US008088971B2

(12) United States Patent
Song et al.

(10) Patent No.: US 8,088,971 B2
(45) Date of Patent: Jan. 3, 2012

(54) EXPRESSION ENHANCING INTRON SEQUENCES

(75) Inventors: Hee-Sook Song, Raleigh, NC (US); Marc Morra, Bronx, NY (US); Liqun Xing, Chapel Hill, NC (US); Hongmei Jia, Apex, NC (US)

(73) Assignee: BASF Plant Science GmbH (DE)

( * ) Notice: Subject to any disclaimer, the term of this patent is extended or adjusted under 35 U.S.C. 154(b) by 868 days.

(21) Appl. No.: 11/885,988

(22) PCT Filed: Mar. 7, 2006

(86) PCT No.: PCT/EP2006/060513
§ 371 (c)(1),
(2), (4) Date: Apr. 3, 2008

(87) PCT Pub. No.: WO2006/094976
PCT Pub. Date: Sep. 14, 2006

(65) Prior Publication Data
US 2009/0144863 A1    Jun. 4, 2009

Related U.S. Application Data

(60) Provisional application No. 60/659,482, filed on Mar. 8, 2005.

(51) Int. Cl.
*C12N 15/82* (2006.01)
*A01H 5/00* (2006.01)

(52) U.S. Cl. ............... 800/278; 536/24.1; 435/320.1; 435/419; 435/468; 800/295; 800/298

(58) Field of Classification Search .................... None
See application file for complete search history.

(56) References Cited

FOREIGN PATENT DOCUMENTS

| EP | 0769553 A1 | 4/1997 |
| EP | 1134285 A1 | 9/2001 |
| EP | 1149915 | 10/2001 |

OTHER PUBLICATIONS

Callis et al. Introns increase gene expression in cultured maize cells. (1987) Genes & Development; vol. 1; pp. 1183-1200.*
Osterman et al. Z. mays alcohol dehydrogenase (ADH-1 C-m allele) gene, complete cds. (1993) GenBank Accession M32984; pp. 1-3.*
Goodall et al. The AU-rich sequences present in the introns of plant nuclear pre-mRNAs are required for splicing. (1989) Cell; vol. 58; pp. 473-483 (Abstract Only).*
Maiti et al. Promoter/leader deletion anaylsis and plant expression vectors with the figwort mosic virus (FMV) full length transcript (FLt) promoter conatining single or double enhancer domains. (1997) Transgen. Res.; vol. 6:143-156.*
Donald et al. Mutation of either G box or I box sequences profoundly affects expression from the *Arabidopsis* rbcS-1A promoter. (1990) EMBO J.; vol. 9; pp. 1717-1726.*
Benfey et al. The cauliflower mosaic virus 35S promoter: combinatorial regulation of transcription in plants. (1990) Science; vol. 250; pp. 959-966.*
Kim et al. A 20 nucleotide upstream element is essential for the nopaline synthase (nos) promoter activity. (1994) Plant Mol. Biol.; vol. 24; pp. 105-117.*
Stalberg et al. Deletion anaylsis of a 2S seed storage protein promoter of *Brassica napus* in transgenic tobacco. (1993) Plant Molecular Biology; vol. 23; pp. 671-683.*
Chen et al. Sequence organization and conservation in sh2/a1-homologous regions of sorghum and rice. (1998) Genetics; vol. 148; pp. 435-444.*
Brendel, V., et al., "Prediction of Locally Optimal Splice Sites in Plant Pre-mRNA with Applications to Gene Identification in *Arabidopsis thaliana* Genomic DNA", Nucleic Acids Research, vol. 26, No. 20, (1998), pp. 4748-4757.
Brendel, V., et al., "Gene Structure Prediction From Consensus Spliced Alignment of Multiple ESTs Matching the Same Genomic Locus", Bioinformatics, vol. 20, No. 7, (2004) pp. 1157-1169.
Callis, J., et al., "Introns Increase Gene Expression in Cultured Maize Cells", Genes & Development, vol. 1, (1987), pp. 1183-1200.
Chee, P. P., et al., Expression of a Bean Storage Protein 'Phaseolin Minigene' in Foreign Plant Tissues, Gene, vol. 41, (1986). pp. 47-57.
Christensen, A. H., "Maize Polyubiquitin Genes: Structure, Thermal Perturbation of Expression and Transcript Splicing, and Promoter Activity Following Transfer to Protoplasts by Electroporation", Plant Molecular Biology, vol. 18, (1992), pp. 675-689.
Clancy, M., et al., "Splicing of the Maize *Sh1* First Intron is Essential for Enhancement of Gene Expression, and a T-Rich Motif Increases Expression Without Affecting Splicing", Plant Physiology, vol. 130, (2002), pp. 918-929.
Dean, C., et al., "Sequences Downstream of Translation Start Regulate Quantitative Expression of Two Petunia *rbcS* Genes", The Plant Cell, vol. 1, (1989), pp. 201-208.
Dennis, E.S., et al., "Molecular Analysis of the Alcohol Dehydrogenase (*Adh1*) Gene of Maize", Nucleic Acids Research, vol. 12, No. 9, (1984), pp. 3983-4000.
Jeon, J.-S., et al., "Tissue-Preferential Expression of a Rice α-Tubulin Gene, *OsTubA1*, Mediated by the First Intron", Plant Physiology, vol. 123, (2000), pp. 1005-1014. Kuhlemeier, C, et al., "Upstream Sequences Determine the Difference in Transcript Abundance of Pea *rbsS* Genes", Mol. Gen. Genet, vol. 212, (1988), pp. 405-411.
Leon, P., et al., "Transient Gene Expression in Protoplasts of *Phaseolus vulgaris* Isolated from a Cell Suspension Culture", Plant Physiol, vol. 95, (1991), pp. 968-972.

(Continued)

*Primary Examiner* — Cathy Kingdon Worley
(74) *Attorney, Agent, or Firm* — Connolly Bove Lodge & Hutz LLP

(57) ABSTRACT

The invention relates to methods for the identification and use of introns with gene expression enhancing properties. The teaching of this invention enables the identification of introns causing intron-mediated enhancement (IME) of gene expression. The invention furthermore relates to recombinant expression construct and vectors comprising said IME-introns operably linked with a promoter sequence and a nucleic acid sequence. The present invention also relates to transgenic plants and plant cells transformed with these recombinant expression constructs or vectors, to cultures, parts or propagation material derived there from, and to the use of same for the preparation of foodstuffs, animal feeds, seed, pharmaceuticals or fine chemicals, to improve plant biomass, yield, or provide desirable phenotypes.

20 Claims, 11 Drawing Sheets

OTHER PUBLICATIONS

Luehrsen, K. R., et al., "Intron Enhancement of Gene Expression and the Splicing Efficiency of Introns in Maize Cells", Mol. Gen. Genet, vol. 225, No. 1, (1991), pp. 81-93.

Mascarenhas, D., et al., "Intron-Mediated Enhancement of Heterologous Gene Expression in Maize", Plant Molecular Biology, vol. 15, No. 6, (1990), pp. 913-920.

McElroy, D., et al., "Isolation of an Efficient Actin Promoter for Use in Rice Transformation", The Plant Cell, vol. 2, (1990), pp. 163-171.

Norris, S. R., et al., "The Intron of *Arabidopsis thaliana* Polyubiquitin Genes is Conserved in Location and is a Quantitative Determinant of Chimeric Gene Expression", Plant Molecular Biology, vol. 21, (1993), pp. 895-906.

Pavy, N., et al., "Evaluation of Gene Prediction Software Using a Genomic Data Set: Application of *Arabidopsis thaliana* Sequences", Bioinformatics, vol. 15, No. 11, (1999), pp. 887-899.

Pertea, M., et al., "GeneSplicer: A New Computational Method for Splice Site Prediction", Nucleic Acids Research, vol. 29, No. 5, (2001), pp. 1185-1190.

Rethmeier, N., et al., "Intron-Mediated Enhancement of Transgene Expression in Maize is a Nuclear, Gene-Dependent Process", The Plant Journal, vol. 12, No. 4, (1997), pp. 895-899.

Rose, A. B., "Requirements for Intron-Mediated Enhancement of Gene Expression in *Arabidopsis*", RNA, vol. 8, No. 11, (2002), pp. 1444-1453.

Rose, A.B., et al., "Introns Act Post-Transcriptionally to Increase Expression of the *Arabidopsis thaliana* Tryptophan Pathway Gene *PAT1*", The Plant Journal, vol. 11, No. 3, (1997), pp. 455-464.

Rose, A. B., et al., "Intron-Mediated Enhancement of Gene Expression Independent of Unique Intron Sequences and Splicing", Plant Physiology, vol. 122, No. 2, (2000), pp. 535-542.

Vancanneyt, G., et al., "Construction of an Intron-Containing Marker Gene: Splicing of the Intron in Transgenic Plants and its Use in Monitoring Early Events in *Agrobacterium*-Mediated Plant Transformation", Mol. Gen. Genet, vol. 220, (1990), pp. 245-250.

Sinibaldi, R.M., et al., "Intron Splicing and Intron-mediated Enhanced Expression in Monocots", Progress in Nucleic Acid Research and Molecular Biology, vol. 42, (1992), pp. 229-257.

Vasil, V., et al., "Increased Gene Expression by the First Intron of Maize *Shrunken-1* Locus in Grass Species", Plant Physiol., vol. 91, (1989), pp. 1575-1579.

Xu, Y., et al., "Rice Triosephosphate Isomerase Gene 5' Sequence Directs β-Glucuronidase Activity in Transgenic Tobacco but Requires an Intron for Expression in Rice", Plant Physiol., vol. 106, (1994), pp. 459-467.

Zanor, M. I., et al., "Isolation and Expression of a Barle β-1,3-Glucanase Isoenzyme II Gene", DNA Sequence, vol. 10, No. 6, (2000), pp. 395-398.

"*O. sativa* salT gene", Database EMBL, Accession No. Z25811, Sep. 1, 1993.

"nbxb0017J19f CUGI Rice BAC Library *Oryza sativa* genomic clone nbxb0017J19f, genomic survey sequence," Database EMBL Accession No. AQ257076, Oct. 23, 1998.

"*O. sativa* RSs2 gene for sucrose-UDP glucosyltransferase (isozyme 2)," Database EMBL Accession No. X59046, Feb. 11, 1992.

"OG_BBa0030I22.r OG_BBa *Oryza glaberrima* genomic clone OG_BBa0030I22 3', genomic survey sequence," Database EMBL Accession No. CW671613, Oct. 30, 2004.

"*Oryza sativa* chromosome 3 BAC OSJNBa0090P23 genomic sequence, complete sequence," Database EMBL Accession No. AC084380, Nov. 1, 2000.

"*Oryza sativa* chromosome 3 BAC OSJNBa0091P11 genomic sequence, complete sequence," Database EMBL Accession No. AC073556, Jul. 3, 2000.

"*Oryza sativa* Indica Group genomic DNA, BAC end sequence, BAC clone:K0117E12_F," Database EMBL Accession No. AG850239, Nov. 4, 2004.

"*Oryza sativa* Indica Group sucrose transporter (SUT1) gene, complete cds," Database EMBL Accession No. AF280050, Aug. 2, 2000.

"*Oryza sativa* Japonica Group chromosome 3 clone OSJNAa0091P11, complete sequence," Database EMBL Accession No. AC144491, Apr. 26, 2003.

"*Oryza sativa* Japonica Group DNA, clone:T27990T, 3' flanking sequence of Tos17 insertion in rice strain NG0596," Database EMBL Accession No. AB157286, Dec. 23, 2003.

"*Oryza sativa* Japonica Group genomic DNA, chromosome 1, BAC clone:B1015E06," Database EMBL Accession No. AP003197, Feb. 22, 2001.

"*Oryza sativa* Japonica Group genomic DNA, chromosome 1, PAC clone:P0489A05," Database EMBL Accession No. AP003105, Jan. 19, 2001.

"*Oryza sativa* Japonica Group genomic DNA, chromosome 1, PAC clone:P0700A11," Database EMBL Accession No. AP003300, Feb. 22, 2001.

"*Oryza sativa* MADS-box protein (MADS3) mRNA, complete cds," Database EMBL Accession No. L37528, Jul. 5, 1995.

Aoki, N., et al., "The Sucrose Transporter Gene Family in Rice," Plant Cell Physiol. (2003), vol. 44, No. 3, pp. 223-232.

European Search Report in EP-09176170, dated May 18, 2011.
European Search Report in EP-09176171, dated May 18, 2011.
European Search Report in EP-09176172, dated May 19, 2011.
European Search Report in EP-09176173, dated May 19, 2011.

Fiume, E., et al., "Introns are key regulatory elements of rice tubulin expression," *Planta* (2004), vol. 218, pp. 693-703.

Huang, J.-W., et al., "Complete Structures of Three Rice Sucrose Synthase Isogenes and Differential Regulation of Their Expressions," *Biosci. Biotech. Biochem.* (1996), vol. 60, No. 2, pp. 233-239.

Kang, H.-G., et al., "Phenotypic alterations of petal and sepal by ectopic expression of a rice MADS box gene in tobacco," Plant Molecular Biology (1995), vol. 29, pp. 1-10.

Katagiri, S., et al., "End Sequencing and Chromosomal in silico Mapping of BAC Clones Derived from an *indica* Rice Cultivar, Kasalath," Breeding Science (2004), vol. 54, pp. 273-279.

Sayion, Y., et al., "Expression and Characterization of Rice Sucrose Synthase in *Escherichia coli*," *Food Science and Agricultural Chemistry* (Apr. 1999), vol. 1, No. 2, pp. 122-128.

Snowden, K.C., et al., "Intron position affects expression from the *tpi* promoter in rice," *Plant Molecular Biology* (1996), vol. 31, pp. 689-692.

Wang, A.-Y., et al., "Differentially and Developmentally Regulated Expression of Three Rice Sucrose Synthase Genes," *Plant Cell Physiol.* (1999), vol. 40, No. 8, pp. 800-807.

Wang, A.-Y., et al., "Presence of three rice sucrose synthase genes as revealed by cloning and sequencing of cDNA," *Plant Molecular Biology* (1992), vol. 18, pp. 1191-1194.

Yu, W.-P., et al., "Isolation and sequences of rice sucrose synthase cDNA and genomic DNA," *Plant Molecular Biology* (1992), vol. 18, pp. 139-142.

* cited by examiner

```perl
#!/usr/local/bin/perl -w
intron.pl open(IN,$ARGV[0]) or die "can't find output";

while (defined(my $file=<IN> )) { start of a single annotation if ($file=~/LOCUS.*?\s+(\d+)\sbp(.*)/) {
        my $length=$1;
        my $mol=1;
                $mol=0 if $2 =~ /circular/;
                my @cdslist=();
                my @start=();
        my $order=0; # order=1: complementary coding.
                my @title=();
                my @title0=();
                my @intron=();
                my $id="";
                my @terminator=();
                my @promoter=();
                my @utr5=();
                my @utr3=();
                my @origin=();
                my $tab="";
                my $organism="";
        while (defined(my $line=<IN> )) {
                $line=$tab.$line;

if ($line =~ /^VERSION.*?\s+(GI:\d+)/) {
        $id=$1;

}elsif ($line =~ /^\s{2}ORGANISM\s+(.*)/){ if($1=~/Oryza sativa/i){
                        $organism="rice";
                }elsif($1=~/Zea mays/i) {
                        $organism="maize";
                    }elsif($1=~/Glycine max/i){
                        $organism="soybean";
                    }else {
                       $1=~/(\w+)/;
                            $organism=$1;
                    }
                }elsif($line =~ /^\s{5}(CDS\s*)/){   #extract cds
                    my $test=$';
                    my $gene="N/A";
                            my $start=1;
                            my $product="N/A";
                            my $gi=$id;
                            my @cds=();
                            my @temp=();
                            if ($test =~ /complement/) {
                    $order=1 ;
                }else {
                    $order = 0;
                }
```

Fig. 5a

```perl
while ( my $in=<IN>) {
    if ($in =~ /\s\/(.*)\//) {
        $test=$test;
        if ($1=~/gene="(.*)"/) {
            $gene=$1;
        }elsif($1=~/note="(.*)"/) {
            $product=$1;
        }else {
        last;
        }
    } else {
        $test=$test.$in;
    }
} #close while loop;

$test =~s/\w+\d+\.\d:\d+\.\.\d+//g;
$test =~ s/\D/ /g;
$test =~ s/\s+/ /g;
$test =~ s/^\s+//;
my @sort;
    if ($mol==0) {
        @sort=split(/ /,$test);
    } else {
@sort=sort {$a <=> $b} split(/ /,$test);
    }
# tag complement cds
    if ($order==1) {
@cds = ("complement",@sort);

} elsif ($order==0) {
@cds = @sort;
} #close if loop;
#retreave notation if intron exist;
    if (scalar(@cds) >= 4) { while (my $in=<IN>) {
        $start=1;
if ($in =~ /codon_start=(\d+)/) {
        $start = $1;

}elsif ($in =~ /\/gene="(.*)"/){
        $gene=$1;
    }elsif ($in =~ /\/product=(.*)/){
        $product=$1;
        $product=~ tr/""//d;

}elsif ($in =~ /db_xref="(GI:.*?)"/) {
        $gi = $1;

last ;
} elsif ($in=~ /\/(pseudo)/) {
        $product="pseudo";
        last;
}                    #close if loop
} #close while loop;
push @start, $start;
push @cdslist, \@cds;
```

Fig. 5b

```
# retreave 5'utr if start codon > 1;
                my @tem=();
                            for (my $i=1;$i<=($#cds-1)/2;$i++) {
                                my $title1=">$organism|$gi|Intron_$i ";
                                my           $title2="             $gene|$start|".($cds[2*$i-
1+$order]+1).".".($cds[2*$i+$order]-1)."|$product\n";
                                my @title=($title1,$title2);
                                push @tem, \@title;
                            } #close for loop
                            push @title, \@tem;
                            my    $title0=">$organism|$gi|5UTR_0       $gene|$start|".($cds[$order]-
1).".".($cds[$order]+$start-2)."|$product\n";
                            push @title0, $title0;

} #close if @cds>4 loop

} elsif ($line =~ /^\s{5}terminator/) {

($tab,my $note,my @term)=&getTerminator($line);

push @terminator, $note;
                    push @terminator, \@term;

} elsif ($line =~ /^\s{5}promoter/) {

($tab,my $note,my @prom)=&getTerminator($line);

push @promoter, $note;
                    push @promoter, \@prom;

} elsif ($line =~ /^\s{5}5\DUTR/) {

($tab,my $note,my @temp)=&getTerminator($line);

push @utr5,$note;
                    push @utr5,\@temp;

} elsif ($line =~ /^\s{5}3\DUTR/) {

($tab,my $note,my @temp)=&getTerminator($line);

push @utr3,$note;
                    push @utr3,\@temp;
#get sequence @origin
         }
         if ($line =~ /^(ORIGIN)/) {
              $line="";
                    while (my $code=<IN>) { if ($code =~ /\\//) {
                    last;
                }else{
                                $line=$line.$code;
                            } #close if loop
                 } #close while loop
                    # $line =~ s/\\//g;
                    # print $line,"\n";
```

Fig. 5c

```perl
            $line =~ tr/0-9//d;
                $line =~ tr/ //d;
                $line =~ tr/\n//d;
                                @origin = split(//,$line);

for (my $i=0; $i<=$#cdslist;$i++) { if ($start[$i]>2) { my @first=();
                    my $first;
                    if (${$cdslist[$i]}[0] eq "complement") {
                        my @utr=@origin[$cdslist[$i][1]-1 .. ($cdslist[$i][1]+$start[$i]-2)];
                                print @utr,"\n";
                        $first=&complement(@utr);
                    } else {
                        @first=@origin[$cdslist[$i][0]-1 .. ($cdslist[$i][0]+$start[$i]-2)];
                                $first=join('',@first);
                    } #close if loop for complement print $title0[$i],$first,"\n\n";
            } #close if loop for $start>2;

if (${$cdslist[$i]}[0] eq "complement") {
                        shift @{$cdslist[$i]};
                        for (my $j=1; $j<=($#{$cdslist[$i]}-1)/2;$j++) {
                            my @int=@origin[$cdslist[$i][2*$j-1] .. $cdslist[$i][2*$j]-2];
                                my $int1=&complement(@int);
                                print        $title[$i][$j-1][0],scalar(@int),$title[$i][$j-1][1],    $int1,"\n\n"    if
$#int<5000;
                    } #close 2nd for loop for complement } else {
                        for (my $j=1; $j<=($#{$cdslist[$i]}-1)/2;$j++) {
                                my @int=@origin[$cdslist[$i][2*$j-1] .. $cdslist[$i][2*$j]-2];

if ($mol==0 && $cdslist[$i][2*$j-1] > $cdslist[$i][2*$j]) {
                                @int=(@origin[$cdslist[$i][2*$j-1]    ..    $#origin],    @origin[0    ..
$cdslist[$i][2*$j]-2]);
                            }
                                my $int1=join('',@int);
                            print $title[$i][$j-1][0],scalar(@int),$title[$i][$j-1][1], $int1,"\n\n" if $#int < 5000;
                            }#close 2nd for loop
                    } #close else loop
            } #close 1st for loop my $title1=">$organism|$id|terminator";
                    &getSequence(\@terminator,\@origin,$title1);

$title1=">$organism|$id|promoter";
                    &getSequence(\@promoter,\@origin,$title1);

$title1=">$organism|$id|5utr";
                    &getSequence(\@utr5,\@origin,$title1);

$title1=">$organism|$id|3utr";
                    &getSequence(\@utr3,\@origin,$title1);
```

Fig. 5d

```
            last;
        } else {
            $tab="";
    } #close if $line loop
   } #close while $line loop
   next;

} #close if $file loop

} #close while $file loop
close IN;

#retreave complement sequnce
sub complement{
  my @code=@_;
  my @complemnt=();
  for (my $i=0;$i<=$#code;$i++) {
    if ($code[$#code-$i] eq "t") {
       $complement[$i]= "a";
    } elsif ($code[$#code-$i] eq "a") {
       $complement[$i]= "t";
    } elsif ($code[$#code-$i] eq "c") {
       $complement[$i]= "g";
    } elsif ($code[$#code-$i] eq "g") {
             $complement[$i]= "c";
    } else {
       $complement[$i]=$code[$#code-$i];
    }#close if loop
  } #close for loop
  my $comp=join('',@complement);
  @complement=();
  return $comp;
} #close sub get sequence reference for feature keys
sub getTerminator {
 my $line=$_[0];
 my $order=0;
 if ($line=~/complement/) {
    $order=1;
 } else {
 } #close if loop
 $line =~ s/\d'UTR//;
 $line =~ s/\D/ /g;
 $line =~ s/\s+/ /g;
 $line =~ s/^\s//;
 my @term=split(' ',$line);
    @term=("c",@term) if $order==1;
 my $in;
 read(IN,$in,6);
 my $note =" \n";
```

Fig. 5e

```perl
    if ($in!~/\w/) {
      $note=<IN>;
      $note=~s/\s+V//;
      $note=~s/note=//;
      $note=~ tr/""//d;
    } #close if loop
    return ($in,$note,@term);
} #close sub retreave sequence information for feature keys
sub getSequence {
my @array=@{$_[0]};
my @code=@{$_[1]};
my $id=$_[2];

for (my $i=0; $i<($#array+1)/2;$i++) {
    my $note=$array[2*$i];
    my @term=@{$array[2*$i+1]};
   if ($term[0] eq "c") {
     shift @term;
     for (my $j=0; $j<=($#term-1)/2;$j++) {
       my @comp=@code[($term[2*$j]-1) .. ($term[2*$j+1]-1)];
       my $int1=&complement(@comp);
       my $title=$id."_".($i+1)." ".scalar(@comp)." $term[2*$j]..$term[2*$j+1]|$note";
       print $title, $int1,"\n\n";
     } #close 2nd for loop
   } else {
     for (my $j=0; $j<($#term+1)/2;$j++) {
              my @int=@code[($term[2*$j]-1) .. ($term[2*$j+1]-1)];
       my $int1=join('',@int);
       my $title=$id."_".($i+1)." ".scalar(@int)." $term[2*$j]..$term[2*$j+1]|$note";
              print $title, $int1,"\n\n";
     } #close 2nd for loop
   } #close if loop
  } #close 1st for loop
} #close sub
```

Fig. 5f

EXPRESSION ENHANCING INTRON SEQUENCES

RELATED APPLICATIONS

This application is a national stage application (under 35 U.S.C. 371) of PCT/EP2006/060513 filed Mar. 7, 2006, which claims benefit of U.S. provisional application 60/659,482 filed Mar. 8, 2005.

SUBMISSION ON COMPACT DISC

The contents of the following submission on compact discs are incorporated herein by reference in its entirety: two copies of the Sequence Listing (COPY 1 and COPY 2) and a computer readable form copy of the Sequence Listing (CRF COPY), all on compact disc, each containing: file name: Sequence List-13987-00067-US, date recorded: Sep. 6, 2007, size: 119 KB.

FIELD OF THE INVENTION

The invention relates to methods for the identification and use of introns with gene expression enhancing properties. The teaching of this invention enables the identification of introns causing intron-mediated enhancement (IME) of gene expression. The invention furthermore relates to recombinant expression construct and vectors comprising said IME-introns operably linked with a promoter sequence and a nucleic acid sequence. The present invention also relates to transgenic plants and plant cells transformed with these recombinant expression constructs or vectors, to cultures, parts or propagation material derived there from, and to the use of same for the preparation of foodstuffs, animal feeds, seed, pharmaceuticals or fine chemicals, to improve plant biomass, yield, or provide desirable phenotypes.

BACKGROUND OF THE INVENTION

The aim of plant biotechnology is the generation of plants with advantageous novel properties, such as pest and disease resistance, resistance to environmental stress (e.g., drought), improved qualities (e.g., high yield), or for the production of certain chemicals or pharmaceuticals. Appropriate gene expression rates play an important role in order to obtain the desired phenotypes. The gene expression rate is mainly modulated by the promoter, additional DNA sequence located in the 5' untranscribed and 5' untranslated region and the terminator sequences of a given gene. Promoters are the portion of DNA sequences located at the 5' end a gene which contains signals for RNA polymerases to begin transcription so that a protein synthesis can then proceed. Regulatory DNA sequences positioned in the 5' untranscribed region modulate gene expression in response to specific biotic (e.g. pathogen infection) or abiotic (e.g. salt-, heat-, drought-stress) stimuli. Furthermore, other so called "enhancer' sequences have been identified that elevate the expression level of nearby located genes in a position and orientation independent manner.

Beside the elements located on the untranscribed regions of a gene (e.g. promoter, enhancer), it is documented in a broad range of organisms (e.g. nematodes, insects, mammals and plants) that some introns have gene expression enhancing properties. In plants, the inclusion of some introns in gene constructs leads to increased mRNA and protein accumulation relative to constructs lacking the intron. This effect has been termed "intron mediated enhancement' (IME) of gene expression (Mascarenhas et al., (1990) Plant Mol. Biol. 15:913-920). Introns known to stimulate expression in plants have been identified in maize genes (e.g. tubA1, Adh1, Sh1, Ubi1 (Jeon et al. (2000) Plant Physiol. 123:1005-1014; Callis et al. (1987) Genes Dev. 1:1183-1200; Vasil et al. (1989) Plant Physiol 91:1575-1579; Christiansen et al. (1992) Plant Mol. Biol. 18:675-689]) and in rice genes (e.g. salt, tpi [McElroy et al. (1990) Plant Cell 2: 163-171; Xu et al. (1994) Plant Physiol 106:459-467]). Similarly, introns from dicotyledonous plant genes like those from petunia (e.g. rbcS), potato (e.g. st-ls1) and from *Arabidopsis thaliana* (e.g. ubq3 and pat1) have been found to elevate gene expression rates (Dean et al. (1989) Plant Cell 1:201-208; Leon et al. (1991) Plant Physiol. 95:968-972; Norris et al. (1993) Plant Mol Biol 21:895-906; Rose and Last (1997) Plant J 11:455-464). It has been shown that deletions or mutations within the splice sites of an intron reduce gene expression, indicating that splicing might be needed for IME (Mascarenhas et al. (1990) Plant Mol Biol 15:913-920; Clancy and Hannah (2002) Plant Physiol 130:918-929). However, that splicing per se is not required for a certain IME in dicotyledonous plants has been shown by point mutations within the splice sites of the pat1 gene from *A. thaliana* (Rose and Beliakoff (2000) Plant Physiol 122:535-542).

Enhancement of gene expression by introns is not a general phenomenon because some intron insertions into recombinant expression cassettes fail to enhance expression (e.g. introns from dicot genes (rbcS gene from pea, phaseolin gene from bean and the stls-1 gene from *Solanum tuberosum*) and introns from maize genes (adh1 gene the ninth intron, hsp81 gene the first intron)) (Chee et al. (1986) Gene 41:47-57; Kuhlemeier et al. (1988) Mol Gen Genet 212:405-411; Mascarenhas et al. (1990) Plant Mol Biol 15:913-920; Sinibaldi and Mettler (1992) In W E Cohn, K Moldave, eds, Progress in Nucleic Acid Research and Molecular Biology, Vol 42. Academic Press, New York, pp 229-257; Vancanneyt et al. 1990 Mol Gen Gent 220:245-250). Therefore, not each intron can be employed in order to manipulate the gene expression level of alien genes or endogenous genes in transgenic plants. What characteristics or specific sequence features must be present in an intron sequence in order to enhance the expression rate of a given gene is not known in the prior art and therefore from the prior art it is not possible to predict whether a given plant intron, when used heterologously, will cause IME.

The introduction of a foreign gene into a new plant host does not always result in a high expression of the incoming gene. Furthermore, if dealing with complex traits, it is sometimes necessary to modulate several genes with spatially or temporarily different expression pattern. Introns can principally provide such modulation. However multiple use of the same intron in one plant has shown to exhibit disadvantages. In those cases it is necessary to have a collection of basic control elements for the construction of appropriate recombinant DNA elements. However, the available collection of introns with expression enhancing properties is limited and alternatives are needed.

Thus, there is still a growing demand for basic control elements including promoters, regulatory sequences (e.g., inducible elements, enhancers) or intron sequences that have an impact on gene expression rates. It is therefore an objective of the present invention, to provide a highly reproducible and reliable method for the identification of introns with expression enhancing properties.

This objective is achieved by the methods provided within this invention.

SUMMARY OF THE INVENTION

A first subject matter of the invention therefore relates to a method for identifying an intron with expression enhancing properties in plants comprising selecting an intron from a plant genome, wherein said intron is characterized by at least the following features I) an intron length shorter than 1,000 base pairs, and
II) presence of a 5' splice site comprising the dinucleotide sequence 5'-GT-3' (SEQ ID NO: 78), and
III) presence of a 3' splice site comprising the trinucleotide sequence 5'-CAG-3' (SEQ ID NO: 79), and
IV) presence of a branch point resembling the consensus sequence 5'-CURAY-3' (SEQ ID NO:75) upstream of the 3' splice site, and
V) an adenine plus thymine content of at least 40% over 100 nucleotides down-stream from the 5' splice site, and
VI) an adenine plus thymine content of at least 50% over 100 nucleotides upstream from the 3' splice site, and
VII) an adenine plus thymine content of at least 50%, and a thymine content of at least 30% over the entire intron.

In another embodiment, the invention relates to a method for enriching the number of introns with expression enhancing properties in plants in a population of plant introns to a percentage of at least 50% of said population, said method comprising selecting introns from said population, wherein said introns are characterized by at least the following features I) an intron length shorter than 1,000 base pairs, and
II) presence of a 5' splice site comprising the dinucleotide sequence 5'-GT-3' (SEQ ID NO: 78), and
III) presence of a 3' splice site comprising the trinucleotide sequence 5'-CAG-3' (SEQ ID NO: 79), and
IV) presence of a branch point resembling the consensus sequence 5'-CURAY-3' (SEQ ID NO:75) upstream of the 3' splice site, and
V) an adenine plus thymine content of at least 40% over 100 nucleotides down-stream from the 5' splice site, and
VI) an adenine plus thymine content of at least 50% over 100 nucleotides upstream from the 3' splice site, and
VII) an adenine plus thymine content of at least 50%, and a thymine content of at least 30% over the entire intron.

Preferably, the population of plant introns chosen for the enrichment of introns with gene expression enhancing properties in plants comprises substantially all introns of a plant genome represented in a genomic DNA sequence database or a plant genomic DNA library.

In a preferred embodiment, the intron with gene expression enhancing properties in plants ("IME-intron') is selected by the method of the invention for identifying IME-introns or the method of the invention for enriching the number of IME-introns in a population of plant introns. Preferably, said intron is selected from the group consisting of introns located between two protein encoding exons or introns located within the 5' untranslated region of the corresponding gene.

In a particularly preferred embodiment, the IME-intron is identified or enriched by one of the inventive methods from a group or population of genes representing the 10% fraction of genes with the highest expression rate in a gene expression analysis experiment performed using a plant cell, plant tissue or a whole plant.

The invention furthermore relates to a method wherein the gene sequence information used for the identification or enrichment of IME-introns is present in a DNA sequence database and the selection steps for identifying or enriching said introns are performed using an automated process, preferably by using a computer device and an algorithm that defines the instructions needed for accomplishing the selection steps for identifying or enriching said introns.

Additionally, the invention relates to computer algorithm that defines the instructions needed for accomplishing the selection steps for identifying or enriching IME-introns from a plant genome or a population of introns selected from the group consisting of introns located between two protein encoding exons, and/or introns located within the 5' untranslated region of the corresponding gene and/or introns located in the DNA sequences of genes representing the 10% fraction of genes with the highest expression rate in a gene expression analysis experiment performed using a plant cell, plant tissue and/or a whole plant.

The invention also relates to the computer device or data storage device comprising an algorithm as described above.

In a preferred embodiment, the invention relates to methods for isolating, providing or producing IME-introns comprising the steps of performing an identification or enrichment of IME-introns as described above and providing the sequence information of said IME-introns identified or enriched, and providing the physical nucleotide sequence of said identified or enriched introns and evaluating the gene expression enhancing properties of the isolated introns in an in vivo or in vitro expression experiment, and isolating the IME-introns from the population of introns tested in the in vivo or in vitro expression experiment. Preferably, the evaluation of the gene expression enhancing properties of the IME-intron is done in a plant cell and wherein IME-intron enhances the expression of a given nucleic add at least two-fold.

An additional subject matter of the invention relates to a recombinant DNA expression construct comprising at least one promoter sequence functioning in plants cells, at least one nucleic acid sequence and at least one intron selected from the group consisting of the sequences described by SEQ ID NOs: 1, 2, 3, 5, 6, 7, 10, 11, 12, 13, 14, 15, 16, 17, 18, 19, 20, 21 and 22, and functional equivalents thereof, wherein said promoter sequence and at least one of said intron sequences are functionally linked to said nucleic acid sequence and wherein said intron is heterologous to said nucleic acid sequence or to said promoter sequence.

Furthermore, the invention relates to recombinant expression constructs comprising at least one promoter sequence functioning in plants cells, at least one nucleic acid sequence and at least one functional equivalents of an intron described by any of sequences SEQ ID NOs: 1, 2, 3, 5, 6, 7, 10, 11, 12, 13, 14, 15, 16, 17, 18, 19, 20, 21 and 22, wherein said functional equivalent comprises the functional elements of an intron and is characterized by a) a sequence having at least 50 consecutive base pairs of the intron sequence described by any of SEQ ID NOs: 1, 2, 3, 5, 6, 7, 10, 11, 12, 13, 14, 15, 16, 17, 18, 19, 20, 21 or 22, or
b) having an identity of at least 80% over a sequence of at least 95 consecutive nucleic acid base pairs to a sequences described by any of SEQ ID NOs: 1, 2, 3, 5, 6, 7, 10, 11, 12, 13, 14, 15, 16, 17, 18, 19, 20, 21 or 22, or
c) hybridizing under high stringent conditions with a nucleic acid fragment of at least 50 consecutive base pairs of a nucleic acid molecule described by any of SEQ ID NOs: 1, 2, 3, 5, 6, 7, 10, 11, 12, 13, 14, 15, 16, 17, 18, 19, 20, 21 or 22, wherein said promoter sequence and at least one of said intron sequences are functionally linked to said nucleic acid sequence and wherein said intron is heterologous to said nucleic acid sequence or to said promoter sequence.

In another embodiment, the recombinant DNA expression construct of the invention further contains one or more additional regulatory sequences functionally linked to promoter. Those regulatory sequences can be selected from the group consisting of heat shock responsive-, anaerobic responsive-, pathogen responsive-, drought responsive-, low temperature responsive-, ABA responsive-elements, 5' untranslated gene region, 3' untranslated gene region, transcription terminators, polyadenylation signals and enhancers.

The nucleic acid sequence of the inventive recombinant DNA expression construct may result in the expression of a protein and/or sense, antisense or double-stranded RNA encoded by said nucleic acid sequence.

In another embodiment, the nucleotide sequence encoding the transgenic expression construct of the invention is double-stranded. In yet another embodiment, the nucleotide sequence encoding the transgenic expression construct of the invention is single-stranded.

In yet another alternative embodiment of the invention, the recombinant expression construct comprises a nucleic acid sequence encoding for a selectable marker protein, a screenable marker protein, a anabolic active protein, a catabolic active protein, a biotic or abiotic stress resistance protein, a male sterility protein or a protein affecting plant agronomic characteristics.

The invention relates furthermore to vectors containing a transgenic expression construct of the invention. Additionally, the invention relates to transgenic cells or transgenic non-human-organisms like bacteria, fungi, yeasts or plants comprising an expression vector containing a transgenic expression construct of the invention. In a preferred embodiment, the transgenic cell or transgenic non-human organism transformed with an expression construct of the invention is a monocotyledonous plant or is derived from such a plant. In a yet more preferred embodiment, the monocotyledonous plant is selected from the group consisting of the genera *Hordeum, Avena, Secale, Triticum, Sorghum, Zea, Saccharum,* and *Oryza*. Further embodiments of the invention relate to cell cultures, parts or propagation material derived from non-human-organisms like bacteria, fungi, yeasts and/or plants, preferably monocotyledonous plants, most preferably plants selected from the group consisting of the genera *Hordeum, Avena, Secale, Triticum, Sorghum, Zea, Saccharum,* and *Oryza*, transformed with the inventive vectors or containing the inventive recombinant expression constructs.

The invention furthermore relates to a method for providing an expression cassette for enhanced expression of a nucleic acid sequence in a plant or a plant cell, comprising the step of functionally linking at least one sequence selected from the group consisting of SEQ ID NOs: 1, 2, 3, 5, 6, 7, 10, 11, 12, 13, 14, 15, 16, 17, 18, 19, 20, 21 and 22 to said nucleic acid sequence.

The invention further relates to a method for enhancing the expression of a nucleic acid sequence in a plant or a plant cell, comprising functionally linking at least one sequence selected from the group consisting of SEQ ID NOs: 1, 2, 3, 5, 6, 7, 10, 11, 12, 13, 14, 15, 16, 17, 18, 19, 20, 21 and 22 to said nucleic acid sequence.

An additional embodiment of the invention relates to a method
a) for providing an expression cassette for enhanced expression of a nucleic acid sequence in a plant or a plant cell, or
b) for enhancing the expression of a nucleic acid sequence in a plant or a plant cell said method comprising functionally linking at least one sequence selected from the group consisting of SEQ ID NOs: 1, 2, 3, 5, 6, 7, 10, 11, 12, 13, 14, 15, 16, 17, 18, 19, 20, 21 and 22 to said nucleic acid sequence, wherein furthermore a promoter sequence functional in plants is linked to said nucleic acid sequence.

Preferably, at least one sequence selected from the group consisting of SEQ ID NOs: 1, 2, 3, 5, 6, 7, 10, 11, 12, 13, 14, 15, 16, 17, 18, 19, 20, 21 and 22 is linked to a nucleic acid sequence by insertion into the plant genome via homologous recombination. Preferably, said homologous recombination is comprising at least the steps of a) providing in vivo or in vitro a DNA construct comprising said intron flanked by sequences ("recombination substrate') allowing homologous recombination into a pre-existing expression cassette between the promoter and the nucleic add of said expression cassette, and b) transforming a recipient plant cell comprising said cassette of step a) and regenerating a transgenic plant, wherein said intron has been inserted into the genome of said plant. Preferably, the site of integration into the genome of said plant is determined by the DNA sequence of the recombination substrate of step a), wherein said sequence sharing sufficient homology (as defined herein) with said genomic target DNA sequence allowing the sequence specific integration via homologous recombination at said genomic target DNA locus.

In a preferred embodiment of the invention, said recipient plant or plant cell is a monocotyledonous plant or plant cell, more preferably a plant or plant cell selected from the group consisting of the genera *Hordeum, Avena, Secale, Triticum, Sorghum, Zea, Saccharum,* and *Oryza*, most preferably a maize plant.

Preferably, the nucleic acid sequence to which one of the inventive intron is functionally linked, encodes for a selectable marker protein, a screenable marker protein, an anabolic active protein, a catabolic active protein, a biotic or a biotic stress resistance protein, a male sterility protein or a protein affecting plant agronomic characteristics and/or a sense, antisense, or double-stranded RNA.

Additionally, the invention relate to the use of a transgenic organism of the invention or of cell cultures, parts of transgenic propagation material derived there from for the production of foodstuffs, animal feeds, seeds, pharmaceuticals or fine chemicals.

The invention furthermore relates to a recombinant DNA expression construct comprising a) at least one promoter sequence functioning in plants or plant cells, and b) at least one intron selected from the group of introns with expression enhancing properties in plants or plant cells characterized by at least the following features I) an intron length shorter than 1,000 base pairs, and II) presence of a 5' splice site comprising the dinucleotide sequence 5'-GT-3' (SEQ ID NO: 78), and III) presence of a 3' splice site comprising the trinucleotide sequence 5'-CAG-3' (SEQ ID NO: 79), and IV) presence of a branch point resembling the consensus sequence 5'-CURAY-3' (SEQ ID NO: 75) upstream of the 3' splice site, and V) an adenine plus thymine content of at least 40% over 100 nucleotides down-stream from the 5' splice site, and VI) an adenine plus thymine content of at least 50% over 100 nucleotides upstream from the 3' splice site, and VII) an adenine plus thymine content of at least 55%, and a thymine content of at least 30% over the entire intron, and c) at least one nucleic add sequence, wherein said promoter sequence and at least one of said intron sequences are functionally linked to said nucleic acid sequence and wherein said intron is heterologous to said nucleic acid sequence and/or to said promoter sequence.

BRIEF DESCRIPTION OF THE DRAWINGS

FIG. 5a-f: Computer algorithm for retrieving sequence information from NCBI genebank file.

GENERAL DEFINITIONS

Figure 1:
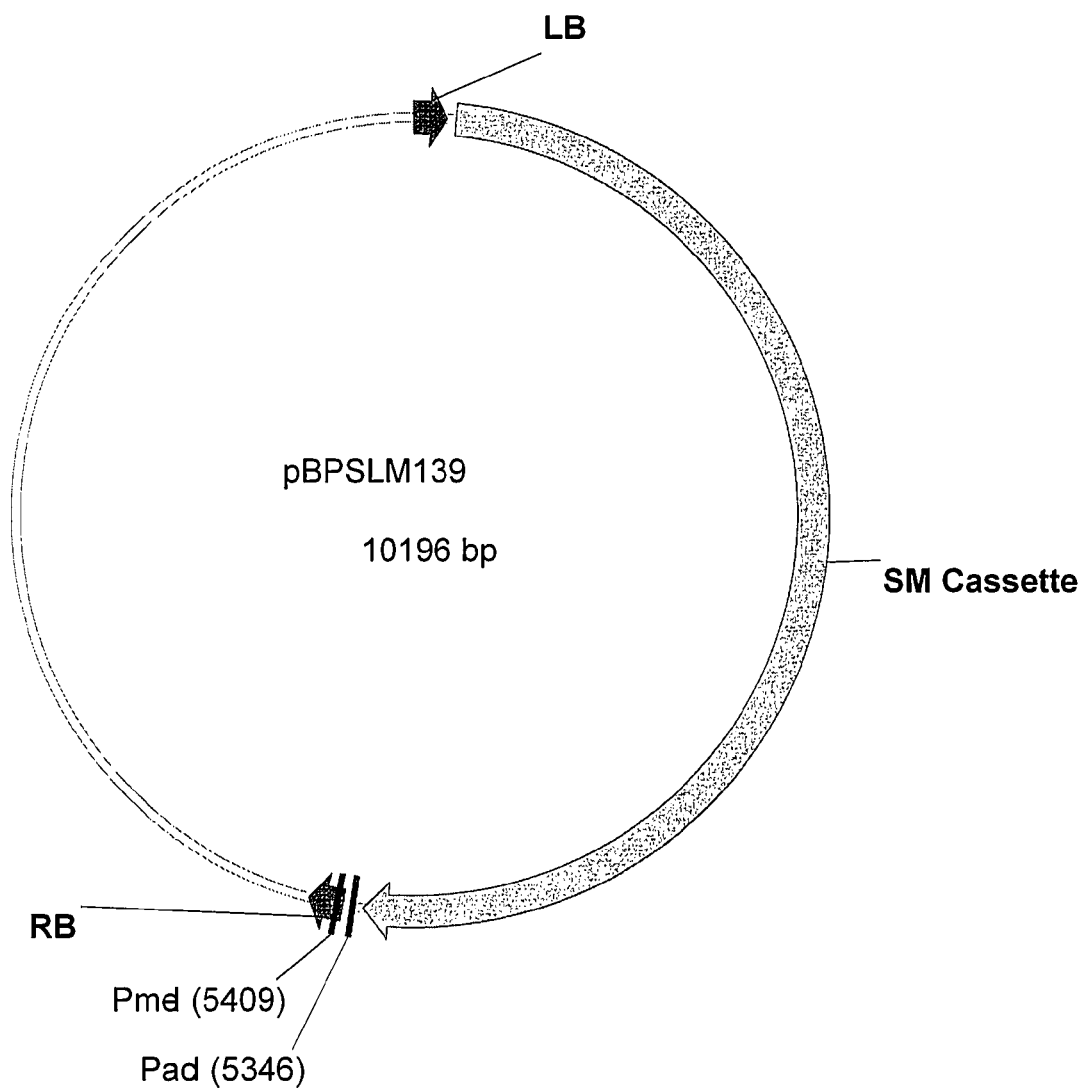
FIG. 1 Map of pBPSMM291 (SEQ ID NO: 109)
This vector comprises the maize ubiquitin promoter, followed by the BPSI.1, then the GUSint ORF (including the potato invertase [PIV]2 intron to prevent bacterial expression), followed by nopaline synthase (NOS) terminator. This vector contains the attL1 and attL2 sites to make it compatible with modification via the Gateway® cloning Technology from Invitrogen™. This vector is based on the pUC based expression vector pBPSMM267. The XmaI-RsrII digested BPSI.1 PCR product was ligated into the XmaI-RsrII digested pBPSMM267 to create pBPSMM291. The vectors pBPSMM293, pBPSMM294 and pBPSMM295 have been created accordingly (see table 6 and 1.6.1).
Figure 2:
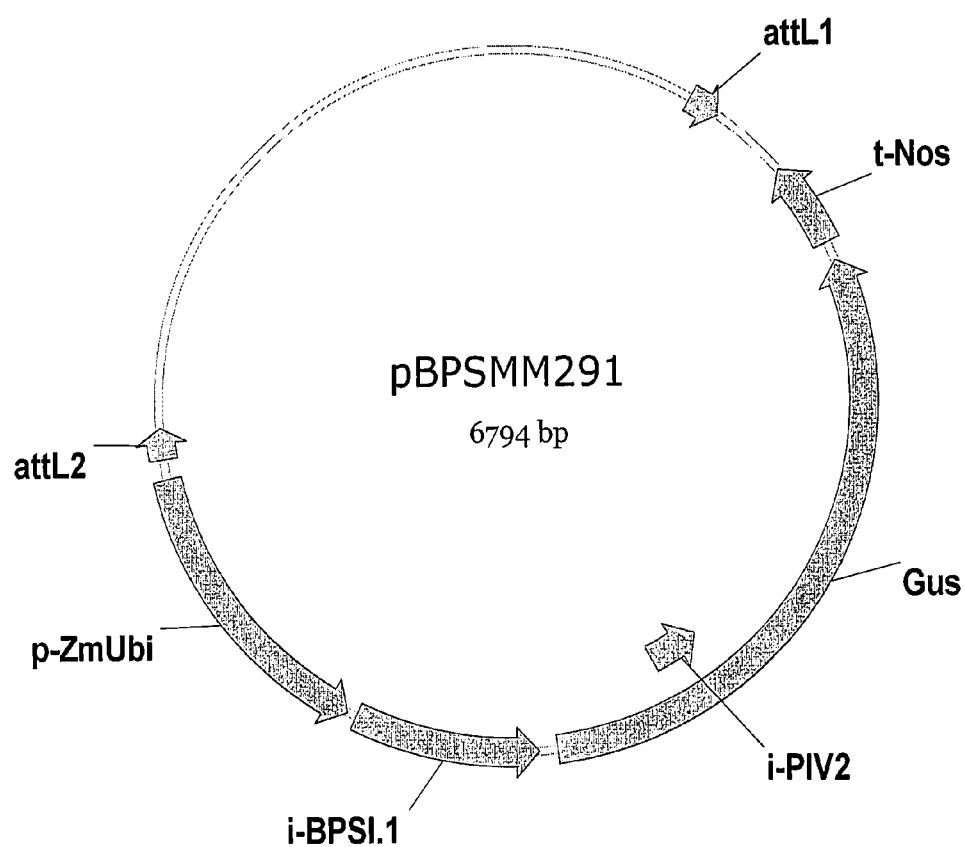
FIG. 2 Map of pBPSMM305 (SEQ ID NO:110)
The expression vector pBPSMM305 comprises the maize lactate dehydrogenase (LDH) promoter without intron driving expression of the GUSint ORF (including the potato invertase [PIV]2 intron to prevent bacterial expression), followed by the NOS terminator. This vector has been used to create the pUC based expression vectors pBPSJB041, pBPSJB042, pBPSJB043, pBPSJB044, pBPSJB045, pBPSJB046 and pBPSJB050 (see examples 2.3).
Figure 3:
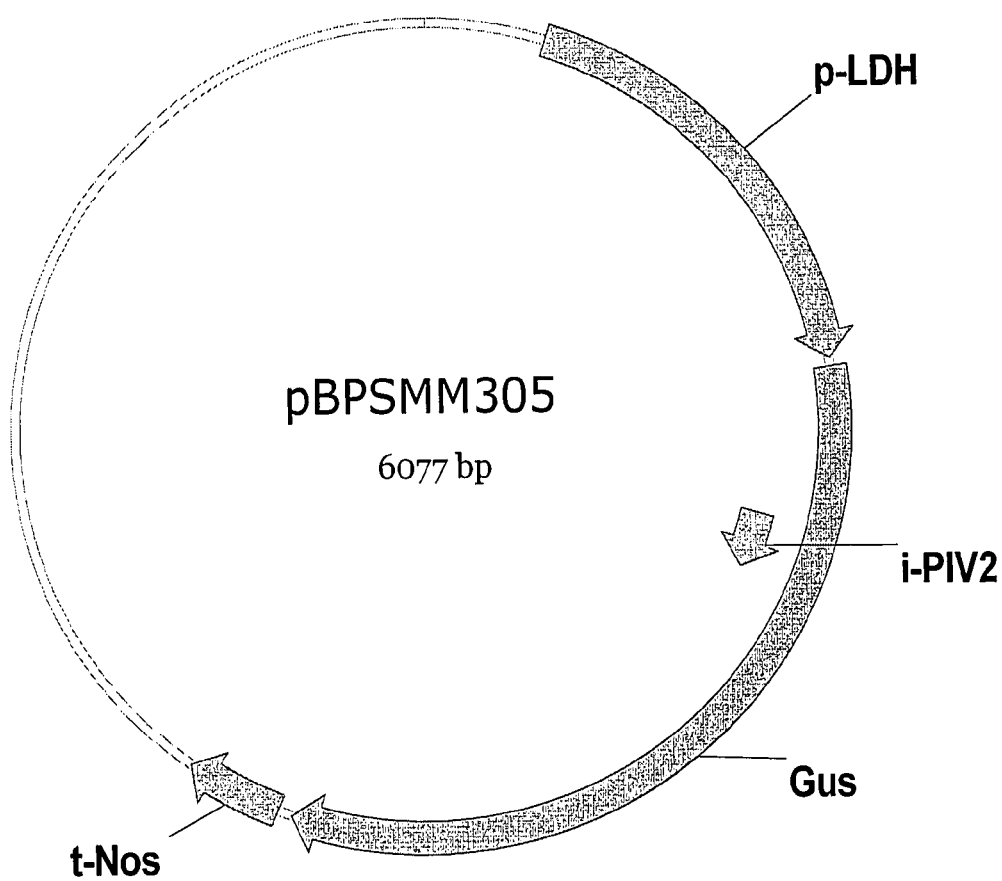
FIG. 3 Map of pBPSMM350 (SEQ ID NO:111):
The vector pBPSMM350 comprises the maize ubiquitin promoter, followed by the BPSI.1, then the GUSint ORF (including the potato invertase [PIV]2 intron to prevent bacterial expression), followed by nopaline synthase (NOS) terminator. The expression cassette has been transferred from the vector pBPSMM291 using the Gateway® cloning Technology from Invitrogen™. The vectors pBPSMM353, pBPSMM312 and pBPSMM310 have been created accordingly (see table 6 and example 1.6.2).
Figure 4:
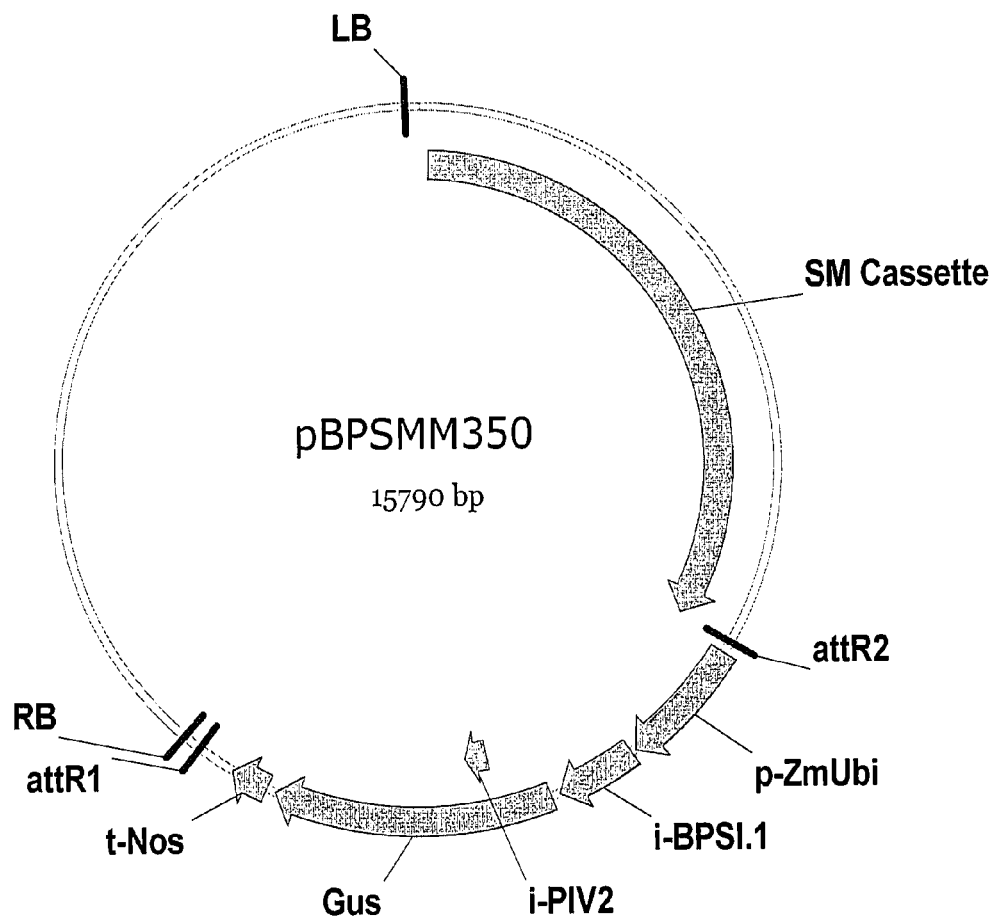
FIG. 4 Map of pBPSLM139 (SEQ ID NO:112):
The vector pBPSLM139 comprises the selectable marker expression cassette. In order to produce the vectors pBPSLI017 to pBPSLI023, PmeI/PacI fragments have been isolated from the vectors pBPSJB-042, -043, -044, -045, 046 and 050 and cloned into the PmeI-PacI digested pBPSLM130 (see example 2.3 and 2.4)
Figure 6:
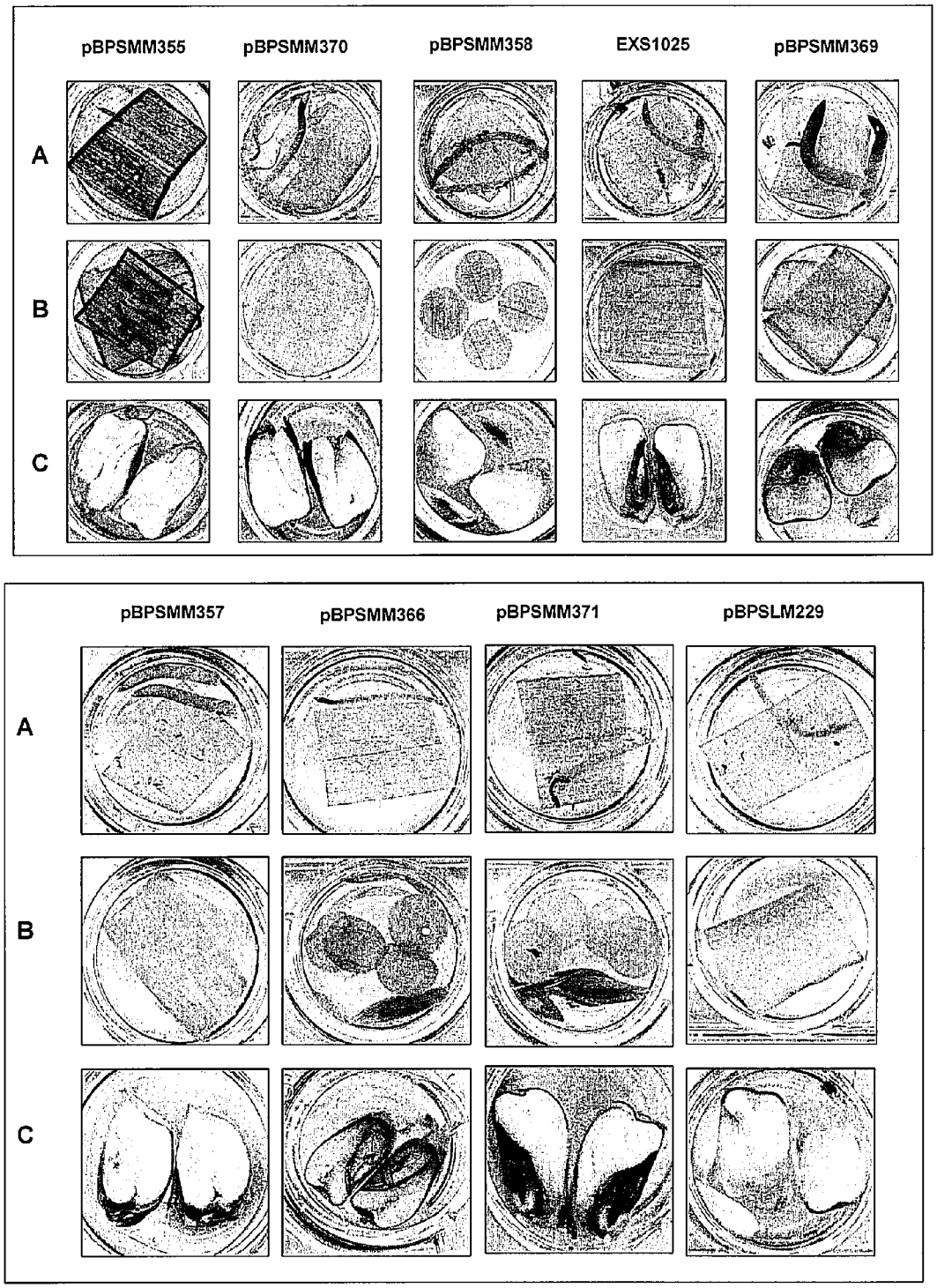
FIG. 6 Transgenic plants containing promoter constructs with BPSI.1 intron (all but pBPSLM229) or BPSI.5 intron (only pBPSLM229) were tested for GUS expression at 5-leaf (A), flowering (B) and seed set (C) stages. Shown are examples of typical staining patterns obtained from at least 15 independent events. All samples were stained for 16 hours in GUS solution. Promoters in the constructs are: rice chloroplast protein 12 (Os.CP12; pBPSMM355), the maize hydroxyproline-rich glycoprotein (Zm.HRGP; pBPSMM370), the rice p-caffeoyl-CoA 3-O-methyltransferase (Os.CCoAMT1; pBPSMM358), the maize Globulin-1 promoter W64A (Zm.Glb1; EXS1025), the putative Rice H+-transporting ATP synthase promoter (Os.V-ATPase; pBPSMM369), Zm.LDH (pBPSMM357), the rice C-8,7 sterol isomerase promoter (Os.C8,7 SI; pBPSMM366), the rice Late Embryogenesis Abundant Protein promoter (Os.Lea; pBPSMM371), and the maize lactate dehydrogenase promoter (ZM.LDH; pBPSLM229).

It is to be understood that this invention is not limited to the particular methodology, protocols, cell lines, plant species or genera, constructs, and reagents described as such it must be noted that as used herein and in the appended claims, the singular forms "a" and "the" include plural reference unless the context clearly dictates otherwise. Thus, for example, reference to "a vector" is a reference to one or more vectors and includes equivalents thereof known to those skilled in the art.

About: the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). As used herein, the word "or" means any one member of a particular list.

*Agrobacterium*: refers to a soil-borne, Gram-negative, rod-shaped phytopathogenic bacterium which causes crown gall. The term "*Agrobacterium*" includes, but is not limited to, the strains *Agrobacterium tumefaciens*, (which typically causes crown gall in infected plants), and *Agrobacterium rhizogenes* (which causes hairy root disease in infected host plants). Infection of a plant cell with *Agrobacterium* generally results in the production of opines (e.g., nopaline, agropine, octopine etc.) by the infected cell. Thus, *Agrobacterium* strains which cause production of nopaline (e.g., strain LBA4301, C58, A208) are referred to as "nopaline-type" *Agrobacteria*; *Agrobacterium* strains which cause production of octopine (e.g., strain LBA4404, Ach5, B6) are referred to as "octopine-type" *Agrobacteria*; and *Agrobacterium* strains which cause production of agropine (e.g., strain EHA105, EHA101, A281) are referred to as "agropine-type" *Agrobacteria*.

Algorithm: as used herein refers to the way computers process information, because a computer program is essentially an algorithm that tells the computer what specific steps to perform (in what specific order) in order to carry out a specified task, such as identification of coding regions of a set of genes. Thus, an algorithm can be considered to be any sequence of operations that can be performed by a computer system. Typically, when an algorithm is associated with processing information, data is read from an input source or device, written to an output sink or device, and/or stored for further use. For any such computational process, the algorithm must be rigorously defined: specified in the way it applies in all possible circumstances that could arise. That is, any conditional steps must be systematically dealt with, case-by-case; the criteria for each case must be clear (and computable). Because an algorithm is a precise list of precise steps, the order of computation will almost always be critical to the functioning of the algorithm. Instructions are usually assumed to be listed explicitly, and are described as starting 'from the top' and going 'down to the bottom', an idea that is described more formally by flow of control. In computer applications, a script is a computer program that automates the sort of task that a user might otherwise do interactively at the keyboard. Languages that are largely used to write such scripts are called scripting languages. Many such languages are quite sophisticated, and have been used to write elaborate programs, which are often still called scripts even if they go well beyond automating simple sequences of user tasks. Computer languages are created for varying purposes and tasks different kinds and styles of programming. Scripting programming languages (commonly called scripting languages or script languages) are computer programming languages designed for "scripting" the operation of a computer. Early script languages were often called batch languages or job control languages.

Examples for script languages are: ACS, ActionScript, Active Server Pages (ASP), AppleScript, Awk, BeanShell (scripting for Java), bash, Brain, CobolScript, csh, ColdFusion, Dylan, Escapade (server side scripting), Euphoria, Groovy, Guile, Haskell, HyperTalk, ICI, IRC script, JavaScript, mIRC script, MS-DOS batch, Nwscript, Perl, PHP, Pike, ScriptBasic.

Antisense: is understood to mean a nucleic acid having a sequence complementary to a target sequence, for example a messenger RNA (mRNA) As used herein, the terms "complementary" or "complementarity" are used in reference to nucleotide sequences related by the base-pairing rules. For example, the sequence 5'-AGT-3' is complementary to the sequence 5'-ACT-3'. Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands.

Sense: is understood to mean a nucleic acid having a sequence that is homologous or identical to a target sequence, for example a sequence which is bound by a protein factor of the spliceosome.

Bombarding, "bombardment and "biolistic bombardment": refer to the process of accelerating particles (microprojectiles) towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are herein incorporated by reference), and are commercially available (e.g., the helium gas-driven microprojectile accelerator (PDS-1000/He) (BioRad).

Cell: refers to a single cell. The term "cells" refers to a population of cells. The population may be a pure population comprising one cell type. Likewise, the population may comprise more than one cell type. In the present invention, there is no limit on the number of cell types that a cell population may comprise. The cells may be synchronize or not synchronized, preferably the cells are synchronized.

Chromosomal DNA or chromosomal DNA-sequence: is to be understood as the genomic DNA of the cellular nucleus independent from the cell cycle status. Chromosomal DNA might therefore be organized in chromosomes or chromatids, they might be condensed or uncoiled. An insertion into the chromosomal DNA can be demonstrated and analyzed by various methods known in the art like e.g., polymerase chain reaction (PCR) analysis, Southern blot analysis, fluorescence in situ hybridization (FISH), and in situ PCR.

Coding region or coding sequence (CDS): when used in reference to a gene refers to the nucleotide sequences which encode the amino adds found in the nascent polypeptide as a result of translation of a mRNA molecule. The coding region is bounded, in eucaryotes, on the 5'-side by the nucleotide triplet "ATG" which encodes the initiator methionine and on the 3'-side by one of the three triplets, which specify stop codons (i.e., TAA, TAG, TGA).

Complement of a nucleic acid sequence: as used herein refers to a nucleotide sequence whose nucleic acids show total complementarity to the nucleic acids of the nucleic add sequence.

Decile: when used in connection with statistical data is any of the 10 values that divide sorted data into 10 equal parts, so that each part represents ⅒th of the sample or population. Thus, the 1st decile cuts off lowest 10% of data, the 9th decile cuts off lowest 90% or the highest 10% of data. A quartile is any of the three values which divide the sorted data set into four equal parts, so that each part represents ¼th of the sample or population (third quartile=upper quartile=cuts off highest 25% of data, or lowest 75%=75th percentile). A percentile is any of the 99 values that divide the sorted data into 100 equal parts, so that each part represents 1/100th of the sample or population. Thus, the 1st percentile cuts off lowest 1% of data, the 98th percentile cuts off lowest 98% of data and the $25^{th}$ percentile cuts off lowest 25% of data.

DNA databases: in the field of bioinformatics, a DNA sequence database is a large collection of DNA sequences stored on a computer. A database can include sequences from only one organism, or it can include sequences from all organisms whose DNA has been sequenced.

Enrichment or enriching: when used in connection with the selection of inventive introns refers to an increase in the success rate of identifying introns with gene expression enhancing properties within a population of introns (e.g. a population of introns representing all introns of a plant genome present in a genomic DNA sequence database). The enrichment is achieved by reducing the number of candidate introns by using the inventive method and the inventive selection criteria. If, as an example, the success rate of identifying an intron with expression enhancing properties from a given population of introns—by using the herein described methods for measuring gene expression enhancement—is one out of ten analyzed introns, enrichment has to be understood as an increase in the number of identified introns with gene expression enhancing properties—by using the inventive method—to at least five out of ten analyzed introns. Therefore, the number of introns needed to be analyzed in order to identify one inventive intron is reduced to two introns by using the inventive method as a preselection or filtering process.

Evaluation of the expression enhancing properties: of an intron can be done using methods known in the art. For example, a candidate intron sequence whose gene expression enhancing effect is to be determined can be inserted into the 5' UTR of a nucleic acid sequence encoding for a reporter gene (e.g., a visible marker protein, a selectable marker protein) under control of an appropriate promoter active in plants or plant cells to generate a reporter vector. The reporter vector and an identical control reporter vector lacking the candidate intron can be introduced into a plant tissue using methods described herein, and the expression level of the reporter gene, in dependence of the presence of the candidate intron, can be measured and compared (e.g., detecting the presence of encoded mRNA or encoded protein, or the activity of a protein encoded by the reporter gene). An intron with expression enhancing properties will result in a higher expression rate than a reference value obtained with an identical control reporter vector lacking the candidate intron under otherwise unchanged conditions.

The reporter gene may express visible markers. Reporter gene systems which express visible markers include β-glucuronidase and its substrate (X-Gluc), luciferase and its substrate (luciferin), and β-galactosidase and its substrate (X-Gal) which are widely used not only to identify transformants, but also to quantify the amount of transient or stable protein expression attributable to a specific vector system (Rhodes (1995) Methods Mol Biol 55:121-131). The assay with β glucuronidase (GUS) being very especially preferred (Jefferson et al., GUS fusions: beta-glucuronidase as a sensitive and versatile gene fusion marker in higher plants. EMBO J. (1987) December 20; 6(13):3901-3907). β-glucuronidase (GUS) expression is detected by a blue color on incubation of the tissue with 5-bromo-4-chloro-3-indolyl-β-D-glucuronic acid. The selectable marker gene may confer antibiotic or herbicide resistance. Examples of reporter genes include, but are not limited to, the dhfr gene, which confers resistance to methotrexate (Wigler (1980) Proc Natl Acad Sci 77:3567-3570); npt, which confers resistance to the aminoglycosides neomycin and G-418 (Colbere-Garapin (1981) J. Mol. Biol. 150:1-14) and als or pat, which confer resistance to chlorsulfuron and phosphinotricin acetyl transferase, respectively.

Expect value when used in the context of DNA sequence alignments or DNA sequence database searches refers to the number of times a certain match or a better one would be expected to occur purely by chance in a search of the entire database. Thus, the lower the Expect value, the greater the similarity between the input sequence and the match. The Expect value (E) is a parameter that describes the number of hits one can "expect" to see just by chance when searching a database of a particular size. It decreases exponentially with the Similarity Score (S) that is assigned to a match between two sequences. The higher the score, the lower the E value. Essentially, the E value describes the random background noise that exists for matches between sequences. The Expect value is used as a convenient way to create a significance threshold for reporting results. An E value of 1 assigned to a hit can be interpreted as meaning that in a database of the current size you might expect to see 1 match with a similar score simply by chance. The E-value is influenced by: a) length of sequence (the longer the query the lower the probability that it will find a sequence in the database by chance), b) size of database (the larger the database the higher the probability that the query will find a match by chance), c) the scoring matrix (the less stringent the scoring matrix the higher the probability that the query will find a sequence in the database by chance).

Expressed sequence tag (EST): refers to a cDNA sequence that has been obtained from a single pass terminal DNA sequencing. An EST sequence denotes a sequence that is derived from a transcript, and hence from a gene that is transcribed.

Expressible nucleic acid sequence: as used in the context of this invention is any nucleic acid sequence that is capable of being transcribed into RNA (e.g. mRNA, antisense RNA, double strand forming RNA etc.) or translated into a particular protein.

Expression: refers to the biosynthesis of a gene product. For example, in the case of a structural gene, expression involves transcription of the structural gene into mRNA and—optionally—the subsequent translation of mRNA into one or more polypeptides.

Functional equivalents: with regard to the inventive introns has to be understood as natural or artificial mutations of said introns described in any of the SEQ ID NOs: 1, 2, 3, 4, 5, 6, 7, 8, 9, 10, 11, 12, 13, 14, 15, 16, 17, 18, 19, 20, 21 or 22. Mutations can be insertions, deletions or substitutions of one or more nucleic acids that do not diminish the expression enhancing properties of said introns. These functional equivalents having a identity of at least 80%, preferably 85%, more preferably 90%, most preferably more than 95%, very especially preferably at least 98% identity but less then 100% identity to the intron sequences as described by any of the SEQ ID NOs: 1, 2, 3, 5, 6, 7, 10, 11, 12, 13, 14, 15, 16, 17, 18, 19, 20, 21 or 22, wherein said identity is determined over a sequence of at least 95 consecutive base pairs, preferably at least 150 consecutive base pairs, more preferably at least 200 consecutive base pairs of the sequence as described by any of the SEQ ID NOs: 1, 2, 3, 5, 6, 7, 10, 11, 12, 13, 14, 15, 16, 17, 18, 19, 20, 21 or 22 and having essentially the same IME effect characteristics as the intron sequences as shown in any of the SEQ ID NOs: 1, 2, 3, 5, 6, 7, 10, 11, 12, 13, 14, 15, 16, 17, 18, 19, 20, 21 or 22.

Functional equivalents are in particular homologs of said introns derived from other plant species. Homologs when used in reference to introns refers to introns with expression enhancing properties isolated from a genomic nucleic acid sequence that encodes for a protein (i) sharing more than 60%, preferably 65%, 70%, 75%, 80%, more preferably 85%, 90%, 95% or most preferably more than 95% sequence identity on amino acid level with proteins that are encoded by genes from which the inventive introns with the SEQ ID NOs: 1, 2, 3, 5, 6, 7, 10, 11, 12, 13, 14, 15, 16, 17, 18, 19, 20, 21 or 22 have been isolated, or (ii) catalyzing the same enzymatic reaction as the proteins encoded by genes from which the inventive introns SEQ ID NOs: 1, 2, 3, 5, 6, 7, 10, 11, 12, 13, 14, 15, 16, 17, 18, 19, 20, 21 or 22 have been isolated, or (iii) showing comparable spatial and temporal expression pattern as the proteins encoded by genes from which the inventive introns SEQ ID NOs: 1, 2, 3, 5, 6, 7, 10, 11, 12, 13, 14, 15, 16, 17, 18, 19, 20, 21 or 22 have been isolated.

"Functional equivalents' as described above might have, compared with the inventive introns a reduced or increased gene expression enhancing effect. In this context, the gene expression enhancing effect of the functional equivalent intron is at least 50% higher, preferably at least 100% higher, especially preferably at least 300% higher, very especially preferably at least 500% higher than a reference value obtained with any of the introns shown in SEQ ID NOs: 1, 2, 3, 5, 6, 7, 10, 11, 12, 13, 14, 15, 16, 17, 18, 19, 20, 21 or 22 under otherwise unchanged conditions.

Functionally linked or operably linked: is to be understood as meaning, for example, the sequential arrangement of a regulatory element (e.g. a promoter) with a nucleic acid sequence to be expressed and, if appropriate, further regulatory elements (such as e.g., a terminator) in such a way that each of the regulatory elements can fulfill its intended function to allow, modify, facilitate or otherwise influence expression of said nucleic acid sequence. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions that are further away, or indeed from other DNA molecules. The terms "functionally linked', "operably linked," "in operable combination," and "in operable order" as used herein with reference to an inventive intron with gene expression enhancing properties refers to the linkage of at least one of said introns to a nucleic acid sequences in a way that the expression enhancing effect is realized and, if functional splice sites have been included, that the intron can be spliced out by the cell factors responsible for the splicing procedure. In a preferred embodiment of the present invention, the intron is introduced into the 5' non coding region of a nucleic acid sequence. Inventive expression constructs, wherein an inventive intron is functionally linked to an nucleic acid sequence are shown in the examples. More preferred arrangements are those in which an intron functioning in intron mediated expression enhancement is inserted between a promoter and a nucleic acid sequence, preferably into the transcribed nucleic acid sequence, or in case of a nucleic acid sequence encoding for a protein, into the 5' untranslated region of a nucleic acid sequence. The distance between the promoter sequence and the nucleic acid sequence to be expressed recombinantly is preferably less than 200 base pairs, especially preferably less than 100 base pairs, very especially preferably less than 50 base pairs. Operable linkage, and an expression cassette, can be generated by means of customary recombination and cloning techniques as are described, for example, in Maniatis T, Fritsch E F and Sambrook J (1989) Molecular Cloning: A Laboratory Manual, Cold Spring Harbor Laboratory, Cold Spring Harbor (NY), in Silhavy T J, Berman M L and Enquist L W (1984) Experiments with Gene Fusions, Cold Spring Harbor Laboratory, Cold Spring Harbor (NY), in Ausubel F M et al. (1987) Current Protocols in Molecular Biology, Greene Publishing Assoc. and Wiley Interscience and in Gelvin et al. (1990) In: Plant Molecular Biology Manual. However, further sequences which, for example, act as a linker with specific cleavage sites for restriction enzymes, or as a signal peptide, may also be positioned between the two sequences. The insertion of sequences may also lead to the expression of fusion proteins. Preferably, the expression construct, consisting of a linkage of promoter, intron and nucleic acid sequence to be expressed, can exist in a vector-integrated form and be inserted into a plant genome, for example by transformation.

Gene: refers to a coding region operably linked to appropriate regulatory sequences capable of regulating the expression of the polypeptide in some manner. A gene includes untranslated regulatory regions of DNA (e.g., promoters, enhancers, repressors, etc.) preceding (upstream) and following (downstream) the coding region (open reading frame, ORF) as well as, where applicable, intervening sequences (i.e., introns) between individual coding regions (i.e., exons). Genes may also include sequences located on both the 5'- and 3'-end of the sequences, which are present on the RNA transcript. These sequences are referred to as "flanking" sequences or regions (these flanking sequences are located 5' or 3' to the non-translated sequences present on the mRNA transcript). The 5'-flanking region may contain regulatory sequences such as promoters and enhancers, which control or influence the transcription of the gene. The 3'-flanking region may contain sequences, which direct the termination of transcription, posttranscriptional cleavage and polyadenylation.

Gene expression enhancing properties, gene expression enhancing effect or intron mediated gene expression enhancement (IME): when made in reference to an intron sequence refers to the ability of the intron to enhance quantitatively the expression level of a nucleic acid sequence (e.g. a gene) that is part of an recombinant/transgenic DNA expression cassette (as defined herein), measured on the basis of the transcribed RNA, mRNA, protein amount or protein activity compared to the otherwise identical expression construct lacking the intron under otherwise unchanged conditions. Gene expression enhancing properties in plants: refers to an intron that is able to enhance quantitatively the expression level of a plant derived nucleic acid sequence in a plant or plant cell and the enhancement of gene expression rate of a non-plant derived nucleic acid in a plant or a plant cell compared to the otherwise identical expression construct lacking the intron under otherwise unchanged conditions. In a preferred embodiment of the invention, the expression enhancing effect is understood as an increase in the RNA steady state level, the protein steady state level or the protein activity of a nucleic acid sequence or the corresponding protein (e.g. a reporter gene or protein) of at least 50%, or at least 100%, or at least 200%, 300%, 400% or at least 500%, 600%, 700%, 800%, 900% or at least 1,000%, or more than 1,000% compared to the otherwise identical expression construct lacking the intron under otherwise unchanged conditions. Furthermore expression enhancing effect or intron mediated enhancement has to be understood as the ability of an intron to change the tissue, organ or cell specific expression pattern of a nucleic acid sequence (e.g. a gene) that is part of an inventive expression cassette. Changing the tissue, organ or cell specific expression pattern of a nucleic acid sequence that is part of an inventive expression cassette refers to the fact that due to the presence of an inventive intron, the expression level (mRNA or encoded protein steady state level, or the activity of a protein) of the respective gene is increased above the detection threshold of the used detection method.

Gene silencing: can be realized by antisense or double-stranded RNA or by co-suppression (sense-suppression). The skilled worker knows that he can use alternative cDNA or the corresponding gene as starting template for suitable antisense constructs. The 'antisense' nucleic acid is preferably complementary to the coding region of the target protein or part thereof. However, the 'antisense' nucleic add may also be complementary to the non-coding region or part thereof. Starting from the sequence information on a target protein, an antisense nucleic acid can be designed in the manner with which the skilled worker is familiar, taking into consideration Watson s and Crick s rules of base pairing. An antisense nucleic add can be complementary to the entire or part of the nucleic acid sequence of a target protein.

Likewise encompassed is the use of the above-described sequences in sense orientation, which, as is known to the skilled worker, can lead to co-suppression (sense-suppression). It has been demonstrated that expression of sense nucleic acid sequences can reduce or switch off expression of the corresponding gene, analogously to what has been described for antisense approaches (Goring (1991) Proc. Natl Acad. Sci. USA 88:1770-1774; Smith (1990) Mol. Gen. Genet. 224:447-481; Napoli (1990) Plant Cell 2:279-289; Van der Krol (1990) Plant Cell 2:291-299). In this context, the construct introduced may represent the gene to be reduced fully or only in part. The possibility of translation is not necessary. Especially preferred is the use of gene regulation methods by means of double-stranded RNAi ('double-stranded RNA interference'). Such methods are known to the person skilled in the art (e.g., Matzke 2000; Fire 1998; WO 99/32619; WO 99/53050; WO 00/68374; WO 00/44914; WO 00/44895; WO 00/49035; WO 00/63364). The processes and methods described in the references stated are expressly referred to.

Genome and genomic DNA of an organism as used herein is the whole hereditary information of an organism that is encoded in the DNA (or, for some viruses, RNA). This includes both the genes and the non-coding sequences. Said genomic DNA comprises the DNA of the nucleus (also referred to as chromosomal DNA) but also the DNA of the plastids (e.g., chloroplasts) and other cellular organelles (e.g., mitochondria). Preferably the terms genome or genomic DNA is referring to the chromosomal DNA of the nucleus. The term "chromosomal DNA' or "chromosomal DNA-sequence" is to be understood as the genomic DNA of the cellular nucleus independent from the cell cycle status. Chromosomal DNA might therefore be organized in chromosomes or chromatids, they might be condensed or uncoiled. An insertion into the chromosomal DNA can be demonstrated and analyzed by various methods known in the art like e.g., polymerase chain reaction (PCR) analysis, Southern blot analysis, fluorescence in situ hybridization (FISH), and in situ PCR.

Heterologous: with respect to a nucleic acid sequence refers to a nucleotide sequence, which is ligated to a nucleic acid sequence to which it is not ligated in nature, or to which it is ligated at a different location in nature.

Hybridizing: as used herein includes "any process by which a strand of nucleic acid joins with a complementary strand through base pairing." (Coombs 1994, Dictionary of Biotechnology, Stockton Press, New York N.Y.). Hybridization and the strength of hybridization (i.e., the strength of the association between the nucleic acids) is impacted by such factors as the degree of complementarity between the nucleic acids, stringency of the conditions involved, the Tm of the formed hybrid, and the G:C ratio within the nucleic acids. As used herein, the term "Tm" is used in reference to the "melting temperature." The melting temperature is the temperature at which a population of double-stranded nucleic acid molecules becomes half dissociated into single strands. The equation for calculating the Tm of nucleic acids is well known in the art. As indicated by standard references, a simple estimate of the Tm value may be calculated by the equation: Tm=81.5+ 0.41 (% G+C), when a nucleic acid is in aqueous solution at 1 M NaCl [see e.g., Anderson and Young, Quantitative Filter Hybridization, in Nucleic Acid Hybridization (1985)]. Other references include more sophisticated computations, which take structural as well as sequence characteristics into account for the calculation of Tm. The person skilled in the art knows well that numerous hybridization conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high hybridization stringency Those skilled in the art know that higher stringencies are preferred to reduce or eliminate non-specific binding between the nucleotide sequence of an inventive intron and other nucleic add sequences, whereas lower stringencies are preferred to detect a larger number of nucleic add sequences having different homologies to the inventive nucleotide sequences. Such conditions are described by, e.g., Sambrook (Molecular Cloning; A Laboratory Manual, 2nd Edition, Cold Spring Harbor Laboratory Press, Cold Spring Harbor, N.Y. (1989)) or in Current Protocols in Molecular Biology, John Wiley & Sons, N.Y. (1989) 6.3.1-6.3.6. Preferred hybridization condition are disclose in the detailed description.

Identity: when used in relation to nucleic adds refers to a degree of complementarity. Identity between two nucleic acids is understood as meaning the identity of the nucleic acid sequence over in each case the entire length of the sequence, which is calculated by comparison with the aid of the program algorithm GAP (Wisconsin Package Version 10.0, University of Wisconsin, Genetics Computer Group (GCG), Madison, USA) with the parameters being set as follows:

| Gap Weight: 12 | Length Weight: 4 |
|---|---|
| Average Match: 2,912 | Average Mismatch: −2,003 |

For example, a sequence with at least 95% identity to the sequence SEQ ID NO. 1 at the nucleic acid level is understood as meaning the sequence that, upon comparison with the sequence SEQ ID NO. 1 by the above program algorithm with the above parameter set, has at least 95% identity. There may be partial identity (i.e., partial identity of less then 100%) or complete identity (i.e., complete identity of 100%).

Introducing a recombinant DNA expression construct: in plant cells refers to a recombinant DNA expression construct that will be introduced into the genome of a plant by transformation and is stably maintained. The term "introducing' encompasses for example methods such as transfection, transduction or transformation.

Identification, "Identifying' or "selecting': with regard to transformation of plants has to be understood as a screening procedure to identify and select those plant cells in which the recombinant expression construct has been introduced stably into the genome. "Identifying' with regard to an intron with gene expression enhancing properties refers to a process for the selection of said intron out of a population of introns. Preferably, "identifying' refers to an in silico selection process, more preferably to an automated in silico selection process, using the selection criteria of the inventive methods. Such an in silico identification process can comprise for instance the steps of (1) generating an intron sequence database on the basis of DNA sequences present in a DNA sequence database (e.g. genomic DNA databases publicly available via the internet),
(2) screening of the generated intron DNA sequence database—or other genomic DNA sequences containing databases—for introns with gene expression enhancing properties using the criteria according to the inventive method, wherein the steps for retrieving or generating the DNA sequences, the generation of an intron specific DNA sequence database and the screening of these DNA sequences—using the criteria according to the inventive method—will be performed with the aid of appropriate computer algorithms and computer devices.

Intron: refers to sections of DNA (intervening sequences) within a gene that do not encode part of the protein that the gene produces, and that is spliced out of the mRNA that is transcribed from the gene before it is exported from the cell nucleus. Intron sequence refers to the nucleic acid sequence of an intron. Thus, introns are those regions of DNA sequences that are transcribed along with the coding sequence (exons) but are removed during the formation of mature mRNA. Introns can be positioned within the actual coding region or in either the 5 or 3 untranslated leaders of the pre-mRNA (unspliced mRNA). Introns in the primary transcript are excised and the coding sequences are simultaneously and precisely ligated to form the mature mRNA. The junctions of introns and exons form the splice site. The sequence of an intron begins with GU and ends with AG. Furthermore, in plants, two examples of AU-AC introns have been described: the fourteenth intron of the RecA-like protein gene and the seventh intron of the G5 gene from *Arabidopsis thaliana* are AT-AC introns. Pre-mRNAs containing introns have three short sequences that are beside other sequences—essential for the intron to be accurately spliced. These sequences are the 5' splice-site, the 3 splice-site, and the branchpoint. mRNA splicing is the removal of intervening sequences (introns) present in primary mRNA transcripts and joining or ligation of exon sequences. This is also known as cis-splicing which joins two exons on the same RNA with the removal of the intervening sequence (intron). The functional elements of an intron comprising sequences that are recognized and bound by the specific protein components of the spliceosome (e.g. splicing consensus sequences at the ends of introns). The interaction of the functional elements with the spliceosome results in the removal of the intron sequence from the premature mRNA and the rejoining of the exon sequences. Introns have three short sequences that are essential—although not sufficient—for the intron to be accurately spliced. These sequences are the 5' splice site, the 3' splice site and the branch point. The branchpoint sequence is important in splicing and splice-site selection in plants. The branchpoint sequence is usually located 10-60 nucleotides upstream of the 3' splice site. Plant sequences exhibit sequence deviations in the branchpoint, the consensus sequences being 5-CURAY-3 (SEQ ID NO:75) or 5-YURAY-3 (SEQ ID NO: 76).

"IME-intron' or intron mediated enhancement (IME)-intron: when made in reference to an intron sequence refers to an intron with gene expression enhancing properties in plants as defined herein (see gene expression enhancing properties, gene expression enhancing effect or intron mediated gene expression enhancement).

Isolation or isolated: when used in relation to an intron or gene, as in "isolation of an intron sequence' or "isolation of a gene" refers to a nucleic acid sequence that is identified within and isolated/separated from its chromosomal nucleic acid sequence context within the respective source organism. Isolated nucleic add is nucleic acid present in a form or setting that is different from that in which it is found in nature. In contrast, non-isolated nucleic acids are nucleic acids such as DNA and RNA, which are found in the state they exist in nature. For example, a given DNA sequence (e.g. a gene) is found on the host cell chromosome in proximity to neighboring genes; intron sequences, are imbedded into the nucleic acid sequence of a gene in an alternating sequence of introns and exons. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (i.e., the nucleic add sequence may be single-stranded). Alternatively, it may contain both the sense and anti-sense strands (i.e., the nucleic acid sequence may be double-stranded).

Nucleic acid: refers to deoxyribonucleotides, ribonucleotides or polymers or hybrids thereof in single- or double-stranded, sense or antisense form. Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" can be used to describe a "gene", "cDNA', 'DNA' "mRNA", "oligonucleotide," and "polynucleotide".

Nucleic add sequence: as used herein refers to the consecutive sequence of deoxyribonucleotides or ribonucleotides (nucleotides) of a DNA fragment (oligonucleotide, polynucleotide, genomic DNA, cDNA etc.) as it can made be available by DNA sequencing techniques as a list of abbreviations, letters, characters or words, which represent nucleotides.

Organ: with respect to a plant (or "plant organ') means parts of a plant and may include (but shall not limited to) for example roots, fruits, shoots, stem, leaves, anthers, sepals, petals, pollen, seeds, etc.

Otherwise unchanged conditions: means for example—that the expression which is initiated by one of the expression constructs to be compared is not modified by combination with additional genetic control sequences, for example enhancer sequences and is done in the same environment (e.g., the same plant species) at the same developmental stage and under the same growing conditions.

Plant: is generally understood as meaning any single- or multi-celled organism or a cell, tissue, organ, part or propagation material (such as seeds or fruit) of same which is capable of photosynthesis. Included for the purpose of the invention are all genera and species of higher and lower plants of the Plant Kingdom. Annual, perennial, monocotyledonous and dicotyledonous plants are preferred. The term includes the mature plants, seed, shoots and seedlings and their derived parts, propagation material (such as seeds or microspores), plant organs, tissue, protoplasts, callus and other cultures, for example cell cultures, and any other type of plant cell grouping to give functional or structural units. Mature plants refer to plants at any desired developmental stage beyond that of the seedling. Seedling refers to a young immature plant at an early developmental stage. Annual, biennial, monocotyledonous and dicotyledonous plants are preferred host organisms for the generation of transgenic plants. The expression of genes is furthermore advantageous in all ornamental plants, useful or ornamental trees, flowers, cut flowers, shrubs or lawns. Plants which may be mentioned by way of example but not by limitation are angiosperms, bryophytes such as, for example, Hepaticae (liverworts) and Musci (mosses); Pteridophytes such as ferns, horsetail and club mosses; gymnosperms such as conifers, cycads, ginkgo and Gnetatae; algae such as Chlorophyceae, Phaeophpyceae, Rhodophyceae, Myxophyceae, Xanthophyceae, Bacillariophyceae (diatoms), and Euglenophyceae. Preferred are plants which are used for food or feed purpose such as the families of the Leguminosae such as pea, alfalfa and soya; Gramineae such as rice, maize, wheat, barley, sorghum, millet, rye, triticale, or oats; the family of the Umbelliferae, especially the genus *Daucus*, very especially the species *carota* (carrot) and *Apium*, very especially the species *Graveolens dulce* (celery) and many others; the family of the Solanaceae, especially the genus *Lycopersicon*, very especially the species *esculentum* (tomato) and the genus *Solanum*, very especially the species *tuberosum* (potato) and *melongena* (egg plant), and many others (such as tobacco); and the genus *Capsicum*, very especially the species *annuum* (peppers) and many others; the family of the Leguminosae, especially the genus *Glycine*, very especially the species *max* (soybean), alfalfa, pea, lucerne, beans or peanut and many others; and the family of the Cruciferae (Brassicacae), especially the genus *Brassica*, very especially the species *napus* (oil seed rape), *campestris* (beet), oleracea cv Tastie (cabbage), oleracea cv Snowball Y (cauliflower) and oleracea cv Emperor (broccoli); and of the genus *Arabidopsis*, very especially the species *thaliana* and many others; the family of the Compositae, especially the genus *Lactuca*, very especially the species *sativa* (lettuce) and many others; the family of the Asteraceae such as sunflower, Tagetes, lettuce or *Calendula* and many other; the family of the Cucurbitaceae such as melon, pumpkin/squash or zucchini, and linseed. Further preferred are cotton, sugar cane, hemp, flax, chillies, and the various tree, nut and wine species.

Providing: when used in relation to an intron as in "physically providing an intron' refers to the cloning of the DNA sequence representing said intron from a plant of interest and the provision of such an intron physically in an appropriate vector or plasmid for further cloning work and the subsequent application of said intron according to the invention.

Producing: when used in relation to an intron as in "producing an intron' refers to the synthesis of DNA molecules on the basis of DNA sequence information of an inventive intron.

Promoter, promoter element, or promoter sequence: as used herein, refers to a DNA sequence which when ligated to a nucleotide sequence of interest is capable of controlling the transcription of the nucleotide sequence of interest into mRNA. Thus, a promoter is a recognition site on a DNA sequence that provide an expression control element for a gene and to which RNA polymerase specifically binds and initiates RNA synthesis (transcription) of that gene. A promoter is typically, though not necessarily, located 5' (i.e., upstream) of a nucleotide sequence of interest (e.g., proximal to the transcriptional start site of a structural gene). Promoters may be tissue specific or cell specific. The term "tissue specific" as it applies to a promoter refers to a promoter that is capable of directing selective expression of a nucleotide sequence of interest to a specific type of tissue (e.g., petals) in the relative absence of expression of the same nucleotide sequence of interest in a different type of tissue (e.g., roots). Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. In contrast, a "regulatable" promoter is one which is capable of directing a level of transcription of an operably linked nuclei acid sequence in the presence of a stimulus (e.g., heat shock, chemicals, light, etc.) which is different from the level of transcription of the operably linked nucleic acid sequence in the absence of the stimulus. A promoter sequence functioning in plants is understood as meaning, in principle, any promoter which is capable of governing the expression of genes, in particular foreign genes, in plants or plant parts, plant cells, plant tissues or plant cultures. In this context, expression can be, for example, constitutive, inducible or development-dependent. A constitutive promoter is a promoter where the rate of RNA polymerase binding and initiation is approximately constant and relatively independent of external stimuli. Usable promoters are constitutive promoters (Benfey et al. (1989) EMBO J. 8:2195-2202), such as those which originate from plant viruses, such as 35S CAMV (Franck et al. (1980) Cell 21:285-294), 19S CaMV (see also U.S. Pat. No. 5,352, 605 and WO 84/02913), 34S FMV (Sanger et al. (1990) Plant. Mol. Biol., 14:433-443), the parsley ubiquitin promoter, or plant promoters such as the Rubisco small subunit promoter described in U.S. Pat. No. 4,962,028 or the plant promoters PRP1 [Ward et al. (1993) Plant. Mol. Biol. 22: 361-6], SSU, PGEL1, OCS [Leisner (1988) Proc Natl Acad Sci USA 85(5): 2553-2557], lib4, usp, mas [Comai (1990) Plant Mol Biol 15(3):373-381], STLS1, ScBV (Schenk (1999) Plant Mol Biol 39(6):1221-1230), B33, SAD1 or SAD2 (flax promoters, Jain et al. (1999) Crop Science 39(6):1696-1701) or nos [Shaw et al. (1984) Nucleic Acids Res. 12(20):7831-7846]. An inducible promoter is a promoter where the rate of RNA polymerase binding and initiation is modulated by external stimuli. Such stimuli include light, heat, anaerobic stress, alteration in nutrient conditions, presence or absence of a metabolite, presence of a ligand, microbial attack, wounding and the like (for a review, see Gatz (1997) Annu. Rev. Plant Physiol. Plant Mol. Biol. 48:89-108). Chemically inducible promoters are particularly suitable when it is desired to express the gene in a time-specific manner. Examples of such promoters are a salicylic acid inducible promoter (WO 95/19443), and abscisic acid-inducible promoter (EP 335 528), a tetracycline-inducible promoter (Gatz et al. (1992) Plant J. 2:397-404), a cyclohexanol- or ethanol-inducible promoter (WO 93/21334) or others as described herein. A viral promoter is a promoter with a DNA sequence substantially similar to the promoter found at the 5' end of a viral gene. A typical viral promoter is found at the 5' end of the gene coding for the p21 protein of MMTV described by Huang et al. ((1981) Cell 27:245). A synthetic promoter is a promoter that was chemically synthesized rather than biologically derived. Usually synthetic promoters incorporate sequence changes that optimize the efficiency of RNA polymerase initiation. A temporally regulated promoter is a promoter where the rate of RNA polymerase binding and initiation is modulated at a specific time during development. Examples of temporally regulated promoters are given in Chua et al. [(1989) Science 244:174-181]. A spatially regulated promoter is a promoter where the rate of RNA polymerase binding and initiation is modulated in a specific structure of the organism such as the leaf, stem or root. Examples of spatially regulated promoters are given in Chua et al. [(1989) Science 244:174-181]. A spatiotemporally regulated promoter is a promoter where the rate of RNA polymerase binding and initiation is modulated in a specific structure of the organism at a specific time during development. A typical spatiotemporally regulated promoter is the EPSP synthase-35S promoter described by Chua et al. [(1989) Science 244:174-181]. Suitable promoters are furthermore the oilseed rape napin gene promoter (U.S. Pat. No. 5,608,152), the *Vicia faba* USP promoter (Bäumlein et al. (1991) Mol Gen Genet 225(3):459-67), the *Arabidopsis* oleosin promoter (WO 98/45461), the *Phaseolus vulgaris* phaseolin promoter (U.S. Pat. No. 5,504, 200), the *Brassica* Bce4 promoter (WO 91/13980), the bean arc5 promoter, the carrot DcG3 promoter, or the Legumin B4 promoter (LeB4; Bäumlein et al. (1992) Plant Journal 2(2): 233-9), and promoters which bring about the seed-specific expression in monocotyledonous plants such as maize, barley, wheat, rye, rice and the like. Advantageous seed-specific promoters are the sucrose binding protein promoter (WO 00/26388), the phaseolin promoter and the napin promoter. Suitable promoters which must be considered are the barley Ipt2 or Ipt1 gene promoter (WO 95/15389 and WO 95/23230), and the promoters described in WO 99/16890 (promoters from the barley hordein gene, the rice glutelin gene, the rice oryzin gene, the rice prolamin gene, the wheat gliadin gene, the wheat glutelin gene, the maize zein gene, the oat glutelin gene, the sorghum kasirin gene and the rye secalin gene). Further suitable promoters are Amy32b, Amy 6-6 and Aleurain [U.S. Pat. No. 5,677,474], Bce4 (oilseed rape) [U.S. Pat. No. 5,530,149], glycinin (soya) [EP 571 741], phosphoenolpyruvate carboxylase (soya) [JP 06/62870], ADR12-2 (soya) [WO 98/08962], isocitrate lyase (oilseed rape) [U.S. Pat. No. 5,689,040] or α-amylase (barley) [EP 781 849]. Other promoters which are available for the expression of genes in plants are leaf-specific promoters such as those described in DE-A 19644478 or light-regulated promoters such as, for example, the pea petE promoter. Further suitable plant promoters are the cytosolic FBPase promoter or the potato ST-LSI promoter (Stockhaus et al. (1989) EMBO J. 8:2445), the *Glycine max* phosphoribosylpyrophosphate amidotransferase promoter (GenBank Accession No. U87999) or the node-specific promoter described in EP A 0 249 676. Other suitable promoters are those which react to biotic or abiotic stress conditions, for example the pathogen-induced PRP1 gene promoter (Ward et al. (1993) Plant. Mol. Biol. 22:361-366), the tomato heat-inducible hsp80 promoter (U.S. Pat. No. 5,187,267), the potato chill-inducible alpha-amylase promoter (WO 96/12814) or the wound-inducible pinII promoter (EP-A-0 375 091) or others as described herein. Other promoters, which are particularly suitable, are those that bring about plastid-specific expression. Suitable promoters such as the viral RNA polymerase promoter are described in WO 95/16783 and WO 97/06250, and the *Arabidopsis* cIpP promoter, which is described in WO 99/46394. Other promoters, which are used for the strong expression of heterologous sequences in as many tissues as possible, in particular also in leaves, are, in addition to several of the abovementioned viral and bacterial promoters, preferably, plant promoters of actin or ubiquitin genes such as, for example, the rice actin1 promoter. Further examples of constitutive plant promoters are the sugarbeet V-ATPase promoters (WO 01/14572).

Examples of synthetic constitutive promoters are the Super promoter (WO 95/14098) and promoters derived from G-boxes (WO 94/12015). If appropriate, chemical inducible promoters may furthermore also be used, compare EP-A 388186, EP-A 335528, WO 97/06268. The above listed promoters can be comprise other regulatory elements that affect gene expression in response to plant hormones (Xu et al., 1994, Plant Cell 6(8):1077-1085) biotic or abiotic environmental stimuli, such as stress conditions, as exemplified by drought (Tran et al. (2004) Plant Cell 16(9):2481-2498), heat, chilling, freezing, salt stress, oxidative stress (U.S. Pat. No. 5,290,924) or biotic stressors like bacteria, fungi or viruses.

Polypeptide, peptide, oligopeptide, gene product, expression product and protein: are used interchangeably herein to refer to a polymer or oligomer of consecutive amino acid residues.

Recombinant or transgenic DNA expression construct: with respect to, for example, a nucleic acid sequence (expression construct, expression cassette or vector comprising said nucleic acid sequence) refers to all those constructs originating by experimental manipulations in which either
a) said nucleic acid sequence, or
b) a genetic control sequence linked operably to said nucleic add sequence (a), for example a promoter, or
c) (a) and (b)
is not located in its natural genetic environment or has been modified by experimental manipulations, an example of a modification being a substitution, addition, deletion, inversion or insertion of one or more nucleotide residues. Natural genetic environment refers to the natural chromosomal locus in the organism of origin, or to the presence in a genomic library. In the case of a genomic library, the natural genetic environment of the nucleic acid sequence is preferably retained, at least in part. The environment flanks the nucleic acid sequence at least at one side and has a sequence of at least 50 bp, preferably at least 500 bp, especially preferably at least 1,000 bp, very especially preferably at least 5,000 bp, in length. A naturally occurring expression construct—for example the naturally occurring combination of a promoter with the corresponding gene—becomes a transgenic expression construct when it is modified by non-natural, synthetic "artificial" methods such as, for example, mutagenesis. Such methods have been described (U.S. Pat. No. 5,565,350; WO 00/15815). Recombinant polypeptides or proteins: refer to polypeptides or proteins produced by recombinant DNA techniques, i.e., produced from cells transformed by an exogenous recombinant DNA construct encoding the desired polypeptide or protein. Recombinant nucleic acids and polypeptide may also comprise molecules which as such does not exist in nature but are modified, changed, mutated or otherwise manipulated by man. An important use of the intron sequences of the invention will be the enhancement of the expression of a nucleic acid sequence, which encodes a particular protein, a polypeptide or DNA sequences that interfere with normal transcription or translation, e.g. interference- or antisense-RNA. In one embodiment of the present invention, the recombinant DNA expression construct confers expression of one or more nucleic acid molecules. Said recombinant DNA expression construct according to the invention advantageously encompasses a promoter functioning in plants, additional regulatory or control elements or sequences functioning in plants, an intron sequence with expression enhancing properties in plants and a terminator functioning in plants. Additionally, the recombinant expression construct might contain additional functional elements such as expression cassettes conferring expression of e.g. positive and negative selection markers, reporter genes, recombinases or endonucleases effecting the production, amplification or function of the expression cassettes, vectors or recombinant organisms according to the invention. Furthermore, the recombinant expression construct can comprise nucleic acid sequences homologous to a plant gene of interest having a sufficient length in order to induce a homologous recombination (HR) event at the locus of the gene of interest after introduction in the plant. A recombinant transgenic expression cassette of the invention (or a transgenic vector comprising said transgenic expression cassette) can be produced by means of customary recombination and cloning techniques as are described (for example, in Maniatis 1989, Molecular Cloning: A Laboratory Manual, 2nd Ed., Cold Spring Harbor Laboratory, Cold Spring Harbor (NY); Silhavy 1984,) Experiments with Gene Fusions, Cold Spring Harbor Laboratory, Cold Spring Harbor, N.Y.; and in Ausubel 1987, Current Protocols in Molecular Biology, Greene Publishing Assoc. and Wiley Interscience). The introduction of an expression cassette according to the invention into an organism or cells, tissues, organs, parts or seeds thereof (preferably into plants or plant cells, tissue, organs, parts or seeds) can be effected advantageously using vectors, which comprise the above described nucleic acids, promoters, introns, terminators, regulatory or control elements and functional elements.

Regeneration: as used herein, means growing a whole plant from a plant cell, a group of plant cells, a plant part or a plant piece (e.g., from a protoplast, callus, protocorm-like body, or tissue part).

Regulatory sequence: refers to promoters, enhancer or other segments of DNA where regulatory proteins such as transcription factors bind and thereby influencing the transcription rate of a given gene.

Substantially all introns of a plant genome represented in a genomic DNA sequence database or genomic DNA library: refers to more than 80%, preferably to more than 90%, more preferably to more than 95%, still more preferably more than 98% of all introns present in the genome of the plant used as a source for the preparation of the genomic DNA sequence database or genomic DNA library. The construction of genomic libraries and the subsequent sequencing of the genomic DNA and the construction of a genomic or genome DNA sequence database using the obtained sequence information is well established in the art (Mozo et al. (1998) Mol. Gen. Genet. 258:562-570; Choi et al. (1995) Weeds World 2:17-20; Lui et al. (1999) Proc. Natl. Acad. Sci. USA 96:6535-6540; The *Arabidopsis* Genome initiative, Nature 402:761-777 (1999); The *Arabidopsis* Genome initiative, Nature 408:796-826 (2000).

Structural gene: as used herein is intended to mean a DNA sequence that is transcribed into mRNA which is then translated into a sequence of amino acids characteristic of a specific polypeptide.

Sufficient length: with respect to a homology sequence comprised in a DNA-construct (e.g., the homology sequence A or B) is to be understood to comprise sequences of a length of at least 100 base pair, preferably at least 250 base pair, more preferably at least 500 base pair, especially preferably at least 1,000 base pair, most preferably at least 2,500 base pair. The term "sufficient homology' with respect to a homology sequence comprised in a DNA-construct (e.g., the homology sequence A or B) is to be understood to comprise sequences having a homology to the corresponding target sequence comprised in the chromosomal DNA (e.g., the target sequence A or B) of at least 70%, preferably at least 80%, more preferably at least 90%, especially preferably at least 95%, more especially preferably at least 99%, most preferably 100%, wherein said homology extends over a length of at least 50 base pair, preferably at least 100 base pair, more preferably at least 250 base pair, most preferably at least 500 base pair.

Target region/sequence: of a nucleic acid sequence is a portion of a nucleic acid sequence that is identified to be of interest. A "coding region" of a nucleic acid sequence is the portion of the nucleic acid sequence, which is transcribed and translated in a sequence-specific manner to produce into a particular polypeptide or protein when placed under the control of appropriate regulatory sequences. The coding region is said to encode such a polypeptide or protein.

Tissue: with respect to a plant (or "plant tissue') means arrangement of multiple plant cells including differentiated and undifferentiated tissues of plants. Plant tissues may constitute part of a plant organ (e.g., the epidermis of a plant leaf) but may also constitute tumor tissues and various types of cells in culture (e.g., single cells, protoplasts, embryos, calli, protocorm-like bodies, etc.). Plant tissue may be in planta, in organ culture, tissue culture, or cell culture.

Transforming or transformation: as used herein refers to the introduction of genetic material (e.g., a transgene) into a cell. Transformation of a cell may be stable or transient. The term "transient transformation" or "transiently transformed" refers to the introduction of one or more transgenes into a cell in the absence of integration of the transgene into the host cell's genome. Transient transformation may be detected by, for example, enzyme-linked immunosorbent assay (ELISA) which detects the presence of a polypeptide encoded by one or more of the transgenes. Alternatively, transient transformation may be detected by detecting the activity of the protein (e.g., β-glucuronidase) encoded by the transgene (e.g., the uidA gene) as demonstrated herein [e.g., examples 1.6 and 2.4, histochemical assay of GUS enzyme activity by staining with X-gluc which gives a blue precipitate in the presence of the GUS enzyme; and a chemiluminescent assay of GUS enzyme activity using the GUS-Light kit (Tropix)]. The term "transient transformant" refers to a cell which has transiently incorporated one or more transgenes. In contrast, the term "stable transformation" or "stably transformed" refers to the introduction and integration of one or more transgenes into the genome of a cell, preferably resulting in chromosomal integration and stable heritability through meiosis. Stable transformation of a cell may be detected by Southern blot hybridization of genomic DNA of the cell with nucleic acid sequences, which are capable of binding to one or more of the transgenes. Alternatively, stable transformation of a cell may also be detected by the polymerase chain reaction of genomic DNA of the cell to amplify transgene sequences. The term "stable transformant" refers to a cell that has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene. Transformation also includes introduction of genetic material into plant cells in the form of plant viral vectors involving extra-chromosomal replication and gene expression, which may exhibit variable properties with respect to meiotic stability.

Transgenic or recombinant: when used in reference to a cell refers to a cell which contains a transgene, or whose genome has been altered by the introduction of a transgene. The term "transgenic" when used in reference to a tissue or to a plant refers to a tissue or plant, respectively, which comprises one or more cells that contain a transgene, or whose genome has been altered by the introduction of a transgene. Trans-genic cells, tissues and plants may be produced by several methods including the introduction of a "transgene" comprising nucleic acid (usually DNA) into a target cell or integration of the transgene into a chromosome of a target cell by way of human intervention, such as by the methods described herein.

Wild-type, natural or of natural origin: means with respect to an organism, polypeptide, or nucleic acid sequence, that said organism polypeptide, or nucleic acid sequence is naturally occurring or available in at least one naturally occurring organism polypeptide, or nucleic acid sequence which is not changed, mutated, or otherwise manipulated by man.

Vector: is a DNA molecule capable of replication in a host cell. Plasmids and cosmids are exemplary vectors. Furthermore, the terms "vector" and "vehicle" are used interchangeably in reference to nucleic acid molecules that transfer DNA segment(s) from one cell to another, whereby the cells not necessarily belonging to the same organism (e.g. transfer of a DNA segment form an *Agrobacterium* cell to a plant cell).

The term "expression vector" as used herein refers to a recombinant DNA molecule containing a desired coding sequence and appropriate nucleic acid sequences necessary for the expression of the operably linked coding sequence in a particular host organism.

DETAILED DESCRIPTION OF THE INVENTION

The teaching of the present invention enables the identification of introns causing intron mediated enhancement (IME) of gene expression. Furthermore, the present invention provides isolated plant introns that, if functionally combined with a promoter functioning in plants and a nucleic acid fragment, can enhance the expression rate of said nucleic acid in a plant or a plant cell.

A first embodiment of the present invention relates to a method for identifying an intron with plant gene expression enhancing properties comprising selecting an intron from a plant genome, wherein said intron is characterized by at least the following features I) an intron length shorter than 1,000 base pairs, and
II) presence of a 5' splice site comprising the dinucleotide sequence 5'-GT-3' (SEQ ID NO: 78), and
III) presence of a 3' splice site comprising the trinucleotide sequence 5'-CAG-3' (SEQ ID NO: 79), and
IV) presence of a branch point resembling the consensus sequence 5'-CURAY-3' (SEQ ID NO:75) upstream of the 3' splice site, and
V) an adenine plus thymine content of at least 40% over 100 nucleotides down-stream from the 5' splice site, and
VI) an adenine plus thymine content of at least 50% over 100 nucleotides upstream from the 3' splice site, and
VII) an adenine plus thymine content of at least 50%, and a thymine content of at least 30% over the entire intron.

In another embodiment, the invention relates to a method for enriching the number of introns with expression enhancing properties in plants in a population of plant introns to a percentage of at least 50% of said population, said method comprising selecting introns from said population, said introns are characterized by at least the following features I) an intron length shorter than 1,000 base pairs, and
II) presence of a 5' splice site comprising the dinucleotide sequence 5'-GT-3' (SEQ ID NO: 78), and
III) presence of a 3' splice site comprising the trinucleotide sequence 5'-CAG-3' (SEQ ID NO: 79), and
IV) presence of a branch point resembling the consensus sequence 5'-CURAY-3' (SEQ ID NO:75) upstream of the 3' splice site, and
V) an adenine plus thymine content of at least 40% over 100 nucleotides down-stream from the 5' splice site, and VI) an adenine plus thymine content of at least 50% over 100 nucleotides upstream from the 3' splice site, and VII) an adenine plus thymine content of at least 50%, and a thymine content of at least 30% over the entire intron.

The inclusion of any of the inventive introns described by SEQ ID NOs: 1, 2, 3, 5, 6, 7, 10, 11, 12, 13, 14, 15, 16, 17, 18, 19, 20, 21 or 22 into the 5' untranslated region (UTR) of the β-glucuronidase gene (GUS) driven by the Zea mays Ubiquitin promoter has led to strong expression enhancement of the reporter gene in maize protoplasts (Black Mexican Sweet) suspension cells and stable transformed plants (see examples). Furthermore, it could be shown that the gene expression enhancement properties of said introns are comparable to those known from the literature (e.g. the first intron of the Zea mays Ubiquitin gene, used as positive control in the expression assays).

In a preferred embodiment, the number of introns—with gene expression enhancing properties identified within a population of introns by applying the method of the invention for enrichment is enriched to a percentage of at least 50%, preferably at least 55%, more preferably at least 60%, especially preferably at least 65%, or very especially preferably at least 70% (i.e., a given population of 100 introns pre-selected by using the inventive method will comprise at least 50, preferably at least 55, more preferably at least 60, especially preferably at least 65 or 70 introns with gene expression enhancing properties). More preferably, the number of introns—with gene expression enhancing properties identified within a population of introns by applying the method of the invention for enrichment is enriched to a percentage of at least 50%, wherein the selected introns, if part of an recombinant DNA expression construct leads to an increase in the gene expression of a given gene of at least 300% compared to the otherwise identical expression construct lacking the intron under otherwise unchanged conditions. Most preferably, the enrichment is at least 60% percent, wherein the selected introns, increasing the transcription of a gene driven by a given promoter of at least 200%. Especially preferably, the enrichment is at least 70%, wherein the selected introns, increasing the transcription of a gene driven by a given promoter of at least 50%.

Preferably, the length of an inventive IME-intron is preferably shorter than 1,000 base pairs, more preferably shorter than 900 bp, most preferably shorter than 800 bp. In a preferred embodiment, the branchpoint sequence of the intron identified by a method of the invention is described by the nucleotide sequences 5'-CURAY-3' (SEQ ID NO. 75) or 5'-YURAY-3' (SEQ ID NO. 76), wherein the U and A are essential nucleotides, and purines and pyrimidines are preferred nucleotides at positions 3 and 5 respectively. In position 1, pyrimidines are preferred but also C is preferred to U. The sequence context of the 5 splice-site surrounding the GT dinucleotide may vary. Preferred are 5 splice-sites of the sequence 5'-RR/GT(RT)(RT)(GY)-3' (SEQ ID NO. 77), wherein R stands for the nucleotides G or A, Y stands for the nucleotides C or T. The nucleotides given in brackets describing alternative nucleotides at the respective position.

In a preferred embodiment of the invention, the adenine/thymine (AT) content of an inventive intron over the entire sequence is at least 50%, more preferably at least 55%, even more preferably at least 60%.

In a preferred embodiment of the invention the populations of plant introns to which the inventive methods will be applied comprises a) substantially all introns of a plant genome represented in a DNA sequence database or b) a plant genomic DNA library. In an additional embodiment of the invention, the population of introns to which the inventive methods will be applied to is selected from the group consisting of a) introns located between two protein encoding exons, and b) introns located within the 5' untranslated region of the corresponding gene. In order to identify an intron with expression enhancing properties in plants or plant cells located within a coding region (between two protein encoding exons) or in the 5' untranslated region of a given gene, the coding regions and the 5' untranslated regions from a set of genes (e.g., present in a sequence database) can be screened for the presence of introns located in said regions and the identified introns are subsequently screened using one of the inventive methods. Such an in silico identification process using bioinformatics tools known to the persons skilled in the art can be performed by screening a) specific DNA sequence databases (e.g., containing solely coding regions or the 5' untranslated regions), or b) other publicly accessible genomic DNA sequences containing databases. In a preferred embodiment of the invention, the introns with expression enhancing properties located in the 5' untranslated regions are identified by a method comprising the steps of:

a. identifying a coding sequences within a set of genes present in a sequence database, and b. identifying EST sequences corresponding to the genes identified under (a), and c. comparing said coding sequences and EST sequences with the genomic sequence of the respective genes, and d. selecting EST sequences comprising the 5' untranslated region, and e. identifying introns located in said 5' untranslated regions.

Preferably, the steps of retrieving or generating DNA sequences or the generation of specific DNA sequence database and screening the same (e.g. using the criteria according to the inventive methods) can be performed with the aid of appropriate bioinformatic computer algorithms and appropriate computer devices known to a skilled person. In a preferred embodiment, the introns where selected from a population of introns derived from monocotyledonous plants, especially preferred are monocotyledonous plants selected from the group consisting of the genera Hordeum, Avena, Secale, Triticum, Sorghum, Zea, Saccharum and Oryza.

In a furthermore preferred embodiment of the invention, the population of introns to which the inventive methods will be applied are selected from a population of plant genes representing the 10% fraction ($9^{th}$ decile) of genes with the highest expression rate in a gene expression analysis experiment performed using a plant cell, plant tissue or a whole plant.

To allow the determination of gene expression levels, a number of different techniques have been proposed (Milosavljevic, A. et al. (1996) Genome Res. 6:132 141; Shoemaker, D. et al. (1996) Nature Genet. 14:450 456; Sikela, J. M. and Auffray, C. (1993) Nature Genet. 3:189 191; Meier-Ewert S. et al. (1998) Nucleic Acids Research 26(9):2216-2223). Therefore, a number of different gene expression analysis systems could be employed in accordance with the instant invention, including, but not limited to microarray analysis, "digital northern', clone distribution analysis of cDNA libraries using the "DNA sequencing by hybridization method' (Strezoska, Z. et al. (1991) Proc. Natl. Acad. Sci. USA 88:10089-10093) and Serial Analysis of Gene Expression (SAGE, Velculescu, V. E. et al. (1995) Science 270:484-487).

By using the cDNA microarray hybridization technology the expression profiles of thousands of genes can be monitored at once. The DNA array analysis has become a standard technique in the molecular biology laboratory for monitoring gene expression. Arrays can be made either by the mechanical spotting of pre-synthesized DNA products or by the de novo synthesis of oligonucleotides on a solid substrate, usually a derivatized glass slide. Typically arrays are used to detect the presence of mRNAs that may have been transcribed from different genes and which encode different proteins. The RNA is extracted from many cells, or from a single cell type, then converted to cDNA or cRNA. The copies may be "amplified" by (RT-) PCR. Fluorescent tags are enzymatically incorporated into the newly synthesized strands or can be chemically attached to the new strands of DNA or RNA. A cDNA or cRNA molecule that contains a sequence complementary to one of the single-stranded probe sequences will hybridize, or stick, via base pairing to the spot at which the complementary probes are affixed. The spot will then fluoresce when examined using a microarray scanner. Increased or decreased fluorescence intensity indicates that cells in the sample have recently transcribed, or ceased transcription, of a gene that contains the probed sequence. The intensity of the fluorescence is proportional to the number of copies of a particular mRNA that were present and thus roughly indicates the activity or expression level of that gene. Microarrays (and the respective equipment needed to perform the expression analysis experiments) that can be employed in accordance with the present invention are commercially available. The GeneChip *Arabidopsis* ATH1 Genome Array, produced from Affimetrix (Santa Clara, Calif.), contains more than 22,500 probe sets representing approximately 24,000 genes. The array is based on information from the international *Arabidopsis* sequencing project that was formally completed in December 2000 (http://www.affymetrix.com). Thus, the expression rate of the analyzed genes can be ranked (according to the intensity of the fluorescence of the respective genes after the hybridization process) and the genes belonging to the 10% of genes showing the highest gene expression rate can be identified by using microarray analysis.

Databases containing microarray expression profiling results are publicly available via the internet e.g. the Nottingham *Arabidopsis* Stock Center s microarray database or the OSMID (osmotic stress microarray information) database. The Nottingham *Arabidopsis* Stock Center s microarray database containing a wide selection of microarray data from Affimetrix gene chips (http://affymetrix.arabidopsis). The OSMID database (http://www.osmid.org) contains the results of approximately 100 microarray experiments performed at the University of Arizona. This includes analysis of NaCl, cold, and drought treatments of *Arabidopsis thaliana*, rice (*Oryza sativa*), barley, (*Hordeum vulgaris*), ice plant (*Mesembryanthemum crystallinum*), and corn (*Zea mays*). Thus, by using the expression profiles present in sequence/expression databases the expression rate of genes can be ranked (according to the clone distribution of the respective cDNA in the library) and genes belonging to the 10% of genes showing the highest (abundance) gene expression rate can be identified.

"Digital Northern are generated by partly sequencing thousands of randomly selected clones from relevant cDNA libraries. Differentially expressed genes can then be detected from variations in the counts of their cognate sequence tags. The sequence tag-based method consists of generating a large number (thousands) of expressed sequence tags (ESTs) from 3'-directed regional non-normalized cDNA libraries. The concept of a "digital Northern comparison is the following: a number of tags is reported to be proportional to the abundance of cognate transcripts in the tissue or cell type used to make the cDNA library. The variation in the relative frequency of those tags, stored in computer databases, is then used to point out the differential expression of the corresponding genes (Okubo et al. 1992; Matsubara and Okubo 1994). The SAGE method is a further development of this technique, which requires only nine nucleotides as a tag, therefore allowing a larger throughput. Thus, the expression rate of the analyzed genes by using the "digital Northern' method can be ranked (according to the abundance of the tags of the respective gene in the cDNA library) and the genes belonging to the 10% of genes showing the highest (abundance) gene expression rate can be identified.

Using the "sequencing by hybridization method' described in the U.S. Pat. No. 5,667,972, U.S. Pat. No. 5,492,806, U.S. Pat. No. 5,695,940, U.S. Pat. No. 5,972,619, U.S. Pat. No. 6,018,041, U.S. Pat. No. 6,451,996, U.S. Pat. No. 6,309,824 it is possible to perform in silico clone distribution analysis of complete cDNA libraries. The entire content of said US patents is incorporated by reference. This technology is commercially available and customized experiments can be conducted in collaboration with the company HySeq Inc. To determine done distribution by using the "sequencing by hybridization method', or "HySeq-technology' plants are grown under a variety of conditions and treatments, and then tissues at different developmental stages are collected. This is done in a strategic manner so the probability of harvesting all expressible genes in at least one or more of the libraries is maximized.

mRNA is then extracted from each of the collected samples and used for the library production. The libraries can be generated from mRNA purified on oligo dT columns. Colonies from transformation of the cDNA library into *E. coli* are randomly picked and placed into microtiter plates and subsequently spotted DNA onto a surface. The cDNA inserts from each clone from the microtiter plates are PCR amplified and spotted onto a nylon membrane. A battery of 288 $^{33}$-P radio-labeled seven-mer oligonucleotides are then sequentially hybridized to the membranes. After each hybridization a blot image is captured during a phosphorimage scan to generate a profile for each single oligonucleotide. Absolute identity is maintained by barcoding for image cassette, filter and orientation within the cassette. The filters are then treated using relatively mild conditions to strip the bound probes and then returned to the hybridization chambers for another round. The hybridization and imaging cycle is repeated until the set of 288 oligomers is completed. After completion of hybridizations, each spot (representing a cDNA insert) will have recorded the amount of radio signal generated from each of the 288 seven-mer oligonucleotides. The profile of which oligomers bound, and to what degree, to each single cDNA insert (a spot on the membrane) is defined as the signature generated from that clone. Each clone's signature is compared with all other signatures generated from the same organism to identify clusters of related signatures. This process "sorts' all of the clones from an organism into so called "clusters' before sequencing. In the clustering process, complex or tissue specific cDNA libraries are "mined' using a series of 288 seven base-pair oligonucleotides. By collecting data on the hybridization signature of these oligos, the random set of clones in a library can be sorted into "clusters'. A cluster is indicative for the abundance of each gene in a particular library and is therefore a measure of the gene expression rate of an individual gene. Thus, the expression rate of genes can be ranked using the 'HySeq' technology and the genes belonging to the 10% of genes showing the highest (abundance) gene expression rate can be identified.

The genes, cDNAs or expressed sequence tags chosen for the identification of the inventive introns, belonging to the 10%, preferably 5%, more preferably 3% most preferably 1% of genes showing the highest gene expression rate in a gene expression analysis experiment, wherein the gene expression rate can be calculated indirectly by using the above described methods. In a preferred embodiment of the invention, the nucleic acid sequences of the genes belonging to the 10% of genes showing the highest gene expression rate where used to isolate the complete genomic DNA sequence including the intron sequences—of the respective genes by screening of e.g. appropriate DNA sequences containing databases, or genomic DNA or genomic DNA libraries using hybridization methods or RACE cloning techniques (rapid amplification of cDNA ends), or chromosome walking techniques. After sequence determination of the isolated complete genomic DNA of the respective candidate gene, the intron sequences present in said genes were screened using the above described criteria to identify those introns, having expression enhancing properties. The described in silico methods for the selection of introns with expression enhancing properties have a high probability of success, but the efficiency of the described methods may be further increased by combination with other methods. Therefore, in one preferred embodiment of the invention independent validation of the genes representing the 10% of genes showing the highest gene expression rate in a gene expression analysis experiment is done using alternative gene expression analysis tools, like Northern analysis, or real time PCR analysis (see examples).

In a preferred embodiment of the invention the method for the identification or enrichment of introns with gene expression enhancing properties in plants is applied to DNA sequence databases using an automated process, more preferably using a computer device and an algorithm that defines the instructions needed for accomplishing the selection steps for identifying or enriching introns with gene expression enhancing properties in plants within the screened population of DNA sequences. A further embodiment of the invention is a computer algorithm that defines the instructions needed for accomplishing the selection steps for identifying or enriching introns with plant gene expression enhancing properties as described above. Useful computer algorithms are well known in the art of bioinformatics or computational biology. Bioinformatics or computational biology is the use of mathematical and informational techniques to analyze sequence data (e.g. generation of sequence data, sequence alignments, screening of sequence data) usually by creating or using computer programs, mathematical models or both. One of the main areas of bioinformatics is the data mining and analysis of data gathered from different sources. Other areas are sequence alignment, protein structure prediction. Another aspect of bioinformatics in sequence analysis is the automatic search for genes or regulatory sequences within a genome (e.g. intron sequences within a stretch of genomic DNA). Sequence databases can be searched using a variety of methods. The most common is probably searching for a sequence similar to a certain target gene whose sequence is already known to the user. A useful program is the BLAST (Basic Local Alignment Search Tool) program a method of this type. BLAST is an algorithm for comparing biological sequences, such as DNA sequences of different genes. Given a library or database of sequences, a BLAST search enables a researcher to look for specific sequences. The BLAST algorithm and a computer program that implements it were developed by Stephen Altschul at the U.S. National Center for Biotechnology Information (NCBI) and is available on the web at http://www.ncbi.nlm.nih.gov/BLAST. The BLAST program can either be downloaded and run as a command-line utility "blastall" or accessed for free over the web. The BLAST web server, hosted by the NCBI, allows anyone with a web browser to perform similarity searches against constantly updated databases of proteins and DNA that include most of the newly sequenced organisms. BLAST is actually a family of programs (all included in the blastall executable) including beside others the Nucleotide-nucleotide BLAST (BLASTN). This program, given a DNA query, returns the most similar DNA sequences from the DNA database that the user specifies. A person skilled in the art knows how to produce or retrieve sequence Data from e.g. public sequence database and to design algorithms to screen the set of sequences in a customized way (see examples).

Additionally, the invention relates to computer algorithm that defines the instructions needed for accomplishing the selection steps for identifying or enriching introns with gene expression enhancing properties in plants from a plant genome or a population of introns selected from the group consisting of introns located between two protein encoding exons, and/or introns located within the 5' untranslated region of the corresponding gene and/or introns located in the DNA sequences of genes representing the 10% fraction of genes with the highest expression rate in a gene expression analysis experiment performed using a plant cell, plant tissue and/or a whole plant. Another embodiment of the invention is a computer device or data storage device comprising the algorithm. A storage device can be a hard disc" (or "hard drive") or an optical data storage medium like a CD-ROM ("Compact Disc Read-Only Memory" (ROM) or DVD (digital versatile disc) or any other mechanically, magnetically, or optically data storage medium.

Another embodiment of the invention relates to a method for isolating, providing or producing an intron with gene expression enhancing properties in plants comprising the steps of
a) performing an identification or enrichment of introns with gene expression enhancing properties in plants as described above and providing the sequence information of said identified or enriched introns, and
b) providing the physical nucleotide sequence of said introns identified or enriched under a) and
c) evaluating the gene expression enhancing properties of the intron sequence provided under b) in an in vivo or in vitro expression experiment, and
d) isolating introns from said expression experiment c), which demonstrate expression enhancing properties.

Preferably, evaluation of the gene expression enhancing properties of the isolated introns comprises,
c1) providing a recombinant expression constructs by functionally linking an individual nucleotide sequence from step b) with at least one promoter sequence functioning in plants or plant cells, and at least one readily quantifiable nucleic acid sequence, and
c2) introducing said recombinant DNA expression construct in plant cells and evaluating the gene expression enhancing properties of the isolated intron.

Preferably, the evaluation of the gene expression enhancing properties is done in a plant cell or stable transformed plants and wherein said isolated intron enhances expression of a given gene at least twofold (see examples).

An additional subject matter of the invention relates to a recombinant DNA expression construct comprising at least one promoter sequence functioning in plants cells, at least one nucleic acid sequence and at least one intron selected from the group consisting of the sequences described by SEQ ID NOs: 1, 2, 3, 5, 6, 7, 10, 11, 12, 13, 14, 15, 16, 17, 18, 19, 20, 21 and 22, and functional equivalents thereof, wherein said promoter sequence and at least one of said intron sequences are functionally linked to said nucleic acid sequence and wherein said intron is heterologous to said nucleic acid sequence or to said promoter sequence. Furthermore, the invention relates to recombinant expression constructs comprising at least one promoter sequence functioning in plants cells, at least one nucleic acid sequence and at least one functional equivalents of an intron described by any of sequences SEQ ID NOs: 1, 2, 3, 5, 6, 7, 10, 11, 12, 13, 14, 15, 16, 17, 18, 19, 20, 21 and 22.

Preferably, said functional equivalents comprising the functional elements of an intron, wherein said promoter sequence and at least one of said intron sequences are functionally linked to said nucleic acid sequence and wherein said intron is heterologous to said nucleic acid sequence or to said promoter sequence. More preferably, the functional equivalent is further characterized by
i) having at least 50 consecutive base pairs of the intron sequence described by any of SEQ ID NOs: 1, 2, 3, 5, 6, 7, 10, 11, 12, 13, 14, 15, 16, 17, 18, 19, 20, 21 or 22, or
ii) having an identity of at least 80% over a sequence of at least 95 consecutive nucleic acid base pairs to a sequences described by any of SEQ ID NOs: 1, 2, 3, 5, 6, 7, 10, 11, 12, 13, 14, 15, 16, 17, 18, 19, 20, 21 or 22 or
iii) hybridizing under high stringent conditions with a nucleic acid fragment of at least 50 consecutive base pairs of a nucleic acid molecule described by any of SEQ ID NOs: 1, 2, 3, 5, 6, 7, 10, 11, 12, 13, 14, 15, 16, 17, 18, 19, 20, 21 or 22, In a preferred embodiment of the invention, the introns comprising at least 50 bases pairs, more preferably at least 40 bases pairs, most preferably 30 bases pairs of the sequences/exons 5' and 3' adjacent to the 5' and 3' splice sites of the intron, respectively. In another embodiment of the in, the recombinant DNA expression construct of the invention further comprises one or more additional regulatory sequences functionally linked to a promoter. Those regulatory sequences can be selected from the group consisting of heat shock-, anaerobic responsive-, pathogen responsive-, drought responsive-, low temperature responsive-, ABA responsive-elements, 5-untranslated gene region, 3-untranslated gene region, transcription terminators, polyadenylation signals and enhancers. Cis- and trans-acting factors involved in ABA-induced gene expression have been reviewed by Bray (1997) Trends Plant Sci. 2:48 54; Busk et al. (1998) Plant Mol. Biol. 37:425 435 and Shinozaki and Yamaguchi-Shinozaki (2000) Curr. Opin. Plant Biol. 3:217 223). Many ABA-inducible genes contain a conserved, ABA-responsive, cis-acting element named ABRE (ABA-responsive element; PyACGTGGC) in their promoter regions (Guiltinan et al (1990) Science 250:267 271; Mundy et al., (1990) Proc. Natl. Acad. Sci. USA 87:406 410). The promoter region of the rd29A gene was analyzed, and a novel cis-acting element responsible for dehydration- and cold-induced expression was identified at the nucleotide sequence (Yamaguchi-Shinozaki and Shinozaki (1994) Plant Cell 6:251 264.). A 9-bp conserved sequence, TACCGACAT, termed the dehydration-responsive element (DRE), is essential for the regulation of dehydration responsive gene expression. DRE-related motifs have been reported in the promoter regions of cold- and drought-inducible genes such as kin1, cor6.6, and rd17 (Wang et al. (1995) Plant Mol. Biol. 28:605 617; Iwasaki et al. (1997) Plant Physiol. 115:1287). The thermoinducibility of the heat shock genes is attributed to activation of heat shock factors (HSF). HSF act through a highly conserved heat shock promoter element (HSE) that has been defined as adjacent and inverse repeats of the motif 5'-nGAAn-3' (Amin et al., (1988) Mol Cell Biol 8:3761-3769). Examples for defense or pathogen response elements are the W-box (TTGACY) and W-box-like elements, representing binding sites for plant-specific WRKY transcription factors involved in plant development and plant responses to environmental stresses (Eulgem et al. (2000) Trends Plant Sci 5:199 206; Robatzek S et al. (2001) Plant J 28:123 133), and the Myc-element (CACATG) (Rushton P J et al. (1998) Curr Opin Plant Biol 1:311 315). Such regulatory sequences or elements that can be employed in conjunction with a described promoter, encompass the 5-untranslated regions, enhancer sequences and plant polyadenylation signals. Examples of translation enhancers, which may be mentioned, are the tobacco mosaic virus 5 leader sequence (Gallie et al. (1987) Nucl Acids Res 15:8693-8711), the enhancer from the octopine synthase gene and the like. Furthermore, they may promote tissue specificity (Rouster J et al. (1998) Plant J 15:435-440). The recombinant DNA expression construct will typically include the gene of interest along with a 3' end nucleic acid sequence that acts as a signal to terminate transcription and subsequent polyadenylation of the RNA. Preferred plant polyadenylation signals are those, which essentially correspond to T-DNA polyadenylation signals from *Agrobacterium tumefaciens*, in particular gene 3 of the T-DNA (octopine synthase) of the Ti plasmid pTiACHS (Gielen et al. (1984) EMBO J 3:835-46) or functional equivalents thereof. Examples of terminator sequences, which are especially suitable, are the OCS (octopin synthase) terminator and the NOS (nopaline synthase) terminator. An expression cassette and the vectors derived from it may comprise further functional elements. The term functional element is to be understood in the broad sense and refers to all those elements, which have an effect on the generation, amplification or function of the expression cassettes, vectors or recombinant organisms according to the invention. The following may be mentioned by way of example, but not by limitation:

1. Selection Markers

Selection markers are useful to select and separate successfully transformed or homologous recombined cells. To select cells which have successfully undergone homologous recombination, or else to select transformed cells, it is, also typically necessary to introduce a selectable marker, which confers resistance to a biocide (for example herbicide), a metabolism inhibitor such as 2-deoxyglucose-6-phosphate (WO 98/45456) or an antibiotic to the cells which have successfully undergone recombination. The selection marker permits the selection of the transformed cells from untransformed ones (McCormick et al. (1986) Plant Cell Reports 5:81-84).

1.1 Negative Selection Markers

Selection markers confer a resistance to a biocidal compound such as a metabolic inhibitor (e.g., 2-deoxyglucose-6-phosphate, WO 98/45456), antibiotics (e.g., kanamycin, G 418, bleomycin or hygromycin) or herbicides (e.g., phosphinothricin or glyphosate). Especially preferred negative selection markers are those which confer resistance to herbicides. Examples which may be mentioned are:
Phosphinothricin acetyltransferases (PAT; also named Bialophos resistance; bar; de Block et al. (1987) EMBO J 6:2513-2518)
5-enolpyruvylshikimate-3-phosphate synthase (EPSPS) conferring resistance to Glyphosate (N-(phosphonomethyl)glycine),
Glyphosate degrading enzymes (Glyphosate oxidoreductase; gox),
Dalapon inactivating dehalogenases (deh)
sulfonylurea- and imidazolinone-inactivating acetolactate synthases (for example mutated ALS variants with, for example, the S4 and/or Hra mutation)
Bromoxynil degrading nitrilases (bxn)
Kanamycin- or G418-resistance genes (NPTII; NPTI) coding e.g., for neomycin phosphotransferases, 2-Desoxyglucose-6-phosphate phosphatase (DOG$_R$1-Gene product; WO 98/45456; EP 0 807 836) conferring resistance against 2-desoxyglucose (Randez-Gil et al., 1995 Yeast 11:1233-1240).

Additional suitable negative selection marker are the aadA gene, which confers resistance to the antibiotic spectinomycin, the streptomycin phosphotransferase (SPT) gene, which allows resistance to streptomycin and the hygromycin phosphotransferase (HPT) gene, which mediates resistance to hygromycin. Especially preferred are negative selection markers that confer resistance against the toxic effects imposed by D-amino adds like e.g., D-alanine and D-serine (WO 03/060133; Erikson 2004). Especially preferred as negative selection marker in this contest are the daol gene (EC: 1.4. 3.3: GenBank Acc.-No.: U60066) from the yeast *Rhodotorula gracilis* (*Rhodosporidium toruloides*) and the *E. coli* gene dsdA (D-serine dehydratase (D-serine deaminase) [EC: 4.3. 1.18; GenBank Acc.-No.: J01603).

1.2) Counter Selection Marker

Counter selection markers are especially suitable to select organisms with defined deleted sequences comprising said marker (Koprek T et al. (1999) Plant J 19(6): 719-726). Examples for counter selection marker comprise thymidin kinases (TK), cytosine deaminases (Gleave A P et al. (1999) Plant Mol. Biol. 40(2):223-35; Perera R J et al. (1993) Plant Mol. Biol 23(4): 793-799; Stougaard J. (1993) Plant J 3:755-761), cytochrom P450 proteins (Koprek et al. (1999) Plant J 16:719-726), haloalkandehalogenases (Naested H (1999) Plant J 18:571-576), iaaH gene products (Sundaresan V et al. (1995) Genes & Development 9:1797-1810), cytosine deaminase codA (Schlaman H R M and Hooykaas P J J (1997) Plant J 11:1377-1385), or tms2 gene products (Fedoroff N V & Smith D L, 1993, Plant J 3:273-289).

1.3 Positive Selection Marker

Furthermore, positive selection marker can be employed. Genes like isopentenyltransferase from *Agrobacterium tumefaciens* (strain: PO22; Genbank Acc.-No.: AB025109) may as a key enzyme of the cytokinin biosynthesis facilitate regeneration of transformed plants (e.g., by selection on cytokinin-free medium). Corresponding selection methods are described (Ebinuma 2000a,b). Additional positive selection markers, which confer a growth advantage to a transformed plant in comparison with a non-transformed one, are described e.g., in EP-A 0 601 092. Growth stimulation selection markers may include (but shall not be limited to) β-Glucuronidase (in combination with e.g., a cytokinin glucuronide), mannose-6-phosphate isomerase (in combination with mannose), UDP-galactose-4-epimerase (in combination with e.g., galactose), wherein mannose-6-phosphate isomerase in combination with mannose is especially preferred.

2) Reporter Genes

Reporter genes encode readily quantifiable proteins and, via their color or enzyme activity, make possible an assessment of the transformation efficacy, the site of expression or the time of expression. Very especially preferred in this context are genes encoding reporter proteins (Schenborn E and Groskreutz D. (1999) Mol. Biotechnol. 13(1):2944) such as the green fluorescent protein (GFP) (Sheen et al., (1995) Plant Journal 8(5):777-784; Haseloff et al. (1997) Proc Natl Acad Sci USA 94(6):2122-2127; Reichel et al. (1996) Proc Natl Acad Sci USA 93(12):5888-5893; Tian et al. (1997) Plant Cell Rep 16:267-271; WO 97/41228; Chui W L et al. (1996) Curr Biol 6:325-330; Leffel S M et al. (1997) Biotechniques. 23(5):912-8), chloramphenicoltransferase, a luciferase (Ow et al. (1986) Science 234:856-859; Millar et al. (1992) Plant Mol Biol Rep 10:324-414), the aequorin gene (Prasher et al. (1985) Biochem Biophys Res Commun 126(3):1259-1268), β galactosidase, R locus gene (encoding a protein which regulates the production of anthocyanin pigments (red coloring) in plant tissue and thus makes possible the direct analysis of the promoter activity without addition of further auxiliary substances or chromogenic substrates; Dellaporta et al. (1988) In: Chromosome Structure and Function: Impact of New Concepts, 18th Stadler Genetics Symposium 11:263-282), with β glucuronidase being very especially preferred (Jefferson et al. (1987) EMBO J. 6:3901-3907).

3) Origins of replication, which ensure amplification of the expression cassettes or vectors according to the invention in, for example, *E. coli*. Examples which may be mentioned are ORI (origin of DNA replication), the pBR322 ori or the P15A ori (Sambrook et al.: Molecular Cloning. A Laboratory Manual, 2nd ed. Cold Spring Harbor Laboratory Press, Cold Spring Harbor, N.Y., 1989).

4) Elements which are necessary for *Agrobacterium*-mediated plant transformation, such as, for example, the right or left border of the T-DNA or the vir region.

The inventive recombinant expression construct contains expressible nucleic acid sequences in addition to, or other than, nucleic acid sequences encoding for marker proteins. In a preferred embodiment of the invention the recombinant DNA expression construct comprises an nucleic acid sequence encodes for i) a protein or ii) a sense, antisense, or double-stranded RNA sequence. In a further preferred embodiment of the present invention, the recombinant DNA expression construct contains a nucleic acid sequence encoding a protein. In yet another embodiment of the invention the recombinant DNA expression construct may contain a DNA for the purpose of expressing RNA transcripts that function to affect plant phenotype without being translated into a protein. Such non protein expressing sequences comprising antisense RNA molecules, sense RNA molecules, RNA molecules with ribozyme activity, double strand forming RNA molecules (RNAi). The transgenic expression constructs of the invention can be employed for suppressing or reducing expression of endogenous target genes by "gene silencing'. The skilled worker knows preferred genes or proteins whose suppression brings about an advantageous phenotype. Examples may include but are not limited to down-regulation of the β-sub-unit of *Arabidopsis* G protein for increasing root mass (Ullah et al. (2003) Plant Cell 15:393-409), inactivating cyclic nucleotide-gated ion channel (CNGC) for improving disease resistance (WO 2001007596), and down-regulation of 4-coumarate-CoA ligase (4CL) gene for altering lignin and cellulose contents (US 2002138870). In yet another preferred embodiment of the invention, the transgenic expression constructs of the invention contain nucleic acids, which when transcribed, produce RNA enzymes (Ribozymes) which can act as endonucleases and catalyze the cleavage of RNA molecules with selected sequences. The cleavage of the selected RNA can result in the reduced production of their encoded polypeptide products. Ribozymes have specific catalytic domains that possess endonuclease activity (Kim and Ceck 1987, Proc. Natl. Acad. Sci. USA, 84:8788-8792; Gerlach et al., 1987, Nature, 328:802-805; Forster and Symons, 1987, Cell, 49:211-220). Several different ribozyme motifs have been described with RNA cleavage activity (Symons, 1992, Annu. Rev. Biochem., 61: 641-671). Examples include sequences from group 1 self splicing introns including Tobacco Ringspot Virus (Prody et al., 1986, Science, 231: 1577-1580). Other suitable ribozymes include sequences from RNaseP with cleavage activity (Yan et al. (1992) Proc. Natl. Acad. Sci. USA 87:4144-4148), hairpin ribozyme structures (Berzal-Herranz et al. (1992) Genes and Devel. 98:1207-1210) and Hepatitis Delta virus based ribozyme (U.S. Pat. No. 5,625,047). The general design and optimization of ribozymes directed RNA cleavage activity has been discussed on detail (Haseloff and Gerlach (1988) Nature 224: 585-591; Symons (1992) Annu. Rev. Biochem. 61: 641-671). The choice of a particular nucleic acid sequence to be delivered to a host cell or plant depends on the aim of the transformation. In general, the main goal of producing transgenic plants is to add some beneficial traits to the plant.

In another embodiment of the invention, the recombinant expression construct comprises a nucleic add sequence encoding for a selectable marker protein, a screenable marker protein, a anabolic active protein, a catabolic active protein, a biotic or abiotic stress resistance protein, a male sterility protein or a protein affecting plant agronomic characteristics. Such traits include, but are not limited to, herbicide resistance or tolerance, insect resistance or tolerance, disease resistance or tolerance (viral, bacterial, fungal, nematode); stress tolerance, as exemplified by tolerance to drought, heat, chilling, freezing, salt stress, oxidative stress; increased yield, food content, male sterility, starch quantity and quality, oil content and quality, vitamin content and quality (e.g. vitamin E) and the like. One may desire to incorporate one or more nucleic acid sequences conferring any of such desirable traits. Furthermore, the recombinant expression constructs of the invention can comprise artificial transcription factors (e.g. of the zinc finger protein type; Beerli (2000) Proc Natl Acad Sci USA 97(4):1495-500). These factors attach to the regulatory regions of the endogenous genes to be expressed or to be repressed and, depending on the design of the factor, bring about expression or repression of the endogenous gene. The following may be mentioned by way of example but not by way of limitation as nucleic acid sequences or polypeptides which can be used for these applications:

Improved protection of the plant embryo against abiotic stresses such as drought, high or low temperatures, for example by overexpressing the antifreeze polypeptides from *Myoxocephalus scorpius* (WO 00/00512), *Myoxocephalus octodecemspinosus*, the *Arabidopsis thaliana* transcription activator CBF1, glutamate dehydrogenases (WO 97/12983, WO 98/11240), a late embryogenesis gene (LEA), for example from barley (WO 97/13843), calcium-dependent protein kinase genes (WO 98/26045), calcineurins (WO 99/05902), farnesyl transferases (WO 99/06580, Pei 1998), ferritin (Deak 1999), oxalate oxidase (WO 99/04013; Dunwell 1998), DREB1A factor (dehydration response element B 1A; Kasuga 1999), mannitol or trehalose synthesis genes, such as trehalose-phosphate synthase or trehalose-phosphate phosphatase (WO 97/42326), or by inhibiting genes such as the trehalase gene (WO 97/50561). Especially preferred nucleic acids are those which encode the transcriptional activator CBF1 from *Arabidopsis thaliana* (GenBank Acc. No.: U77378) or the *Myoxocephalus octodecemspinosus* antifreeze protein (GenBank Acc. No.: AF306348), or functional equivalents of these. For expression in plants, the nucleic acid molecule must be linked operably to a suitable promoter. The plant specific promoter, regulatory element and the terminator of the inventive recombinant expression construct needs not be of plant origin, and may originate from viruses or microorganisms, in particular for example from viruses which attack plant cells.

An additional subject matter of the invention is the introduction of an inventive intron sequence into a target nucleic acid sequence via homologous recombination (HR). As a prerequisite for the HR between the recombinant expression construct and the genomic target nucleic acid sequence, the recombinant expression construct must contain fragments of the target nucleic acid sequence of sufficient length and homology. In a preferred embodiment of the invention, the intron sequences that has to be inserted into the gene of interest via HR is (within the recombinant expression construct) placed between a pair of DNA sequences identical to the region 5' and 3' to the preferred place of insertion. In this case, the recombinant expression construct can comprises only the intron sequence and the nucleic acid sequences needed to induce the HR event. In a preferred embodiment of the invention, the intron sequence that is flanked by the nucleic acid sequence of the target DNA, contains an expression cassette that enables the expression of an selectable marker protein which allows the selection of transgenic plants in which a homologues or illegitimate recombination had occurred subsequent to the transformation. The expression cassette driving the expression of the selection marker protein can be flanked by HR control sequences that are recognized by specific endonucleases or recombinases, facilitating the removal of the expression cassette from the genome. Such so called marker excision methods e.g. the cre/lox technology permit a tissue-specific, if appropriate inducible, removal of the expression cassette from the genome of the host organism (Sauer B (1998) Methods. 14(4):381-92). In this method, specific flanking sequences (lox sequences), which later allow removal by means of cre recombinase, are attached to the target gene.

Specifically, the present invention relates to transgenic expression cassettes comprising the following introns with gene expression enhancing properties in plants:
1) The sequence of the first intron (BPSI.1, SEQ ID NO: 1) isolated from the *Oryza sativa* metallothioneine-like gene (Gene Bank accession No. AP002540, *Oryza sativa* (Japonica cultivar group) genomic DNA, Chromosome 1, PAC clone: P0434B04, gene_id="P0434B04.31, protein_id="BAB44010.1", complement joined sequences: 142304 . . . 142409, 143021 . . . 143098, 143683 . . . 143747; Hsieh, H. M. et al., RNA expression patterns of a type 2 metallothioneine-like gene from rice. Plant Mol. Biol. 32 (3), 525-529 (1996)). The gene comprises two introns and three exons. The first intron of the *Oryza sativa* metallothioneine-like gene (BPSI.1, SEQ ID NO:1) is flanked by the 5' (5'-GU-3', base pair (bp) 1-2 in SEQ ID NO:1) and 3' (5'-CAG-3', bp 582-584 in SEQ ID NO:1) splice sites. In a preferred embodiment of the invention, the first intron of the *Oryza sativa* metallothioneine-like gene (BPSI.1, SEQ ID NO:1) comprises at least 28 bases pairs, more preferably at least 40 bases pairs, most preferably at least 50 base pairs of the sequences 5' and 3' adjacent to the 5' and 3' splice sites of the intron, respectively (SEQ ID NO: 82). On nucleotide level, the *Oryza sativa* metallothionein-like gene shares high homology or identity with the coding region of orthologous genes from other monocotyledonous or dicotyledonous plants e.g. 89% identity to the *Zea mays* CL1155_3 mRNA sequence (acc. No. AY109343), 88% identity to the *Poa secunda* metallothionein-like protein type 2 mRNA (acc. No. AF246982.1), 93% identity to the *Triticum aestivum* metallothioneine mRNA, partial coding sequence (acc. No. AF470355.1), 89% identity to the *Nicotiana plumbaginifolia* metallothionein-like protein mRNA (acc. No. NPU35225), 86% identity to the *Brassica oleracea* cultivar Green King metallothioneine-like protein 2 (acc. No. AF200712), 95% and 88% identity to the *Hordeum vulgare* subsp. *vulgare* partial mRNA for metallothioneine type 2 mt2b (acc. No. HVU511346) and mtb2a (acc. No. HVU511345) genes, respectively (identities have been calculated using the BLASTN 2.2.9 algorithm [May 1, 2004] Altschul, Stephen F. et al., (1997), Gapped BLAST and PSI-BLAST: a new generation of protein database search programs, Nucleic Acids Res. 25:3389-3402).

2) The sequence of the first intron (BPSI.2, SEQ ID NO:2) isolated from the *Oryza sativa* Sucrose UDP Glucosyltransferase-2 gene (Gene Bank accession No. AC084380, *Oryza sativa* (Japonica cultivar group) genomic DNA, chromosome 3, BAC OSJNBa0090P23, gene ID="OSJNBa0090P23.15", Protein ID=AAK5219.1, complement join (nucleotide 62884 to. 65255, 65350 . . . 65594, 65693 . . . 66011, 66098 . . . 66322, 66427 . . . 66593, 66677 . . . 66793, 66881 . . . 67054, 67136 . . . 67231, 67316 . . . 67532, 67652 . . . 67770, 67896 . . . 68088, 68209 . . . 68360, 68456 . . . 68585, 69314 . . . 69453 and 70899 . . . 72082). The gene comprises 13 introns and 14 exons. The first intron of the *Oryza sativa* Sucrose UDP Glucosyltransferase-2 gene (BPSI.2, SEQ ID NO: 2) is flanked by the 5' (5'-GU-3', bp 1-2 in SEQ ID NO:2) and 3' (5'-CAG-3', bp 726-728 in SEQ ID NO: 2) splice sites. In a preferred embodiment of the invention, the first intron of the *Oryza sativa* Sucrose UDP Glucosyltransferase-2 gene (SEQ ID NO:2) comprises at least 19 bases pairs of the sequence 5' to the 5'-splice site and 23 bases pairs of the sequences/exons 3' to the 3'-splice site of the intron (SEQ ID NO: 83). In a particularly preferred embodiment the intron BPSI.2 comprises at least 40 bases pairs, more preferably at least 50 bases pairs of the sequences 5' and 3' adjacent to the 5' and 3' splice sites of the intron, respectively 3) The sequence of the second intron isolated from the *Oryza sativa* Sucrose UDP Glucosyltransferase-2 gene (BPSI.3, SEQ ID NO:3). Said the second intron is flanked by the 5' (5'-GU-3', bp 1-2 in SEQ ID NO:3) and 3' (5'-CAG-3', bp 93-95 in SEQ ID NO: 3) splice sites.

In a preferred embodiment of the invention, the second intron of the *Oryza sativa* Sucrose UDP Glucosyltransferase-2 gene (SEQ ID NO:3) comprises at least 25 bases pairs of the sequence 5' to the 5'-splice site and 30 bases pairs of the sequences 3' to the 3'-splice site of the intron (SEQ ID NO: 84). In a particularly preferred embodiment the intron BPSI.3 comprises at least 40 bases pairs, more preferably at least 50 bases pairs of the sequences 5' and 3' adjacent to the 5' and 3' splice sites of the intron, respectively. On nucleotide level, the *Oryza sativa* Sucrose UDP Glucosyltransferase-2 gene shares high homology or identity with the coding region of orthologous genes from other monocotyledonous or dicotyledonous plants e.g. 88% identity to the *Zea mays* sucrose synthase (Sus1) mRNA (acc. No. L22296.1), 85% identity to the *Triticum aestivum* mRNA for sucrose synthase type 2 (acc. No. AJ000153), 85% identity to the *H. vulgare* mRNA for sucrose synthase (acc No. X69931), 80% identity to the *Saccharum officinarum* sucrose synthase-2 mRNA (acc No. AF263384.1), 95% identity to the Rice mRNA for sucrose synthase (S464 gene), partial sequence (acc. No. D10418), 79% identity to the *Glycine max* sucrose synthase mRNA (acc. No. AF03231). Identities have been calculated using the BLASTN 2.2.9 algorithm [May 1, 2004] Altschul, Stephen F. et al., (1997), Gapped BLAST and PSI-BLAST: a new generation of protein database search programs, Nucleic Acids Res. 25:3389-3402).

4) The sequence of the eighth intron (BPSI.5, SEQ ID NO:5) isolated from the *Oryza sativa* gene encoding for the Sucrose transporter (Gene Bank accession No. AF 280050). Said the eighth intron (SEQ ID NO:5) is flanked by the 5' (5'-GU-3', bp 1-2 in SEQ ID NO:5) and 3' (5'-CAG-3', bp 223-225 in SEQ ID NO: 5) splice sites. In a preferred embodiment of the invention, the eighth intron of the *Oryza sativa* gene encoding for the Sucrose transporter (SEQ ID NO:5) comprises at least 35 bases pairs of the sequence 5' to the 5'-splice site and 30 bases pairs of the sequences 3' to the 3'-splice site of the intron (SEQ ID NO: 86). In a particularly preferred embodiment the intron BPSI.5 comprises at least 40 bases pairs, more preferably at least 50 bases pairs of the sequences 5' and 3' adjacent to the 5' and 3' splice sites of the intron, respectively. In a more preferred embodiment, the 5' and 3' splice sites of the eighth intron (BPSI.5, SEQ ID NO:5) are modified in order to match the plant consensus sequences for 5' splice sites 5'-AG:: GTAAGT-3' (SEQ ID NO: 80) and 3' splice sites 5'-CAG:: GT-3' (SEQ ID NO: 81) using a PCR mutagenesis approach (SEQ ID NO:87).

5) The sequence of the fourth intron (BPSI.6, SEQ ID NO:6) isolated from the *Oryza sativa* gene (Gene Bank accession No. BAA94221) encoding for an unknown protein with homology to the *A. thaliana* chromosome II sequence from clones T22013, F12K2 encoding for a putative lipase (AC006233). Said the fourth intron (SEQ ID NO:6) is flanked by the 5' (5'-GU-3', bp 1-2 in SEQ ID NO:6) and 3' (5'-CAG-3', bp 768-770 in SEQ ID NO:6) splice sites. In a preferred embodiment of the invention, the fourth intron of the *Oryza sativa* gene (accession No. BAA94221) (SEQ ID NO:6) comprises at least 34 bases pairs of the sequence 5' to the 5'-splice site and 34 bases pairs of the sequences 3' to the 3'-splice site of the intron (SEQ ID NO: 88). In a particularly preferred embodiment the intron BPSI.6 comprises at least 40 bases pairs, more preferably at least 50 bases pairs of the sequences 5' and 3' adjacent to the 5' and 3' splice sites of the intron, respectively. In a more preferred embodiment, the 5' and 3' splice sites of fourth intron (BPSI.6, SEQ ID NO:6) are modified in order to match the plant consensus sequences for 5' splice sites 5'-AG::GTAAGT-3' (SEQ ID NO: 80) and 3' splice sites 5'-CAG::GT-3' (SEQ ID NO: 81) using a PCR mutagenesis approach (SEQ ID NO:89).

6) The sequence of the fourth intron (BPSI.7, SEQ ID NO:7) isolated from the *Oryza sativa* gene (accession No. BAB90130) encoding for a putative cinnamyl-alcohol dehydrogenase. Said the fourth intron (SEQ ID NO:7) is flanked by the 5' (5'-GU-3', bp 1-2 in SEQ ID NO:7) and 3' (5'-CAG-3', 713-715 bp in SEQ ID NO: 7) splice sites. In a preferred embodiment of the invention, the fourth intron of the *Oryza sativa* gene (accession No. BAB90130) (SEQ ID NO:7) comprises at least 34 bases pairs of the sequence 5' to the 5'-splice site and 26 bases pairs of the sequences 3' to the 3'-splice site of the intron (SEQ ID NO: 90). In a particularly preferred embodiment the intron BPSI.7 comprises at least 40 bases pairs, more preferably at least 50 bases pairs of the sequences 5' and 3' adjacent to the 5' and 3' splice sites of the intron, respectively. In a more preferred embodiment, the 5' and 3' splice sites of the fourth intron (BPSI.7, SEQ ID NO:7) are modified in order to match the plant consensus sequences for 5' splice sites 5'-AG::GTAAGT-3' (SEQ ID NO: 80) and 3' splice sites 5'-CAG::GT-3' (SEQ ID NO: 81) using a PCR mutagenesis approach (SEQ ID NO:91).

7) The sequence of the third intron (BPSI.10, SEQ ID NO:10) isolated from the *Oryza sativa* gene (accession No. AP003300) encoding for a putative protein kinase. Said the third intron (SEQ ID NO:10) is flanked by the 5' (5'-GU-3', bp 1-2 in SEQ ID NO:10) and 3' (5'-CAG-3', 536-538 bp in SEQ ID NO: 10) splice sites. In a preferred embodiment of the invention, the third intron of the *Oryza sativa* gene (accession No. AP003300) (SEQ ID NO:10) comprises at least 31 bases pairs of the sequence 5' to the 5'-splice site and 31 bases pairs of the sequences 3' to the 3'-splice site of the intron (SEQ ID NO: 94). In a particularly preferred embodiment the intron BPSI.10 comprises at least 40 bases pairs, more preferably at least 50 bases pairs of the sequences 5' and 3' adjacent to the 5' and 3' splice sites of the intron, respectively. In a more preferred embodiment, the 5' and 3' splice sites of the third intron (BPSI.10, SEQ ID NO:10) are modified in order to match the plant consensus sequences for 5' splice sites 5'-AG::GTAAGT-3' (SEQ ID NO: 80) and 3' splice sites 5'-CAG::GT-3' (SEQ ID NO: 81) using a PCR mutagenesis approach (SEQ ID NO:95).

8) The sequence of the first intron (BPSI.11, SEQ ID NO:11) isolated from the *Oryza sativa* gene (accession No. L37528) encoding for a MADS3 box protein. Said the first intron (SEQ ID NO:11) is flanked by the 5' (5'-GU-3', bp 1-2 in SEQ ID NO:11) and 3' (5'-CAG-3', bp 329-331 in SEQ ID NO: 11) splice sites. In a preferred embodiment of the invention, the first intron of the *Oryza sativa* gene (accession No. L37528) (SEQ ID NO:11) comprises at least 35 bases pairs of the sequence 5' to the 5'-splice site and 34 bases pairs of the sequences 3' to the 3'-splice site of the intron (SEQ ID NO: 96). In a particularly preferred embodiment the intron BPSI.11 comprises at least 40 bases pairs, more preferably at least 50 bases pairs of the sequences 5' and 3' adjacent to the 5' and 3' splice sites of the intron, respectively. In a more preferred embodiment, the 5' and 3' splice sites of the first intron (BPSI.11, SEQ ID NO:11) are modified in order to match the plant consensus sequences for 5' splice sites 5'-AG::GTAAGT-3' (SEQ ID NO: 80) and 3' splice sites 5'-CAG::GT-3' (SEQ ID NO: 81) using a PCR mutagenesis approach (SEQ ID NO:97).

9) The sequence of the first intron (BPSI.12, SEQ ID NO:12) isolated from the *Oryza sativa* gene (accession No. CB625805) encoding for a putative Adenosylmethionine decarboxylase. Said the first intron (SEQ ID NO:12) is flanked by the 5' (5'-GU-3', bp 1-2 in SEQ ID NO:12) and 3' (5'-CAG-3', bp 959-961 in SEQ ID NO: 12) splice sites. In a preferred embodiment of the invention, the first intron of the *Oryza sativa* gene (accession No. CB625805) (SEQ ID NO:12) comprises at least 26 bases pairs of the sequence 5' to the 5'-splice site and 26 bases pairs of the sequences 3' to the 3'-splice site of the intron (SEQ ID NO: 98). In a particularly preferred embodiment the intron BPSI.12 comprises at least 40 bases pairs, more preferably at least 50 bases pairs of the sequences 5' and 3' adjacent to the 5' and 3' splice sites of the intron, respectively.

10) The sequence of the first intron (BPSI.13, SEQ ID NO:13) isolated from the *Oryza sativa* gene (accession No. CF297669) encoding for an Aspartic proteinase. Said the first intron (SEQ ID NO:13) is flanked by the 5' (5'-GU-3', bp 1-2 in SEQ ID NO:13) and 3' (5'-CAG-3', bp 593-595 in SEQ ID NO: 13) splice sites. In a preferred embodiment of the invention, the first intron of the *Oryza sativa* gene (accession No. CF297669) (SEQ ID NO:13) comprises at least 26 bases pairs of the sequence 5' to the 5'-splice site and 24 bases pairs of the sequences 3' to the 3'-splice site of the intron (SEQ ID NO: 99). In a particularly preferred embodiment the intron BPSI.13 comprises at least 40 bases pairs, more preferably at least 50 bases pairs of the sequences 5' and 3' adjacent to the 5' and 3' splice sites of the intron, respectively.

11) The sequence of the first intron (BPSI.14, SEQ ID NO:14) isolated from the *Oryza sativa* gene (accession No. CB674940) encoding for a Lec14b protein. Said the first intron (SEQ ID NO:14) is flanked by the 5' (5'-GU-3', bp 1-2 in SEQ ID NO:14) and 3' (5'-CAG-3', bp 143-145 in SEQ ID NO: 14) splice sites. In a preferred embodiment of the invention, the first intron of the *Oryza sativa* gene (accession No. CB674940) (SEQ ID NO:14) comprises at least 26 bases pairs of the sequence 5' to the 5'-splice site and 25 bases pairs of the sequences 3' to the 3'-splice site of the intron (SEQ ID NO: 100). In a particularly preferred embodiment the intron BPSI.14 comprises at least 40 bases pairs, more preferably at least 50 bases pairs of the sequences 5' and 3' adjacent to the 5' and 3' splice sites of the intron, respectively.

12) The sequence of the first intron (BPSI.15, SEQ ID NO:15) isolated from the 5 UTR of the *Oryza sativa* gene (accession No. BAD37295.1) encoding for a putative SalT protein precursor. Said the first intron (SEQ ID NO:15) is flanked by the 5' (5'-GU-3', bp 1-2 in SEQ ID NO:15) and 3' (5'-CAG-3', bp 312-314 in SEQ ID NO: 15) splice sites. In a preferred embodiment of the invention, the first intron of the *Oryza sativa* gene (accession No. BAD37295.1) (SEQ ID NO:15) comprises at least 26 bases pairs of the sequence 5' to the 5'-splice site and 25 bases pairs of the sequences 3' to the 3'-splice site of the intron (SEQ ID NO: 101). In a particularly preferred embodiment the intron BPSI.15 comprises at least 40 bases pairs, more preferably at least 50 bases pairs of the sequences 5' and 3' adjacent to the 5' and 3' splice sites of the intron, respectively.

13) The sequence of the first intron (BPSI.16, SEQ ID NO:16) isolated from the *Oryza sativa* gene (accession No. BX928664) encoding for a putative reticulon. Said the first intron (SEQ ID NO:16) is flanked by the 5' (5'-GU-3', bp 1-2 in SEQ ID NO:16) and 3' (5'-CAG-3', bp 650-652 in SEQ ID NO: 16) splice sites. In a preferred embodiment of the invention, the first intron of the *Oryza sativa* gene (accession No. BX928664) (SEQ ID NO:16) comprises at least 26 bases pairs of the sequence 5' to the 5'-splice site and 23 bases pairs of the sequences 3' to the 3'-splice site of the intron (SEQ ID NO: 102). In a particularly preferred embodiment the intron BPSI.16 comprises at least 40 bases pairs, more preferably at least 50 bases pairs of the sequences 5' and 3' adjacent to the 5' and 3' splice sites of the intron, respectively.

14) The sequence of the first intron (BPSI.17, SEQ ID NO:17) isolated from the *Oryza sativa* gene (accession No. AA752970) encoding for a glycolate oxidase. Said the first intron (SEQ ID NO:17) is flanked by the 5' (5'-GU-3', bp 1-2 in SEQ ID NO:17) and 3' (5'-CAG-3', bp 266-268 in SEQ ID NO:17) splice sites. In a preferred embodiment of the invention, the first intron of the *Oryza sativa* gene (accession No. AA752970) (SEQ ID NO:17) comprises at least 26 bases pairs of the sequence 5' to the 5'-splice site and 35 bases pairs of the sequences 3' to the 3'-splice site of the intron (SEQ ID NO: 103). In a particularly preferred embodiment the intron BPSI.17 comprises at least 40 bases pairs, more preferably at least 50 bases pairs of the sequences 5' and 3' adjacent to the 5' and 3' splice sites of the intron, respectively.

15) The sequence of the first intron (BPSI.18, SEQ ID NO:18) isolated from the *Oryza sativa* clone GI 40253643 (accession No. AK064428) is similar to AT4g33690. Said the first intron (SEQ ID NO:18) is flanked by the 5' (5'-GU-3', bp 1-2 in SEQ ID NO:18) and 3' (5'-CAG-3', bp 544-546 in SEQ ID NO:18) splice sites. In a preferred embodiment of the invention, the first intron of the *Oryza sativa* gene (accession No. AK064428) (SEQ ID NO:18) comprises at least 26 bases pairs of the sequence 5' to the 5'-splice site and 21 bases pairs of the sequences 3' to the 3'-splice site of the intron (SEQ ID NO: 104). In a particularly preferred embodiment the intron BPSI.18 comprises at least 40 bases pairs, more preferably at least 50 bases pairs of the sequences 5' and 3' adjacent to the 5' and 3' splice sites of the intron, respectively.

16) The sequence of the first intron (BPSI.19, SEQ ID NO:19) isolated from the *Oryza sativa* clone GI 51091887 (accession No. AK062197)). Said the first intron (SEQ ID NO:19) is flanked by the 5' (5'-GU-3', bp 1-2 in SEQ ID NO:19) and 3' (5'-CAG-3', bp 810-812 in SEQ ID NO:19) splice sites. In a preferred embodiment of the invention, the first intron of the

*Oryza sativa* gene (accession No. AK062197) (SEQ ID NO:19) comprises at least 26 bases pairs of the sequence 5' to the 5'-splice site and 26 bases pairs of the sequences 3' to the 3'-splice site of the intron (SEQ ID NO: 105). In a particularly preferred embodiment the intron BPSI.19 comprises at least 40 bases pairs, more preferably at least 50 bases pairs of the sequences 5' and 3' adjacent to the 5' and 3' splice sites of the intron, respectively.

17) The sequence of the first intron (BPSI.20, SEQ ID NO:20) isolated from the *Oryza sativa* gene (accession No. CF279761) encoding for a hypothetical protein clone (GI 33657147). Said the first intron (SEQ ID NO:20) is flanked by the 5' (5'-GU-3', bp 1-2 in SEQ ID NO:20) and 3' (5'-CAG-3', bp 369-371 in SEQ ID NO:20) splice sites. In a preferred embodiment of the invention, the first intron of the *Oryza sativa* gene (accession No. CF279761) (SEQ ID NO:20) comprises at least 26 bases pairs of the sequence 5' to the 5'-splice site and 27 bases pairs of the sequences 3' to the 3'-splice site of the intron (SEQ ID NO: 106). In a particularly preferred embodiment the intron BPSI.20 comprises at least 40 bases pairs, more preferably at least 50 bases pairs of the sequences 5' and 3' adjacent to the 5' and 3' splice sites of the intron, respectively.

18) The sequence of the first intron (BPSI.21, SEQ ID NO:21) isolated from the *Oryza sativa* gene (accession No. CF326058) encoding for a putative membrane transporter. Said the first intron (SEQ ID NO:21) is flanked by the 5' (5'-GU-3', bp 1-2 in SEQ ID NO:21) and 3' (5'-CAG-3', bp 720-722 in SEQ ID NO:21) splice sites. In a preferred embodiment of the invention, the first intron of the *Oryza sativa* gene (accession No. CF326058) (SEQ ID NO:21) comprises at least 26 bases pairs of the sequence 5' to the 5'-splice site and 25 bases pairs of the sequences 3' to the 3'-splice site of the intron (SEQ ID NO: 107). In a particularly preferred embodiment the intron BPSI.21 comprises at least 40 bases pairs, more preferably at least 50 bases pairs of the sequences 5' and 3' adjacent to the 5' and 3' splice sites of the intron, respectively.

19) The sequence of the first intron (BPSI.22, SEQ ID NO:22) isolated from the *Oryza sativa* gene (accession No. C26044) encoding for a putative ACT domain repeat protein. Said the first intron (SEQ ID NO:22) is flanked by the 5' (5'-GU-3', bp 1-2 in SEQ ID NO:22) and 3' (5'-CAG-3', bp 386-388 in SEQ ID NO:22) splice sites. In a preferred embodiment of the invention, the first intron of the *Oryza sativa* gene (accession No. C26044) (SEQ ID NO:22) comprises at least 26 bases pairs of the sequence 5' to the 5'-splice site and 28 bases pairs of the sequences 3' to the 3'-splice site of the intron (SEQ ID NO: 108). In a particularly preferred embodiment the intron BPSI.22 comprises at least 40 bases pairs, more preferably at least 50 bases pairs of the sequences 5' and 3' adjacent to the 5' and 3' splice sites of the intron, respectively.

TABLE 1

Genes from which the introns of the invention are preferably isolated, putative function of said genes, cDNA and the protein encoded by said genes.

| Intron | Rice GI number | Accesion No. | SEQ ID NO. | Sequence homology |
|---|---|---|---|---|
| BPSI.1 | | AP002540 | 1 | metallothioneine-like gene |
| BPSI.2 | | AC084380 | 2 | Sucrose UDP Glucosyltransferase-2 gene, first Intron |
| BPSI.3 | | AC084380 | 3 | Sucrose UDP Glucosyltransferase-2 gene, second Intron |
| BPSI.4 | | AC084380 | 4 | Sucrose UDP Glucosyltransferase-2 gene, third Intron |
| BPSI.5 | 9624451 | AF280050 | 5 | Sucrose transporter |
| BPSI.6 | 7523493 | BAA94221 | 6 | Similar to *A. thaliana* chromosome II sequence from clones T22O13, F12K2; putative lipase (AC006233) |
| BPSI.7 | 20161203 | BAB90130 | 7 | putative cinnamyl-alcohol dehydrogenase |
| BPSI.10 | 20160990 | AP003300 | 10 | Putative protein kinase |
| BPSI.11 | 886404 | L37528 | 11 | MADS3 box protein |
| BPSI.12 | 29620794 | CB625805 | 12 | putative Adenosylmethionine decarboxylase |
| BPSI.13 | 33666702 | CF297669 | 13 | Aspartic proteinase |
| BPSI.14 | 29678665 | CB674940 | 14 | Lec14b protein |
| BPSI.15 | 51535011 | BAD37295 | 15 | putative SaIT protein precursor |
| BPSI.16 | 41883853 | BX928664 | 16 | Putative Reticulon |
| BPSI.17 | 2799981 | AA752970 | 17 | Glycolate oxidase |
| BPSI.18 | 40253643 | AK06442 | 18 | Putative non-coding (Similar to AT4g33690) |
| BPSI.19 | 51091887 | AK062197 | 19 | Putative non-coding |
| BPSI.20 | 33657147 | CF279761 | 20 | Hypothetical protein |
| BPSI.21 | 33800379 | CF326058 | 21 | Putative membrane transporter |
| BPSI.22 | 2309889 | C26044 | 22 | Putative ACT domain repeat protein |

It is disclosed by the examples of this invention, that the inventive introns with the SEQ ID NOs: 1, 2, 3, 5, 6, 7, 10 and 11 have an impact on the expression rate of the GUS gene in transient expression assays and stable transformed plants, respectively. It could be shown that the inclusion of said Introns into the 5' UTR of the GUS gene has led to a strong enhancement in the expression rate of this gene in transiently and stable transformed cell, respectively, compared to a control construct that lacks the first intron (see examples 1.6.1 (table 7), 1.6.2 (table 8), 2.4 (table 15).

The expression enhancing properties of the introns with the SEQ ID NOs: 12, 13, 14, 15, 16, 17, 18, 19, 20, 21 or 22 can be demonstrated by performing the above described transient or stable expression assays.

Functional equivalents of the inventive introns can be identified via homology searches in nucleic add databases or via DNA hybridization (screening of genomic DNA libraries) using a fragment of at least 50 consecutive base pairs of the nucleic acid molecule described by any of the SEQ ID NOs: 1, 2, 3, 5, 6, 7, 10, 11, 12, 13, 14, 15, 16, 17, 18, 19, 20, 21 or 22 and stringent hybridization conditions. In a preferred embodiment of the present invention the stringent hybridizing conditions can be chosen as follows: The hybridization puffer contains Formamide, NaCl and PEG 6000 (Polyethyleneglykol MW 6000). Formamide has a destabilizing effect on double strand nucleic acid molecules, thereby, when used in hybridization buffer, allowing the reduction of the hybridization temperature to 42° C. without reducing the hybridization stringency. NaCl has a positive impact on the renaturation-rate of a DNA duplex and the hybridization efficiency of a DNA probe with its complementary DNA target. PEG increases the viscosity of the hybridization buffer, which has in principle a negative impact on the hybridization efficiency. The composition of the hybridization buffer is as follows:

250 mM Sodium phosphate-buffer pH 7.2
1 mM EDTA (ethylenediaminetetraacetic acid)
7% SDS (g/v) (sodium dodecyl sulfate)
250 mM NaCl (Sodiumchloride)
10 µg/ml single stranded DNA
5% Polyethylenglykol (PEG) 6000
40% Formamide The hybridization is preferably performed over night at 42° C. In the morning, the hybridized filter will be washed 3× for 10 minutes with 2×SSC+0.1% SDS. Hybridization should advantageously be carried out with fragments of at least 50, 60, 70 or 80 bp, preferably at least 90 bp. In an especially preferred embodiment, the hybridization should be carried out with the entire nucleic acid sequence with conditions described above.

Combination of the introns of the invention with different plant promoters has clearly demonstrated their expression enhancing and/or modulating properties. In a preferred embodiment of the invention the recombinant DNA expression construct comprises (functionally linked to an intron of the invention) a promoter sequence functioning in plants or plant cells selected from the group consisting of a) the rice chloroplast protein 12 (Os.CP12) promoter as described by nucleotide 1 to 854 of SEQ ID NO: 113 (the 'fragment'), or a sequence having at least 60% (preferably at least 70% or 80%, more preferably at least 90% or 95%, most preferably at least 98% or 99%) identity to said fragment, or a sequence hybridizing under stringent conditions (preferably under conditions equivalent to the high stringency conditions defined in the paragraph above) to said fragment, or a sequence comprising at least 50 (preferably at least 100, more preferably at least 200 or 300, most preferably at least 400 or 500) consecutive nucleotides of said fragment, and b) the maize hydroxyproline-rich glycoprotein (Zm.HRGP) promoter as described by nucleotide 1 to 1184 of SEQ ID NO: 114, or a sequence having at least 60% (preferably at least 70% or 80%, more preferably at least 90% or 95%, most preferably at least 98% or 99%) identity to said fragment, or a sequence hybridizing under stringent conditions (preferably under conditions equivalent to the high stringency conditions defined in the paragraph above) to said fragment, or a sequence comprising at least 50 (preferably at least 100, more preferably at least 200 or 300, most preferably at least 400 or 500) consecutive nucleotides of said fragment, and c) the rice p-caffeoyl-CoA 3-O-methyltransferase (Os.C-CoAMT1) promoter as described by nucleotide 1 to 1034 of SEQ ID NO: 115, or a sequence having at least 60% (preferably at least 70% or 80%, more preferably at least 90% or 95%, most preferably at least 98% or 99%) identity to said fragment, or a sequence hybridizing under stringent conditions (preferably under conditions equivalent to the high stringency conditions defined in the paragraph above) to said fragment, or a sequence comprising at least 50 (preferably at least 100, more preferably at least 200 or 300, most preferably at least 400 or 500) consecutive nucleotides of said fragment, and d) the maize Globulin-1 (Zm.Glb1) promoter (W64A) as described by nucleotide 1 to 1440 of SEQ ID NO: 116, or a sequence having at least 60% (preferably at least 70% or 80%, more preferably at least 90% or 95%, most preferably at least 98% or 99%) identity to said fragment, or a sequence hybridizing under stringent conditions (preferably under conditions equivalent to the high stringency conditions defined in the paragraph above) to said fragment, or a sequence comprising at least 50 (preferably at least 100, more preferably at least 200 or 300, most preferably at least 400 or 500) consecutive nucleotides of said fragment, and e) the putative Rice H+-transporting ATP synthase (Os.V-ATPase) promoter as described by nucleotide 1 to 1589 of SEQ ID NO: 117, or a sequence having at least 60% (preferably at least 70% or 80%, more preferably at least 90% or 95%, most preferably at least 98% or 99%) identity to said fragment, or a sequence hybridizing under stringent conditions (preferably under conditions equivalent to the high stringency conditions defined in the paragraph above) to said fragment, or a sequence comprising at least 50 (preferably at least 100, more preferably at least 200 or 300, most preferably at least 400 or 500) consecutive nucleotides of said fragment, and f) the putative rice C-8,7 sterol isomerase (Os.C8,7 SI) promoter as described by nucleotide 1 to 796 of SEQ ID NO: 118, or a sequence having at least 60% (preferably at least 70% or 80%, more preferably at least 90% or 95%, most preferably at least 98% or 99%) identity to said fragment, or a sequence hybridizing under stringent conditions (preferably under conditions equivalent to the high stringency conditions defined in the paragraph above) to said fragment, or a sequence comprising at least 50 (preferably at least 100, more preferably at least 200 or 300, most preferably at least 400 or 500) consecutive nucleotides of said fragment, and g) the maize lactate dehydrogenase (Zm.LDH) promoter as described by nucleotide 1 to 1062 of SEQ ID NO: 119, or a sequence having at least 60% (preferably at least 70% or 80%, more preferably at least 90% or 95%, most preferably at least 98% or 99%) identity to said fragment, or a sequence hybridizing under stringent conditions (preferably under conditions equivalent to the high stringency conditions defined in the paragraph above) to said fragment, or a sequence comprising at least 50 (preferably at least 100, more preferably at least 200 or 300, most preferably at least 400 or 500) consecutive nucleotides of said fragment, and h) the rice Late Embryogenesis Abundant (Os.Lea) promoter as described by nucleotide 1 to 1386 of SEQ ID NO: 121, or a sequence having at least 60% (preferably at least 70% or 80%, more preferably at least 90% or 95%, most preferably at least 98% or 99%) identity to said fragment, or a sequence hybridizing under stringent conditions (preferably under conditions equivalent to the high stringency conditions defined in the paragraph above) to said fragment, or a sequence comprising at least 50 (preferably at least 100, more preferably at least 200 or 300, most preferably at least 400 or 500) consecutive nucleotides of said fragment.

Preferably said expression construct is comprising a combination of one of the above defined promoters with at least one intron selected from the group consisting of i) the BPSI.1 intron as described by nucleotide 888 to 1470 of SEQ ID NO: 113 or a sequence having at least 60% (preferably at least 70% or 80%, more preferably at least 90% or 95%, most preferably at least 98% or 99%) identity to said fragment, or a sequence hybridizing under stringent conditions (preferably under conditions equivalent to the high stringency conditions defined above) to said fragment, or a sequence comprising at least 50 (preferably at least 100, more preferably at least 200 or 300, most preferably at least 400 or 500) consecutive nucleotides of said fragment and ii) the BPSI.5 intron as described by nucleotide 1068 to 1318 of SEQ ID NO: 120, or a sequence having at least 60% (preferably at least 70% or 80%, more preferably at least 90% or 95%, most preferably at least 98% or 99%) identity to said fragment, or a sequence hybridizing under stringent conditions (preferably under conditions equivalent to the high stringency conditions defined above) to said fragment, or a sequence comprising at least 50 (preferably at least 100, more preferably at least 200 or 300, most preferably at least 400 or 500) consecutive nucleotides of said fragment.

More preferably expression construct is comprising a combination of promoter and intron selected from the group consisting of i) sequences as described by any of SEQ ID NO: 113, 114, 115, 116, 117, 118, 119, 120, or 121, and ii) sequences having at least 50 (preferably at least 100, more preferably at least 200 or 300, most preferably at least 400 or 500) consecutive nucleotides of a sequence described by any of SEQ ID NOs: 113, 114, 115, 116, 117, 118, 119, 120, or 121, and iii) sequences having an identity of at least 60% (preferably at least 70% or 80%, more preferably at least 90% or 95%, most preferably at least 98% or 99%) to a sequence described by any of SEQ ID NOs: 113, 114, 115, 116, 117, 118, 119, 120, or 121, and iv) sequences hybridizing under stringent conditions (preferably under conditions equivalent to the high stringency conditions defined above) with sequence described by any of SEQ ID NOs: 113, 114, 115, 116, 117, 118, 119, 120, or 121.

A preferred subject matter of the invention, is a vector, preferably a plant transformation vector, containing an inventive recombinant expression construct. The expression cassette can be introduced into the vector via a suitable restriction cleavage site. The plasmid formed is first introduced into E. coli. Correctly transformed E. coli are selected, grown, and the recombinant plasmid is obtained by the methods familiar to the skilled worker. Restriction analysis and sequencing may serve to verify the cloning step. Preferred vectors are those, which make possible stable integration of the expression cassette into the host genome. An expression construct according to the invention can advantageously be introduced into cells, preferably into plant cells, using vectors. In one embodiment, the methods of the invention involve transformation of organism or cells (e.g. plants or plant cells) with a transgenic expression vector comprising at least a transgenic expression cassette of the invention. The methods of the invention are not limited to the expression vectors disclosed herein. Any expression vector which is capable of introducing a nucleic acid sequence of interest into a plant cell is contemplated to be within the scope of this invention. Typically, expression vectors comprise the transgenic expression cassette of the invention in combination with elements which allow cloning of the vector into a bacterial or phage host. The vector preferably, though not necessarily, contains an origin of replication which is functional in a broad range of prokaryotic hosts. A selectable marker is generally, but not necessarily, included to allow selection of cells bearing the desired vector. Preferred are those vectors that allowing a stable integration of the expression construct into the host genome. In the case of injection or electroporation of DNA into plant cells, the plasmid used need not meet any particular requirements. Simple plasmids such as those of the pUC series can be used. If intact plants are to be regenerated from the transformed cells, it is necessary for an additional selectable marker gene to be present on the plasmid. A variety of possible plasmid vectors are available for the introduction of foreign genes into plants, and these plasmid vectors contain, as a rule, a replication origin for multiplication in E. coli and a marker gene for the selection of transformed bacteria. Examples are pBR322, pUC series, M13 mp series, pACYC184 and the like. The expression construct can be introduced into the vector via a suitable restriction cleavage site. The plasmid formed is first introduced into E. coli. Correctly transformed E. coli are selected and grown, and the recombinant plasmid is obtained by methods known to the skilled worker. Restriction analysis and sequencing can be used for verifying the cloning step.

Depending on the method by which DNA is introduced, further genes may be necessary on the vector plasmid.

*Agrobacterium tumefaciens* and *A. rhizogenes* are plant-pathogenic soil bacteria, which genetically transform plant cells. The Ti and Ri plasmids of *A. tumefaciens* and *A. rhizogenes*, respectively, carry genes responsible for genetic transformation of the plant (Kado (1991) Crit Rev Plant Sci 10:1). Vectors of the invention may be based on the *Agrobacterium* Ti- or Ri-plasmid and may thereby utilize a natural system of DNA transfer into the plant genome. As part of this highly developed parasitism *Agrobacterium* transfers a defined part of its genomic information (the T-DNA; flanked by about 25 bp repeats, named left and right border) into the chromosomal DNA of the plant cell (Zupan (2000) Plant J 23(1): 11-28). By combined action of the so-called vir genes (part of the original Ti-plasmids) said DNA-transfer is mediated. For utilization of this natural system, Ti-plasmids were developed which lack the original tumor inducing genes ("disarmed vectors"). In a further improvement, the so called "binary vector systems", the T-DNA was physically separated from the other functional elements of the Ti-plasmid (e.g., the vir genes), by being incorporated into a shuttle vector, which allowed easier handling (EP-A 120 516; U.S. Pat. No. 4,940,838). These binary vectors comprise (beside the disarmed T-DNA with its border sequences), prokaryotic sequences for replication both in *Agrobacterium* and *E. coli*. It is an advantage of *Agrobacterium*-mediated transformation that in general only the DNA flanked by the borders is transferred into the genome and that preferentially only one copy is inserted. Descriptions of *Agrobacterium* vector systems and methods for *Agrobacterium*-mediated gene transfer are known in the art (Miki 1993, "Procedures for Introducing Foreign DNA into Plants" in METHODS IN PLANT MOLECULAR BIOLOGY AND BIOTECHNOLOGY; pp. 67-88; Gruber 1993, "Vectors for Plant Transformation," in METHODS IN PLANT MOLECULAR BIOLOGY AND BIOTECHNOLOGY; pp. 89-119; Moloney (1989) Plant Cell Reports 8: 238-242). The use of T-DNA for the transformation of plant cells has been studied and described intensively (EP 120516; Hoekema 1985, In: The Binary Plant Vector System, Offsetdrukkerij Kanters B. V., Alblasserdam, Chapter V; Fraley (1985) CRC Crit. Rev. Plant. Sci. 4:1-45; and An (1985) EMBO J. 4:277-

287). Various binary vectors are known, some of which are commercially available such as, for example, pBIN19 (Clontech Laboratories, Inc. U.S.A.). Hence, for *Agrobacterium*-mediated transformation the transgenic expression construct of the invention is integrated into specific plasmids, either into a shuttle or intermediate vector, or into a binary vector. If a Ti or Ri plasmid is to be used for the transformation, at least the right border, but in most cases the right and left border, of the Ti or Ri plasmid T-DNA is linked to the transgenic expression construct to be introduced in the form of a flanking region. Binary vectors are preferably used. Binary vectors are capable of replication both in *E. coli* and in *Agrobacterium*. They may comprise a selection marker gene and a linker or polylinker (for insertion of e.g. the expression construct to be transferred) flanked by the right and left T-DNA border sequence. They can be transferred directly into *Agrobacterium* (Holsters (1978) Mol Gen Genet 163:181-187). The selection marker gene permits the selection of transformed *agrobacteria* and is, for example, the nptII gene, which confers resistance to kanamycin. The *Agrobacterium* which acts as host organism in this case should already contain a plasmid with the vir region. The latter is required for transferring the T-DNA to the plant cell. An *Agrobacterium* transformed in this way can be used for transforming plant cells. The use of T-DNA for transforming plant cells has been studied and described intensively (EP 120 516; Hoekema (1985) Nature 303:179-181; An (1985) EMBO J. 4:277-287; see also below). Common binary vectors are based on "broad host range"-plasmids like pRK252 (Bevan (1984) Nucl Acid Res 12:8711-8720) or pTJS75 (Watson (1985) EMBO J 4(2):277-284) derived from the P-type plasmid RK2. Most of these vectors are derivatives of pBIN19 (Bevan 1984, Nucl Acid Res 12:8711-8720). Various binary vectors are known, some of which are commercially available such as, for example, pBI101.2 or pBIN19 (Clontech Laboratories, Inc. USA). Additional vectors were improved with regard to size and handling (e.g. pPZP; Hajdukiewicz (1994) Plant Mol Biol 25:989-994). Improved vector systems are described also in WO 02/00900. In a preferred embodiment, *Agrobacterium* strains for use in the practice of the invention include octopine strains, e.g., LBA4404 or agropine strains, e.g., EHA101 or EHA105. Suitable strains of *A. tumefaciens* for DNA transfer are for example EHA101pEHA101 (Hood (1986) J Bacteriol 168:1291-1301), EHA105-[pEHA105] (Li (1992) Plant Mol Biol 20:1037-1048), LBA4404-[pAL4404] (Hoekema (1983) Nature 303:179-181), C58C1-[pMP90] (Koncz (1986) Mol Gen Genet 204:383-396), and C58C1[pGV2260] (Deblaere (1985) Nucl Acids Res 13:4777-4788. Other suitable strains are *Agrobacterium tumefaciens* C58, a nopaline strain. Other suitable strains are *A. tumefaciens* C58C1 (Van Larebeke (1974) Nature 252:169-170, A136 (Watson (1975) J. Bacteriol 123:255-264) or LBA4011 (Klapwijk (1980) J. Bacteriol. 141:128-136 In a preferred embodiment, the *Agrobacterium* strain used to transform the plant tissue pre-cultured with the plant phenolic compound contains a L,L-succinamopine type Ti-plasmid, preferably disarmed, such as pEHA101. In another preferred embodiment, the *Agrobacterium* strain used to transform the plant tissue pre-cultured with the plant phenolic compound contains an octopine-type Ti-plasmid, preferably disarmed, such as pAL4404. Generally, when using octopine-type Ti-plasmids or helper plasmids, it is preferred that the virF gene be deleted or inactivated (Jarchow (1991) Proc. Natl. Acad. Sci. USA 88:10426-10430). In a preferred embodiment, the *Agrobacterium* strain used to transform the plant tissue pre-cultured with the plant phenolic compound such as acetosyringone. The method of the invention can also be used in combination with particular *Agrobacterium* strains, to further increase the transformation efficiency, such as *Agrobacterium* strains wherein the vir gene expression and/or induction thereof is altered due to the presence of mutant or chimeric virA or virG genes (e.g. Hansen (1994) Proc. Natl. Acad. Sci. USA 91:7603-7607; Chen 1991 J. Bacteriol. 173:1139-1144; Scheeren-Groot (1994) J. Bacteriol 176:6418-6426). A binary vector or any other vector can be modified by common DNA recombination techniques, multiplied in *E. coli*, and introduced into *Agrobacterium* by e.g., electroporation or other transformation techniques (Mozo (1991) Plant Mol. Biol. 16:917-918). *Agrobacterium* is grown and used as described in the art. The vector comprising *Agrobacterium* strain may, for example, be grown for 3 days on YP medium (5 g/L yeast extract, 10 g/L peptone, 5 g/L Nail, 15 g/L agar, pH 6.8) supplemented with the appropriate antibiotic (e.g., 50 mg/L spectinomycin). Bacteria are collected with a loop from the solid medium and resuspended.

An additional subject matter of the invention relates to transgenic non-human organisms transformed with at least one vector containing a transgenic expression construct of the invention. In a preferred embodiment the invention relates to bacteria, fungi, yeasts, more preferably to plants or plant cell. In a preferred embodiment of the invention, the transgenic organism is a monocotyledonous plant. In a yet more preferred embodiment, the monocotyledonous plant is selected from the group consisting of the genera *Hordeum, Avena, Secale, Triticum, Sorghum, Zea, Saccharum* and *Oryza*, very especially preferred are plants selected from the group consisting of *Hordeum vulgare, Triticum aestivum, Triticum aestivum* subsp.spelta, *Triticale, Avena sativa, Secale cereale, Sorghum bicolor, Saccharum officinarum, Zea mays* and *Oryza sativa* transformed with the inventive vectors or containing the inventive recombinant expression constructs. Preferred bacteria are bacteria of the genus *Escherichia, Erwinia, Agrobacterium, Flavobacterium, Alcaligenes* or *cyanobacteria*, for example of the genus *Synechocystis*. Especially preferred are microorganisms which are capable of infecting plants and thus of transferring the constructs according to the invention. Preferred microorganisms are those from the genus *Agrobacterium* and, in particular, the species *Agrobacterium tumefaciens*. Preferred yeasts are *Candida, Saccharomyces, Hansenula* or *Pichia*. Preferred fungi are *Aspergillus, Trichoderma, Ashbya, Neurospora, Fusarium, Beauveria* or other fungi. Plant organisms are furthermore, for the purposes of the invention, other organisms which are capable of photosynthetic activity such as, for example, algae or cyanobacteria, and also mosses. Preferred algae are green algae such as, for example, algae of the genus *Haematococcus, Phaedactylum tricornatum, Volvox* or *Dunaliella*. Furthermore the invention relates cell cultures, tissues, organs (e.g., leaves, roots and the like in the case of plant organisms), or propagation material derived from transgenic non-human organisms like bacteria, fungi, yeasts, plants or plant cells transformed with at least one vector containing a transgenic expression construct of the invention.

An additional subject matter of the invention relates to a method for providing an expression cassette for enhanced expression of a nucleic acid in a plant or a plant cell, comprising the step of functionally linking the inventive introns to a plant expression cassette not comprising said intron. In a yet another preferred embodiment, the invention relates to a method for enhancing the expression of a nucleic acid sequence in a plant or a plant cell, comprising functionally linking the inventive introns to said nucleic acid sequence. Preferably, the method for providing an expression cassette for enhanced expression of a nucleic acid in a plant or a plant cell and the method for enhancing the expression of a nucleic add sequence in a plant or a plant cell further comprises the steps of i) providing an recombinant expression cassette, wherein the nucleic acid sequence is functionally linked with a promoter sequence functional in plants and with an intron sequence selected from the group consisting of SEQ ID NOs: 1, 2, 3, 5, 6, 7, 10, 11, 12, 13, 14, 15, 16, 17, 18, 19, 20, 21 and 22,
ii) introducing said recombinant expression into a plant cell or a plant,
iii) identifying or selecting the transgenic plant cell comprising said transgenic expression construct. In another preferred embodiment, the above-described method further comprises the steps of
iv) regenerating transgenic plant tissue from the transgenic plant cell. In an alternative preferred embodiment, the method further comprises
v) regenerating a transgenic plant from the transgenic plant cell.

The generation of a transformed organism or a transformed cell requires introducing the DNA in question into the host cell in question. A multiplicity of methods is available for this procedure, which is termed transformation (see also Keown (1990) Methods in Enzymology 185:527-537). For example, the DNA can be introduced directly by microinjection or by bombardment via DNA-coated microparticles. Also, the cell can be permeabilized chemically, for example using polyethylene glycol, so that the DNA can enter the cell by diffusion. The DNA can also be introduced by protoplast fusion with other DNA-containing units such as minicells, cells, lysosomes or liposomes. Another suitable method of introducing DNA is electroporation, where the cells are permeabilized reversibly by an electrical pulse. Methods for introduction of a transgenic expression construct or vector into plant tissue may include but are not limited to, e.g., electroinjection (Nan (1995) In "Biotechnology in Agriculture and Forestry," Ed. Y. P. S. Bajaj, Springer-Verlag Berlin Heidelberg 34:145-155; Griesbach (1992) Hort Science 27:620); fusion with liposomes, lysosomes, cells, minicells or other fusible lipid-surfaced bodies (Fraley (1982) Proc. Natl. Acad. Sci. USA 79:1859-1863); polyethylene glycol (Krens (1982) Nature 296:72-74); chemicals that increase free DNA uptake; transformation using virus, and the like. Furthermore, the biolistic method with the gene gun, electroporation, incubation of dry embryos in DNA-containing solution, and microinjection may be employed. Protoplast based methods can be employed (e.g., for rice), where DNA is delivered to the protoplasts through liposomes, PEG, or electroporation (Shimamoto (1989) Nature 338:274-276; Datta (1990) Bio/Technology 8:736-740). Transformation by electroporation involves the application of short, high-voltage electric fields to create "pores" in the cell membrane through which DNA is taken-up. These methods are for example—used to produce stably transformed monocotyledonous plants (Paszkowski (1984) EMBO J 3:2717-2722; Shillito (1985) Bio/Technology, 3:1099-1103; Fromm (1986) Nature 319:791-793) especially from rice (Shimamoto (1989) Nature 338:274-276; Datta (1990) Bio/Technology 8:736-740; Hayakawa (1992) Proc Natl Acad Sci USA 89:9865-9869). Particle bombardment or "biolistics" is a widely used method for the transformation of plants, especially monocotyledonous plants. In the "biolistics" (microprojectile-mediated DNA delivery) method microprojectile particles are coated with DNA and accelerated by a mechanical device to a speed high enough to penetrate the plant cell wall and nucleus (WO 91/02071). The foreign DNA gets incorporated into the host DNA and results in a transformed cell. There are many variations on the "biolistics" method (Sanford (1990) Physiologia Plantarium 79:206-209; Fromm (1990) Bio/Technology 8:833-839; Christou (1988) Plant Physiol 87:671-674; Sautter (1991) Bio/Technology 9:1080-1085). The method has been used to produce stably transformed monocotyledonous plants including rice, maize, wheat, barley, and oats (Christou (1991) Bio/Technology 9:957-962; Gordon-Kamm (1990) Plant Cell 2:603-618; Vasil (1992) Bio/Technology 10:667-674, (1993) Bio/Technology 11:1153-1158; Wan (1994) Plant Physiol. 104:3748; Somers (1992) Bio/Technology 10:1589-1594). In addition to these 'direct' transformation techniques, transformation can also be effected by bacterial infection by means of *Agrobacterium tumefaciens* or *Agrobacterium rhizogenes*. These strains contain a plasmid (Ti or Ri plasmid) which is transferred to the plant following *Agrobacterium* infection. Part of this plasmid, termed T-DNA (transferred DNA), is integrated into the genome of the plant cell (see above for description of vectors). To transfer the DNA to the plant cell, plant explants are cocultured with a transgenic *Agrobacterium tumefaciens* or *Agrobacterium rhizogenes*. Starting from infected plant material (for example leaf, root or stem sections, but also protoplasts or suspensions of plant cells), intact plants can be generated using a suitable medium which may contain, for example, antibiotics or biocides for selecting transformed cells. The plants obtained can then be screened for the presence of the DNA introduced, in this case the expression construct according to the invention. As soon as the DNA has integrated into the host genome, the genotype in question is, as a rule, stable and the insertion in question is also found in the subsequent generations. The plants obtained can be cultured and hybridized in the customary fashion. Two or more generations should be grown in order to ensure that the genomic integration is stable and hereditary. The abovementioned methods are described (for example, in Jenes (1983) Techniques for Gene Transfer, in: Transgenic Plants, Vol. 1, Engineering and Utilization, edited by Kung & Wu, Academic Press 128-143; and in Potrykus (1991) Ann Rev Plant Physiol Plant Mol Biol 42:205-225). One of skill in the art knows that the efficiency of transformation by *Agrobacterium* may be enhanced by using a number of methods known in the art. For example, the inclusion of a natural wound response molecule such as acetosyringone (AS) to the *Agrobacterium* culture has been shown to enhance transformation efficiency with *Agrobacterium tumefaciens* (Shahla (1987) Plant Mol. Biol. 8:291-298). Alternatively, transformation efficiency may be enhanced by wounding the target tissue to be transformed. Wounding of plant tissue may be achieved, for example, by punching, maceration, bombardment with microprojectiles, etc. (see, e.g., Bidney (1992) Plant Molec. Biol. 18:301-313). A number of other methods have been reported for the transformation of plants (especially monocotyledonous plants) including, for example, the "pollen tube method" (WO 93/18168; Luo (1988) Plant Mol. Biol. Rep. 6:165-174), macro-injection of DNA into floral tillers (Du (1989) Genet Manip Plants 5:8-12), injection of *Agrobacterium* into developing caryopses (WO 00/63398), and tissue incubation of seeds in DNA solutions (Töpfer (1989) Plant Cell 1:133-139). Direct injection of exogenous DNA into the fertilized plant ovule at the onset of embryogenesis was disclosed in WO 94/00583. WO 97/48814 disclosed a process for producing stably transformed fertile wheat and a system of transforming wheat via *Agrobacterium* based on freshly isolated or precultured immature embryos, embryogenic callus and suspension cells.

As a rule, the expression construct integrated contains a selection marker, which imparts a resistance to a biocide (for example a herbicide) or an antibiotic such as kanamycin, G 418, bleomycin, hygromycin or phosphinotricin and the like to the transformed plant. The selection marker permits the selection of transformed cells from untransformed cells (McCormick 1986) Plant Cell Reports 5:81-84). The plants obtained can be cultured and hybridized in the customary fashion. Two or more generations should be grown in order to ensure that the genomic integration is stable and hereditary. The abovementioned methods are described (for example, in Jenes 1983; and in Potrykus 1991). As soon as a transformed plant cell has been generated, an intact plant can be obtained using methods known to the skilled worker. Accordingly, the present invention provides transgenic plants. The transgenic plants of the invention are not limited to plants in which each and every cell expresses the nucleic acid sequence of interest under the control of the promoter sequences provided herein. Included within the scope of this invention is any plant which contains at least one cell which expresses the nucleic acid sequence of interest (e.g., chimeric plants). It is preferred, though not necessary, that the transgenic plant comprises the nucleic acid sequence of interest in more than one cell, and more preferably in one or more tissue. Once transgenic plant tissue, which contains an expression vector, has been obtained, transgenic plants may be regenerated from this transgenic plant tissue using methods known in the art. Species from the following examples of genera of plants may be regenerated from transformed protoplasts: *Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyamus, Lycopersicon, Nicotiana, Solanum, Petunia, Digitalis, Majorana, Ciohorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Pisum, Lolium, Zea, Triticum, Sorghum*, and *Datura*. For regeneration of transgenic plants from transgenic protoplasts, a suspension of transformed protoplasts or a Petri plate containing transformed explants is first provided. Callus tissue is formed and shoots may be induced from callus and subsequently rooted. Alternatively, somatic embryo formation can be induced in the callus tissue. These somatic embryos germinate as natural embryos to form plants. The culture media will generally contain various amino acids and plant hormones, such as auxin and cytokinins. It is also advantageous to add glutamic acid and proline to the medium, especially for such species as corn and alfalfa. Efficient regeneration will depend on the medium, on the genotype, and on the history of the culture. These three variables may be empirically controlled to result in reproducible regeneration. Plants may also be regenerated from cultured cells or tissues. Dicotyledonous plants which have been shown capable of regeneration from transformed individual cells to obtain transgenic whole plants include, for example, apple (*Malus pumila*), blackberry (*Rubus*), Blackberry/raspberry hybrid (*Rubus*), red raspberry (*Rubus*), carrot (*Daucus carota*), cauliflower (*Brassica oleracea*), celery (*Apium graveolens*), cucumber (*Cucumis sativus*), eggplant (*Solanum melongena*), lettuce (*Lactuca sativa*), potato (*Solanum tuberosum*), rape (*Brassica napus*), wild soybean (*Glycine canescens*), soybean (*Glycine max*), strawberry (*Fragaria ananassa*), tomato (*Lycopersicon esculentum*), walnut (*Juglans regia*), melon (*Cucumis melo*), grape (*Vitis vinifera*), and mango (*Mangifera indica*). Monocotyledonous plants which have been shown capable of regeneration from transformed individual cells to obtain transgenic whole plants include, for example, rice (*Oryza sativa*), rye (*Secale cereale*), and maize (*Zea mays*).

In addition, regeneration of whole plants from cells (not necessarily transformed) has also been observed in: apricot (*Prunus armeniaca*), asparagus (*Asparagus officinalis*), banana (hybrid *Musa*), bean (*Phaseolus vulgaris*), cherry (hybrid *Prunus*), grape (*Vitis vinifera*), mango (*Mangifera indica*), melon (*Cucumis melo*), ochra (*Abelmoschus esculentus*), onion (hybrid *Allium*), orange (*Citrus sinensis*), papaya (*Carrica papaya*), peach (*Prunus persica*), plum (*Prunus domestica*), pear (*Pyrus communis*), pineapple (*Ananas comosus*), watermelon (*Citrullus vulgaris*), and wheat (*Triticum aestivum*). The regenerated plants are transferred to standard soil conditions and cultivated in a conventional manner. After the expression vector is stably incorporated into regenerated transgenic plants, it can be transferred to other plants by vegetative propagation or by sexual crossing. For example, in vegetatively propagated crops, the mature transgenic plants are propagated by the taking of cuttings or by tissue culture techniques to produce multiple identical plants. In seed propagated crops, the mature transgenic plants are self crossed to produce a homozygous inbred plant which is capable of passing the transgene to its progeny by Mendelian inheritance. The inbred plant produces seed containing the nucleic acid sequence of interest. These seeds can be grown to produce plants that would produce the selected phenotype. The inbred plants can also be used to develop new hybrids by crossing the inbred plant with another inbred plant to produce a hybrid.

Confirmation of the transgenic nature of the cells, tissues, and plants may be performed by PCR analysis, antibiotic or herbicide resistance, enzymatic analysis and/or Southern blots to verify transformation. Progeny of the regenerated plants may be obtained and analyzed to verify whether the transgenes are heritable. Heritability of the transgene is further confirmation of the stable transformation of the transgene in the plant. The resulting plants can be bred in the customary fashion. Two or more generations should be grown in order to ensure that the genomic integration is stable and hereditary. Corresponding methods are described, (Jenes 1993; Potrykus 1991).

Also in accordance with the invention are cells, cell cultures, tissues, parts, organs, such as, for example, roots, leaves and the like in the case of transgenic plant organisms derived from the above-described transgenic organisms, and transgenic propagation material such as seeds or fruits.

Preferably, the method for enhancing the expression of a nucleic acid sequence in a plant or a plant cell further comprises, linking the introns with expression enhancing properties to the expression cassette by insertion via homologous recombination comprising the following steps:

a) providing in vivo or in vitro a DNA construct comprising said introns flanked by sequences allowing homologous recombination into a pre-existing expression cassette between the promoter and the nucleic acid of said expression cassette, b) transforming a recipient plant cell comprising said cassette, c) regenerating a transgenic plant where said intron has been inserted into the genomic DNA of said promoter nucleic acid construct via homologous recombination.

Two different ways for the integration of DNA molecules into genomes are possible: Either regions of sequence identity between the partners are used (homologous recombination (HR), "gene targeting") or no sequence-specific requirements have to be fulfilled (illegitimate recombination also referred to as non-homologous end joining (NHEJ)). Gene targeting (GT) is the generation of specific mutations in a genome by homologous recombination-mediated integration of foreign DNA sequences. In contrast to natural recombination processes, one of the recombination partners is artificial and introduced by transformation in gene targeting. The integration of transformed DNA follows pre-existing recombination pathways. Homologous recombination is a reaction between any pair of DNA sequences having a similar sequence of nucleotides, where the two sequences interact (recombine) to form a new recombinant DNA species. The frequency of homologous recombination increases as the length of the shared nucleotide DNA sequences increases, and is higher with linearized plasmid molecules than with circularized plasmid molecules. Homologous recombination can occur between two DNA sequences that are less than identical, but the recombination frequency declines as the divergence between the two sequences increases. Introduced DNA sequences can be targeted via homologous recombination by linking a DNA molecule of interest to sequences sharing homology with endogenous sequences of the host cell. Once the DNA enters the cell, the two homologous sequences can interact to insert the introduced DNA at the site where the homologous genomic DNA sequences were located. Therefore, the choice of homologous sequences contained on the introduced DNA will determine the site where the introduced DNA is integrated via homologous recombination. For example, if the DNA sequence of interest is linked to DNA sequences sharing homology to a single copy gene of a host plant cell, the DNA sequence of interest will be inserted via homologous recombination at only that single specific site. However, if the DNA sequence of interest is linked to DNA sequences sharing homology to a multicopy gene of the host eucaryotic cell, then the DNA sequence of interest can be inserted via homologous recombination at each of the specific sites where a copy of the gene is located. For example, if one wishes to insert a foreign gene into the genomic site where a selected gene is located, the introduced DNA should contain sequences homologous to the selected gene. A double recombination event can be achieved by flanking each end of the DNA sequence of interest (the sequence intended to be inserted into the genome) with DNA sequences homologous to the selected gene. A homologous recombination event involving each of the homologous flanking regions will result in the insertion of the foreign DNA. Thus only those DNA sequences located between the two regions sharing genomic homology become integrated into the genome.

In the case of gene targeting via homologous recombination, the inventive intron that has to be introduced in the chromosome, preferably in the 5' UTR of a gene (a pre-existing expression cassette), is (for example) located on a DNA construct and is 5' and 3' flanked by nucleic add sequences of sufficient homology to the target DNA (such an construct is called "gene targeting substrate') in which the intron should be integrated. Said flanking regions must be sufficient in length for making possible recombination. They are, as a rule, in the range of several hundred bases to several kilo bases in length (Thomas K R and Capecchi M R (1987) Cell 51:503; Strepp et al. (1998) Proc Natl Acad Sci USA 95(8):4368-4373). In a preferred embodiment of the invention, the gene targeting substrate comprises an selection marker that is co-integrated with the intron into the genomic region of interest, allowing the selection of recombination events. Preferably, the gene targeting substrate is integrated via a double cross over event between pairs of homologous DNA sequences of sufficient length and homology resulting in the insertion of the intron sequence (and if desired additional nucleic acid sequences e.g. selection marker). Using homologous recombination, a intron of the invention can be placed in the 5' non coding region of the target gene (e.g., an endogenous plant gene) to be transgenically expressed, by linking said intron to DNA sequences which are homologous to, for example, endogenous sequences upstream and/or downstream of the reading frame of the target gene. After a cell has been transformed with the DNA construct in question, the homologous sequences can interact and thus place the intron of the invention at the desired site so that the intron sequence of the invention becomes operably linked to the target gene and constitutes an expression construct of the invention. For homologous recombination or gene targeting, the host organism—for example a plant—is transformed with the recombination construct using the methods described herein, and clones, which have successfully undergone recombination, are selected, for example using a resistance to antibiotics or herbicides. If desirable to target the nucleic acid sequence of interest to a particular locus on the plant genome, site-directed integration of the nucleic acid sequence of interest into the plant cell genome may be achieved by, for example, homologous recombination using Agrobacterium-derived sequences. Generally, plant cells are incubated with a strain of Agrobacterium which contains a targeting vector in which sequences that are homologous to a DNA sequence inside the target locus are flanked by Agrobacterium transfer-DNA (T-DNA) sequences, as previously described (U.S. Pat. No. 5,501,967, the entire contents of which are herein incorporated by reference).

One of skill in the art knows that homologous recombination may be achieved using targeting vectors which contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known. Gene targeting is a relatively rare event in higher eucaryotes, especially in plants. Random integrations into the host genome predominate. One possibility of eliminating the randomly integrated sequences and thus increasing the number of cell clones with a correct homologous recombination is the use of a sequence-specific recombination system as described in U.S. Pat. No. 6,110,736, by which unspecifically integrated sequences can be deleted again, which simplifies the selection of events which have integrated successfully via homologous recombination.

An efficient variant of gene targeting has been reported for *Drosophila melanogaster* (Rong and Golic 2000 Science. 2000 Jun. 16; 288(5473):2013-8). In this method the construct for targeting is integrated into the host genome flanked by two recognition sites of a site-specific recombinase and includes a site for a rare cutting restriction endonuclease. By induced expression of the site-specific recombinase a DNA circle is excised from the genome. This circle is then linearized after the restriction enzyme (in this case I-SceI) has been expressed resulting in an "activated' DNA molecule with both ends homologous to the target sequence. In the female germ line of *Drosophila*, gene targeting occurred in about one out of 500 cells. Selection of gene targeting events from events of illegitimate recombination can be facilitated by certain combinations of positive and negative selection techniques (WO 99/20780).

Counter selection is a powerful approach in mammalian and plant systems to enrich for gene targeting events. In plants the bacterial codA gene as a cell autonomous negative selection marker can be used for selection in tissue culture (Schlaman and Hooykaas Plant J 11:1377-1385, 1997; Thykjaer et al., Plant Mol. Biol. 1997 November; 35(4):523-30.). Negative selection in plants allowed a more than a thousand-fold suppression of random integration (Risseeuw et al., Plant J. 1997 April; 11(4):717-28; Gallego et al., Plant Mol. Biol. 1999 January; 39(1):83-93; Terada et al., Nat. Biotechnol. 2002 October; 20(10):1030-4. Epub 2002 Sep. 9.). Exploratory approaches to increase gene targeting in plants comprise expression of proteins like RecA (WO 97/08331) or RecA-homologues derived from other species like e.g., Rad52 (WO 01/68882) or RecA/VirE2 fusion-proteins (WO 01/38504). Use of poly(ADPribose)polymerase inhibitors has demonstrated an increased HR in plants (Puchta H et al. (1995) Plant J 7:203-210). Initiation of sequence-unspecific DNA double-strand breaks was also found to increase efficiency of HR in plants (Puchta H et al. (1995) Plant J 7(2), 203-210; Lebel E G et al. (1993) Proc Natl Acad Sci USA 90(2):422-426). However, sequence-unspecific induction of DNA strand breaks is disadvantageous because of the potential mutagenic effect. Sequence-specific induction of DNA strand-breaks may also increase efficiency of HR but is limited to artificial scenarios (Siebert R and Puchta H (2002) Plant Cell 14(5):1121-1131).

It is specifically contemplated by the inventors that one could employ techniques for the site-specific integration or excision of transformation constructs prepared in accordance with the instant invention. An advantage of site-specific integration or excision is that it can be used to overcome problems associated with conventional transformation techniques, in which transformation constructs typically randomly integrate into a host genome in multiple copies. This random insertion of introduced DNA into the genome of host cells can be lethal if the foreign DNA inserts into an essential gene. In addition, the expression of a transgene may be influenced by "position effects" caused by the surrounding genomic DNA. Further, because of difficulties associated with plants possessing multiple transgene copies, including gene silencing, recombination and unpredictable inheritance, it is typically desirable to control the copy number of the inserted DNA, often only desiring the insertion of a single copy of the DNA sequence. Site-specific integration or excision of transgenes or parts of transgenes can be achieved in plants by means of homologous recombination (see, for example, U.S. Pat. No. 5,527,695). The DNA-constructs utilized within the method of this invention may comprise additional nucleic acid sequences. Said sequences may be for example localized in different positions with respect to the homology sequences. Preferably, the additional nucleic acid sequences are localized between two homology sequences and may be introduced via homologous recombination into the chromosomal DNA, thereby resembling an insertion mutation of said chromosomal DNA. However, the additional sequences may also be localized outside of the homology sequences (e.g., at the 5- or 3-end of the DNA-construct). In cases where the additional sequence resembles a counter selection marker this may allow a distinction of illegitimate insertion events from correct insertion events mediated by homologous recombination. Corresponding negative markers are described below and suitable methods are well known in the art (WO 99/20780).

In a preferred embodiment of the invention, efficiency of the method of the invention may be further increased by combination with other methods suitable for increasing homologous recombination. Said methods may include for example expression of HR enhancing proteins (like e.g., RecA; WO 97/08331; Reiss B et al. (1996) Proc Natl Acad Sci USA 93(7):3094-3098; Reiss B et al. (2000) Proc Natl Acad Sci USA 97(7):3358-3363) or treatment with PARP inhibitors (Puchta H et al. (1995) Plant J. 7:203-210). Various PARP inhibitors suitable for use within this invention are known to the person skilled in the art and may include for example preferably 3-Aminobenzamid, 8-Hydroxy-2-methylquinazolin-4-on (NU1025), 1,11b-Dihydro-[2H]benzopyrano[4,3,2-de]isoquinolin-3-on (GPI 6150), 5-Aminoisoquinolinon, 3,4-Dihydro-5-[4-(1-piperidinyl) butoxy]-1(2H)-isoquinolinon or compounds described in WO 00/26192, WO 00/29384, WO 00/32579, WO 00/64878, WO 00/68206, WO 00/67734, WO 01/23386 or WO 01/23390. Furthermore, the method may be combined with other methods facilitation homologous recombination and/or selection of the recombinants like e.g., positive/negative selection, excision of illegitimate recombination events or induction of sequence-specific or unspecific DNA double-strand breaks. In a preferred embodiment, the method for enhancing the expression of a nucleic acid sequence in a plant or a plant cell further via linking the intron with expression enhancing properties to the expression cassette by insertion via homologous recombination is applied to monocotyledonous plants or plant cells, more preferably to plants selected from the group consisting of the genera *Hordeum, Avena, Secale, Triticum, Sorghum, Zea, Saccharum*, and *Oryza*, most preferably a maize plant.

The nucleic acid sequence in which one of the inventive intron is inserted and functionally linked (via the inventive methods), encodes for a selectable marker protein, a screenable marker protein, a anabolic active protein, a catabolic active protein, a biotic or abiotic stress resistance protein, a male sterility protein or a protein affecting plant agronomic characteristics as described above and/or a sense, antisense, or double-stranded RNA as described above. In a preferred embodiment of the present invention, said nucleic acid sequence encodes a protein. In yet another embodiment of the invention the method is applied to recombinant DNA expression construct that contain a DNA for the purpose of expressing RNA transcripts that function to affect plant phenotype without being translated into a protein. Such non protein expressing sequences comprising antisense RNA molecules, sense RNA molecules, RNA molecules with ribozyme activity, double strand forming RNA molecules (RNAi) as described above.

Additionally, a further subject matter of the invention relates to the use of the above describes transgenic organism or of cell cultures, parts of transgenic propagation material derived there from, produced with the inventive method, for the production of foodstuffs, animal feeds, seeds, pharmaceuticals or fine chemicals. Preferred is furthermore the use of transgenic organisms for the production of pharmaceuticals or fine chemicals, where a host organism is transformed with one of the above-described expression constructs, and this expression construct contains one or more structural genes which encode the desired fine chemical or catalyze the biosynthesis of the desired fine chemical, the transformed host organism is cultured, and the desired fine chemical is isolated from the culture medium. This process can be used widely for fine chemicals such as enzymes, vitamins, amino acids, sugars, fatty acids, natural and synthetic flavorings, aroma substances and colorants. Especially preferred is the production of tocopherols and tocotrienols, carotenoids, oils, polyunsaturated fatty acids etc. Culturing the transformed host organisms, and isolation from the host organisms or the culture medium, is performed by methods known to the skilled worker. The production of pharmaceuticals such as, for example, antibodies, vaccines, enzymes or pharmaceutically active proteins is described (Hood (1999) Curr Opin Biotechnol. 10(4):382-6; Ma (1999) Curr Top Microbiol. Immunol. 236:275-92; Russel (1999) Current Topics in Microbiology and Immunology 240:119-138; Cramer et al. (1999) Current Topics in Microbiology and Immunology 240:95-118; Gavilondo (2000) Biotechniques 29(1):128-138; Holliger (1999) Cancer & Metastasis Reviews 18(4):411-419).

Furthermore the present invention relates to recombinant DNA expression construct comprising at least one promoter sequence functioning in plants or plant cells, at least one intron with expression enhancing properties in plants or plant cells characterized by VIII) an intron length shorter than 1,000 base pairs, and
IX) presence of a 5' splice site comprising the dinucleotide sequence 5'-GT-3' (SEQ ID NO: 78), and
X) presence of a 3' splice site comprising the trinucleotide sequence 5'-CAG-3' (SEQ ID NO: 79), and
XI) presence of a branch point resembling the consensus sequence 5'-CURAY-3' (SEQ ID NO: 75) upstream of the 3' splice site, and
XII) an adenine plus thymine content of at least 40% over 100 nucleotides down-stream from the 5' splice site, and
XIII) an adenine plus thymine content of at least 50% over 100 nucleotides upstream from the 3' splice site, and
XIV) an adenine plus thymine content of at least 55%, and a thymine content of at least 30% over the entire intron, and at least one nucleic acid sequence, wherein said promoter sequence and at least one of said intron sequences are functionally linked to said nucleic acid sequence and wherein said intron is heterologous to said nucleic acid sequence and/or to said promoter sequence.

Sequences

1. SEQ ID NO: 1 BPSI.1: Sequence of the first intron isolated from the *Oryza sativa* metallothioneine-like gene (accession No. AP002540)
2. SEQ ID NO: 2 BPSI.2: Sequence of the first intron isolated from the *Oryza sativa* Sucrose UDP Glucosyltransferase-2 gene (accession No. AC084380)
3. SEQ ID NO: 3 BPSI.3: Sequence of the second intron isolated from the *Oryza sativa* Sucrose UDP Glucosyltransferase-2 gene (accession No. AC084380)
4. SEQ ID NO: 4 BPSI.4: Sequence of the third intron isolated from the *Oryza sativa* Sucrose UDP Glucosyltransferase-2 gene (accession No. AC084380)
5. SEQ ID NO: 5 BPSI.5: Sequence of the eighth intron isolated from the *O. sativa* gene encoding for the Sucrose transporter (accession No. AF 280050).
6. SEQ ID NO: 6 BPSI.6: Sequence of fourth intron isolated from the *Oryza sativa* gene (accession No. BAA94221) encoding for an unknown protein with homology to the *A. thaliana* chromosome II sequence from clones T22013, F12K2 encoding for a putative lipase (AC006233).
7. SEQ ID NO: 7 BPSI.7: Sequence of the fourth intron isolated from the *Oryza sativa* gene (accession No. BAB90130) encoding for a putative cinnamyl-alcohol dehydrogenase.
8. SEQ ID NO: 8 BPSI.8: Sequence of the second intron isolated from the *Oryza sativa* gene (accession No. AC084766) encoding for a putative ribonucleoprotein.
9. SEQ ID NO: 9 BPSI.9: Sequence of the fifth intron isolated from the *Oryza sativa* clone GI 12061241.
10. SEQ ID NO: 10 BPSI.10: Sequence of the third intron isolated from the *O. sativa* gene (accession No. AP003300) encoding for a putative protein kinase.
11. SEQ ID NO: 11 BPSI.11: Sequence of the first intron isolated from the *O. sativa* gene (accession No. L37528) encoding for a MADS3 box protein.
12. SEQ ID NO: 12 BPSI.12: Sequence of the first intron isolated from the *Oryza sativa* gene (accession No. CB625805) encoding for a putative Adenosylmethionine decarboxylase.
13. SEQ ID NO: 13 BPSI.13: Sequence of the first intron isolated from the *O. sativa* gene (accession No. CF297669) encoding for an Aspartic proteinase.
14. SEQ ID NO: 14 BPSI.14: Sequence of the first intron isolated from the *O. sativa* gene (accession No. CB674940) encoding for a Lec14b protein.
15. SEQ ID NO: 15 BPSI.15: Sequence of the first intron isolated from the *Oryza sativa* gene (accession No. BAD37295.1) encoding for a putative SalT protein precursor
16. SEQ ID NO: 16 BPSI.16: Sequence of the first intron isolated from the *O. sativa* gene (accession No. BX928664) encoding for a putative Reticulon.
17. SEQ ID NO: 17 BPSI.17: Sequence of the first intron isolated from the *O. sativa* gene (accession No. M752970) encoding for a glycolate oxidase.
18. SEQ ID NO: 18 BPSI.18: Sequence of the first intron isolated from the *Oryza sativa* clone (accession No. AK06442 encoding putative non-coding
19. SEQ ID NO: 19 BPSI.19: Sequence of the first intron isolated from the *Oryza sativa* clone (accession No. AK062197) encoding putative non-coding
20. SEQ ID NO: 20 BPSI.20 sequence of the first intron isolated from the *O. sativa* gene (accession No. CF279761) encoding for a hypothetical protein.
21. SEQ ID NO: 21 BPSI.21 Sequence of the first intron isolated from the *Oryza sativa* gene (accession No. CF326058) encoding for a putative membrane transporter.
22. SEQ ID NO: 22 BPSI.22: Sequence of the first intron isolated from the *Oryza sativa* gene (accession No. C26044) encoding for a putative ACT domain repeat protein
23. SEQ ID NO: 23 Sucrose-UDP glucosyltransferase 2 forward (for) primer
24. SEQ ID NO: 24 Sucrose-UDP glucosyltransferase 2 reverse (rev) primer
25. SEQ ID NO: 25 Putative Bowman-Kirk trypsin inhibitor (for) primer
26. SEQ ID NO: 26 Putative Bowman-Kirk trypsin inhibitor rev primer
27. SEQ ID NO: 27 Hypothetical protein Acc. No. CF279761 (for) primer
28. SEQ ID NO: 28 Hypothetical protein Acc. No. CF279761 rev primer
29. SEQ ID NO: 29 Phenylalanine ammonia-lyase (for) primer
30. SEQ ID NO: 30 Phenylalanine ammonia-lyase rev primer
31. SEQ ID NO: 31 Metallothioneine-like protein 1 (for) primer
32. SEQ ID NO: 32 Metallothioneine-like protein 1 rev primer
33. SEQ ID NO: 33 Catalase (for) primer
34. SEQ ID NO: 34 Catalase rev primer
35. SEQ ID NO: 35 Putative stress-related protein (for) primer
36. SEQ ID NO: 36 Putative stress-related protein rev primer
37. SEQ ID NO: 37 Putative translation initiation factor SUI1 (for) primer
38. SEQ ID NO: 38 Putative translation initiation factor SUI1 rev primer
39. SEQ ID NO: 39 Polyubiquitin (for) primer
40. SEQ ID NO: 40 Polyubiquitin rev primer
41. SEQ ID NO: 41 Glutathione S-transferase II (for) primer 42. SEQ ID NO: 42 Glutathione S-transferase II rev primer
43. SEQ ID NO: 43 Metallothioneine-like protein 2 (for) primer
44. SEQ ID NO: 44 Metallothioneine-like protein 2 rev primer
45. SEQ ID NO: 45 Translational initiation factor elF1 (for) primer
46. SEQ ID NO: 46 Translational initiation factor elF1 rev primer
47. SEQ ID NO: 47 OSJNBa0024F24.10 (unknown protein) (for) primer
48. SEQ ID NO: 48 OSJNBa0024F24.10 (unknown protein) rev primer
49. SEQ ID NO: 49 Protein similar to Histone 3.2-614 (for) primer
50. SEQ ID NO: 50 Protein similar to Histone 3.2-614 rev primer
51. SEQ ID NO: 51 OSJNBa0042L16.3 (for) primer
52. SEQ ID NO: 52 OSJNBa0042L16.3 rev primer
53. SEQ ID NO: 53 BPSI.1-5' primer
54. SEQ ID NO: 54 BPSI.1-3' primer
55. SEQ ID NO: 55 BPSI.2-5' primer
56. SEQ ID NO: 56 BPSI.2-3' primer
57. SEQ ID NO: 57 BPSI.3-5' primer
58. SEQ ID NO: 58 BPSI.3-3' primer
59. SEQ ID NO: 59 BPSI.4-5' primer
60. SEQ ID NO: 60 BPSI.4-3' primer
61. SEQ ID NO: 61 BPSI.5-5' primer
62. SEQ ID NO: 62 BPSI.5-3' primer
63. SEQ ID NO: 63 BPSI.6-5' primer
64. SEQ ID NO: 64 BPSI.6-3' primer
65. SEQ ID NO: 65 BPSI.7-5' primer
66. SEQ ID NO: 66 BPSI.7-3' primer
67. SEQ ID NO: 67 BPSI.8-5' primer
68. SEQ ID NO: 68 BPSI.8-3' primer
69. SEQ ID NO: 69 BPSI.9-5' primer
70. SEQ ID NO: 70 BPSI.9-3' primer
71. SEQ ID NO: 71 BPSI.10-5' primer
72. SEQ ID NO: 72 BPSI.10-3' primer
73. SEQ ID NO: 73 BPSI.11-5' primer
74. SEQ ID NO: 74 BPSI.11-3' primer
75. SEQ ID NO: 75 5'-CURAY-3' plant branchpoint consensus sequences 1
76. SEQ ID NO: 76 5'-YURAY-3' plant branchpoint consensus sequences 2
77. SEQ ID NO: 77 5'-(AG)(AG)/GT(AGT)(AGT)(GTC)-3' preferred 5 splice-site
78. SEQ ID NO: 78 5' splice site dinucleotide 5'-GT-3'
79. SEQ ID NO: 79 3' splice site trinucleotide 5'-CAG-3'
80. SEQ ID NO: 80 5' splice site plant consensus sequence 5'-AG::GTAAGT-3'
81. SEQ ID NO: 81 3' splice site plant consensus sequence 5'-CAG::GT-3'
82. SEQ ID NO: 82 Sequence of the first intron isolated from the *Oryza sativa* metallothioneine-like gene (accession No. AP002540) including sequences 5' and 3' adjacent to the 5' and 3' splice sites of the intron sequence BPSI.1 (SEQ ID NO:1)
83. SEQ ID NO: 83 Sequence of the first intron isolated from the *O. sativa* Sucrose UDP Glucosyltransferase-2 gene (accession No. AC084380) including sequences 5' and 3' adjacent to the 5' and 3' splice sites of the intron sequence BPSI.2 (SEQ ID NO:2)
84. SEQ ID NO: 84 Sequence of the second intron isolated from the *O. sativa* Sucrose UDP Glucosyltransferase-2 gene (accession No. AC084380) including sequences 5' and 3' adjacent to the 5' and 3' splice sites of the intron sequence BPSI.3 (SEQ ID NO:3)
85. SEQ ID NO: 85 Sequence of the third intron isolated from the *O. sativa* Sucrose UDP Glucosyltransferase-2 gene (accession No. AC084380) including sequences 5' and 3' adjacent to the 5' and 3' splice sites of the intron sequence BPSI.4 (SEQ ID NO:4)
86. SEQ ID NO: 86 Sequence of the eighth intron isolated from the *Oryza sativa* gene encoding for the Sucrose transporter (GenBank accession No. AF 280050) including sequences 5' and 3' adjacent to the 5' and 3' splice sites of the intron sequence BPSI.5 (SEQ ID NO:5)
87. SEQ ID NO: 87 Sequence of the eighth intron isolated from the *Oryza sativa* gene encoding for the Sucrose transporter (accession No. AF 280050) including modified 5' and 3' splice sites and sequences 5' and 3' adjacent to the 5' and 3' splice sites of the intron sequence BPSI.5 (SEQ ID NO:5)
88. SEQ ID NO: 88 Sequence of the fourth intron isolated from the *Oryza sativa* gene encoding for an unknown protein with homology to the *A. thaliana* chromosome II sequence from clones T22013, F12K2 encoding for a putative lipase (AC006233) including sequences 5' and 3' adjacent to the 5' and 3' splice sites of the intron sequence BPSI.6 (SEQ ID NO:6)
89. SEQ ID NO: 89 Sequence of the fourth intron isolated from the *Oryza sativa* gene encoding for an unknown protein with homology to the *A. thaliana* chromosome II sequence from clones T22013, F12K2 encoding for a putative lipase (AC006233) including modified 5' and 3' splice sites and sequences 5' and 3' adjacent to the 5' and 3' splice sites of the intron sequence BPSI.6 (SEQ ID NO:6)
90. SEQ ID NO: 90 Sequence of the fourth intron isolated from the *Oryza sativa* gene (accession No. BAB90130) encoding for a putative cinnamyl-alcohol dehydrogenase including sequences 5' and 3' adjacent to the 5' and 3' splice sites of the intron sequence BPSI.7 (SEQ ID NO:7)
91. SEQ ID NO: 91 Sequence of the fourth intron isolated from the *Oryza sativa* gene (accession No. BAB90130) encoding for a putative cinnamyl-alcohol dehydrogenase including modified 5' and 3' splice sites and sequences 5' and 3' adjacent to the 5' and 3' splice sites of the intron sequence BPSI.7 (SEQ ID NO:7)
92. SEQ ID NO: 92 Sequence of the second intron isolated from the *Oryza sativa* gene (accession No. AC084766) encoding for a putative ribonucleoprotein including sequences 5' and 3' adjacent to the 5' and 3' splice sites of the intron sequence BPSI.8 (SEQ ID NO:8)
93. SEQ ID NO: 93 Sequence of the second intron isolated from the *Oryza sativa* gene (accession No. AC084766) encoding for a putative ribonucleoprotein including modified 5' and 3' splice sites and sequences 5' and 3' adjacent to the 5' and 3' splice sites of the intron sequence BPSI.8 (SEQ ID NO:8)
94. SEQ ID NO: 94 Sequence of the third intron isolated from the *Oryza sativa* gene (accession No. AP003300) encoding for a putative protein including sequences 5' and 3' adjacent to the 5' and 3' splice sites of the intron sequence BPSI.10 (SEQ ID NO:10)
95. SEQ ID NO: 95 Sequence of the third intron isolated from the *Oryza sativa* gene (accession No. AP003300) encoding for a putative protein including modified 5' and 3' splice sites and sequences 5' and 3' adjacent to the 5' and 3' splice sites of the intron sequence BPSI.10 (SEQ ID NO:10)
96. SEQ ID NO: 96 Sequence of the first intron isolated from the *Oryza sativa* gene (accession No. L37528) encoding for a MADS3 box protein including sequences 5' and 3' adjacent to the 5' and 3' splice sites of the intron sequence BPSI.11 (SEQ ID NO:11)
97. SEQ ID NO: 97 Sequence of the first intron isolated from the *Oryza sativa* gene (accession No. L37528) encoding for a MADS3 box protein including modified 5' and 3' splice sites and sequences 5' and 3' adjacent to the 5' and 3' splice sites of the intron sequence BPSI.11 (SEQ ID NO:11)
98. SEQ ID NO: 98 Sequence of the first intron isolated from the *Oryza sativa* gene (accession No. CB625805) encoding for a putative Adenosylmethionine decarboxylase including sequences 5' and 3' adjacent to the 5' and 3' splice sites of the intron sequence BPSI.12 (SEQ ID NO:12)
99. SEQ ID NO: 99 Sequence of the first intron isolated from the *Oryza sativa* gene (accession No. CF297669) encoding for a Aspartic proteinase including sequences 5' and 3' adjacent to the 5' and 3' splice sites of the intron sequence BPSI.13 (SEQ ID NO:13)
100. SEQ ID NO: 100 Sequence of the first intron isolated from the *Oryza sativa* gene (accession No. CB674940) encoding for a Lec14b protein including sequences 5' and 3' adjacent to the 5' and 3' splice sites of the intron sequence BPSI.14 (SEQ ID NO:14)
101. SEQ ID NO: 101 Sequence of the first intron isolated from the *O. sativa* gene (accession No. CA128696) encoding for a putative mannose-binding rice lectin including sequences 5' and 3' adjacent to the 5' and 3' splice sites of the intron sequence BPSI.15 (SEQ ID NO:15)
102. SEQ ID NO: 102 Sequence of the first intron isolated from the *Oryza sativa* gene (accession No. BX928664) encoding for a putative Reticulon including sequences 5' and 3' adjacent to the 5' and 3' splice sites of the intron sequence BPSI.16 (SEQ ID NO:16)
103. SEQ ID NO: 103 Sequence of the first intron isolated from the *Oryza sativa* gene (accession No. AA752970) encoding for a glycolate oxidase including sequences 5' and 3' adjacent to the 5' and 3' splice sites of the intron sequence BPSI.17 (SEQ ID NO:17)
104. SEQ ID NO: 104 Sequence of the first intron isolated from the *Oryza sativa* clone GI 34763855 including sequences 5' and 3' adjacent to the 5' and 3' splice sites of the intron sequence BPSI.18 (SEQ ID NO:18)
105. SEQ ID NO: 105 Sequence of the first intron isolated from the *Oryza sativa* clone GI 32533738 including sequences 5' and 3' adjacent to the 5' and 3' splice sites of the intron sequence BPSI.19 (SEQ ID NO:19)
106. SEQ ID NO: 106 Sequence of the first intron isolated from the *Oryza sativa* gene (accession No. CF279761) encoding for a hypothetical protein including sequences 5' and 3' adjacent to the 5' and 3' splice sites of the intron sequence BPSI.20 (SEQ ID NO:20).
107. SEQ ID NO: 107 Sequence of the first intron isolated from the *O. sativa* gene (accession No. CF326058) encoding for a putative membrane transporter including sequences 5' and 3' adjacent to the 5' and 3' splice sites of the intron sequence BPSI.21 (SEQ ID NO:21).
108. SEQ ID NO: 108 Sequence of the first intron isolated from the *O. sativa* gene (accession No. C26044) encoding for a putative ACT domain repeat protein including sequences 5' and 3' adjacent to the 5' and 3' splice sites of the intron sequence BPSI.22 (SEQ ID NO:22).
109. SEQ ID NO: 109 Binary vector pBPSMM291
110. SEQ ID NO: 110 Binary vector pBPSMM305
111. SEQ ID NO: 111 Binary vector pBPSMM350
112. SEQ ID NO: 112 Binary vector pBPSLM139
113. SEQ ID NO: 113 Artificial sequence: cassette from vector pBPSMM355 (OsCP12::BPSI.1) comprising Os CP12 promoter (bp 1-854) and BPSI.1 intron (bp 888-1470).
114. SEQ ID NO: 114 Artificial sequence: cassette from vector pBPSMM355 (ZmHRGP::BPSI.1) comprising Maize [HRGP] hydroxyproline-rich glycoprotein (extensin) 5'/UTR promoter (bp 1-1184) and *Oryza sativa* BPSI.1 intron (bp 1217-1799)
115. SEQ ID NO: 115 Artificial sequence: cassette from vector pBPSMM358 (OsC-CoAMT1::BPSI.1) comprising p-caffeoyl-CoA 3-O-methyltransferase [CoA-O-Methyl] promoter (bp 1-1034) and BPSI.1 intron (1119-1701)
116. SEQ ID NO: 116 Artificial sequence: cassette from vector EXS1025 (ZmGlobulin1::BPSI.1) comprising Maize Globulin-1 [ZmGlb1] promoter (W64A) (bp 1-1440) and BPSI.1 intron (1443-1999)
117. SEQ ID NO: 117 Artificial sequence: cassette from vector pBPSMM369 (OsV-ATPase::BPSI.1) comprising putative Rice H+-transporting ATP synthase 5'/UTR promoter (1-1589) and BPSI.1 intron (1616-2198)
118. SEQ ID NO: 118 Artificial sequence: cassette from vector pBPSMM366 (OsC8,7SI:BPSI.1) comprising Putative Rice C-8,7 Sterol isomerase promoter (1-796) and BPSI.1 intron (827-1409)
119. SEQ ID NO: 119 Artificial sequence: cassette from vector pBPSMM357 (ZmLDH::BPSI.1) comprising maize gene Lactate Dehydrogenase 5'/UTR promoter (bp 1-1062) and BPSI.1 intron (bp 1095-1677).
120. SEQ ID NO: 120 Artificial sequence: cassette from vector pBPSLM229 (ZmLDH::BPSI.5) comprising maize gene Lactate Dehydrogenase 5'/UTR promoter (bp 1-1062) and BPSI.5 intron (bp 1068-1318)
121. SEQ ID NO: 121 Artificial sequence: cassette from vector pBPSMM371 (Os-Lea::BPSI.1) comprising rice Lea (Late Embryogenesis Abundant) promoter (bp 1-1386) and BPSI.1 intron (bp 1387-2001)

EXAMPLES

Chemicals

Unless indicated otherwise, chemicals and reagents in the Examples were obtained from Sigma Chemical Company (St. Louis, Mo.), restriction endonucleases were from New England Biolabs (Beverly, Mass.) or Roche (Indianapolis, Ind.), oligonucleotides were synthesized by MWG Biotech Inc. (High Point, N.C.), and other modifying enzymes or kits regarding biochemicals and molecular biological assays were from Clontech (Palo Alto, Calif.), Pharmacia Biotech (Piscataway, N.J.), Promega Corporation (Madison, Wis.), or Stratagene (La Jolla, Calif.). Materials for cell culture media were obtained from Gibco/BRL (Gaithersburg, Md.) or DIFCO (Detroit, Mich.). The cloning steps carried out for the purposes of the present invention, such as, for example, restriction cleavages, agarose gel electrophoresis, purification of DNA fragments, transfer of nucleic acids to nitrocellulose and nylon membranes, linking DNA fragments, transformation of *E. coli* cells, growing bacteria, multiplying phages and sequence analysis of recombinant DNA, are carried out as described by Sambrook (1989). The sequencing of recombinant DNA molecules is carried out using ABI laser fluorescence DNA sequencer following the method of Sanger (Sanger 1977).

Example 1

Identification and Characterization of IME-Introns in Highly Expressing Genes 1.1 Identification of Strongly and Constitutively Expressed *Oryza sativa* Gene Candidates.

Using the above described "sequencing by hybridization method' in silico clone distribution analysis of rice cDNA libraries have been performed.

The rice cDNA done distribution profiles were derived from about 7.6 million rice cDNA clones, which were generated over 23 rice cDNA libraries of different tissues at different developmental stages and biotic/abiotic treatments. Method for the production of cDNA libraries are well known in the art (e.g. Gubler U, and Hoffman B J. (1983) A simple and very efficient method for generating cDNA libraries. Gene 25(2-3):263-269; Jung-Hwa Oh et al. (2003) An improved method for constructing a full-length enriched cDNA library using small amounts of total RNA as a starting material. EXPERIMENTAL and MOLECULAR MEDICINE 35(6):586-590; Lanfranchi et al. (1996) Identification of 4370 expressed sequence tags from a 3'-end-specific cDNA library of human skeletal muscle by DNA sequencing and filter hybridization. Genome Res. 6(1):3542). Furthermore, a comprehensive description of cDNA library construction is provided in 1) Cowell and Austin. cDNA Library Protocols. In Methods in Molecular Biology, Volume 69, October 1996, Humana Press, Scientific and medical publishers, ISBN: 0-89603-383-X; and 2) Ying, Shao-Yao. Generation of cDNA Libraries, Methods and Protocols. In Methods in Molecular Biology, Volume 221, February 2003, Humana Press, Scientific and medical publishers, ISBN: 1-58829-066-2.

All of the clones were clustered into a total of 300,408 rice clusters using the above described (see "sequencing by hybridization method', or "HySeq-technology') high-throughput technology of 288 plant-specific 7 mer-oligonucleotide fingerprinting. For each generated cluster, clones have further been clustered into different variants using more stringent cutoff value of the hybridization pattern similarity, leading to 335,073 rice done variants. Therefore, within each variant for given cluster, clones are more homogeneous. The distribution of rice cDNA clones over the 23 normalized cDNA libraries for given variants provides the rice variant expression profiles. The normalized cDNA library was produced by first adjusting the original library clone size to the average done size of all of the 23 libraries, then adjusting the number of clones per variant in that library based on the adjusted total number of clones in that library.

Rice clones are selected from the rice clusters for sequencing to generate rice EST data. In using the clones distribution profiles of 335,073 rice variants, 145 variants were selected based on the number of clones exceeding top 1% of the clone distribution across the entire library for over each of 23 libraries, and genes were identified using the homologs to the EST sequences derived from the variants. These candidate genes showed strong, constitutive, and ubiquitous expression. The rice EST sequences homolog to these candidate genes were mapped to the rice genomic DNA sequences. Top 15 candidates out of 145 were selected based on availability of genomic sequences, annotation, and high level of expression (Table 2).

TABLE 2

Gene candidates for potential IME-introns

| Candidate gene | Annotation |
|---|---|
| 1 | sucrose-UDP glucosyltransferase 2 |
| 2 | putative Bowman-Kirk trypsin inhibitor |
| 3 | Hypothetical Protein |
| 4 | phenylalanine ammonia-lyase |
| 5 | metallothioneine-like protein 1 |
| 6 | Catalase |
| 7 | putative stress-related protein |
| 8 | putative translation initiation factor SUI1 |
| 9 | Polyubiquitin |
| 10 | glutathione S-transferase II |
| 11 | metallothioneine-like protein 2 |
| 12 | translational initiation factor eIF1 |
| 13 | OSJNBa0024F24.10 (Unknown Protein) |
| 14 | Similar to Histone 3.2-614 |
| 15 | OSJNBa0042L16.3 |

1.2 Validation of Highly Expressing Gene Candidates Using Real Time RT-PCR

Expression levels of the endogenous genes representing these 15 candidates were measured at the mRNA levels using LightCycler. Total RNA was extracted from rice plants at various developmental stages and tissues with and without drought stress (6, 12, 24, and 48 hr by withholding water) using Qiagen RNeasy Plant Mini Kit (Cat. No 74904). Quality and quantity of the RNA were determined using Molecular Probes RiboGreen Kit (Cat. No. R-11490) on the Spectra MAX Gemini. One μg of RNA was used for RT-PCR (Roche RT-PCR AMV kit, Cat. No. 1483188) in the reaction solution I (1 μg RNA, 2 μL 10× Buffer, 4 μL 25 mM MgCl$_2$, 2 μL 1 mM dNTPs, 2 μL 3.2 μg Random Primers, 1 μL 50 units RNase Inhibitor, 0.8 μL 20 units AMV-RT polymerase, fill to 20 μL with sterile water) under the optimized PCR program (25° C. 10 min, 42° C. 1 hr, 99° C. 5 min, 4° C. stop reaction).

The RT-PCR samples were used for the LightCycler reaction (11.6 μL sterile water, 2.4 μL 25 mM MgCl$_2$, 2 μL SYBR Green Polymerase mix, 2 μL 10 mM Specific Primer Mix, 2 μL RT-PCR reaction product) under the optimized program (95° C. 5 min, 95° C. 30 sec, 61° C. 40 sec, 72° C. 40 sec and repeat steps 2-4 for 30 cycles, 72° C. 10 min, and 4° C. stop reaction) provided by Roche (LightCycler FastStart DNA Master SYBR Green I, Cat. No. 3003230).

TABLE 3

Primer sequences of the gene candidates

| Gene | Primers | SEQ ID NO. |
|---|---|---|
| Sucrose-UDP glucosyltransferase 2 | Fwd: 5-tttgtgcagcccgctttctacgag | 23 |
| | Rev: 5-acggccaacgggacggtgcta | 24 |
| Putative Bowman-Birk trypsin inhibitor | Fwd: 5-gtcctcgccggcatcgtcac | 25 |
| | Rev: 5-cagaacggcgggttgatcc | 26 |

TABLE 3-continued

Primer sequences of the gene candidates

| Gene | Primers | SEQ ID NO. |
|---|---|---|
| Hypothetical protein Acc. No. CF279761 | Fwd: 5-agctcgctcgcggtctt<br>Rev: 5-acagggcccaagtcgtgtgc | 27<br>28 |
| Phenylalanine ammonia-lyase | Fwd: 5-aggtctcgccatcgtcaatg<br>Rev: 5-cgagacgggcgttgt | 29<br>30 |
| Methallothioneine-like protein 1 | Fwd: 5-ggctgcggaggatgcaagatg<br>Rev: 5-ggggttgcaggtgcagttgtcg | 31<br>32 |
| Catalase | Fwd: 5-ggcgtcaacacctacacctt<br>Rev: 5-tgcactgcagcatcttgtcgtc | 33<br>34 |
| Putative stress-related protein | Fwd: 5-ggtggatgccacggtgcaagag<br>Rev: 5-ggggaggtactgtgctc | 35<br>36 |
| Putative translation initiation factor SUI1 | Fwd: 5-tgcggaagccaatgctga<br>Rev. 5-ccagccctgaactaggaacgtc | 37<br>38 |
| Polyubiquitin | Fwd: 5-tcaggggaggcatgcaaa<br>Rev: 5-tgcataccaccacggagacgaa | 39<br>40 |
| Glutathione S-transferase II | Fwd: 5-cgatttctccaaaggcgagcac<br>Rev: 5-tgcgggtatgcgtccaaca | 41<br>42 |
| Metallothioneine-like protein 2 | Fwd: 5-acagccaccaccaagaccttcg<br>Rev: 5-ctgcagctggtgccacacttgc | 43<br>44 |
| Translational initiation factor eIF1 | Fwd: 5-tcccaactgccttcgatccctt<br>Rev: 5-tggacagtggtcaggctcttacgg | 45<br>46 |
| OSJNBa0024F24.10 (unknown protein) | Fwd: 5-gagttctaccagttcagcgacc<br>Rev: 5-aacccgaaggcgttgac | 47<br>48 |
| Similar to Histone 3.2-614 | Fwd: 5-agaccgcccgcaagtc<br>Rev: 5-cttgggcatgatggtgacgc | 49<br>50 |
| OSJNBa0042L16.3 | Fwd: 5-ccaagagggagtgctgtatgcca<br>Rev: 5-acgaggaccaccacggtacccat | 51<br>52 |

Standardizing the concentration of RNA (1 µg) in each of the RT-PCR reactions was sufficient to directly compare the samples if the same primers were used for each Lightcycler reaction. The output results were a number that corresponds to the cycle of PCR at which the sample reaches the inflection point in the log curve generated. The lower the cycle numbers the higher the concentration of target RNA present in the sample. Each sample was repeated in triplicate and an average was generated to produce the sample "crosspoint' value. The lower the crosspoint, the stronger the target gene was expressed in that sample. (*Roche Molecular Biochemicals* LightCycler System: Reference Guide May 1999 version) Based on the LightCycler results, 11 candidates were selected (Table 4).

TABLE 4

LightCycler results representing expression of the rice gene candidates at the mRNA levels.

| Gene candidates [strong & constitutive expression] | Drought stressed rice root (R) and shoot (S) (hr with holding water) | | | | | | | | Well-watered conditions | | | |
|---|---|---|---|---|---|---|---|---|---|---|---|---|
| | R6 | R12 | R24 | R48 | S6 | S12 | S24 | S48 | seedling | Panicle during flowering stage | shoots | flowers |
| Unknown | 21.1 | 21.6 | N/A | 20.3 | 20.5 | 21.7 | N/A | 21.0 | 23.3 | 22.7 | 21.4 | 23.7 |
| Catalase | 21.2 | 22.7 | 26.7 | 26.0 | 21.9 | 21.7 | N/A | 27.8 | 22.8 | 31 | 20.6 | 23.5 |
| GSTII | 20.6 | 20.3 | 23.3 | 23.7 | 21.8 | 23.2 | N/A | 20.6 | 24.4 | 22.6 | 22.1 | 24.8 |
| Hypothetical Protein | 31 | 31 | 31 | 31 | 31 | 31 | 31 | 31 | 31 | 31 | 27.4 | 27.0 |
| Metallothioneine 1 | 20.1 | 21.5 | 16.5 | 16.3 | 18.3 | 19.8 | N/A | 19.2 | 21.0 | 22.5 | 20.6 | 20.6 |
| Metallothioneine2 | 20.2 | 20.8 | 23.8 | 24.8 | 18.5 | 18.7 | N/A | 18.7 | 19.9 | 17.8 | 21.2 | 19.2 |
| PolyUbuiquitin | 19.5 | 19.1 | 19.4 | 20.4 | 19.1 | 20.4 | N/A | 19.8 | 22.8 | 20.7 | 20.0 | 22.6 |

TABLE 4-continued

LightCycler results representing expression of the rice gene candidates at the mRNA levels.

| Gene candidates [strong & constitutive expression] | Drought stressed rice root (R) and shoot (S) (hr with holding water) | | | | | | | | Well-watered conditions | | | |
|---|---|---|---|---|---|---|---|---|---|---|---|---|
| | | | | | | | | | | Panicle during flowering | | |
| | R6 | R12 | R24 | R48 | S6 | S12 | S24 | S48 | seedling | stage | shoots | flowers |
| Stress Related Protein | 24.1 | 23.9 | 23.7 | 24.0 | 23.4 | 23.4 | N/A | 23.3 | 24.6 | 24.0 | 23.6 | 24.9 |
| Sucrose-UDP glucoryltransferase 2 | 21.3 | 21.9 | 26.6 | 26.7 | 20.7 | 20.9 | 27.2 | 22.6 | 20.9 | 19.1 | 20.7 | 26.0 |
| SUI1 | 21.3 | 21.1 | 23.1 | 23.6 | 21.9 | 22.8 | N/A | 21.7 | 24.4 | 23.8 | 22.9 | 30.2 |
| TIF | 23.6 | 23.6 | N/A | 22.9 | 22.1 | 23.3 | N/A | 23.1 | 24.6 | 23.8 | 22.8 | 23.7 |
| Trypsin Inhibitor | 24.0 | 23.8 | 24.5 | 25.0 | 22.8 | 23.3 | 23.5 | 23.2 | 26.2 | 23.8 | 23.2 | 23.05 |

The numbers represent PCR cycle that reaches the start of the exponential curve of the PCR product. Lower the number indicates that higher the expression of the endogenous gene is.

1.3 Identification of IME-Introns

Candidate introns were isolated using the public available genomic DNA sequences (e.g. http://www.ncbi.nlm.nih.gov/genomes/PLANTS/PlantList.html), leading to a total of 20 introns, mostly first, second, and/or third introns from the targeted genes. These intron sequences were screened by the following IME criteria:

5' splice site GT, 3' splice site CAG

At least 40% AT rich over 100 nucleotides downstream from the 5' splice site GT

At least 50% AT rich over 100 nucleotides upstream from the 3' splice site CAG

At least 55% AT rich and 35% T rich over the entire intron

CURAY branch point

Intron size less than 1 kb

Selected intron candidates can retain up to 50 bp exon sequences upstream and downstream of the 5' and 3' splice sites, respectively.

After screening the intron sequences against the IME criteria described above, four out of the 20 candidates were chosen and named as follows.

TABLE 5

The intron candidates

| Intron name | Annotation |
|---|---|
| BPSI.1 (SEQ ID No. 1) | Metallothioneine1 first intron |
| BPSI.2 (SEQ ID No. 2) | Sucrose-UDP glucosyltransferase2 first intron |
| BPSI.3 (SEQ ID No. 3) | Sucrose-UDP glucosyltransferase2 second intron |
| BPSI.4 (SEQ ID No. 4) | Sucrose-UDP glucosyltransferase2 third intron |

1.4 Isolation of the Intron Candidates

Genomic DNA from rice was extracted using the Qiagen DNAeasy Plant Mini Kit (Qiagen). Genomic DNA regions containing introns of interest were isolated using conventional PCR. Approximately 0.1 µg of digested genomic DNA was used for the regular PCR reaction (see below). The primers were designed based on the rice genomic sequences. One µL of the diluted digested genomic DNA was used as the DNA template in the primary PCR reaction. The reaction comprised six sets of primers (Table 6) in a mixture containing Buffer 3 following the protocol outlined by an Expand Long PCR kit (Cat #1681-842, Roche-Boehringer Mannheim). The isolated DNA was employed as template DNA in a PCR amplification reaction using the following primers:

TABLE 6

Primer sequences

| Primer name | Sequence |
|---|---|
| BPSI.1-5 (SEQ ID No. 53) | 5-cccgggcaccctgcggagggtaagatccgatcacc |
| BPSI.1-3 (SEQ ID No. 54) | 5-cggaccggtacatcttgcatctgcatgtac |
| BPSI.2-5 (SEQ ID No. 55) | 5-cccgggcacccttcaccaggttcgtgctgatttag |
| BPSI.2-3 (SEQ ID No. 56) | 5-cggaccgaaccagcctgcgcaaataacag |
| BPSI.3-5 (SEQ ID No. 57) | 5-cccgggcacctcctgaggagtgcacaggtttg |
| BPSI.3-3 (SEQ ID No. 58) | 5-cggaccgggagataacaatcccctcctgcatg |
| BPSI.4-5 (SEQ ID No. 59) | 5-cccgggcacccagcttgtggaagaagggtatg |
| BPSI.4-3 (SEQ ID No. 60) | 5-cggaccggttgttggtgctgaaatatacatc |

Amplification was carried out in the PCR reaction (5 μL 10× Advantage PCR Mix [Eppendorf], 5 μL genomic DNA [corresponds to approximately 80 ng], 2.5 mM of each dATP, dCTP, dGTP and dTTP [Invitrogen:dNTP mix], 1 μL of 20 μM 5-intron specific primer 20 μM, 1 μL of 20 μM 3 intron specific primer, 1 μL TripleMaster DNA Polymerase mix [Eppendorf], in a final volume of 50 μL) under the optimized PCR program (1 cycle with 15 sec at 94° C. and 1 min at 80° C. 35 cycles with 15 sec at 94° C., 1 min at 58° C. and 1 min at 72° C.) provided by Thermocycler (T3 Thermocycler Biometra).

The PCR product was applied to an 1% (w/v) agarose gel and separated at 80V. The PCR products were excised from the gel and purified with the aid of the Qiagen Gel Extraction Kit (Qiagen, Hilden, Germany). The PCR product can be cloned directly into vector pCR4-TOPO (Invitrogen) following the manufacturer s instructions i.e. the PCR product obtained was inserted into a vector having T overhangs with its A overhangs and a topoisomerase.

1.5 Vector Construction

The base vector to which the intron candidates were clone in was pBPSMM267. This vector comprises the maize ubiquitin promoter with no intronic sequence, followed by multiple cloning sites (MCS) to be used for addition of introns of interest, then the GUSint ORF (including the potato invertase [PIV]2 intron to prevent bacterial expression), followed by nopaline synthase (NOS) terminator. The intron-containing expression vectors were generated by ligation of XmaI-RsrII digested intron PCR products into XmaI-RsrII linearized pBPSMM267, thereby resulting in the following vectors (Table 7).

TABLE 7

GUS chimeric constructs containing introns in the 5 UTR

| pUC-based expression vector | Binary vector | Composition of the expression cassette (promoter::intron::reporter gene::terminator) |
|---|---|---|
| pBPSMM291 | pBPSMM350 | Zm.ubiquitin promoter::BPSI.1::GUS::NOS3 |
| pBPSMM293 | pBPSMM353 | Zm.ubiquitin promoter::BPSI.2::GUS::NOS3 |
| pBPSMM294 | pBPSMM312 | Zm.ubiquitin promoter::BPSI.3::GUS::NOS3 |
| pBPSMM295 | pBPSMM310 | Zm.ubiquitin promoter::BPSI.4::GUS::NOS3 |

1.6 Plant Analysis for Identifying IME-Introns

These experiments were performed by bombardment of plant tissues or culture cells (Example 4.1), or by *Agrobacterium*-mediated transformation (Example 4.3). The target tissues for these experiments can be plant tissues (e.g. leaf or root), cultured cells (e.g. maize BMS), or plant tissues (e.g. immature embryos) for *Agrobacterium* protocols.

1.6.1 Transient Assays

To identify IME-introns, four introns (BPSI.1, 2, 3, and 4) were tested using Microprojectile bombardment. The maize ubiquitin promoter (Zm.ubiquitin) without any intronic sequence was used as basal expression (negative control). Introns of interest were cloned into the 5 UTR region of Zm.ubiquitin promoter. Maize ubiquitin intron was used as a positive control to measure the relative levels of expression enhanced by introns of interest based on GUS expression. Strong enhancement with BPSI.1 and BPSI.2 introns was detected (Table 8). BPSI.3 intron showed medium enhancement levels of GUS expression. No expression was detected with BPSI.4 intron.

TABLE 8

Transient GUS expression testing for intron-mediated enhancement

| Intron candidates | GUS expression* | |
|---|---|---|
| Zm.ubiquitin promoter alone (negative control) | ++ | 50%** |
| Zm.ubiquitin promoter + Zm.ubiquitin intron 1 (positive control) | ++++ | 100% |
| Zm.ubiquitin promoter + BPSI.1 (pBPSMM291) | ++++ | 100% |
| Zm.ubiquitin promoter + BPSI.2 (pBPSMM293) | ++++ | 100% |
| Zm.ubiquitin promoter + BPSI.3 (pBPSMM294) | +++ | 80% |
| Zm.ubiquitin promoter + BPSI.4 (pBPSMM295) | – | 0% |

*GUS histochemical assays: a range of GUS activities (– no expression to ++++ high expression),
**Relative GUS expression compared to the expression controlled by maize ubiquitin promoter fused with Zm.ubiquitin intron.

1.6.2 Analysis of IME-Intron Candidates in Stably Transformed Maize

The binary vectors pBPSMM350, pBPSMM353, pBPSMM312, and pBPSMM310 (Table 7), were transformed into maize using *Agrobacterium*-mediated transformation (Example 4.3). The levels and patterns of GUS expression controlled by BPSI.1, BPSI.2, BPSI.3, or BPSI.4 intron were compared with those controlled by Zm.ubiquitin intron. BPSI.1, BPSI.2 and BPSI.3 introns enhanced expression in roots, leaves, and kernels throughout the various development stages at a similar level to that observed in transient assays (Table 9). Expression of Zm.ubiquitin promoter without intron was undetectable in roots and leaves and was limited in kernels to the endosperm. Expression of Zm.ubiqutin promoter with BPSI.4 intron exhibited the same expression patterns as those controlled by Zm.ubiquitin promoter without intron. This result indicates that a transient assay can be used as a model system and is therefore one of the important screening systems to identify introns that function in intron-mediated enhancement (IME) in stable transformed plants. However, the results obtained with the transient assays should be validated by the production of stable transformed transgenic plants.

TABLE 9

GUS expression in transgenic maize plants

| Developmental stage | Organs | Zmubiquitin promoter::Zmubiquitin intron | Zmubiquitin promoter::no intron | Zmubiquitin promoter::BPSI.1 (pPSMM350) |
|---|---|---|---|---|
| Five leaf | Roots | ++++ | – | ++++ |
| | Leaves | ++++ | – | +++ |

TABLE 9-continued

| GUS expression in transgenic maize plants | | | | |
|---|---|---|---|---|
| Flowering | Leaves | ++++ | − | +++ |
| Late reproductive | Kernels | ++++ | ++** | +++ |

| Developmental stage | Organs | Zmubiquitin promoter::BPSI.2 (pBPSMM353) | Zmubiquitin promoter::BPSI.3 (pBPSMM312) | Zmubiquitin promoter::BPSI.4 (pBPSMM310) |
|---|---|---|---|---|
| Five leaf | Roots | +++ | +++ | − |
|  | Leaves | +++ | ++ | − |
| Flowering | Leaves | +++ | +++ | − |
| Late reproductive | Kernels | +++ | +++ | ++** |

*GUS histochemical assays: a range of GUS activities (− no expression to ++++ high expression),
**only in endosperm,
ND: not determined Example 2

IME-Introns Located in the Annotated DNA Sequences 2.1 In Silico Screening System The in silico intron-screening system for identifying introns that have the functional IME comprises three major components: (1) Generate intron sequence database and screen for intron candidates using the functional IME criteria (indicated in Example 1.3); (2) Define the expression profiles of these candidate genes from which introns were selected; (3) Further examine the selected gene structures by conducting a mapping of EST sequences onto the genomic region where the candidate genes resided.

More than 30,000 annotated rice and maize genomic sequences were downloaded from NCBI. Intron, 5- and 3-UTR, promoter and terminator sequences were isolated (in silico) from those annotated genes and their corresponding sequence databases were generated (Table 10, 11). From the generated intron sequence database, more than 111,800 introns (i.e., 106049 rice introns, 4587 maize introns) were screened for potential intron regulatory enhancement elements based on the functional IME criteria (see 1.3). A total of 108 potential intron candidates have been identified, and the protein sequences of the intron candidate genes were retrieved from NCBI. The rice (we do not disclose maize sequences) homolog EST sequences were identified from the cDNA libraries described in example 1 using the BLASTx algorithm (this program compares the six-frame conceptual translation products of a nucleotide query sequence (both strands) against protein sequences) at an E-value of $1.0e^{-20}$ against those protein sequences. Using the rice variant expression profiling data (see example 1), the introns whose genes were homolog to the rice genes with desirable expression profiling, such as constitutive and tissue specific expression pattern, were selected as final in silico identified intron candidates for lab experimental test.

The rice UniGenes, which was derived from the EST sequence assembly, were updated using the combined public rice EST data and the EST data obtained using the databases described in example 1, and the UniGene expression profiling data was generated using the rice variant expression profiling data over the 23 different libraries described in example 1. The newly updated rice UniGene expression profiling data were used to help select the final 108-intron candidates. Perl scripts have been written to isolate intron, 5- and 3-UTR, terminator, and promoter sequences from the entire NCBI rice and maize annotated gnomic DNA sequences for creating corresponding sequence databases, to screen for functional IME, and to compare the expression profiling data (see example 5). The introns were retrieved from the CDS (coding sequences) features of the annotated genes. A total of 106,049 rice introns and 4,587 maize introns have been retrieved (Table 10) from more that 30,000 annotated genes as the data summarized in Table 11 and 12.

TABLE 10

| Rice/maize sequence database summary | | |
|---|---|---|
|  | Rice | Maize |
| Intron | 106049 | 4587 |
| 5' UTR | 129 | 236 |
| 3' UTR | 142 | 694 |
| Terminator | 7 | 5 |
| Promoter | 69 | 239 |

TABLE 11

| Rice and maize gene summary* | | |
|---|---|---|
| Average | Rice | Maize |
| gene length | 2471 | 3223 |
| intron length | 399 | 279 |
| extron length | 309 | 388 |
| intron/gene | 3.9 | 2.61 |
| extron/gene | 4 | 2.45 |
| GC/intron | 39% | 40.8% |
| GC/extron | 54.8% | 55.3% |

*Intron or extron without gene names were excluded from the calculation.

TABLE 12

| Total number of genes in the database | | |
|---|---|---|
| Species | Gene Name | Gene Identifier |
| Rice | 30059 | 30249 |
| Maize | 1281 | 3549 |

Furthermore, The full length coding sequences of all 108 candidate genes, in which introns were isolated, were downloaded from NCBI and blasted against the Hyseq rice and maize UniGenes to identify Hyseq rice and maize homolog sequences, using BLASTN and $1.0e^{-20}$ cutoff E-value. Top hits of rice UniGenes were selected, and the gene expression profiling data was examined. The EST sequences, identified as homolog to the coding sequences of selected intron candidate genes, were retrieved and mapped along with the intron candidate gene sequences to the rice genomic regions. Based on the UniGene expression profiling data and the candidate gene structures, annotated and confirmed by the EST sequence alignments, nine introns were finally selected from a total of 108 intron candidates and are subject to the real time RT-PCR expression test. Among the nine introns, four showed a constitutive expression pattern, three preferably expressed in the early seed-developed stage, one preferably expressed in root, and one was induced in the drought condition (Table 13).

TABLE 13

Intron candidates selected based on the second in silico screening system

| Intron | Rice GI number | Sequence homology |
| --- | --- | --- |
| BPSI.5 (SEQ ID No. 5) | 9624451 | Sucrose transporter |
| BPSI.6 (SEQ ID No. 6) | 7523493 | Similar to *Arabidopsis thaliana* chromosome II sequence from clones T22O13, F12K2; putative lipase (AC006233) |
| BPSI.7 (SEQ ID No. 7) | 20161203 | putative cinnamyl-alcohol dehydrogenase |
| BPSI.8 (SEQ ID No. 8) | 18921322 | Putative ribonucleoprotein |
| BPSI.9 (SEQ ID No. 9) | 12061241 | putative mitochondrial carrier protein |
| BPSI.10 (SEQ ID No. 10) | 20160990 | Putative protein kinase |
| BPSI.11 (SEQ ID No. 11) | 886404 | 5 UTR intron (1$^{st}$) MADS3 box protein |

2.2 Isolation of the Intron Candidates

Genomic DNA from rice was extracted using the Qiagen DNAeasy Plant Mini Kit (Qiagen). Genomic DNA regions containing introns of interest were isolated using conventional PCR. Approximately 0.1 µg of digested genomic DNA was used for the regular PCR reaction (see below). The primers were designed based on the rice genomic sequences. Five µL of the diluted digested genomic DNA was used as the DNA template in the PCR reaction. PCR was performed using the TripleMaster PCR System (Eppendorf, Hamburg, Germany) as described by the manufacturer.

TABLE 14

Primers used for amplification of widely expressed intron candidates

| Primers | Sequence |
| --- | --- |
| BPSI.5-5 (SEQ ID No. 61) | 5-cggggtacgagctctctggtggctgaggtaagttctgttattacc |
| BPSI.5-3 (SEQ ID No. 62) | 5-cggggatccggacaggaaaacctgaaaacaggg |
| BPSI.6-5 (SEQ ID No. 63) | 5-cggggtaccgagctcgacgatttaggtaagtcattattgtctc |
| BPSI.6-3 (SEQ ID No. 64) | 5-cggggatcctcactgaaacctgcagtgtagg |
| BPSI.7-5 (SEQ ID No. 65) | 5-cggggtaccgagctcgatcctaaggtaagcactctagctg |
| BPSI.7-3 (SEQ ID No. 66) | 5-cggggatccgtaactcaacctgttttttta |
| BPSI.8-5 (SEQ ID No. 67) | 5-cggggtaccgagctccaatggctaggtaagtatatgcttcc |
| BPSI.8-3 (SEQ ID No. 68) | 5-cggggatcccccatcaagtacctgttttaag |
| BPSI.9-5 (SEQ ID No. 69) | 5-cgggtaccgagctcgaatacctaggtaagtccatctc |
| BPSI.9-3 (SEQ ID No. 70) | 5-cggggatcccacacaagcgacctggaaaaataagc |
| BPSI.10-5 (SEQ ID No. 71) | 5-cgggtaccgagctcccatcttttaggtaagtatctttgcg |
| BPSI.10-3 (SEQ ID No. 72) | 5-cggggatccggtaaagaacctgtttaatac |
| BPSI.11-5 (SEQ ID No. 73) | 5-cggggtaccgagctctgaacaggaaggtaagttctggctttcttgc |
| BPSI.11-3 (SEQ ID No. 74) | 5-ggggatcctcagatcgacctggacacaaacgc |

Amplification was carried out in the PCR reaction (5 µL 10× Advantage PCR Mix [Eppendorf], 5 µL genomic DNA [corresponds to approximately 80 ng], 2.5 mM of each dATP, dCTP, dGTP and dTTP [Invitrogen:dNTP mix], 1 µL of 20 µM 5-intron specific primer 20 pM, 1 µL of 20 µM 3 intron specific primer, 1 µL TripleMaster DNA Polymerase mix [Eppendorf], in a final volume of 50 µL) under the optimized PCR program (1 cycle with 15 sec at 94° C. and 1 min at 80° C. 35 cycles with 15 sec at 94° C., 1 min at 58° C. and 1 min at 72° C.) provided by Thermocycler (T3 Thermocycler Biometra).

A QIAspin column was used to purify the PCR products as directed by the manufacturer (Qiagen, Valencia, Calif.), and the amplified introns were used directly for cloning into expression vectors, as described below.

2.3 Vector Construction

The base expression vector for these experiments was pBPSMM305, which comprises the maize lactate dehydrogenase (LDH) promoter without intron driving expression of the GUSint gene followed by the NOS terminator. The LDH promoter has been demonstrated to direct undetectable levels of GUS expression by colorimetric staining in the absence of an intron capable of providing IME.

Intron PCR products were digested with SacI & BamHI and cloned into pBPSMM305 linearized with SacI & BamHI, generating the following LDH:intron:GUS expression vectors.

TABLE 15

GUS chimeric constructs containing introns in the 5 UTR

| pUC-based expression vector | Composition of the expression cassette (promoter::intron::reporter gene::terminator) |
|---|---|
| pBPSJB041 (pBPSLI017) | ZmLDH promoter::BPSI.5::GUS::NOS3 |
| pBPSJB042 (pBPSLI018) | ZmLDH promoter::BPSI.6::GUS::NOS3 |
| pBPSJB043 (pBPSLI019) | ZmLDH promoter::BPSI.7::GUS::NOS3 |
| pBPSJB044 (pBPSLI020) | ZmLDH promoter::BPSI.8::GUS::NOS3 |
| pBPSJB045 (pBPSLI021) | ZmLDH promoter::BPSI.9::GUS::NOS3 |
| pBPSJB046 (pBPSLI022) | ZmLDH promoter::BPSI.10::GUS::NOS3 |
| pBPSJB050 (pBPSLI023) | ZmLDH promoter::BPSI.11::GUS::NOS3 |

Binary vector pBPSLI017 comprises the expression cassette containing the BPSI.5 intron and was generated by ligating in the PmeI-PacI fragment from pBPSJB041 into pBPSLM139 linearized with PmeI and PacI.

Binary vector pBPSLI018 comprises the expression cassette containing the BPSI.6 intron and was generated by ligating in the PmeI-PacI fragment from pBPSJB042 into pBPSLM139 linearized with PmeI and PacI.

Binary vector pBPSLI019 comprises the expression cassette containing the BPSI.7 intron and was generated by ligating in the PmeI-PacI fragment from pBPSJB043 into pBPSLM139 linearized with PmeI and PacI.

Binary vector pBPSLI020 comprises the expression cassette containing the BPSI.8 intron and was generated by ligating in the PmeI-PacI fragment from pBPSJB044 into pBPSLM139 linearized with PmeI and PacI.

Binary vector pBPSLI021 comprises the expression cassette containing the BPSI.9 intron and was generated by ligating in the PmeI-PacI fragment from pBPSJB045 into pBPSLM139 linearized with PmeI and PacI.

Binary vector pBPSLI022 comprises the expression cassette containing the BPSI.10 intron and was generated by ligating in the PmeI-PacI fragment from pBPSJB046 into pBPSLM139 linearized with PmeI and PacI.

Binary vector pBPSLI023 comprises the expression cassette containing the BPSI.11 intron and was generated by ligating in the PmeI-PacI fragment from pBPSJB050 into pBPSLM139 linearized with PmeI and PacI.

2.4 Transient Assays for Identifying the Intron Functioning IME

These experiments were performed by bombardment of plant tissues or culture cells (Example 4.1), or by *Agrobacterium*-mediated transformation (Example 4.3). The target tissues for these experiments can be plant tissues (e.g. leaf or root), cultured cells (e.g. maize BMS), or plant tissues (e.g. immature embryos) for *Agrobacterium* protocols. Characterization of these introns for their ability to direct IME in conjunction with the LDH promoter was undertaken via transient expression by bombardment of expression vectors into maize leaf tissue and liquid-cultured BMS cells, respectively.

The maize lactate dehydrogenase promoter (ZmLDH) without any intronic sequence was used as basal expression (negative control). Introns of interest were cloned into the 5 UTR region of ZmLDH promoter. Maize ubiquitin intron was used as a positive control to measure the relative levels of expression enhanced by introns of interest based on GUS expression.

Due to the very low background (no detectable GUS expression) of the ZmLDH promoter in the absence of intron, the presence of any GUS staining indicates that a particular intron is capable of providing IME. Of the introns tested, BPSI.10 and BPSI.11 introns consistently yielded the highest GUS expression, at a level comparable to the LDH::Zm.ubiquitin intron construct. In addition to these introns, BPSI.5, BPSI.6, and BPSI.7 introns consistently resulted in an intermediate level of GUS expression in between LDH alone and LDH::Zm.ubiquitin intron. Comparable results were obtained in maize leaves and BMS cells, indicating that the tested introns confer IME in green and non-green tissues (Table 16).

TABLE 16

Transient GUS expression testing for intron-mediated enhancement

| | GUS expression* | |
|---|---|---|
| Intron candidates | leaves | BMS |
| No intron (Zm.LDH promoter alone) | − | − |
| Zm.LDH + Zm.ubiquitin intron (positive control) | ++++ | ++++ |
| Zm.LDH promoter + BPSI.5 | ++ | ++ |
| Zm.LDH promoter + BPSI.6 | +++ | +++ |
| Zm.LDH promoter + BPSI.7 | +++ | +++ |
| Zm.LDH promoter + BPSI.8 | − | + |
| Zm.LDH promoter + BPSI.9 | − | − |
| Zm.LDH promoter + BPSI.10 | ++++ | +++ |
| Zm.LDH promoter + BPSI.11 | ++++ | ND |

*GUS histochemical assays: a range of GUS activities (− no expression to ++++ high expression),
ND: not determined.

Example 3

Identification of IME-Introns Located in the 5' Untranslated Region 3.1 In Silico Screening System The in silico intron screening system for identifying introns that have the functional IME located in the '5 UTR comprises three major components: (1) Genome mapping of the entire rice CDS, released from Institute of Genome Research on Oct. 2, 2003 and the EST sequence collections; (2) identification and selection of the introns located in the 5 UTR using both the functional IME criteria and the rice cDNA clone distribution profiles; (3) validation of the selected 5 UTR introns by examining the sequence alignments among the genomic DNA, CDS and ESTs, the gene model, sequence reading frame and intron splicing sites A total of 56,056 annotated rice CDS were mapped onto the Japonica rice genome in which both rice CDS and genomic DNA sequences were obtained from The Institute of Genome Research. Additional 422,882 rice EST sequences of public and in-house sources were also mapped onto the rice genome. A splicing alignment software, GeneSeqer (version Sep. 2, 2003 from Iowa State University Research foundation), was used to conduct the entire genome mapping. Since both EST and CDS were mapped onto their corresponding genomic regions, the sequence alignment coordinators [coordinators are the start and/or end positions of the genomic sequences where CDS/EST sequences aligned to] derived from the CDS mapping and the EST mapping on the same genomic region provide opportunity to identify the alignment extension of the EST sequences along the genomic DNA beyond the start codon of the CDS. Such sequence alignment extension from the EST sequences beyond CDS indicates the identification of the 5 UTRs, which have not been contained in the CDS, but in the EST sequences. The system selects these EST sequences, which extend the sequence alignment beyond the CDS along the gnome for up to 5 k base long for 5 URT intron screening. For any predicted exons, the last exon in the predicated 5 UTR region must aligned at the same position of the 1st exon of the CDS. The gnome mapping results have identified 461 genes that have their 5 UTR containing at least one intron.

Further stringent screen criteria that required at least 3 EST sequences confirming the same predicted 5 UTR introns were used to select the gene candidates, leading to identify 87 gene candidates. Those identified EST sequences, which were considered as the same transcript as the rice CDS, were used to retrieve the rice cDNA clone distribution data or the microarray expression data in which either the clones of those identified EST sequences have been spotted on the rice microarray chip or homolog to those identified EST sequences were identified on the chip. For given the rice cDNA clone distribution profile, a gene, which has a cluster/variant size of more than 100 clones distributed over 23 cDNA libraries, was considered highly expressed. For given the microarray expression, a gene, which has hybridization signal intensity exceeding the top 25% percentile within the same sample, was also considered highly expressed.

In addition to the gene expression criteria used for gene candidate selection, the IME criteria (indicated in Example 1.3) were applied.

Furthermore, a validation of the selected candidate genes was conducted by examining the coincidence of the sequence alignments between EST, CDS sequences and genomic DNA sequence. Clearly the EST sequences needed to support the gene model predicted from the CDS. Any conflict of the sequence alignments between EST and CDS would result in the deselecting the candidate genes. Using those criteria, a final list of 11 introns was selected (Table 17).

TABLE 17

Intron candidates selected based on the third in silico screening system

| Intron | Rice GI number | Sequence homology |
|---|---|---|
| BPSI.12 (SEQ ID No. 12) | 29620794 | Putative adenosylmethionine decarboxy-lase |
| BPSI.13 (SEQ ID No. 13) | 33666702 | Aspartic proteinase |
| BPSI.14 (SEQ ID No. 14) | 29678665 | Lec14b protein |
| BPSI.15 (SEQ ID No. 15) | 35009827 | Putative mannose-binding rice lectin |
| BPSI.16 (SEQ ID No. 16) | 41883853 | Putative reticulon |
| BPSI.17 (SEQ ID No. 17) | 2799981 | Glycolate oxidase |
| BPSI.18 (SEQ ID No. 18) | 34763855 | Similar to AT4g33690/T16L1_180 |
| BPSI.19 (SEQ ID No. 19) | 32533738 | N/A |
| BPSI.20 (SEQ ID No. 20) | 33657147 | Hypothetical protein |
| BPSI.21 (SEQ ID No. 21) | 33800379 | Putative membrane transporter |
| BPSI.22 (SEQ ID No. 22) | 2309889 | Putative ACT domain repeat protein |

3.2 Isolation of Introns

Genomic DNA containing introns of interest is isolated using conventional PCR amplification with sequence specific primers (see 1.4) followed by cloning into a PCR cloning vector in the art.

3.3 Vector Construction

Introns are PCR amplified from rice genomic DNA using primers that engineer a SacI site on the 5 end of the intron and a BamHI site on the 3 end of the sequence. The PCR products are digested with SacI and BamHI and ligated into pBPSMM305 linearized with SacI and BamHI to generate pUC-based expression vectors comprising the Zm.LDH promoter::Intron candidate::GUSint::NOS terminator.

Binary vectors for stable plant transformation are constructed by digesting the pUC expression vectors with PmeI and PacI and ligating into pBPSLM139 digested with PmeI and PacI.

3.4 Transient Assays for Identifying IME-Introns.

These experiments are performed by bombardment of plant tissues or culture cells (Example 4.1), or by *Agrobacterium*-mediated transformation (Example 4.3). The target tissues for these experiments can be plant tissues (e.g. leaf or root), cultured cells (e.g. maize BMS), or plant tissues (e.g. immature embryos) for *Agrobacterium* protocols.

Example 4

Assays for Identifying IME-Introns

These experiments are performed by bombardment of plant tissues or culture cells (Example 4.1), by PEG-mediated (or similar methodology) introduction of DNA to plant protoplasts (Example 4.2), or by *Agrobacterium*-mediated transformation (Example 4.3). The target tissue for these experiments can be plant tissues (e.g. leaf tissue), cultured plant cells (e.g. maize Black Mexican Sweetcorn (BMS), or plant embryos for *Agrobacterium* protocols.

4.1 Transient Assay Using Microprojectile Bombardment

The plasmid constructs are isolated using Qiagen plasmid kit (cat#12143). DNA is precipitated onto 0.6 µM gold particles (Bio-Rad cat#165-2262) according to the protocol described by Sanford et al. (1993) and accelerated onto target tissues (e.g. two week old maize leaves, BMS cultured cells, etc.) using a PDS-1000/He system device (Bio-Rad). All DNA precipitation and bombardment steps are performed under sterile conditions at room temperature.

Black Mexican Sweet corn (BMS) suspension cultured cells are propagated in BMS cell culture liquid medium [Murashige and Skoog (MS) salts (4.3 g/L), 3% (w/v) sucrose, myo-inositol (100 mg/L), 3 mg/L 2,4-dichlorophenoxyacetic acid (2,4-D), casein hydrolysate (1 g/L), thiamine (10 mg/L) and L-proline (1.15 g/L), pH 5.8]. Every week 10 mL of a culture of stationary cells are transferred to 40 mL of fresh medium and cultured on a rotary shaker operated at 110 rpm at 27° C. in a 250 mL flask.

60 mg of gold particles in a siliconized Eppendorf tube are resuspended in 100% ethanol followed by centrifugation in a Mini centrifuge C1200 (National Labnet Co. Woodbridge, N.J.) for 30 seconds. The pellet is rinsed once in 100% ethanol and twice in sterile water with centrifugation after each wash. The pellet is finally resuspended in 1 mL sterile 50% glycerol. The gold suspension is then divided into 50 µL aliquots and stored at 4° C. The following reagents are added to one aliquot: 5 µL of 1 µg/µL total DNA, 50 µL 2.5M $CaCl_2$, 20 µL 0.1M spermidine, free base. The DNA solution is vortexed for 1 minute and placed at −80° C. for 3 min followed by centrifugation for 10 seconds in a Mini centrifuge C1200. The supernatant is removed. The pellet is carefully resuspended in 1 mL 100% ethanol by flicking the tube followed by centrifugation for 10 seconds. The supernatant is removed and the pellet is carefully resuspended in 50 µL of 100% ethanol and placed at −80° C. until used (30 min to 4 hr prior to bombardment). If gold aggregates are visible in the solution the tubes are sonicated for one second in a waterbath sonicator just prior to use.

For bombardment, two-week-old maize leaves are cut into pieces approximately 1 cm in length and placed ad-axial side up on osmotic induction medium M-N6-702 [N6 salts (3.96 g/L), 3% (w/v) sucrose, 1.5 mg/L 2,4-dichlorophenoxyacetic acid (2,4-D), casein hydrolysate (100 mg/L), and L-proline (2.9 g/L), MS vitamin stock solution (1 mL/L), 0.2 M mannitol, 0.2 M sorbitol, pH 5.8]. The pieces are incubated for 1-2 hours.

In the case of BMS cultured cells, one-week-old suspension cells are pelleted at 1000 g in a Beckman/Coulter Avanti J25 centrifuge and the supernatant is discarded. Cells are placed onto round ash-free No 42 Whatman filters as a 1/16 inch thick layer using a spatula. The filter papers holding the plant materials are placed on osmotic induction media at 27° C. in darkness for 1-2 hours prior to bombardment. Just before bombardment the filters are removed from the medium and placed onto on a stack of sterile filter paper to allow the calli surface to partially dry.

Each plate is shot with 6 µL of gold-DNA solution twice, at 1,800 psi for the leaf materials and at 1,100 psi for the BMS cultured cells. To keep the position of plant materials, a sterilized wire mesh screen is laid on top of the sample. Following bombardment, the filters holding the samples are transferred onto M-N6-702 medium lacking mannitol and sorbitol and incubated for 2 days in darkness at 27° C. prior to transient assays. Transient expression levels of the reporter genes are determined by GUS staining, quantification of luminescence or RT-PCR using the protocols in the art. GUS staining is done by incubating the plant materials in GUS solution [100 mM NaHPO4, 10 mM EDTA, 0.05% Triton X100, 0.025% X-Gluc solution (5-bromo-4-chloro-3-indolyl-beta-D-glucuronic acid dissolved in DMSO), 10% methanol, pH 7.0] at 37° C. for 16-24 hours. Plant tissues are vacuum-infiltrated 2 times for 15 minutes to aid even staining.

Transient expression levels of the reporter genes are determined by staining, enzyme assays or RT-PCR using the protocols in the art.

4.2 Transient Assay Using Protoplasts

Isolation of protoplasts is conducted by following the protocol developed by Sheen (1990). Maize seedlings are kept in the dark at 25° C. for 10 days and illuminated for 20 hours before protoplast preparation. The middle part of the leaves are cut to 0.5 mm strips (about 6 cm in length) and incubated in an enzyme solution containing 1% (w/v) cellulose RS, 0.1% (w/v) macerozyme R10 (both from Yakult Honsha, Nishinomiya, Japan), 0.6 M mannitol, 10 mM Mes (pH 5.7), 1 mM $CaCl_2$, 1 mM $MgCl_2$, 10 mM β-mercaptoethanol, and 0.1% BSA (w/v) for 3 hr at 23° C. followed by gentle shaking at 80 rpm for 10 min to release protoplasts. Protoplasts are collected by centrifugation at 100×g for 2 min, washed once in cold 0.6 M mannitol solution, centrifuged, and resuspended in cold 0.6 M mannitol ($2\times10^6$/mL).

A total of 50 µg plasmid DNA in a total volume of 100 µL sterile water is added into 0.5 mL of a suspension of maize protoplasts ($1\times10^6$ cells/mL) and mix gently. 0.5 mL PEG solution (40% PEG 4,000, 100 mM $CaNO_3$, 0.5 mannitol) is added and pre-warmed at 70° C. with gentle shaking followed by addition of 4.5 mL MM solution (0.6 M mannitol, 15 mM $MgCl_2$, and 0.1% MES). This mixture is incubated for 15 minutes at room temperature. The protoplasts are washed twice by pelleting at 600 rpm for 5 min and resuspending in 1.0 mL of MMB solution [0.6 M mannitol, 4 mM Mes (pH 5.7), and brome mosaic virus (BMV) salts (optional)] and incubated in the dark at 25° C. for 48 hr. After the final wash step, collect the protoplasts in 3 mL MMB medium, and incubate in the dark at 25° C. for 48 hr. Transient expression levels of the reporter gene are determined quantification of expression of reporter genes or RT-PCR using the protocols in the art in order to determine potentially intron candidates that function in intron-mediated enhancement.

4.3 *Agrobacterium*-Mediated Transformation in Dicotyledonous and Monocotyle-Donous Plants 4.3.1 Transformation and Regeneration of Transgenic *Arabidopsis thaliana* (Columbia) Plants To generate transgenic *Arabidopsis* plants, *Agrobacterium tumefaciens* (strain C58C1 pGV2260) is transformed with the various vector constructs described above. The Agrobacterial strains are subsequently used to generate transgenic plants. To this end, a single transformed *Agrobacterium* colony is incubated overnight at 28° C. in a 4 mL culture (medium: YEB medium with 50 µg/mL kanamycin and 25 µg/mL rifampicin). This culture is subsequently used to inoculate a 400 mL culture in the same medium, and this is incubated overnight (28° C., 220 rpm) and spun down (GSA rotor, 8,000 rpm, 20 min). The pellet is resuspended in infiltration medium (½ MS medium; 0.5 g/L MES, pH 5.8; 50 g/L sucrose). The suspension is introduced into a plant box (Duchefa), and 100 ml of SILWET L-77 (heptamethyltrisiloxan modified with polyalkylene oxide; Osi Specialties Inc., Cat. P030196) is added to a final concentration of 0.02%. In a desiccator, the plant box with 8 to 12 plants is exposed to a vacuum for 10 to 15 minutes, followed by spontaneous aeration. This is repeated twice or 3 times. Thereupon, all plants are planted into flowerpots with moist soil and grown under long-day conditions (daytime temperature 22 to 24° C., nighttime temperature 19° C.; relative atmospheric humidity 65%). The seeds are harvested after 6 weeks.

As an alternative, transgenic *Arabidopsis* plants can be obtained by root transformation. White root shoots of plants with a maximum age of 8 weeks are used. To this end, plants that are kept under sterile conditions in 1 MS medium (1% sucrose; 100 mg/L inositol; 1.0 mg/L thiamine; 0.5 mg/L pyridoxine; 0.5 mg/L nicotinic acid; 0.5 g MES, pH 5.7; 0.8% agar) are used. Roots are grown on callus-inducing medium for 3 days (1× Gamborg s B5 medium; 2% glucose; 0.5 g/L mercaptoethanol; 0.8% agar; 0.5 mg/L 2,4-D (2,4-dichlorophenoxyacetic acid); 0.05 mg/L kinetin). Root sections 0.5 cm in length are transferred into 10 to 20 mL of liquid callus-inducing medium (composition as described above, but without agar supplementation), inoculated with 1 mL of the above-described overnight *Agrobacterium* culture (grown at 28° C., 200 rpm in LB) and shaken for 2 minutes. After excess medium has been allowed to run off, the root explants are transferred to callus-inducing medium with agar, subsequently to callus-inducing liquid medium without agar (with 500 mg/L betabactyl, SmithKline Beecham Pharma GmbH, Munich), incubated with shaking and finally transferred to shoot-inducing medium (5 mg/L 2-isopentenyladenine phosphate; 0.15 mg/L indole-3-acetic acid; 50 mg/L kanamycin; 500 mg/L betabactyl). After 5 weeks, and after 1 or 2 medium changes, the small green shoots are transferred to germination medium (1 MS medium; 1% sucrose; 100 mg/L inositol; 1.0 mg/L thiamine; 0.5 mg/L pyridoxine; 0.5 mg/L nicotinic acid; 0.5 g MES, pH 5.7; 0.8% agar) and regenerated into plants.

4.3.2 Transformation and Regeneration of Crop Plants

The *Agrobacterium*-mediated plant transformation using standard transformation and regeneration techniques may also be carried out for the purposes of transforming crop plants (Gelvin & Schilperoort (1995) Plant Molecular Biology Manual, $2^{nd}$ Edition, Dordrecht: Kluwer Academic Publ. ISBN 0-7923-2731-4; Glick & Thompson (1993) Methods in Plant Molecular Biology and Biotechnology, Boca Raton: CRC Press, ISBN 0-8493-5164-2). For example, oilseed rape can be transformed by cotyledon or hypocotyl transformation (Moloney (1989) Plant Cell Reports 8: 238-242). The use of antibiotics for the selection of *agrobacteria* and plants depends on the binary vector and the *Agrobacterium* strain used for the transformation. The selection of oilseed rape is generally carried out using kanamycin as selectable plant marker. The *Agrobacterium*-mediated gene transfer in linseed (*Linum usitatissimum*) can be carried out using for example a technique described by Mlynarova (1994) Plant Cell Report 13:282-285. The transformation of soybean can be carried out using, for example, a technique described in EP A10 424 047 or in EP A10 397 687, U.S. Pat. No. 5,376,543, U.S. Pat. No. 5,169,770. The transformation of maize or other monocotyledonous plants can be carried out using, for example, a technique described in U.S. Pat. No. 5,591,616. The transformation of plants using particle bombardment, polyethylene glycol-mediated DNA uptake or via the silicon carbonate fiber technique is described, for example, by Freeling & Walbot (1993) 'The maize handbook' ISBN 3-540-97826-7, Springer Verlag New York).

Example 5

Computer Algorithm for Retrieving Sequence Information from NCBI Genebank File The target feature keys are intron, terminator, promoter, UTR. The following script (written in computer language Pearl) is giving an example for a computer algorithm of the invention suitable to identify suitable intron sequences based of database information (see also FIG. 5*a-f*):

```perl
#!/usr/local/bin/perl -w
intron.pl
open(IN,$ARGV[0]) or die "can't find output";
    while (defined(my $file=<IN> )) {
start of a single annotation
    if ($file=~/LOCUS.*?\s+(\d+)\sbp(.*)/) {
            my  $length=$1;
            my  $mol=1;
            $mol=0 if $2 =~ /circular/;
        my  @cdslist=( );
        my  @start=( );
        my  $order=0; # order=1: complementary coding.
        my  @title=( );
        my  @title0=( );
        my  @intron=( );
        my  $id="";
        my  @terminator=( );
        my  @promoter=( );
        my  @utr5=( );
        my  @utr3=( );
        my  @origin=( );
        my  $tab="";
        my  $organism="";
            while (defined(my $line=<IN> )) {
            $line=$tab.$line;
            if ($line =~ /^VERSION.*?\s+(GI:\d+)/) {
                    $id=$1;
            }elsif ($line =~ /^\s{2}ORGANISM\s+(.*)/){
                if($1=~/Oryza sativa/i){
                    $organism="rice";
                    }elsif($1=~/Zea mays/i) {
                    $organism="maize";
                }elsif($1=~/Glycine max/i){
                    $organism="soybean";
                }else {
                    $1=~/(\w+)/;
                    $organism=$1;
                }
            }elsif($line =~ /^\s{5}(CDS\s*)/){   #extract cds
                my  $test=$';
                my  $gene="N/A";
        my  $start=1;
        my  $product="N/A";
        my  $gi=$id;
```

```perl
        my  @cds=( );
        my  @temp=( );
        if   ($test =~ /complement/) {
                    $order=1 ;
                }else {
                    $order = 0;
                }
                while ( my $in=<IN>) {
                if ($in =~ /^\s\/(.*)/) {
                    $test=$test;
                    if ($1=~/gene="(.*)"/) {
                        $gene=$1;
                    }elsif($1=~/note="(.*)"/) {
                        $product=$1;
                    }else {
                    last;
                    }
                } else {
                    $test=$test.$in;
                }
            } #close while loop;
                $test =~s/\w+\d+\.\d:\d+\.\.\d+//g;
                $test =~ s/\D/ /g;
                    $test =~ s/\s+/ /g;
                    $test =~ s/^\s+//;
            my @sort;
            if ($mol==0) {
                @sort=split(/ /,$test);
            } else {
                    @sort=sort {$a <=> $b} split(/ /,$test);
            }
# tag complement cds
            if ($order==1) {
                @cds = ("complement",@sort);
            } elsif ($order==0) {
                @cds = @sort;
            } #close if loop;
#retreave notation if intron exist;
            if (scalar(@cds) >= 4) {
                while (my $in=<IN>) {
                $start=1;
                    if ($in =~ /codon_start=(\d+)/) {
                    $start = $1;
                }elsif ($in =~ /\/gene="(.*)"/){
                    $gene=$1;
                }elsif ($in =~ /\/product=(.*)/){
                    $product=$1;
                    $product=~ tr/""//d;
                }elsif ($in =~ /db_xref="(GI:.*?)"/) {
                    $gi = $1;
                    last ;
                    } elsif ($in=~ /\/(pseudo)/) {
                    $product="pseudo";
                last;
                }   #close if loop
                }   #close while loop;
                push @start, $start;
                push @cdslist, \@cds;
# retreave 5'utr if start codon > 1;
                my @tem=( );
                for (my $i=1;$i<=($#cds-1)/2;$i++) {
                    my $title1=">$organism|$gi|Intron_$i ";
                    my    $title2="   $gene|$start|".($cds[2*$i-1+$order]+1)."..".($cds[2*$i+$order]-1)."|$product\n";
                    my @title=($title1,$title2);
                    push @tem, \@title;
                } #close for loop
                push @title, \@tem;
                my         $title0=">$organism|$gi|5UTR_0 $gene|$start|".($cds[$order]-1)."..".($cds[$order]+$start-2)."|$product\n";
                push @title0, $title0;
                } #close if @cds>4 loop
            } elsif ($line =~ /^\s{5}terminator/) {
                ($tab,my $note,my @term)=&getTerminator($line);
                push @terminator, $note;
                push @terminator, \@term;
```

```
        } elsif ($line =~ /^\s{5}promoter/) {
            ($tab,my $note,my @prom)=&getTerminator($line);
            push @promoter, $note;
            push @promoter, \@prom;
        } elsif ($line =~ /^\s{5}5\DUTR/) {
            ($tab,my $note,my @temp)=&getTerminator($line);
            push @utr5,$note;
            push @utr5,\@temp;
        } elsif ($line =~ /^\s{5}3\DUTR/) {
            ($tab,my $note,my @temp)=&getTerminator($line);
            push @utr3,$note;
            push @utr3,\@temp;
#get sequence @origin
        }
        if ($line =~ /^(ORIGIN)/) {
            $line="";
            while (my $code=<IN>) {
                if ($code =~ /\/\//) {
                    last;
                }else{
                    $line=$line.$code;
                } #close if loop
            } #close while loop
        # $line =~ s/\/\//g;
        # print $line,"\n";
            $line =~ tr/0-9//d;
            $line =~ tr/ //d;
            $line =~ tr/\n//d;
            @origin = split(//,$line);
            for (my $i=0; $i<=$#cdslist;$i++) {
                if ($start[$i]>2) {
                    my  @first=( );
                    my  $first;
                    if (${$cdslist[$i]}[0] eq "complement") {
                        my         @utr=@origin[$cdslist[$i][1]-1
($cdslist[$i][1]+$start[$i]-2)];
                        print @utr,"\n";
                        $first=&complement(@utr);
                    } else {
                        @first=@origin[$cdslist[$i][0]-1
($cdslist[$i][0]+$start[$i]-2)];
                        $first=join('',@first);
                    } #close if loop for complement
                    print $title0[$i],$first,"\n\n";
                }   #close if loop for $start>2;
                if (${$cdslist[$i]}[0] eq "complement") {
                    shift @{$cdslist[$i]};
                    for (my $j=1; $j<=($#{$cdslist[$i]}-1)/2;$j++) {
                        my         @int=@origin[$cdslist[$i][2*$j-1]
$cdslist[$i][2*$j]-2];
                        my $int1=&complement(@int);
                        print     $title[$i][$j-1][0],scalar(@int),$title[$i][$j-
1][1], $int1,"\n\n" if $#int<5000;
                    } #close 2nd for loop for complement
                } else {
                    for (my $j=1; $j<=($#{$cdslist[$i]}-1)/2;$j++) {
                        my @int=@origin[$cdslist[$i][2*$j-1] .. $cdslist[$i][2*$j]-
2];
                        if ($mol==0 && $cdslist[$i][2*$j-1] > $cdslist[$i][2*$j]) {
                            @int=(@origin[$cdslist[$i][2*$j-1]     ..      $#origin],
@origin[0 .. $cdslist[$i][2*$j]-2]);
                        }
                        my $int1=join('',@int);
                        print     $title[$i][$j-1][0],scalar(@int),$title[$i][$j-
1][1], $int1,"\n\n" if $#int < 5000;
                    }#close 2nd for loop
                } #close else loop
            } #close 1st for loop
            my $title1=">$organism|$id|terminator";
            &getSequence(\@terminator,\@origin,$title1);
            $title1=">$organism|$id|promoter";
            &getSequence(\@promoter,\@origin,$title1);
            $title1=">$organism|$id|5utr";
            &getSequence(\@utr5,\@origin,$title1);
            $title1=">$organism|$id|3utr";
            &getSequence(\@utr3,\@origin,$title1);
            last;
        } else {
            $tab="";
        } #close if $line loop
    } #close while $line loop
    next;
    } #close if $file loop
} #close while $file loop
close IN;
#retreave complement sequnce
sub complement{
    my @code=@_;
    my @complemnt=( );
    for (my $i=0;$i<=$#code;$i++) {
        if ($code[$#code-$i] eq "t") {
            $complement[$i]= "a";
        } elsif ($code[$#code-$i] eq "a") {
            $complement[$i]= "t";
        } elsif ($code[$#code-$i] eq "c") {
            $complement[$i]= "g";
        } elsif ($code[$#code-$i] eq "g") {
            $complement[$i]= "c";
        } else {
            $complement[$i]=$code[$#code-$i];
        }#close if loop
    } #close for loop
    my $comp=join('',@complement);
    @complement=( );
    return $comp;
} #close sub
get sequence reference for feature keys
sub getTerminator {
    my $line=$_[0];
    my $order=0;
    if ($line=~/complement/) {
        $order=1;
    } else {
    } #close if loop
    $line =~ s/\d'UTR//;
    $line =~ s/\D/ /g;
    $line =~ s/\s+/ /g;
    $line =~ s/^\s//;
    my @term=split(' ',$line);
    @term=("c",@term) if $order==1;
    my $in;
    read(IN,$in,6);
    my $note =" \n";
    if ($in!~/\w/) {
        $note=<IN>;
        $note=~s/\s+\///;
        $note=~s/note=//;
        $note=~ tr/'"//d;
    } #close if loop
    return ($in,$note,@term);
} #close sub
retreave sequence information for feature keys
sub getSequence {
    my @array=@{$_[0]};
    my @code=@{$_[1]};
    my $id=$_[2];
    for (my $i=0; $i<($#array+1)/2;$i++) {
        my $note=$array[2*$i];
        my @term=@{$array[2*$i+1]};
        if ($term[0] eq "c") {
            shift @term;
            for (my $j=0; $j<=($#term-1)/2;$j++) {
                my @comp=@code[($term[2*$j]-1) .. ($term[2*$j+1]-1)];
                my $int1=&complement(@comp);
                my       $title=$id."_".($i+1)."    ".scalar(@comp)."
$term[2*$j]..$term[2*$j+1]|$note";
                print $title, $int1,"\n\n";
            } #close 2nd for loop
        } else {
            for (my $j=0; $j<($#term+1)/2;$j++) {
```

-continued

```
    my @int=@code[($term[2*$j]-1) .. ($term[2*$j+1]-1)];
        my $int1=join('',@int);
        my      $title=$id."_".($i+1)."      ".scalar(@int)."
    $term[2*$j]..$term[2*$j+1]|$note";
        print $title, $int1,"\n\n";
        } #close 2nd for loop
    } #close if loop
    } #close 1st for loop
} #close sub
```

Example 6

Expression of Tissue-Specific Promoters in Combination with IME-Introns

BPSI.1 and BPSI.5 have been fused with various monocot promoters and demonstrated that most of these promoters without IME-intron did not show GUS expression, but IME-introns have enhanced expression.

6.1 Os.CP12 Promoter::BPSI.1 Intron::GUS::NOS Terminator (pBPSMM355)

pBPSMM355 shows strong leaf-specific expression. This expression was detected in all tested developmental stages. No expression was detected in any other tissue tested.

6.2 Zm.HRGP Promoter::BPSI.1 Intron::GUS::NOS Terminator (pBPSMM370)

pBPSMM370 is strongly expressed in roots. Significant expression was also detected in silk and in the outermost layers of the kernel that include the aleuron layer and seed coat. This expression was strongest around the base of the kernel. Staining in silk was strongest in the region close to the attachment point with the kernel and was detected at very early developmental stages.

6.3 Os.CCoAMT1 Promoter::BPSI.1 Intron::GUS::NOS Terminator (pBPSMM358)

Os.Caffeoyl-CoA-O-methyltransferase (CCoAMT1) promoter in combination with BPSI.1 (pBPSMM358) showed embryo-specific expression in T1 and T2 kernels. The expression level was low but very specific. No expression was detected in any other tissue tested.

6.4 Zm.Globulin1 Promoter::BPSI.1 Intron::GUS::NOS Terminator (EXS1025)

EXS1025 is strongly expressed in the embryo. This expression starts between 5 days after pollination (DAP) and 10DAP. Expression is strongest in the scutellum and weaker in the embryo axis (plumule with leaves and internodes, primary root).

Significant expression was also detected in the outermost layers of the kernel that include the aleuron layer. Expression is strongest at stages 15DAP to 25DAP and weaker at 30DAP. Weak expression was sometimes detected in the endosperm. No expression could be detected in any other organ including pollen.

6.5 Os.V-ATPase Promoter::BPSI.1 Intron::GUS::NOS Terminator (pBPSMM369)

pBPSMM369 is strongly expressed in roots. This expression was detected in all tested stages. Significant expression was also detected in all parts of the kernels and in pollen. Weak expression was detected in the leaves at early developmental stages and at flowering. This expression was variable in strength and was in several plants at the detection limit. In general, expression was higher in homozygous T1 plants than in the heterozygous T0.

6.6 Zm.LDH Promoter::BPSI.1 Intron::GUS::NOS Terminator (pBPSMM357)

pBPSMM357 shows weak activity in kernels. Expression in kernels was mainly located in and around the embryo. Very weak expression was also detected in roots.

6.7 Os.C8,7SI Promoter::BPSI.1 Intron::GUS::NOS Terminator (pBPSMM366)

Os.C-8,7-sterol-isomerase promoter containing BPSI.1 (pBPSMM366) shows weak activity in roots and good expression in kernels.

6.8 Os.Lea Promoter::BPSI.1 Intron::GUS::NOS Terminator (pBPSMM371)

Os.Lea promoter in combination with BPSI.1 (pBPSMM371) showed strong embryo-specific expression in kernels. Some expression could be detected in root tips but no expression was detected in any other tissue tested.

6.9 Zm.LDH Promoter::BPSI.5 Intron::GUS::NOS Terminator (pBPSLM229)

pBPSLM229 shows weak expression in endosperm and aleuron layer, mainly at the top side of the kernel. No expression was detected in any other tissue tested.

What is claimed is:

1. A recombinant DNA expression construct comprising
   a) at least one promoter sequence functioning in a plant or plant cell;
   b) at least one intron comprising the sequence of SEQ ID NO: 1 or a functional equivalent thereof; and
   c) at least one nucleic acid sequence,
wherein the at least one promoter sequence and the at least one intron or functional equivalent thereof are functionally linked to the at least one nucleic acid sequence, and
wherein said intron is heterologous to said nucleic acid sequence and/or to said promoter sequence, and
wherein the functional equivalent thereof comprises a sequence having at least 80% sequence identity to the full-length sequence of SEQ ID NO: 1 and comprises
   i) an intron length shorter than 1000 base pairs, and
   ii) a 5' splice site comprising the dinucleotide sequence 5'-GT-3' (SEQ ID NO: 78), and
   iii) a 3' splice site comprising the trinucleotide sequence 5'-CAG-3' (SEQ ID NO: 79), and
   iv) a branch point resembling the consensus sequence 5'-CURAY-3' (SEQ ID NO: 75) upstream of the 3' splice site.

2. The recombinant DNA expression construct of claim 1, wherein the functional equivalent further comprises
   i) an adenine plus thymine content of at least 40% over 100 nucleotides downstream from the 5' splice site, and
   ii) an adenine plus thymine content of at least 50% over 100 nucleotides upstream from the 3' splice site, and
   iii) an adenine plus thymine content of at least 55%, and a thymine content of at least 30% over the entire intron.

3. The recombinant DNA expression construct of claim 1, wherein the intron comprises the sequence of SEQ ID NO: 3.

4. The recombinant DNA expression construct of claim 1, wherein said nucleic acid encodes
   i) a protein or
   ii) a sense, antisense, or double-stranded RNA sequence.

5. The recombinant DNA expression construct of claim 1, wherein said promoter sequence functioning in a plant or plant cell is selected from the group consisting of
   a) a promoter comprising nucleotides 1 to 854 of SEQ ID NO: 113, or a sequence having at least 95% identity to nucleotides 1 to 854 of SEQ ID NO: 113, or a sequence comprising at least 300 consecutive nucleotides of SEQ ID NO: 113;
   b) a promoter comprising nucleotides 1 to 1184 of SEQ ID NO: 114, or a sequence having at least 95% identity to nucleotides 1 to 1184 of SEQ ID NO: 114, or a sequence comprising at least 300 consecutive nucleotides of SEQ ID NO: 114;
   c) a promoter comprising nucleotides 1 to 1034 of SEQ ID NO: 115, or a sequence having at least 90% identity to nucleotides 1 to 1034 of SEQ ID NO: 115, or a sequence comprising at least 200 consecutive nucleotides of SEQ ID NO: 115;
   d) a promoter comprising nucleotides 1 to 1440 of SEQ ID NO: 116, or a sequence having at least 95% identity to nucleotides 1 to 1440 of SEQ ID NO: 116, or a sequence comprising at least 300 consecutive nucleotides of SEQ ID NO: 116;
e) a promoter comprising nucleotides 1 to 1589 of SEQ ID NO: 117, or a sequence having at least 90% identity to nucleotides 1 to 1589 of SEQ ID NO: 117, or a sequence comprising at least 200 consecutive nucleotides of SEQ ID NO: 117;
f) a promoter comprising nucleotides 1 to 796 of SEQ ID NO: 118, or a sequence having at least 95% identity to nucleotides 1 to 796 of SEQ ID NO: 118, or a sequence comprising at least 300 consecutive nucleotides of SEQ ID NO: 118;
g) a promoter comprising nucleotides 1 to 1062 of SEQ ID NO: 119, or a sequence having at least 95% identity to nucleotides 1 to 1062 of SEQ ID NO: 119, or a sequence comprising at least 300 consecutive nucleotides of SEQ ID NO: 119; and
h) a promoter comprising nucleotides 1 to 1386 of SEQ ID NO: 121, or a sequence having at least 95% identity to nucleotides 1 to 1386 of SEQ ID NO: 121, or a sequence comprising at least 300 consecutive nucleotides of SEQ ID NO: 121.

6. An expression vector comprising the recombinant expression construct of claim 1.

7. A transgenic cell or transgenic non-human organism or a cell culture, part or propagation material derived therefrom comprising the recombinant expression construct of claim 1, wherein the cell or organism is from a bacterium or plant.

8. The transgenic cell or non-human organism of claim 7, wherein said cell or organism is a monocotyledonous plant cell or organism selected from the group consisting of the genera Hordeum, Avena, Secale, Triticum, Sorghum, Zea, Saccharum, and Oryza.

9. A transgenic cell or transgenic non-human organism or a cell culture, part or propagation material derived therefrom comprising the expression vector of claim 6, wherein the cell or organism is from a bacterium or plant.

10. A method for providing an expression cassette for enhanced expression of a nucleic acid sequence in a plant or a plant cell or a plant cell culture, part or propagation material derived therefrom or for enhancing the expression of a nucleic acid sequence in a plant or a plant cell or a plant cell culture, part or propagation material derived therefrom, comprising functionally linking at least one intron to a nucleic acid sequence to be expressed,
wherein expression of the nucleic acid is enhanced relative to a plant or plant cell or a plant cell culture, part or propagation material derived therefrom that does not comprise the at least one intron,
wherein the at least one intron comprises the sequence of SEQ ID NO: 1 or a functional equivalent thereof,
wherein the functional equivalent thereof comprises a sequence having at least 80% sequence identity to the full-length sequence of SEQ ID NO: 1 and comprises
i) an intron length shorter than 1000 base pairs, and
ii) a 5' splice site comprising the dinucleotide sequence 5'-GT-3' (SEQ ID NO: 78), and
iii) a 3' splice site comprising the trinucleotide sequence 5'-CAG-3' (SEQ ID NO: 79), and
iv) a branch point resembling the consensus sequence 5'-CURAY-3' (SEQ ID NO: 75) upstream of the 3' splice site.

11. The method of claim 10, wherein said nucleic acid encodes for a selectable marker protein, a screenable marker protein, a anabolic active protein, a catabolic active protein, a biotic or abiotic stress resistance protein, a male sterility protein, or a protein affecting plant agronomic characteristics or a sense, antisense, or double-stranded RNA.

12. The method of claim 10, wherein the functional equivalent comprises a sequence having at least 95% sequence identity to the full-length sequence of SEQ ID NO: 1.

13. The method of claim 10, wherein the at least one intron comprises the sequence of SEQ ID NO: 1.

14. The method of claim 10, further comprising linking a promoter functional in plants to the nucleic acid sequence.

15. The method of claim 10, wherein the plant or plant cell or plant cell culture, part or propagation material derived therefrom are from a monocot.

16. The recombinant DNA expression construct of claim 1, wherein the functional equivalent comprises a sequence having at least 90% sequence identity to the full-length sequence of SEQ ID NO: 1.

17. The recombinant DNA expression construct of claim 1, wherein the functional equivalent comprises a sequence having at least 95% sequence identity to the full-length sequence of SEQ ID NO: 1.

18. The recombinant DNA expression construct of claim 1, wherein the at least one intron comprises the sequence of SEQ ID NO: 1.

19. A method for producing a transgenic plant or plant cell comprising transforming a plant or plant cell with the recombinant expression construct of claim 1, and optionally regenerating a plant from the transformed plant cell.

20. The method of claim 19, wherein the plant or plant cell is from a monocotyledonous plant or plant cell.

* * * * *

SEQUENCE LISTING

<160> NUMBER OF SEQ ID NOS: 121

<210> SEQ ID NO 1
<211> LENGTH: 584
<212> TYPE: DNA
<213> ORGANISM: Oryza sativa
<220> FEATURE:
<221> NAME/KEY: Intron
<222> LOCATION: (1)..(584)
<223> OTHER INFORMATION: BPSI.1

<400> SEQUENCE: 1
gtaagatccg atcaccatct tctgaatttc tgttcttgat ctgtcatgta taataactgt      60
ctagtcttgg tgttggtgag atggaaattc ggtggatctc ggaagggata ttgttcgttt     120
gctggggttt tttttgtgtg ttgtgatccg taatgaattt gtgtttatcc atgttgttga     180
tcttggtatg tattcatgac atattgacat gcatgtgttg tatgtgtcat atgtgtgcct     240
ctccttggga tttgttttgg ataatagaac atgttatgga ctcaatagtc tgtgaacaaa     300

```
tctttttta   gatggtggcc   aaatctgatg   atgatctttc   ttgagaggaa   aaagttcatg      360
atagaaaaat  cttttttgag   atggtggctt   aatgtgatga   tgatcttact   tgagaggaaa      420
aaaaagattc  attataggag   attttgattt   agctcctttc   caccgttatt   aaatgaggag      480
catgcatgct  gatggctgat   aaggatctga   tttttttat    cccctcttct   ttgaacagac      540
aagaaatagg  ctctgaattt   ctgattgatt   atttgtacat   gcag                         584

<210> SEQ ID NO 2
<211> LENGTH: 728
<212> TYPE: DNA
<213> ORGANISM: Oryza sativa

<400> SEQUENCE: 2
gttcgtgctg   atttagtgat   ttcccagcat   tagattttgt   tggtttctag   tctactgcct      60
tcagatgtta   ctgtattttc   ttttagaagg   agatgttcat   ataggatctt   tgttgttgag     120
attgttagat   ctggccagga   atggctcata   tttactgaat   tggatgcaat   cattttgtag     180
tcactttttt   tttaagtttc   tgattagaat   gaatatttaa   gtgcggcctt   ctgcagccaa     240
gattttgtac   aaacctagta   ctactgaata   atgatgaaat   atacaaatgt   agttttggat     300
tactgtggac   tggtagtgct   agatctgact   gcatgtgcat   gttatttata   ttatatatac     360
ggtttacaaa   ctgaatacaa   gtaatgaatt   ctgcactggt   acagatgctt   gttgtggtag     420
caaagtttca   caaaaaaat    aaaaaaccta   catcttacta   gatctattgg   cgcgagcgcg     480
tagatctgat   tatcgcgcat   atttcattaa   gtccaattaa   atggtcaaaa   ctaatcattt     540
catatctaca   atgaaatttt   taattcatct   caatgcaaac   agatcatata   tggtcttttt     600
aagtggctaa   tagcaaattt   tcttattatg   cgcaaatgct   caagtgctaa   aattatctta     660
ttgagatatt   tataggctga   gttgatagat   ctggcctgat   atttttgttg   acactgttat     720
ttgcgcag                                                                        728

<210> SEQ ID NO 3
<211> LENGTH: 95
<212> TYPE: DNA
<213> ORGANISM: Oryza sativa

<400> SEQUENCE: 3
gtttgaatca   gattcagatt   tcattgcatc   acagagatcc   atctttactc   taccgcttgc      60
tctaacttaa   cttgtaattg   tttttatca    tgcag                                    95

<210> SEQ ID NO 4
<211> LENGTH: 120
<212> TYPE: DNA
<213> ORGANISM: Oryza sativa

<400> SEQUENCE: 4
gtatgaaatc   tgcataattg   ggatactaaa   aacatatatt   cttaaaattt   aaaacttaat      60
tttattattt   ttctttttatc  gatatatatg   tcattgtaat   atctctgatg   tatatttcag     120

<210> SEQ ID NO 5
<211> LENGTH: 225
<212> TYPE: DNA
<213> ORGANISM: Oryza sativa

<400> SEQUENCE: 5
gtaagttctg   ttattacctc   ataaactgcc   tgctgataat   actttaacaa   tgtgctaata      60
ttagtctttg   taataagata   gtactatact   gaaaatattt   tagcgagtat   gagtaattta     120
```

```
acttacatat tgtattgctg ttcctctttt ttcaaccctg tcatattggt tgctttttt   180 cacagcctaa catgctcttg tttggtcatt ttccctgtt ttcag                    225

<210> SEQ ID NO 6
<211> LENGTH: 770
<212> TYPE: DNA
<213> ORGANISM: Oryza sativa

<400> SEQUENCE: 6
gtgagtcatt attgtctcat tatttgatcg atctctgatt ctctgattct tttcttttta    60
agcttaattg gcagccggat ggctgcaaat ccccatcgaa ggtaaatgct tgccttatat   120
atatgagtat ctctctactt tctccatcct aaaatagttt agtacgtata atactatatt   180
agaaataatc taatataatg aatctcagat atcattatta tttatgttg taatttgtgt    240 gtatatatca ttggtctgat gtactacttt cctttcatat tataagtttc tcttttttcg   300 ctattttttct actcaatttt ctttagattt gactaggttc ataaaaaaat taacaatatt   360
tgcaacgcta aattagtttc attaaatata acattgagag aaattttggg tacatgagaa   420
tgtacctgaa gatacctaaa ttttacacta aaagttttga tttctcaaga tacttattag   480
tatatggagg tactaagttt tatactagaa aatatgtatc tcttagtact ttttcaagaa   540
tgataaaatt actctaatat taaatatatt ttgataatat gtttgctttg tgttaaaaat   600
attactatat tttctttata aacttaacta aacttaaaaa ggtttaacta ataaaatagt   660
gaaagcgacc tataacaatt ataaatggag ggagcagtag cgtgaaatct gaatataatt   720
attttctctc tttctgacgt cactagctaa cttggtcacc tacactgcag              770

<210> SEQ ID NO 7
<211> LENGTH: 715
<212> TYPE: DNA
<213> ORGANISM: Oryza sativa

<400> SEQUENCE: 7
gtgagcacta tagctgtttg atgcaaaatc ataattgctg tatgttactg taatagattg    60
atctggacat ataaaaacga tcctgatgtc acttatttt ttccttcaag atgtattgca   120
gtatggaagc agctttatgc agaattttag tgcttatagg caattttcta aaggagttct   180
caggataatg attattcatg tatactgagc ttaaatatat gcagtgttaa taggcaacaa   240
ctatccgttg ttataggtgc agtaatatac ttcactgtgc attgcccttg gtatcctttt   300
attaattatg catttggtgc agtactgtac tgtactgtac tgtactgtac tgtgcactgt   360
tgttggtatc ctttattgat cgtgcatttg gattgccttt ttttaattcc aaggtttctc   420
ttgggagtat ttgtgtagga ctcatgcata tatcacttat gttccatttt ataatctttc   480
accctgtatc taattccttt aatttatgaa aaatataatc cagatattcc ctagttttaa   540
caacattgaa tatttgaatg ttagaacatg atttacattc atttggctaa ctattttttt    600
aacaagtgat ctcacatgtt gactgaagtt tcataagtaa acagtattat cttgttttct   660
tctatatatt tacatttttc acgctgattt actccttgtt ttttaaaaaa aacag         715

<210> SEQ ID NO 8
<211> LENGTH: 334
<212> TYPE: DNA
<213> ORGANISM: Oryza sativa

<400> SEQUENCE: 8
gtgagtatat gcttccatac ttctaagtca ttattttgc tccatgttgg tatatgggct     60
```

-continued

```
ggctaaaaat atattgcata aagtgcgctc ctatttcatc tctttggttt gcatgctgtg    120
gcttgcattc tttcaagata actgtagctg aggttgctcg atatgaacct gcttgcttgt    180
tttaatcctt gtttgctttt agcttattca tgactagaaa acaaacttta atttactctt    240
ttctggcatg ttgctggaca tatgttgtgt tatatcctat acaacatcat tgaattgtgc    300
ttaactaatt tgctgatttc atttcttaaa acag                                334
```

<210> SEQ ID NO 9
<211> LENGTH: 355
<212> TYPE: DNA
<213> ORGANISM: Oryza sativa

<400> SEQUENCE: 9

```
gtaagtccat ctcttttttt tccaggtgtc ggtatagtag tgtactgtac gttctattct     60
tgtaaccaac atttccaatg cattttgcat ccatatatta ctacagttca agtgattaaa    120
tttgtgacat gagaaaattt atcttatttt gaacttaagg tgtatcagtg tatgttctca    180
tgttgtcaac ttgtcatcgt cagtgctaaa gcagacactt ttttttttcct tccgacagag    240 tggaactagt gttgtttcat gaataacatc atgaagcatg caaattaatg ctttcttctt    300
aaattcttgg caaatggact ctaactgtat attgcttctg tgcttatttt tccag         355
```

<210> SEQ ID NO 10
<211> LENGTH: 538
<212> TYPE: DNA
<213> ORGANISM: Oryza sativa

<400> SEQUENCE: 10

```
gtaagaatct tgcgtccta ctgtcagtca tttttttctt cccatttgtt gccaacagtt      60
tggagttctt tcattgttca cggtagcagt ttttcttgta gtacctgcat ttttatatgc    120
acttttctat attgtactct gctctagtga tgtagttgat tatttatttt attcatattt    180
tgtagcaatt ctgttgtact gtatacttga atgtctgaca gtttggcatt taagagttca    240
ttaagaaatg gctgacacct tactaactgt tcattacgat ttctggcagt caataagggt    300
gttaggtggt gctatgttac atgtttccaa ttccaaatga tgtattttg gtgttttatt     360 attaccgact aaataccttg ggtgcaactc tttgttctcc tcctttagac aatgtagttt    420
atgcactgtt attgctgtgt tgcgttaaat ttggcccaac tgtttcattt cagtataact    480
ctattctgaa gtgtcttgta tttatctgat atttgtcttg gataattgta ttaaacag     538
```

<210> SEQ ID NO 11
<211> LENGTH: 331
<212> TYPE: DNA
<213> ORGANISM: Oryza sativa

<400> SEQUENCE: 11

```
gtaaattctg gctttcttgc ttttggataa attttgcttc ctttcttaac ttgagcacaa     60
gcttgtgtta tatgtggtgt gaaatcttgg ttgccatgtt gtgaggattt agctagagag    120
tcaagaaaga ggaatatatg ctttatgtag ataggagtag gatctctggg tctttaaaca    180
tcaccatgac aagcaaagat aagaacagga gagcagttct tgattattat ttttcttctc    240
atcaagaaat taagccggag atagacatgg cagctgcacg cagtgattca cttcttgatt    300
tcttgatttg ggttgttgcg tttgtgtcca g                                   331
```

<210> SEQ ID NO 12
<211> LENGTH: 961

```
<212> TYPE: DNA
<213> ORGANISM: Oryza sativa

<400> SEQUENCE: 12
gtaagatctc gcgcgacctg tttgttcttc ttggtgttct tctgcctagt tacttcgttt      60
gttttatgtt tgatctatag tcttgatgat ctgtgaagac tagttgttgt tttcggtacg     120
gatggtagga aaggtatttt cctttgttta aggaattgca agatctcgcg cgacctgttc     180
ttgatgttct gtctagtact tcgtttgttt gtttgatcta gtatgttaga tgatctatga     240
aaagtagtta ttttcggtac gaatggtagg agaagtattt ccttttgttg gcgtcaaaat     300
ataatcttta atcactcagt cttgtgaatg gtaattctga attcatattt ttcttttctg     360
atctatatcg tgttattctg tttatgattt tttgctgagt agatcccctt gtgctcgatg     420
tatgataagt tatctatatc gtaatagatt cgtatgtcaa aacttagtcg aaattttcga     480
tctcatctct tctgttagcc acaggtggct gattgaaata ttcttcaatt gagtctgaat     540
ttttatgtta tatgcaaata attgtcccgc tccagttcat atgtctgatg aaacatgaat     600
gtaaaggaat taagactttg gttatatgat tcgagtctga attttcttat gcttatgcaa     660
ataatagtcc aaaagaattg gtgatttttt tgtgtagttc atatggttga taaatatgaa     720
tgtgtctcaa aagcaacgaa gattttgatg acaagacaat ctgctatttg agtctgaaat     780
ttcttatgct tttgcaaata atagtcatag tcagaacgaa ttactgaaat ttccctccag     840
ttcatacggt tgatgaaaca tgaatgtatc tctttagtaa ttgaaacttt gacgatcaga     900
caatctgttg cattgcctag tcttgcagat tctcatcgat ccttttaatt cttctctgca     960
g                                                                     961

<210> SEQ ID NO 13
<211> LENGTH: 595
<212> TYPE: DNA
<213> ORGANISM: Oryza sativa

<400> SEQUENCE: 13
gtgagaacga ttgattactt tgctggctgc tcttagctac tactacaact gttttgtctt      60
aatcggttga ttacatctca tatttcatcg gtttagctcg ctctgttaag atttctcacc     120
tcctcttgga tgtattattc atgtatatgt tgtgtggtct ggctaagttt ttggtctgtc     180
ctgataaatg ctgtttaagg attctttctt tgttcttttt tttatggac aaaatataat     240 ctttgtgcct tactgtgaat tgagtctgtt ggctatatcg ttcccggttt attggactat     300
agatgaacat gtaaccctat atgcggttgt gttttctcct tacaaagatc agtagtacct     360
aattcagcta gttagaagtg gtaccaaggc tgtaaatttc catctttttc tctgtgaggt     420
tcatttccct tttaatctct gtttcgtgag aaatacccca ctgtttgact tccagtaaat     480
ctgttctcta tttctagttc agttaacctg ctattattga ttctacaatt taagcataat     540
aaagattaat gtctattagt tttctcaatt gatcatgtgg cacgtatttt agcag          595

<210> SEQ ID NO 14
<211> LENGTH: 145
<212> TYPE: DNA
<213> ORGANISM: Oryza sativa

<400> SEQUENCE: 14
gtgcgaaatt tttttttgtg ggttttttg gctgcttcca tttcgcaatc cactgatgga      60
gtacgttgct agcagtcgtt gcaatttctc agtaatttta ccgatttact atttatgcaa     120
gcttacactg gtgaattttt ttcag                                           145
```

<210> SEQ ID NO 15
<211> LENGTH: 314
<212> TYPE: DNA
<213> ORGANISM: Oryza sativa

<400> SEQUENCE: 15

| | | | | | |
|---|---|---|---|---|---|
| gtactatgaa | tatatgtcta | gttacatttt | gcacttcaat | atatatgtgt | agcttctgcc | 60 |
| cctctgcttg | ttttgcatta | catgtatttg | cttgttggag | aagtagatag | ctatatctta | 120 |
| aacatttaga | tcttattcgg | ttaatcccat | atgcgtgaaa | ttagagggga | ttaattccac | 180 |
| acattattcc | tcttcttccc | taattaaata | accttatagg | tggaattagc | cgaataagtc | 240 |
| aatgattaat | ttttctagtc | ctctcttgtg | agtggattga | ttaattacta | cttagaattg | 300 |
| gctcatatac | gcag | | | | | 314 |

<210> SEQ ID NO 16
<211> LENGTH: 652
<212> TYPE: DNA
<213> ORGANISM: Oryza sativa

<400> SEQUENCE: 16

| | | | | | |
|---|---|---|---|---|---|
| gtaattttt | gctccaaatc | catctccttt | ctcttctttt | ctgctgttac | ccgccgtatc | 60 |
| tttgctttac | cttcttcttt | tttttctctt | tttttttttg | cgaatccatc | ttgctttagt | 120 |
| ttgttgttct | gttccgagta | aaagaatac | ccttgatggc | ctagtctgac | caaaaggag | 180 |
| tgtgaagctc | ttcgaaagga | aaggtttag | acaatacgag | cctcagatgc | tcggttgctt | 240 |
| agtcgatccg | gtggtgaatc | gaacaattta | attcactgat | gctgttaatc | ttttctttta | 300 |
| aaagaaaatt | cctttctgtt | attggtggta | tttcttcaa | cataaacata | tatctgaaga | 360 |
| ttcttcagaa | atgatctgaa | gtctgaagat | ttcagcgtgg | cgccttagct | gatttattgt | 420 |
| aactgtgatg | aatatagcag | cgttgactgg | gtacagtaca | attacttgca | catcctatta | 480 |
| tgtagaaaca | agaaatttga | tgaatataac | aaggaattct | taatgtttat | ggccttaaat | 540 |
| cagcttaaaa | caacactgaa | gccacgttgt | tgttaaatga | aggtgactgc | taccttagtt | 600 |
| catgcgaaaa | tattcagtgc | gacctaacct | aattctactg | aaacgaattc | ag | 652 |

<210> SEQ ID NO 17
<211> LENGTH: 268
<212> TYPE: DNA
<213> ORGANISM: Oryza sativa

<400> SEQUENCE: 17

| | | | | | |
|---|---|---|---|---|---|
| gtaaaaaact | cactggagat | taagaacaat | tattaatttc | attcttgatt | cagtacatgg | 60 |
| tccaatttac | atgctctatt | gaattgatgg | tgtcttaatt | tggaaaacat | tttgcatgga | 120 |
| tggatttcaa | caagtgttct | gatgatgaaa | gcctgactgt | tctttacttt | cttcagacaa | 180 |
| agaatccact | tgcatgtagt | agagggattt | gaagttattc | ttatgttttc | ttggttaaat | 240 |
| caagcagctg | ttttcttgtt | tggtccag | | | | 268 |

<210> SEQ ID NO 18
<211> LENGTH: 546
<212> TYPE: DNA
<213> ORGANISM: Oryza sativa

<400> SEQUENCE: 18

| | | | | | |
|---|---|---|---|---|---|
| gtacgtacga | tgaacaaaga | acaaacccct | aaattgctct | ttctatatgc | gatttctaga | 60 |
| gtatttattt | atttatttat | gagggggat | tccgccgttc | taaattggtg | ggtcatagga | 120 |

```
gagattaggt ccgattgttc tcgtggtgaa attaatacta tgcgctcacg tacgctacct    180
ctggattaat tcaccattca aacaaaatca aggcagaaca aatggtatat atctgctatt    240
tttgtcagcg ccaatctgca aattaacaat gctttacata ttggagagtg tcttgctgtt    300
cttcatgttt gtctcagtta gtcagttagc agcttctttt tttaatttct ttagcgaaat    360
tcgttatatc tggtgacata cggacagggt cgactaatat aggttcatgg tcgcggccta    420
ctgcaatctg catctgcaat ttgattcacg gtctatttgg ctccttcgta gagacattaa    480
aaatattggt tgtgtttgta tgatcaagag aactttcatc tgaactttga ttggttgtgt    540
tcacag                                                                546

<210> SEQ ID NO 19
<211> LENGTH: 812
<212> TYPE: DNA
<213> ORGANISM: Oryza sativa

<400> SEQUENCE: 19
gtaggaaaat tggaagcaat ttaacatgca ttatgcttat caatcatcct gtgcatgcat     60
gtcagctagc ttacttcata gagcattaga gcttatagtt catctgatca gaactagttg    120
tctgggaggt taattatgca tgtgtgttca agaactcagc cagctaataa cccgttctag    180
ggactcgatc atcaagtgca tgaatgcatg gtgtgcatgc ttgaggttca tatggttaat    240
taagatttct cagcaagatt aattgttgat gaaaaaggca agcaaattaa acatatatat    300
gatcttttgg tgtgtgttgc gttgctgttc acaagtggat gtatgtgacc ctgcgtctgc    360
tgttcatttt agttacatat gcctagttgt tattttgtat ggcagttact ttcaagttag    420
ttaaaggctt tctaaacaag ccctatgtat atatatttct gtgttagctt aggcatcatt    480
ttctttacct tttgtacaaa tttccaagtg gtcaaagcaa tcttaactct tccttgctac    540
tagctctttc gcacctgact ttattagaag cttatattat aaaaaatttc tccttccttt    600
ctcgagctgg cgtctgcaaa ataccgattt ttacaagca catgagtcta gtagggtgct     660
ccacccgcat gcaaaaagca aatttggtcg tctataaaaa ccttttgtat agtagtgtgg    720
ttttaattat ttttataatt cgcaaagttg ttttttaactt ggactgttca tttggtgttt    780
tcactagtta atacagtctt ttttttcttc ag                                   812

<210> SEQ ID NO 20
<211> LENGTH: 371
<212> TYPE: DNA
<213> ORGANISM: Oryza sativa

<400> SEQUENCE: 20
gtaagttgat ctctctttct tgcttcaatc tgattgtttc cttgctagtt gaaaactact     60
attatatact ctgtctttcg tccatcttga gtgatatcat gaattgatac acattctcat    120
gaatgaatgt atcaaattcc atctgaaact ctggtagtag ctgcacacac atttcagaat    180
tcagactttg cactagcttt gtgcattgag atagagaaat taccaaagta gatgtaagca    240
tgtaagagtt gttgaaatat gcttacatac aaaaaattgta taaaaatat gattatgaat    300 gtactagtga atagtgatta caagatttaa actcctaatc aattaagttt gcatcattga    360
tgcaagttca g                                                          371

<210> SEQ ID NO 21
<211> LENGTH: 722
<212> TYPE: DNA
<213> ORGANISM: Oryza sativa
```

<400> SEQUENCE: 21

```
gtaagtttat tttgctctaa ttttgggcta ccaattgggt ttatatttct ctagtggtgg    60
tgactggtga gtaattttcc ccttatttta ttgtgttgat gtgaggcctt ggggttttct   120
atctctttgc atcgttttcg ctttcatttg tttagagatt tgttctttga acaaagcatg   180
cagaaatctc tgaggactga agtgtttctc tctgcttgtc actttctccc caattgtgga   240
ataactaaga ggaatcgaca tggggtctag tcttccattc cacaagattt gcatcttccc   300
catgaatctt ccaagaaaat ctgtatctct tacttccttt cttttttctct aggtcttgtc   360
ttgcaaacta ggataaagat acaagttagt agtacaagaa acagtaaagg tgaaagtctt   420
gtgttctttt ccctgcgatt tcttctgaaa aaggtcgcca ttaagaaaaa gctttgcaat   480
ctttggagtg ttcttctcac ccagtggttt ctctgcttgt tctcttctga ttaataacag   540
tagtagctgc tcattaaatt gcatcttttt ttaatttatt taatttctgt tgatgtgaaa   600
cgcatccaat ctcttgcaat caatgtgagg ctttcattgg cgtatgagca taaaaagggg   660
ggaaagaaag gtgggagtct ttaggtttct actcctaaaa attgtttctt tcttatgtgc   720
ag                                                                  722
```

<210> SEQ ID NO 22
<211> LENGTH: 388
<212> TYPE: DNA
<213> ORGANISM: Oryza sativa

<400> SEQUENCE: 22

```
gtatccatcc atctctgctt tctctctccc tgttgtgttg ggctttcttg ttcatgtcct    60
tggaatgtaa agtttggttc ttttttttta tggtaccttt gtccttcctt tcctcttgat   120
ttcatttagt aacggtgtta ggaaggaagg atattctttc tgctctgttc ttgattttgt   180
ttatcaattt tcctttttttt atggctcacc ctctttcaga tattgccata tcagaaataa   240
aaaatctgat tttttttcat atattattca tcatactagt tttaaccttt ttttttttga   300
aaaaaaaata tgagagagaa gaaaaatcag catgtttctt gctgttcatc agaagctgta   360
gtgaaattta atggctgcat gtggacag                                      388
```

<210> SEQ ID NO 23
<211> LENGTH: 24
<212> TYPE: DNA
<213> ORGANISM: Oryza sativa

<400> SEQUENCE: 23

```
tttgtgcagc ccgctttcta cgag                                           24
```

<210> SEQ ID NO 24
<211> LENGTH: 21
<212> TYPE: DNA
<213> ORGANISM: Oryza sativa

<400> SEQUENCE: 24

```
acggccaacg ggacggtgct a                                              21
```

<210> SEQ ID NO 25
<211> LENGTH: 20
<212> TYPE: DNA
<213> ORGANISM: Oryza sativa

<400> SEQUENCE: 25

```
gtcctcgccg gcatcgtcac                                                20
```

<210> SEQ ID NO 26
<211> LENGTH: 19
<212> TYPE: DNA
<213> ORGANISM: Oryza sativa

<400> SEQUENCE: 26
cagaacggcg ggttgatcc                                                19

<210> SEQ ID NO 27
<211> LENGTH: 17
<212> TYPE: DNA
<213> ORGANISM: Oryza sativa

<400> SEQUENCE: 27
agctcgctcg cggtctt                                                  17

<210> SEQ ID NO 28
<211> LENGTH: 20
<212> TYPE: DNA
<213> ORGANISM: Oryza sativa

<400> SEQUENCE: 28
acagggccca agtcgtgtgc                                               20

<210> SEQ ID NO 29
<211> LENGTH: 20
<212> TYPE: DNA
<213> ORGANISM: Oryza sativa

<400> SEQUENCE: 29
aggtctcgcc atcgtcaatg                                               20

<210> SEQ ID NO 30
<211> LENGTH: 15
<212> TYPE: DNA
<213> ORGANISM: Oryza sativa

<400> SEQUENCE: 30
cgagacgggc gttgt                                                    15

<210> SEQ ID NO 31
<211> LENGTH: 21
<212> TYPE: DNA
<213> ORGANISM: Oryza sativa

<400> SEQUENCE: 31
ggctgcggag gatgcaagat g                                             21

<210> SEQ ID NO 32
<211> LENGTH: 22
<212> TYPE: DNA
<213> ORGANISM: Oryza sativa

<400> SEQUENCE: 32
ggggttgcag gtgcagttgt cg                                            22

<210> SEQ ID NO 33
<211> LENGTH: 20
<212> TYPE: DNA
<213> ORGANISM: Oryza sativa

<400> SEQUENCE: 33
ggcgtcaaca cctacacctt                                               20

```
<210> SEQ ID NO 34
<211> LENGTH: 22
<212> TYPE: DNA
<213> ORGANISM: Oryza sativa

<400> SEQUENCE: 34
tgcactgcag catcttgtcg tc                                              22

<210> SEQ ID NO 35
<211> LENGTH: 22
<212> TYPE: DNA
<213> ORGANISM: Oryza sativa

<400> SEQUENCE: 35
ggtggatgcc acggtgcaag ag                                              22

<210> SEQ ID NO 36
<211> LENGTH: 17
<212> TYPE: DNA
<213> ORGANISM: Oryza sativa

<400> SEQUENCE: 36
ggggaggtac tgtgctc                                                    17

<210> SEQ ID NO 37
<211> LENGTH: 18
<212> TYPE: DNA
<213> ORGANISM: Oryza sativa

<400> SEQUENCE: 37
tgcggaagcc aatgctga                                                   18

<210> SEQ ID NO 38
<211> LENGTH: 22
<212> TYPE: DNA
<213> ORGANISM: Oryza sativa

<400> SEQUENCE: 38
ccagccctga actaggaacg tc                                              22

<210> SEQ ID NO 39
<211> LENGTH: 18
<212> TYPE: DNA
<213> ORGANISM: Oryza sativa

<400> SEQUENCE: 39
tcaggggagg catgcaaa                                                   18

<210> SEQ ID NO 40
<211> LENGTH: 22
<212> TYPE: DNA
<213> ORGANISM: Oryza sativa

<400> SEQUENCE: 40
tgcataccac cacggagacg aa                                              22

<210> SEQ ID NO 41
<211> LENGTH: 22
<212> TYPE: DNA
<213> ORGANISM: Oryza sativa

<400> SEQUENCE: 41
cgatttctcc aaaggcgagc ac                                              22
```

<210> SEQ ID NO 42
<211> LENGTH: 19
<212> TYPE: DNA
<213> ORGANISM: Oryza sativa

<400> SEQUENCE: 42
tgcgggtatg cgtccaaca                                                    19

<210> SEQ ID NO 43
<211> LENGTH: 22
<212> TYPE: DNA
<213> ORGANISM: Oryza sativa

<400> SEQUENCE: 43
acagccacca ccaagacctt cg                                                22

<210> SEQ ID NO 44
<211> LENGTH: 22
<212> TYPE: DNA
<213> ORGANISM: Oryza sativa

<400> SEQUENCE: 44
ctgcagctgg tgccacactt gc                                                22

<210> SEQ ID NO 45
<211> LENGTH: 22
<212> TYPE: DNA
<213> ORGANISM: Oryza sativa

<400> SEQUENCE: 45
tcccaactgc cttcgatccc tt                                                22

<210> SEQ ID NO 46
<211> LENGTH: 24
<212> TYPE: DNA
<213> ORGANISM: Oryza sativa

<400> SEQUENCE: 46
tggacagtgg tcaggctctt acgg                                              24

<210> SEQ ID NO 47
<211> LENGTH: 22
<212> TYPE: DNA
<213> ORGANISM: Oryza sativa

<400> SEQUENCE: 47
gagttctacc agttcagcga cc                                                22

<210> SEQ ID NO 48
<211> LENGTH: 17
<212> TYPE: DNA
<213> ORGANISM: Oryza sativa

<400> SEQUENCE: 48
aacccgaagg cgttgac                                                      17

<210> SEQ ID NO 49
<211> LENGTH: 16
<212> TYPE: DNA
<213> ORGANISM: Oryza sativa

<400> SEQUENCE: 49
agaccgcccg caagtc                                                       16

<210> SEQ ID NO 50
<211> LENGTH: 20
<212> TYPE: DNA
<213> ORGANISM: Oryza sativa

<400> SEQUENCE: 50
cttgggcatg atggtgacgc                                          20

<210> SEQ ID NO 51
<211> LENGTH: 24
<212> TYPE: DNA
<213> ORGANISM: Oryza sativa

<400> SEQUENCE: 51
ccaagaggga gtgctgtatg ccaa                                     24

<210> SEQ ID NO 52
<211> LENGTH: 23
<212> TYPE: DNA
<213> ORGANISM: Oryza sativa

<400> SEQUENCE: 52
acgaggacca ccacggtacc cat                                      23

<210> SEQ ID NO 53
<211> LENGTH: 35
<212> TYPE: DNA
<213> ORGANISM: Oryza sativa

<400> SEQUENCE: 53
cccgggcacc ctgcggaggg taagatccga tcacc                         35

<210> SEQ ID NO 54
<211> LENGTH: 30
<212> TYPE: DNA
<213> ORGANISM: Oryza sativa

<400> SEQUENCE: 54
cggaccggta catcttgcat ctgcatgtac                               30

<210> SEQ ID NO 55
<211> LENGTH: 35
<212> TYPE: DNA
<213> ORGANISM: Oryza sativa

<400> SEQUENCE: 55
cccgggcacc cttcaccagg ttcgtgctga tttag                         35

<210> SEQ ID NO 56
<211> LENGTH: 29
<212> TYPE: DNA
<213> ORGANISM: Oryza sativa

<400> SEQUENCE: 56
cggaccgaac cagcctgcgc aaataacag                                29

<210> SEQ ID NO 57
<211> LENGTH: 32
<212> TYPE: DNA
<213> ORGANISM: Oryza sativa

<400> SEQUENCE: 57
cccgggcacc tcctgaggag tgcacaggtt tg                            32

<210> SEQ ID NO 58
<211> LENGTH: 32
<212> TYPE: DNA
<213> ORGANISM: Oryza sativa

<400> SEQUENCE: 58
cggaccggga gataacaatc ccctcctgca tg                               32

<210> SEQ ID NO 59
<211> LENGTH: 32
<212> TYPE: DNA
<213> ORGANISM: Oryza sativa

<400> SEQUENCE: 59
cccgggcacc cagcttgtgg aagaagggta tg                               32

<210> SEQ ID NO 60
<211> LENGTH: 31
<212> TYPE: DNA
<213> ORGANISM: Oryza sativa

<400> SEQUENCE: 60
cggaccggtt gttggtgctg aaatatacat c                                31

<210> SEQ ID NO 61
<211> LENGTH: 46
<212> TYPE: DNA
<213> ORGANISM: Oryza sativa

<400> SEQUENCE: 61
cggggtaccg agctctctgg tggctgaggt aagttctgtt attacc                 46

<210> SEQ ID NO 62
<211> LENGTH: 33
<212> TYPE: DNA
<213> ORGANISM: Oryza sativa

<400> SEQUENCE: 62
cggggatccg gacaggaaaa cctgaaaaca ggg                              33

<210> SEQ ID NO 63
<211> LENGTH: 43
<212> TYPE: DNA
<213> ORGANISM: Oryza sativa

<400> SEQUENCE: 63
cggggtaccg agctcgacga tttaggtaag tcattattgt ctc                   43

<210> SEQ ID NO 64
<211> LENGTH: 31
<212> TYPE: DNA
<213> ORGANISM: Oryza sativa

<400> SEQUENCE: 64
cggggatcct cactgaaacc tgcagtgtag g                                31

<210> SEQ ID NO 65
<211> LENGTH: 40
<212> TYPE: DNA
<213> ORGANISM: Oryza sativa

<400> SEQUENCE: 65
cggggtaccg agctcgatcc taaggtaagc actctagctg                       40

<210> SEQ ID NO 66
<211> LENGTH: 31
<212> TYPE: DNA
<213> ORGANISM: Oryza sativa

<400> SEQUENCE: 66
cggggatccg taactcaacc tgttttttt a                                31

<210> SEQ ID NO 67
<211> LENGTH: 41
<212> TYPE: DNA
<213> ORGANISM: Oryza sativa

<400> SEQUENCE: 67
cggggtaccg agctccaatg gctaggtaag tatatgcttc c                    41

<210> SEQ ID NO 68
<211> LENGTH: 31
<212> TYPE: DNA
<213> ORGANISM: Oryza sativa

<400> SEQUENCE: 68
cggggatccc ccatcaagta cctgttttaa g                               31

<210> SEQ ID NO 69
<211> LENGTH: 38
<212> TYPE: DNA
<213> ORGANISM: Oryza sativa

<400> SEQUENCE: 69
cggggtaccg agctcgaata cctaggtaag tccatctc                        38

<210> SEQ ID NO 70
<211> LENGTH: 35
<212> TYPE: DNA
<213> ORGANISM: Oryza sativa

<400> SEQUENCE: 70
cggggatccc acacaagcga cctggaaaaa taagc                           35

<210> SEQ ID NO 71
<211> LENGTH: 42
<212> TYPE: DNA
<213> ORGANISM: Oryza sativa

<400> SEQUENCE: 71
cggggtaccg agctcccatc ttttaggta agtatctttg cg                    42

<210> SEQ ID NO 72
<211> LENGTH: 30
<212> TYPE: DNA
<213> ORGANISM: Oryza sativa

<400> SEQUENCE: 72
cggggatccg gtaaagaacc tgtttaatac                                 30

<210> SEQ ID NO 73
<211> LENGTH: 46
<212> TYPE: DNA
<213> ORGANISM: Oryza sativa

<400> SEQUENCE: 73
cggggtaccg agctctgaac aggaaggtaa gttctggctt tcttgc               46

-continued

<210> SEQ ID NO 74
<211> LENGTH: 33
<212> TYPE: DNA
<213> ORGANISM: Oryza sativa

<400> SEQUENCE: 74
cggggatcct cagatcgacc tggacacaaa cgc                33

<210> SEQ ID NO 75
<211> LENGTH: 5
<212> TYPE: RNA
<213> ORGANISM: Oryza sativa

<400> SEQUENCE: 75 curay                5

<210> SEQ ID NO 76
<211> LENGTH: 5
<212> TYPE: RNA
<213> ORGANISM: Oryza sativa

<400> SEQUENCE: 76 yuray                5

<210> SEQ ID NO 77
<211> LENGTH: 15
<212> TYPE: DNA
<213> ORGANISM: preferred 5' splice site

<400> SEQUENCE: 77
agaggtagta gtgtc                15

<210> SEQ ID NO 78
<211> LENGTH: 2
<212> TYPE: DNA
<213> ORGANISM: 5' splice site dinucleotide

<400> SEQUENCE: 78 gt                2

<210> SEQ ID NO 79
<211> LENGTH: 3
<212> TYPE: DNA
<213> ORGANISM: 3' splice site trinucleotide

<400> SEQUENCE: 79 cag                3

<210> SEQ ID NO 80
<211> LENGTH: 8
<212> TYPE: DNA
<213> ORGANISM: Oryza sativa

<400> SEQUENCE: 80 aggtaagt                8

<210> SEQ ID NO 81
<211> LENGTH: 5
<212> TYPE: DNA
<213> ORGANISM: Oryza sativa

<400> SEQUENCE: 81 caggt                5

<210> SEQ ID NO 82
<211> LENGTH: 640
<212> TYPE: DNA
<213> ORGANISM: Oryza sativa

<400> SEQUENCE: 82

```
gctgccagtg cggcagcggc tgcggagggt aagatccgat caccatcttc tgaatttctg      60
ttcttgatct gtcatgtata ataactgtct agtcttggtg ttggtgagat ggaaattcgg     120
tggatctcgg aagggatatt gttcgtttgc tggggttttt tttgtgtgtt gtgatccgta     180
atgaatttgt gtttatccat gttgttgatc ttggtatgta ttcatgacat attgacatgc     240
atgtgttgta tgtgtcatat gtgtgcctct ccttgggatt tgttttggat aatagaacat     300
gttatggact caatagtctg tgaacaaatc tttttttaga tggtggccaa atctgatgat     360
gatctttctt gagaggaaaa agttcatgat agaaaaatct ttttgagat ggtggcttaa      420
tgtgatgatg atcttacttg agaggaaaaa aaagattcat tataggagat tttgatttag     480
ctcctttcca ccgttattaa atgaggagca tgcatgctga tggctgataa ggatctgatt     540
tttttatcc cctcttcttt gaacagacaa gaaataggct ctgaatttct gattgattat      600
ttgtacatgc agatgcaaga tgtacccgga gatggctgag                           640
```

<210> SEQ ID NO 83
<211> LENGTH: 770
<212> TYPE: DNA
<213> ORGANISM: Oryza sativa

<400> SEQUENCE: 83

```
tcgtcgccgt cttcaccagg ttcgtgctga tttagtgatt tcccagcatt agattttgtt      60
ggtttctagt ctactgcctt cagatgttac tgtattttct tttagaagga gatgttcata     120
taggatcttt gttgttgaga ttgttagatc tggccaggaa tggctcatat ttactgaatt     180
ggatgcaatc attttgtagt cacttttttt ttaagtttct gattagaatg aatatttaag     240
tgcggccttc tgcagccaag attttgtaca aacctagtac tactgaataa tgatgaaata     300
tacaaatgta gttttggatt actgtggact ggtagtgcta gatctgactg catgtgcatg     360
ttatttatat tatatatacg gtttacaaac tgaatacaag taatgaattc tgcactggta     420
cagatgcttg ttgtggtagc aaagtttcac aaaaaaaata aaaaacctac atcttactag     480
atctattggc gcgagcgcgt agatctgatt atcgcgcata tttcattaag tccaattaaa     540
tggtcaaaac taatcatttc atatctacaa tgaaattttt aattcatctc aatgcaaaca     600
gatcatatat ggtcttttta agtggctaat agcaaatttt cttattatgc gcaaatgctc     660
aagtgctaaa attatcttat tgagatattt ataggctgag ttgatagatc tggcctgata     720
tttttgttga cactgttatt tgcgcaggct ggttaacctc ggaaagggaa                 770
```

<210> SEQ ID NO 84
<211> LENGTH: 150
<212> TYPE: DNA
<213> ORGANISM: Oryza sativa

<400> SEQUENCE: 84

```
tgaggatgtc ctgaggagtg cacaggtttg aatcagattc agatttcatt gcatcacaga      60
gatccatctt tactctaccg cttgctctaa cttaacttgt aattgttttt tatcatgcag     120
gaggggattg ttatctcccc atgggttgcc                                      150
```

```
<210> SEQ ID NO 85
<211> LENGTH: 189
<212> TYPE: DNA
<213> ORGANISM: Oryza sativa

<400> SEQUENCE: 85
cttgcagttc aaggaacagc ttgtggaaga aggtatgaaa tctgcataat tgggatacta      60
aaaacatata ttcttaaaat ttaaaactta attttattat ttttctttta tcgatatata     120
tgtcattgta atatctctga tgtatatttc agcaccaaca acaactttgt gcttgagctg     180
gatttcgag                                                             189

<210> SEQ ID NO 86
<211> LENGTH: 290
<212> TYPE: DNA
<213> ORGANISM: Oryza sativa

<400> SEQUENCE: 86
gtgcaaattt gaaaggtgca tttctggtgg ctgtggtaag ttctgttatt acctcataaa      60
ctgcctgctg ataatacttt aacaatgtgc taatattagt ctttgtaata agatagtact     120
atactgaaaa tattttagcg agtatgagta atttaactta catattgtat tgctgttcct     180
cttttttcaa ccctgtcata ttggttgctt ttttttcacag cctaacatgc tcttgtttgg    240 tcatttttccc ctgttttcag attttcctgt ccctgtgctt ggttataact               290

<210> SEQ ID NO 87
<211> LENGTH: 246
<212> TYPE: DNA
<213> ORGANISM: Oryza sativa

<400> SEQUENCE: 87
tctggtggct gaggtaagtt ctgttattac ctcataaact gcctgctgat aatactttaa      60
caatgtgcta atattagtct ttgtaataag atagtactat actgaaaata ttttagcgag     120
tatgagtaat ttaacttaca tattgtattg ctgttcctct ttttcaaccc tgtcatattg     180 gttgctttt tcacagcct aacatgctct gtttggtca ttttccctg ttttcaggtt         240 ttcctg                                                                246

<210> SEQ ID NO 88
<211> LENGTH: 838
<212> TYPE: DNA
<213> ORGANISM: Oryza sativa

<400> SEQUENCE: 88
gtgagtcatt attgtctcat tatttgatcg atctgtgagt cattattgtc tcattatttg      60
atcgatctct gattctctga ttcttttctt tttaagctta attggcagcc ggatggctgc     120
aaatccccat cgaaggtaaa tgcttgcctt atatatgatg atctctct actttctcca       180 tcctaaaata gtttagtacg tataatacta tattagaaat aatctaatat aatgaatctc     240
agatatcatt attattttat gttgtaattt gtgtgtatat atcattggtc tgatgtacta     300 cttccttc atattataag tttctctttt ttcgctattt ttctactcaa ttttctttag       360
atttgactag gttcataaaa aaattaacaa tatttgcaac gctaaattag tttcattaaa     420
tataacattg agagaaattt ttggtacatg agaatgtacc tgaagatacc taaatttttac    480 actaaaagtt ttgatttctc aagatactta ttagtatatg gaggtactaa gttttatact    540
agaaaatatg tatctcttag tacttttttca agaatgataa aattactcta atattaaata    600
tattttgata atatgtttgc tttgtgttaa aaatattact atattttctt ataaaactta     660
```

```
actaaactta aaaaggttta actaataaaa tagtgaaagc gacctataac aattataaat      720
ggagggagca gtagcgtgaa atctgaatat aattattttc tctctttctg acgtcactag      780
ctaacttggt cacctacact gcagggttca gcgagtcgtc gaagctccgg gcgtgctg       838

<210> SEQ ID NO 89
<211> LENGTH: 788
<212> TYPE: DNA
<213> ORGANISM: Oryza sativa

<400> SEQUENCE: 89
gacgatttag gtaagtcatt attgtctcat tatttgatcg atctctgatt ctctgattct      60
tttcttttta agcttaattg gcagccggat gctgaatccc catcgaaggt aaatgcttgc     120
cttatatata tgagtatctc tctactttct ccatcctaaa atagtttagt acgtataata     180
ctatattaga aataatctaa tataatgaat ctcagatatc attattattt tatgttgtaa     240
tttgtgtgta tatatcattg gtctgatgta ctactttcct ttcatattat aagtttctct     300
tttttcgcta ttttttctact caattttctt tagatttgac taggttcata aaaaaattaa    360
caatatttgc aacgctaaat tagtttcatt aaatataaca ttgagagaaa ttttttggtac   420 atgagaatgt acctgaagat acctaaattt tacactaaaa gttttgatttt ctcaagatac    480 ttattagtat atggaggtac taagtttttat actagaaaat atgtatctct tagtactttt    540
tcaagaatga taaaattact ctaatattaa atatattttg ataatatgtt tgctttgtgt    600
taaaaatatt actatatttt ctttataaac ttaactaaac ttaaaaaggt ttaactaata    660
aaatagtgaa agcgacctat aacaattata aatggaggga gcagtagcgt gaaatctgaa    720
tataattatt ttctctctctttt ctgacgtcac tagctaactt ggtcacctac actgcaggtt    780
tcagtgac                                                               788

<210> SEQ ID NO 90
<211> LENGTH: 775
<212> TYPE: DNA
<213> ORGANISM: Oryza sativa

<400> SEQUENCE: 90
actagtgctg aagcaattct gaagctaatc aatggtgagc actatagctg tttgatgcaa      60
aatcataatt gctgtatgtt actgtaatag attgatctgg acatataaaa acgatcctga     120
tgtcacttat ttttttccctt caagatgtat tgcagtatgg aagcagcttt atgcagaatt    180
ttagtgctta taggcaattt tctaaaggag ttctcaggat aatgattatt catgtatact    240
gagcttaaat atatgcagtg ttaataggca acaactatcc gttgttatag gtgcagtaat    300
atacttcact gtgcattgcc cttggtatcc ttttattaat tatgcatttg gtgcagtact     360
gtactgtact gtactgtact gtactgtgca ctgttgttgg tatcctttat tgatcgtgca    420
tttggattgc cttttttttaa ttccaaggtt tctcttggga gtatttgtgt aggactcatg    480
catatatcac ttatgttcca ttttataatc tttcaccctg tatctaattc ctttaattta    540
tgaaaaatat aatccagata ttccctagtt ttaacaacat tgaatatttg aatgttagaa    600
catgatttac attcatttgg ctaactattt ttttaacaag tgatctcaca tgttgactga    660
agtttcataa gtaaacagta ttatcttgtt ttcttctata tatttacatt tttcacgctg    720
atttactcct tgtttttttaa aaaaaacagg atcatcctcg acatatccta atttc          775

<210> SEQ ID NO 91
<211> LENGTH: 734
```

```
<212> TYPE: DNA
<213> ORGANISM: Oryza sativa

<400> SEQUENCE: 91
gatcctaagg taagtactat agctgtttga tgcaaaatca taattgctgt atgttactgt      60
aatagattga tctggacata taaaaacgat cctgatgtca cttattttt tccttcaaga     120
tgtattgcag tatggaagca gctttatgca gaatttagt gcttataggc aatttctaa      180
aggagttctc aggataatga ttattcatgt atactgagct taaatatatg cagtgttaat    240
aggcaacaac tatccgttgt tataggtgca gtaatatact tcactgtgca ttgcccttgg    300
tatcctttta ttaattatgc atttggtgca gtactgtact gtactgtact gtactgtact    360
gtgcactgtt gttggtatcc tttattgatc gtgcatttgg attgccttt tttaattcca     420
aggtttctct tgggagtatt tgtgtaggac tcatgcatat atcacttatg ttccatttta    480
taatctttca ccctgtatct aattccttta atttatgaaa aatataatcc agatattccc    540
tagttttaac aacattgaat atttgaatgt tagaacatga tttacattca tttggctaac    600
tatttttta acaagtgatc tcacatgttg actgaagttt cataagtaaa cagtattatc     660
ttgttttctt ctatatattt acattttca cgctgattta ctccttgttt tttaaaaaaa     720
acaggttgag ttac                                                       734

<210> SEQ ID NO 92
<211> LENGTH: 400
<212> TYPE: DNA
<213> ORGANISM: Oryza sativa

<400> SEQUENCE: 92
ttgaggcagc tgtcgagcaa ttcaatggct atgtgagtat atgcttccat acttctaagt     60
cattatttt gctccatgtt ggtatatggg ctggctaaaa atatattgca taaagtgcgc    120
tcctatttca tctctttggt ttgcatgctg tggcttgcat tctttcaaga taactgtagc    180
tgaggttgct cgatatgaac ctgcttgctt gttttaatcc ttgtttgctt ttagcttatt    240
catgactaga aaacaaactt taatttactc ttttctggca tgttgctgga catatgttgt    300
gttatatcct atacaacatc attgaattgt gcttaactaa tttgctgatt tcatttctta    360
aaacagatac ttgatgggag atctttgagg gttaactcag                          400

<210> SEQ ID NO 93
<211> LENGTH: 356
<212> TYPE: DNA
<213> ORGANISM: Oryza sativa

<400> SEQUENCE: 93
caatggctag gtaagtatat gcttccatac ttctaagtca ttattttgc tccatgttgg      60
tatatgggct ggctaaaaat atattgcata aagtgcgctc ctatttcatc tctttggttt    120
gcatgctgtg gcttgcattc tttcaagata actgtagctg aggttgctcg atatgaacct    180
gcttgcttgt tttaatcctt gtttgctttt agcttattca tgactagaaa acaaacttta    240
atttactctt ttctggcatg ttgctggaca tatgttgtgt tatatcctat acaacatcat    300
tgaattgtgc ttaactaatt tgctgatttc atttcttaaa acaggtactt gatggg        356

<210> SEQ ID NO 94
<211> LENGTH: 600
<212> TYPE: DNA
<213> ORGANISM: Oryza sativa

<400> SEQUENCE: 94
```

```
cgtggaagct tggagaacca tcttttttagg agtaagaatc tttgcgtcct actgtcagtc    60 attttttttct tcccatttgt tgccaacagt ttggagttct ttcattgttc acggtagcag   120
tttttcttgt agtacctgca ttttttatatg cacttttcta tattgtactc tgctctagtg   180
atgtagttga ttatttattt tattcatatt ttgtagcaat tctgttgtac tgtatacttg   240
aatgtctgac agtttggcat ttaagagttc attaagaaat ggctgacacc ttactaactg   300
ttcattacga tttctggcag tcaataaggg tgttaggtgg tgctatgtta catgtttcca   360
attccaaatg atgtatttt  ggtgttttat tattaccgac taaataccttt gggtgcaact   420 ctttgttctc ctcctttaga caatgtagtt tatgcactgt tattgctgtg ttgcgttaaa   480
tttggcccaa ctgtttcatt tcagtataac tctattctga agtgtcttgt atttatctga   540
tatttgtctt ggataattgt attaaacagg gtctttacct ctcccatggg ccatcagaat   600
```

<210> SEQ ID NO 95
<211> LENGTH: 560
<212> TYPE: DNA
<213> ORGANISM: Oryza sativa

<400> SEQUENCE: 95

```
ccatcttttt aggtaagtat ctttgcgtcc tactgtcagt catttttttc ttcccatttg    60
ttgccaacag tttggagttc tttcattgtt cacggtagca gttttttcttg tagtacctgc   120 atttttatat gcacttttct atattgtact ctgctctagt gatgtagttg attatttatt   180
ttattcatat tttgtagcaa ttctgttgta ctgtatactt gaatgtctga cagtttggca   240
tttaagagtt cattaagaaa tggctgacac cttactaact gttcattacg atttctggca   300
gtcaataagg gtgttaggtg gtgctatgtt acatgtttcc aattccaaat gatgtatttt   360
tggtgtttta ttattaccga ctaaataccct tgggtgcaac tctttgttct cctcctttag   420
acaatgtagt ttatgcactg ttattgctgt gttgcgttaa atttggccca actgtttcat   480
ttcagtataa ctctattctg aagtgtcttg tatttatctg atatttgtct tggataattg   540
tattaaacag gttctttacc                                               560
```

<210> SEQ ID NO 96
<211> LENGTH: 400
<212> TYPE: DNA
<213> ORGANISM: Oryza sativa

<400> SEQUENCE: 96

```
actagttagc atacccatcc atgatgagca tgatggtaaa ttctggcttt cttgcttttg    60
gataaatttt gcttcctttc ttaacttgag cacaagcttg tgttatatgt ggtgtgaaat   120
cttggttgcc atgttgtgag gatttagcta gagagtcaag aaagaggaat atatgcttta   180
tgtagatagg agtaggatct ctgggtcttt aaacatcacc atgacaagca agataagaa   240 caggagagca gttcttgatt attatttttc ttctcatcaa gaaattaagc cggagataga   300
catggcagct gcacgcagtg attcacttct tgatttcttg atttggggttg ttgcgttttgt   360 gtccagaccg atctgagctg cgggccatcg tcgatgacgg                         400
```

<210> SEQ ID NO 97
<211> LENGTH: 352
<212> TYPE: DNA
<213> ORGANISM: Oryza sativa

<400> SEQUENCE: 97

```
tgaacaggaa ggtaagttct ggctttcttg cttttggata aattttgctt cctttcttaa    60
```

```
cttgagcaca agcttgtgtt atatgtggtg tggaatccttg gttgccatgt tgtgaggatt      120
tagctagaga gtcaagaaag aggaatatat gctttatgta gataggagta ggatctctgg      180
gtctttaaac atcaccatga caagcaaaga taagaacagg agagcagttc ttgattatta      240
tttttcttct catcaagaaa ttaagccgga gatagacatg gcagctgcac gcagtgattc      300
acttcttgat tccttgattt gggttgttgc gtttgtgtcc aggtcgatct ga              352
```

<210> SEQ ID NO 98
<211> LENGTH: 1013
<212> TYPE: DNA
<213> ORGANISM: Oryza sativa

<400> SEQUENCE: 98

```
atcgtaactt tatttccgag gaaattgtaa gatctcgcgc gacctgtttg ttcttcttgg       60
tgttcttctg cctagttact tcgtttgttt tatgtttgat ctatagtctt gatgatctgt      120
gaagactagt tgttgttttc ggtacggatg gtaggaaagg tattttcctt tgtttaagga      180
attgcaagat ctcgcgcgac ctgttcttga tgttctgtct agtacttcgt tgtttgttt       240 gatctagtat gttagatgat ctatgaaaag tagttatttt cggtacgaat ggtaggagaa      300 gtatttttcct tgttggcgt caaaatataa tctttaatca ctcagtcttg tgaatggtaa      360
ttctgaattc atatttttct tttctgatct atatcgtgtt attctgttta tgattttttg      420
ctgagtagat ccccttgtgc tcgatgtatg ataagttatc tatatcgtaa tagattcgta      480
tgtcaaaact tagtcgaaat tttcgatctc atctcttctg ttagccacag gtggctgatt      540
gaaatattct tcaattgagt ctgaattttt atgttatatg caaataattg tcccgctcca      600
gttcatatgt ctgatgaaac atgaatgtaa aggaattaag actttggtta tatgattcga      660
gtctgaattt tcttatgctt atgcaaataa tagtccaaaa gaattggtga ttttttttgtg     720 tagttcatat ggttgataaa tatgaatgtg tctcaaaagc aacgaagatt ttgatgacaa      780
gacaatctgc tatttgagtc tgaaatttct tatgcttttg caaataatag tcatagtcag      840
aacgaattac tgaaatttcc ctccagttca tacggttgat gaaacatgaa tgtatctctt      900
tagtaattga aactttgacg atcagacaat ctgttgcatt gcctagtctt gcagattctc      960
atcgatcctt ttaattcttc tctgcagtca acaaattgat gcactaatgg agt            1013
```

<210> SEQ ID NO 99
<211> LENGTH: 645
<212> TYPE: DNA
<213> ORGANISM: Oryza sativa

<400> SEQUENCE: 99

```
cagcacaaca caccaaggaa gctgaggtga gaacgattga ttactttgct ggctgctctt       60
agctactact acaactgttt tgtcttaatc ggttgattac atctcatatt tcatcggttt      120
agctcgctct gttaagattt ctcacctcct cttggatgta ttattcatgt atatgttgtg      180
tggtctggct aagtttttgg tctgtcctga taaatgctgt ttaaggattc tttctttgtt      240 ctttttttt atggacaaaa tataatcttt gtgccttact gtgaattgag tctgttggct      300
atatcgttcc cggtttattg gactatagat gaacatgtaa ccctatatgc ggttgtgttt      360
tctccttaca aagatcagta gtacctaatt cagctagtta gaagtggtac caaggctgta      420
aatttccatc tttttctctg tgaggttcat ttcccttta atctctgttt cgtgagaaat      480 accccactg ttgacttcca gtaaatctgt tctctatttc tagttcagtt aacctgctat      540
tattgattct acaatttaag cataataaag attaatgtct attagttttc tcaattgatc      600
```

```
atgtggcacg tattttagca ggtgcgttga tttcttgata tcatg              645
```

<210> SEQ ID NO 100
<211> LENGTH: 196
<212> TYPE: DNA
<213> ORGANISM: Oryza sativa

<400> SEQUENCE: 100

```
cctctcggca tccagggaaa accaaggtgc gaaatttttt tttgtgggtt tttttggctg    60
cttccatttc gcaatccact gatggagtac gttgctagca gtcgttgcaa tttctcagta   120
attttaccga tttactattt atgcaagctt acactggtga attttttca gggtaaatta   180
ggcctgcgtg attcaa                                                   196
```

<210> SEQ ID NO 101
<211> LENGTH: 365
<212> TYPE: DNA
<213> ORGANISM: Oryza sativa

<400> SEQUENCE: 101

```
tccaagtgtc aagtacttac gaaacggtac tatgaatata tgtctagtta cattttgcac    60
ttcaatatat atgtgtagct tctgcccctc tgcttgtttt gcattacatg tatttgcttg   120
ttggagaagt agatagctat atcttaaaca tttagatctt attcggttaa tcccatatgc   180
gtgaaattag aggggattaa ttccacacat tattcctctt cttccctaat taaataaccct  240
tataggtgga attagccgaa taagtcaatg attaattttt ctagtcctct cttgtgagtg   300
gattgattaa ttactactta gaattggctc atatacgcag aatatgccgg cattggtgaa   360
gatcg                                                               365
```

<210> SEQ ID NO 102
<211> LENGTH: 701
<212> TYPE: DNA
<213> ORGANISM: Oryza sativa

<400> SEQUENCE: 102

```
ttttgttgtt ctgctggtct tgctcggtaa ttttttgctc caaatccatc tcctttctct    60
tcttttctgc tgttacccgc cgtatctttg ctttaccttc ttcttttttt ttctttttt   120
tttttgcgaa tccatcttgc tttagtttgt tgttctgttc cgagtaaaaa gaatacccctt  180
gatggcctag tctgaccaaa aaggagtgtg aagctcttcg aaaggaaaag gtttagacaa   240
tacgagcctc agatgctcgg ttgcttagtc gatccggtgg tgaatcgaac aatttaattc   300
actgatgctg ttaatctttt tctttaaaag aaaattcctt tctgttattg gtggtattt   360
cttcaacata aacatatatc tgaagattct tcagaaatga tctgaagtct gaagatttca   420
gcgtggcgcc ttagctgatt tattgtaact gtgatgaata tagcagcgtt gactgggtac   480
agtacaatta cttgcacatc ctattatgta gaaacaagaa atttgatgaa tataacaagg   540
aattcttaat gtttatggcc ttaaatcagc ttaaaacaac actgaagcca cgttgttgtt   600
aaatgaaggt gactgctacc ttagttcatg cgaaatatt cagtgcgacc taacctaatt    660
ctactgaaac gaattcagcg tgcaaagaga tgccggagca c                       701
```

<210> SEQ ID NO 103
<211> LENGTH: 329
<212> TYPE: DNA
<213> ORGANISM: Oryza sativa

<400> SEQUENCE: 103

```
aggggtcagg cactgcctgc tacaaggtaa aaaactcact ggagattaag aacaattatt      60
aatttcattc ttgattcagt acatggtcca atttacatgc tctattgaat tgatggtgtc     120
ttaatttgga aaacattttg catggatgga tttcaacaag tgttctgatg atgaaagcct     180
gactgttctt tactttcttc agacaaagaa tccacttgca tgtagtagag ggatttgaag     240
ttattcttat gttttcttgg ttaaatcaag cagctgtttt cttgtttggt ccagagtggt     300
gtaggtgatt cggctagctc agcgcgaag                                       329

<210> SEQ ID NO 104
<211> LENGTH: 593
<212> TYPE: DNA
<213> ORGANISM: Oryza sativa

<400> SEQUENCE: 104
ctcgctcccg cgctgtcttc ggtgaggtac gtacgatgaa caaagaacaa accccctaaat    60 tgctctttct atatgcgatt tctagagtat ttatttattt atttatgagg ggggattccg    120
ccgttctaaa ttggtgggtc ataggagaga ttaggtccga ttgttctcgt ggtgaaatta    180
atactatgcg ctcacgtacg ctacctctgg attaattcac cattcaaaca aaatcaaggc    240
agaacaaatg gtatatatct gctatttttg tcagcgccaa tctgcaaatt aacaatgctt    300
tacatattgg agagtgtctt gctgttcttc atgtttgtct cagttagtca gttagcagct    360
tcttttttta atttctttag cgaaattcgt tatatctggt gacatacgga cagggtcgac    420
taatataggt tcatggtcgc ggcctactgc aatctgcatc tgcaatttga ttcacggtct    480
atttggctcc ttcgtagaga cattaaaaat attggttgtg tttgtatgat caagagaact    540
ttcatctgaa ctttgattgg ttgtgttcac agttgctgga gttgagttag aca           593

<210> SEQ ID NO 105
<211> LENGTH: 864
<212> TYPE: DNA
<213> ORGANISM: Oryza sativa

<400> SEQUENCE: 105
agacaaggaa ggccacctcc cctaaggtag gaaaattgga agcaatttaa catgcattat      60
gcttatcaat catcctgtgc atgcatgtca gctagcttac ttcatagagc attagagctt    120
atagttcatc tgatcagaac tagttgtctg ggaggttaat tatgcatgtg tgttcaagaa    180
ctcagccagc taataacccg ttctagggac tcgatcatca agtgcatgaa tgcatggtgt    240
gcatgcttga ggttcatatg gttaattaag atttctcagc aagattaatt gttgatgaaa    300
aaggcaagca aattaaacat atatgatc ttttggtgtg tgttgcgttg ctgttcacaa     360
gtggatgtat gtgaccctgc gtctgctgtt catttagtt acatatgcct agttgttatt    420
ttgtatggca gttactttca agttagttaa aggctttcta acaagccct atgtatatat    480 atttctgtgt tagcttaggc atcattttct ttaccttttg tacaaatttc caagtggtca    540
aagcaatctt aactcttcct tgctactagc tctttcgcac ctgacttat tagaagctta     600 tattataaaa aatttctcct tcctttctcg agctggcgtc tgcaaaaata ccgatttta    660 caagcacatg agtctagtag ggtgctccac ccgcatgcaa aaagcaaatt tggtcgtcta    720 taaaaaccctt ttgtatagta gtgtggtttt aattattttt ataattcgca aagttgtttt    780
taacttggac tgttcatttg gtgttttcac tagttaatac agtcttttt tcttcagag      840 ctcaatgact agtagcacag ggcc                                           864
```

```
<210> SEQ ID NO 106
<211> LENGTH: 424
<212> TYPE: DNA
<213> ORGANISM: Oryza sativa

<400> SEQUENCE: 106
cttattaatt tacctctaca gaagaagtaa gttgatctct ctttcttgct tcaatctgat      60
tgtttccttg ctagttgaaa actactatta tatactctgt ctttcgtcca tcttgagtga     120
tatcatgaat tgatacacat tctcatgaat gaatgtatca aattccatct gaaactctgg     180
tagtagctgc acacacattt cagaattcag actttgcact agctttgtgc attgagatag     240
agaaattacc aaagtagatg taagcatgta agagttgttg aaatatgctt acatacaaaa     300
attgtataaa aaatatgatt atgaatgtac tagtgaatag tgattacaag atttaaactc     360
ctaatcaatt aagtttgcat cattgatgca agttcaggca ttacagacat tgagattcat     420
ttcc                                                                  424

<210> SEQ ID NO 107
<211> LENGTH: 773
<212> TYPE: DNA
<213> ORGANISM: Oryza sativa

<400> SEQUENCE: 107
gcttggagct tgagctttct gaatttgtaa gttatttttg ctctaatttt gggctaccaa      60
ttgggtttat atttctctag tggtggtgac tggtgagtaa ttttcccctt attttattgt     120
gttgatgtga ggcctgggg ttttctatct ctttgcatcg ttttcgcttt catttgttta      180
gagatttgtt ctttgaacaa agcatgcaga atctctgag gactgaagtg tttctctctg      240
cttgtcactt tctccccaat tgtggaataa ctaagaggaa tcgacatggg gtctagtctt     300
ccattccaca agatttgcat cttccccatg aatcttccaa gaaaatctgt atctcttact     360
tcctttcttt ttctctaggt cttgtcttgc aaactaggat aaagatacaa gttagtagta     420
caagaaacag taaaggtgaa agtcttgtgt tcttttccct gcgatttctt ctgaaaaagg     480
tcgccattaa gaaaaagctt tgcaatcttt ggagtgttct tctcacccag tggtttctct     540
gcttgttctc ttctgattaa taacagtagt agctgctcat taaattgcat ctttttttaa     600
tttatttaat ttctgttgat gtgaaacgca tccaatctct tgcaatcaat gtgaggcttt     660
cattggcgta tgagcataaa aagggggaa agaaaggtgg gagtctttag gtttctactc     720
ctaaaaattg tttctttctt atgtgcagca gtcggtgtaa ctaatggggg aga            773

<210> SEQ ID NO 108
<211> LENGTH: 442
<212> TYPE: DNA
<213> ORGANISM: Oryza sativa

<400> SEQUENCE: 108
ggtctcctgc tctgccatgt ccatgggtat ccatccatct ctgctttctc tctccctgtt      60
gtgttgggct ttcttgttca tgtccttgga atgtaaagtt tggttctttt tttttatggt     120
acctttgtcc ttcctttcct cttgatttca tttagtaacg gtgttaggaa ggaaggatat     180
tctttctgct ctgttcttga ttttgttat caattttcct tttttatgg ctcaccctct       240 ttcagatatt gccatatcag aaataaaaaa tctgattttt tttcatatat tattcatcat     300
actagtttta accttttttt ttttgaaaaa aaaatatgag agagaagaaa aatcagcatg     360
tttcttgctg ttcatcagaa gctgtagtga aatttaatgg ctgcatgtgg acagatgaag     420
ggtatggccc tacctgggac ag                                              442
```

```
<210> SEQ ID NO 109
<211> LENGTH: 6794
<212> TYPE: DNA
<213> ORGANISM: puc based expression vector pBPSMM291
<220> FEATURE:
<221> NAME/KEY: terminator
<222> LOCATION: (920)..(1189)
<223> OTHER INFORMATION: polyadenylation signal (terminator) of the
      Nopaline synthase gene
<220> FEATURE:
<221> NAME/KEY: gene
<222> LOCATION: (1250)..(3255)
<223> OTHER INFORMATION: beta-glucoronidase gene containing the potato
      invertase 2 intron. (sequence is complementary)
<220> FEATURE:
<221> NAME/KEY: Intron
<222> LOCATION: (3311)..(3894)
<223> OTHER INFORMATION: inventive Intron BPSI.1 (sequence is
      complementary)
<220> FEATURE:
<221> NAME/KEY: promoter
<222> LOCATION: (3921)..(4856)
<223> OTHER INFORMATION: eukaryotic Promoter: Zea mais ubiquitin
      promoter (sequence is complementary)

<400> SEQUENCE: 109
ctttcctgcg ttatcccctg attctgtgga taaccgtatt accgcctttg agtgagctga      60
taccgctcgc cgcagccgaa cgaccgagcg cagcgagtca gtgagcgagg aagcggaaga     120
gcgcccaata cgcaaaccgc ctctccccgc gcgttggccg attcattaat gcagctggca     180
cgacaggttt cccgactgga aagcgggcag tgagcgcaac gcaattaata cgcgtaccgc     240
tagccaggaa gagtttgtag aaacgcaaaa aggccatccg tcaggatggc cttctgctta     300
gtttgatgcc tggcagttta tggcgggcgt cctgcccgcc accctccggg ccgttgcttc     360
acaacgttca atccgctccc ggcggatttg tcctactcag ggagagcgtt caccgacaaa     420
caacagataa aacgaaaggc ccagtcttcc gactgagcct ttcgttttat ttgatgcctg     480
gcagttccct actctcgcgt taacgctagc atggatgttt tcccagtcac gacgttgtaa     540
aacgacggcc agtcttaagc tcgggcccca aataatgatt ttattttgac tgatagtgac     600
ctgttcgttg caacaaattg atgagcaatg cttttttata atgccaactt tgtacaaaaa     660
agcaggctcc gcggccgccc ccttcaccgc tatcgtttaa actgaaggcg ggaaacgaca     720
atctgatcca agctcaagct gctctagcat tcgccattca ggctgcgcaa ctgttgggaa     780
gggcgatcgg tgcgggcctc ttcgctatta cgccagctgg cgaaagggggg atgtgctgca     840 aggcgattaa gttgggtaac gccagggttt cccagtcac gacgttgtaa aacgacggcc     900
agtgccaagc ttgcatgcca attcccgatc tagtaacata gatgacaccg cgcgcgataa     960
tttatcctag tttgcgcgct atattttgtt ttctatcgcg tattaaatgt ataattgcgg    1020
gactctaatc ataaaaaccc atctcataaa taacgtcatg cattacatgt taattattac    1080
atgcttaacg taattcaaca gaaattatat gataatcatc gcaagaccgg caacaggatt    1140
caatcttaag aaactttatt gccaaatgtt tgaacgatcg gggaaattcg agctcggtag    1200
caattcccga ggctgtagcc gacgatggtg cgccaggaga gttgttgatt cattgtttgc    1260
ctccctgctg cggttttttca ccgaagttca tgccagtcca gcgttttttgc agcagaaaag    1320 ccgccgactt cggtttgcgg tcgcgagtga agatccctt cttgttaccg ccaacgcgca    1380
atatgccttg cgaggtcgca aaatcggcga aattccatac ctgttcaccg acgacggcgc    1440
tgacgcgatc aaagacgcgg tgatacatat ccagccatgc acactgatac tcttcactcc    1500
acatgtcggt gtacattgag tgcagcccgg ctaacgtatc cacgccgtat cggtgatga    1560
```

```
taatcggctg atgcagtttc tcctgccagg ccagaagttc tttttccagt accttctctg   1620
ccgtttccaa atcgccgctt tggacatacc atccgtaata acggttcagg cacagcacat   1680
caaagagatc gctgatggta tcggtgtgag cgtcgcagaa cattacattg acgcaggtga   1740
tcggacgcgt cgggtcgagt ttacgcgttg cttccgccag tggcgaaata ttcccgtgca   1800
cttgcggacg ggtatccggt tcgttggcaa tactccacat caccacgctt gggtggtttt   1860
tgtcacgcgc tatcagctct ttaatcgcct gtaagtgcgc ttgctgagtt tccccgttga   1920
ctgcctcttc gctgtacagt tctttcggct tgttgcccgc ttcgaaacca atgcctaaag   1980
agaggttaaa gccgacagca gcagtttcat caatcaccac gatgccatgt tcatctgccc   2040
agtcgagcat ctcttcagcg taagggtaat gcgaggtacg gtaggagttg gccccaatcc   2100
agtccattaa tgcgtggtcg tgcaccatca gcacgttatc gaatcctttg ccacgtaagt   2160
ccgcatcttc atgacgacca aagccagtaa agtagaacgg tttgtggtta atcaggaact   2220
gttggcccct cactgccact gaccggatgc cgacgcgaag cgggtagata tcacactctg   2280
tctggctttt ggctgtgacg cacagttcat agagataacc ttcacccggt tgccagaggt   2340
gcggattcac cacttgcaaa gtcccgctag tgccttgtcc agttgcaacc acctgttgat   2400
ccgcatcacg cagttcaacg ctgacatcac cattggccac cacctgccag tcaacagacg   2460
cgtggttaca gtcttgcgcg acatgcgtca ccacggtgat atcgtccacc caggtgttcg   2520
gcgtggtgta gagcattacg ctgcgatgga ttccggcata gttaaagaaa tcatggaagt   2580
aagactgctt tttcttgccg ttttcgtcgg taatcaccat tcccggcggg atagtctgcc   2640
agttcagttc gttgttcaca caaacggtga tacctgcaca tcaacaaatt ttggtcatat   2700
attagaaaag ttataaatta aaatatacac acttataaac tacagaaaag caattgctat   2760
atactacatt cttttatttt gaaaaaaata tttgaaatat tatattacta ctaattaatg   2820
ataattatta tatatatatc aaaggtagaa gcagaaactt acgtacactt ttcccggcaa   2880
taacatacgg cgtgacatcg gcttcaaatg gcgtatagcc gccctgatgc tccatcactt   2940
cctgattatt gacccacact ttgccgtaat gagtgaccgc atcgaaacgc agcacgatac   3000
gctggcctgc ccaaccttc ggtataaaga cttcgcgctg ataccagacg ttgcccgcat   3060
aattacgaat atctgcatcg gcgaactgat cgttaaaact gcctggcaca gcaattgccc   3120
ggctttcttg taacgcgctt tcccaccaac gctgatcaat tccacagttt tcgcgatcca   3180
gactgaatgc ccacaggccg tcgagttttt tgatttcacg ggttgggggtt tctacaggac   3240 gtaacataag ggactgacca cccaaacctt aaggcgatcg cgctgaggcg gaccgttgta   3300
catcttgcat ctgcatgtac aaataatcaa tcagaaattc agagcctatt tcttgtctgt   3360
tcaaagaaga ggggataaaa aaaatcagat ccttatcagc catcagcatg catgctcctc   3420
atttaatatc ggtggaaagg agctaaatca aaatctccta taatgaatct ttttttttcct   3480 ctcaagaaag atcatcatca cattaagcca ccatctcaaa aagatttttt ctatcatgaa   3540 cttttttcctc tcaagaaaga tcatcatcag atttggccac catctaaaaa aagatttgtt   3600
cacagactat tgagtccata acatgttcta ttatccaaaa caaatcccaa ggagaggcac   3660
acatatgaca catacaacac atgcatgtca atatgtcatg aatacatacc aagatcaaca   3720
acatggataa acacaaattc tctacggatc acaacacaca aaaaaaccc cagcaaacga   3780 acaatatccc ttccgagatc caccgaattt ccatctcacc aacaccaaga ctagacagtt   3840
attatacatg acagatcaag aacagaaatt cagaagatgg tgatcggatc ttaccctccg   3900
caggtgaagg cccgggggatc tggttgtgtg tgtgtgcgct ccgaacaaca cgaggttggg   3960
```

```
gaaagagggt gtggaggggg tgtctatttta ttacggcggg cgaggaaggg aaagcgaagg    4020
agcggtggga aaggaatccc ccgtagctgc cgtgccgtga gaggaggagg aggccgcctg    4080
ccgtgccggc tcacgtctgc cgctccgcca cgcaatttct ggatgccgac agcggagcaa    4140
gtccaacggt ggagcggaac tctcgagagg ggtccagagg cagcgacaga gatgccgtgc    4200
cgtctgcttc gcttggcccg acgcgacgct gctggttcgc tggttggtgt ccgttagact    4260
cgtcgacggc gtttaacagg ctggcattat ctactcgaaa caagaaaaat gtttccttag    4320 ttttttttaat ttcttaaagg gtatttgttt aattttttagt cactttatttt tattctatttt    4380 tatatctaaa ttattaaata aaaaaactaa aatagagttt tagttttctt aatttagagg    4440
ctaaaataga ataaaataga tgtactaaaa aaattagtct ataaaaacca ttaaccctaa    4500
accctaaatg gatgtactaa taaaatggat gaagtattat ataggtgaag ctatttgcaa    4560
aaaaaaagga gaacacatgc acactaaaaa gataaaactg tagagtcctg ttgtcaaaat    4620
actcaattgt cctttagacc atgtctaact gttcatttat atgattctct aaaacactga    4680
tattattgta gtactataga ttatattatt cgtagagtaa agtttaaata tatgtataaa    4740
gatagataaa ctgcacttca aacaagtgtg acaaaaaaaa tatgtggtaa tttttttataa    4800 cttagacatg caatgctcat tatctctaga gagggggcacg accgggtcac gctgcactgc    4860
aggaattcga tggggatcct ctagagtcga cctgcaggca tgcaagcttg gcgcgccgac    4920
ccagctttct tgtacaaagt tggcattata agaaagcatt gcttatcaat ttgttgcaac    4980
gaacaggtca ctatcagtca aaataaaatc attatttgcc atccagctga tatccccctat    5040 agtgagtcgt attacatggt catagctgtt tcctggcagc tctggcccgt gtctcaaaat    5100
ctctgatgtt acattgcaca agataaaaat atatcatcat gaacaataaa actgtctgct    5160
tacataaaca gtaatacaag gggtgttatg agccatattc aacgggaaac gtcgaggccg    5220
cgattaaatt ccaacatgga tgctgattta tatgggtata aatgggctcg cgataatgtc    5280
gggcaatcag gtgcgacaat ctatcgcttg tatgggaagc ccgatgcgcc agagttgttt    5340
ctgaaacatg gcaaaggtag cgttgccaat gatgttacag atgagatggt cagactaaac    5400
tggctgacgg aatttatgcc tcttccgacc atcaagcatt ttatccgtac tcctgatgat    5460
gcatggttac tcaccactgc gatccccgga aaaacagcat tccaggtatt agaagaatat    5520
cctgattcag gtgaaaatat tgttgatgcg ctggcagtgt tcctgcgccg gttgcattcg    5580
attcctgttt gtaattgtcc ttttaacagc gatcgcgtat ttcgtctcgc tcaggcgcaa    5640
tcacgaatga ataacggttt ggttgatgcg agtgattttg atgacgagcg taatggctgg    5700
cctgttgaac aagtctggaa agaaatgcat aaacttttgc cattctcacc ggattcagtc    5760
gtcactcatg gtgatttctc acttgataac cttattttttg acgaggggaa attaataggt    5820
tgtattgatg ttggacgagt cggaatcgca gaccgatacc aggatcttgc catcctatgg    5880
aactgcctcg gtgagttttc tccttcatta cagaaacggc ttttttcaaaa atatggtatt    5940 gataatcctg atatgaataa attgcagttt catttgatgc tcgatgagtt tttctaatca    6000
gaattggtta attggttgta acactggcag agcattacgc tgacttgacg ggacggcgca    6060
agctcatgac caaaatccct taacgtgagt tacgcgtcgt tccactgagc gtcagacccc    6120
gtagaaaaga tcaaaggatc ttcttgagat cctttttttc tgcgcgtaat ctgctgcttg    6180
caaacaaaaa aaccaccgct accagcggtg gtttgtttgc cggatcaaga gctaccaact    6240 cttttccga aggtaactgg cttcagcaga gcgcagatac caaatactgt ccttctagtg    6300
tagccgtagt taggccacca cttcaagaac tctgtagcac cgcctacata cctcgctctg    6360
```

```
ctaatcctgt taccagtggc tgctgccagt ggcgataagt cgtgtcttac cgggttggac    6420
tcaagacgat agttaccgga taaggcgcag cggtcgggct gaacggggg ttcgtgcaca    6480 cagcccagct tggagcgaac gacctacacc gaactgagat acctcagcg tgagcattga    6540 gaaagcgcca cgcttcccga agggagaaag gcggacaggt atccggtaag cggcagggtc    6600
ggaacaggag agcgcacgag ggagcttcca gggggaaacg cctggtatct ttatagtcct    6660
gtcgggtttc gccacctctg acttgagcgt cgattttgt gatgctcgtc aggggggcgg    6720
agcctatgga aaaacgccag caacgcggcc ttttttacggt tcctggcctt ttgctggcct    6780
tttgctcaca tgtt                                                       6794

<210> SEQ ID NO 110
<211> LENGTH: 6077
<212> TYPE: DNA
<213> ORGANISM: pUC based expression vector pBPSMM305
<220> FEATURE:
<221> NAME/KEY: promoter
<222> LOCATION: (286)..(1350)
<223> OTHER INFORMATION: eukaryotic promoter: promoter of the maize
      lactate dehydrogenase gene
<220> FEATURE:
<221> NAME/KEY: gene
<222> LOCATION: (1369)..(3369)
<223> OTHER INFORMATION: beta-Glucuronidase gene comtaining the potato
      invertase 2 intron
<220> FEATURE:
<221> NAME/KEY: gene
<222> LOCATION: (1369)..(3369)
<223> OTHER INFORMATION: beta-Glucuronidase gene comtaining the potato
      invertase 2 intron
<220> FEATURE:
<221> NAME/KEY: Terminator
<222> LOCATION: (3403)..(3640)
<223> OTHER INFORMATION: Nopaline synthase gene terminator
<220> FEATURE:
<221> NAME/KEY: gene
<222> LOCATION: (4276)..(5136)
<223> OTHER INFORMATION: beta-lactamase gene

<400> SEQUENCE: 110
gcgcccaata cgcaaaccgc ctctccccgc gcgttggccg attcattaat gcagctggca     60
cgacaggttt cccgactgga aagcgggcag tgagcgcaac gcaattaatg tgagttagct    120
cactcattag gcaccccagg ctttacactt tatgcttccg gctcgtatgt tgtgtggaat    180
tgtgagcgga taacaatttc acacaggaaa cagctatgac catgattacg ccaagctatc    240
gtttaaacct taaggcgatc gcgctgaggc ggaccgcacg tggaattcaa caaatggcgt    300
acttatataa ccacaatgta ctggtgctgc gtcattattt tatactacgc atatattatt    360
ataagtagag aaagctcaca aaaccatgcg cgcgcccccc tgtttgcttt cggtcgctaa    420
ttacaccctt tgtatcgttg gttgatgatg gtctccaccg gccgtacgag tcatcgatcg    480
ttgatttatt tttatcaccg acttgcacgc ctttcgaaca aagacgcaac aaaggaaagc    540
gaaagcacga acgaggttgt tccctgacag ttgggcgact aatacaactg caagacactg    600
aataagcagt aaaaatcaat atagattaaa gttaacgaa catgctcaac atcgaatact    660
actcatatgt gttattatta agagaatacc accaaggtag aaaagttaaa ggacctaaac    720
tgttgtgccg ggagagttgt gcgacgaaca gatgtaaata tgataaaata agttcaaagt    780
tcatatagat agcacgatca cacttagggc tagtttgaag ccataaaaat ggaagagatt    840
aaatgagata aaattcactt atttaatttt aaataagaag agagttttaa ccctctcaat    900
tctctccagt attttagctc ctaaactagc tcttacagca gtaaaagacc cttgatggta    960
```

-continued

```
gcgtatgcaa agagaaggaa ctattcaatg aattgttttt ttaatcacta gtagtatggt    1020
gggtaacgtg ttcgtcaacc ggccctatct acttcagttt agtgaagcac taaaccgcac    1080
cttggtatgt tcaaatttaa gattttttt gaaacgaaac aatttaacc agcggctcca    1140 aaccggtgaa gtggtttggt ctttggtgtg gggccaggt attaatggaa ttgaatatat    1200
aaagagcagg gtggtggacc tttccccacc cacgagtcga gtagccattg cccattgcca    1260
ttccttcctt cctccacaga gaaatccgat ccgcggagat ttgacccaac cagatcatat    1320
cacacacgta atcccatccc attccgcccg gagctcggta cccggggatc catgttacgt    1380
cctgtagaaa ccccaacccg tgaaatcaaa aaactgacg gcctgtgggc attcagtctg    1440
gatcgcgaaa actgtggaat tgatcagcgt tggtgggaaa gcgcgttaca agaaagccgg    1500
gcaattgctg tgccaggcag ttttaacgat cagttcgccg atgcagatat tcgtaattat    1560 gcggcaacg tctggtatca gcgcgaagtc tttataccga aaggttgggc aggccagcgt    1620
atcgtgctgc gtttcgatgc ggtcactcat tacggcaaag tgtgggtcaa taatcaggaa    1680
gtgatggagc atcagggcgg ctatacgcca tttgaagccg atgtcacgcc gtatgttatt    1740
gccgggaaaa gtgtacgtaa gtttctgctt ctacctttga tatatatata ataattatca    1800
ttaattagta gtaatataat atttcaaata ttttttcaa aataaagaa tgtagtatat    1860 agcaattgct tttctgtagt ttataagtgt gtatatttta atttataact tttctaatat    1920
atgaccaaaa tttgttgatg tgcaggtatc accgtttgtg tgaacaacga actgaactgg    1980
cagactatcc cgccgggaat ggtgattacc gacgaaaacg gcaagaaaaa gcagtcttac    2040
ttccatgatt tctttaacta tgccggaatc catcgcagcg taatgctcta caccacgccg    2100
aacacctggg tggacgatat caccgtggtg acgcatgtcg cgcaagactg taaccacgcg    2160
tctgttgact ggcaggtggt ggccaatggt gatgtcagcg ttgaactgcg tgatgcggat    2220
caacaggtgg ttgcaactgg acaaggcact agcgggactt tgcaagtggt gaatccgcac    2280
ctctggcaac cgggtgaagg ttatctctat gaactgtgcg tcacagccaa aagccagaca    2340
gagtgtgata tctacccgct tcgcgtcggc atccggtcag tggcagtgaa gggccaacag    2400
ttcctgatta accacaaacc gttctacttt actggctttg tcgtcatga agatgcggac    2460 ttacgtggca aaggattcga taacgtgctg atggtgcacg accacgcatt aatggactgg    2520
attgggccca actcctaccg tacctcgcat tacccttacg ctgaagagat gctcgactgg    2580
gcagatgaac atggcatcgt ggtgattgat gaaactgctg ctgtcggctt aacctctct    2640 ttaggcattg gtttcgaagc gggcaacaag ccgaaagaac tgtacagcga gaggcagtc    2700 aacggggaaa ctcagcaagc gcacttacag gcgattaaag agctgatagc gcgtgacaaa    2760
aaccacccaa gcgtggtgat gtggagtatt gccaacgaac cggatacccg tccgcaagtg    2820
cacgggaata tttcgccact ggcggaagca acgcgtaaac tcgacccgac gcgtccgatc    2880
acctgcgtca atgtaatgtt ctgcgacgct cacaccgata ccatcagcga tctctttgat    2940
gtgctgtgcc tgaaccgtta ttacggatgg tatgtccaaa gcggcgattt ggaaacggca    3000
gagaaggtac tggaaaaaga acttctggcc tggcaggaga aactgcatca gccgattatc    3060
atcaccgaat acggcgtgga tacgttagcc gggctgcact caatgtacac cgacatgtgg    3120
agtgaagagt atcagtgtgc atggctggat atgtatcacc gcgtctttga tcgcgtcagc    3180
gccgtcgtcg gtgaacaggt atggaatttc gccgattttg cgacctcgca aggcatattg    3240
cgcgttggcg gtaacaagaa agggatcttc actcgcgacc gcaaaccgaa gtcggcggct    3300
tttctgctgc aaaaacgctg gactggcatg aacttcggtg aaaaaccgca gcagggaggc    3360
```

```
aaacaatgaa gatcctctag agtcgacctg caggcatgca agcttgtttc ttaagattga   3420
atcctgttgc cggtcttgcg atgattatca tataatttct gttgaattac gttaagcatg   3480
taataattaa catgtaatgc atgacgttat ttatgagatg gttttttatg attagagtcc   3540
cgcaattata catttaatac gcgatagaaa acaaaatata gcgcgcaaac taggataaat   3600
tatcgcgcgc ggtgtcatct atgttactag atcgggaatt ttaattaaag gcctgttaac   3660
agcgctgggc ccgataattc actggccgtc gttttacaac gtcgtgactg ggaaaaccct   3720
ggcgttaccc aacttaatcg ccttgcagca catccccctt tcgccagctg gcgtaatagc   3780
gaagaggccc gcaccgatcg cccttcccaa cagttgcgca gcctgaatgg cgaatggcgc   3840
ctgatgcggt attttctcct tacgcatctg tgcggtattt cacaccgcat atggtgcact   3900
ctcagtacaa tctgctctga tgccgcatag ttaagccagc cccgacaccc gccaacaccc   3960
gctgacgcgc cctgacgggc ttgtctgctc ccggcatccg cttacagaca gctgtgacc    4020
gtctccggga gctgcatgtg tcagaggttt tcaccgtcat caccgaaacg cgcgagacga   4080
aagggcctcg tgatacgcct atttttatag gttaatgtca tgataataat ggtttcttag   4140
acgtcaggtg gcacttttcg gggaaatgtg cgcggaaccc ctatttgttt attttttctaa  4200
atacattcaa atatgtatcc gctcatgaga caataaccct gataaatgct tcaataatat   4260
tgaaaaagga gagtatgag tattcaacat ttccgtgtcg cccttattcc cttttttgcg    4320
gcatttgcc ttcctgtttt tgctcaccca gaaacgctgg tgaaagtaaa agatgctgaa   4380
gatcagttgg gtgcacgagt gggttacatc gaactggatc tcaacagcgg taagatcctt   4440
gagagttttc gccccgaaga acgttttcca atgatgagca cttttaaagt tctgctatgt   4500
ggcgcggtat tatcccgtat tgacgccggg caagagcaac tcggtcgccg catacactat   4560
tctcagaatg acttggttga gtactcacca gtcacagaaa agcatcttac ggatggcatg   4620
acagtaagag aattatgcag tgctgccata accatgagtg ataacactgc ggccaactta   4680
cttctgacaa cgatcggagg accgaaggag ctaaccgctt ttttgcacaa catgggggat   4740
catgtaactc gccttgatcg ttgggaaccg gagctgaatg aagccatacc aaacgacgag   4800
cgtgacacca cgatgcctgt agcaatggca acaacgttgc gcaaactatt aactggcgaa   4860
ctacttactc tagcttcccg gcaacaatta atagactgga tggaggcgga taaagttgca   4920
ggaccacttc tgcgctcggc ccttccggct ggctggttta ttgctgataa atctggagcc   4980
ggtgagcgtg ggtctcgcgg tatcattgca gcactggggc cagatggtaa gccctcccgt   5040
atcgtagtta tctacacgac ggggagtcag gcaactatgg atgaacgaaa tagacagatc   5100
gctgagatag gtgcctcact gattaagcat tggtaactgt cagaccaagt ttactcatat   5160
atactttaga ttgatttaaa acttcatttt taatttaaaa ggatctaggt gaagatcctt   5220
tttgataatc tcatgaccaa aatcccttaa cgtgagtttt cgttccactg agcgtcagac   5280
cccgtagaaa agatcaaagg atcttcttga gatcctttt ttctgcgcgt aatctgctgc    5340
ttgcaaacaa aaaaaccacc gctaccagcg gtggtttgtt tgccggatca agagctacca   5400
actctttttc cgaaggtaac tggcttcagc agagcgcaga taccaaatac tgtccttcta   5460
gtgtagccgt agttaggcca ccacttcaag aactctgtag caccgcctac atacctcgct   5520
ctgctaatcc tgttaccagt ggctgctgcc agtggcgata gtcgtgtct taccgggttg    5580
gactcaagac gatagttacc ggataaggcg cagcggtcgg gctgaacggg gggttcgtgc   5640
acacagccca gcttggagcg aacgacctac accgaactga gatacctaca gcgtgagcta   5700
tgagaaagcg ccacgcttcc cgaagggaga aaggcggaca ggtatccggt aagcggcagg   5760
```

-continued

| | | |
|---|---|---|
| gtcggaacag gagagcgcac gagggagctt ccaggggggaa acgcctggta tctttatagt | 5820 | |
| cctgtcgggt ttcgccacct ctgacttgag cgtcgatttt tgtgatgctc gtcaggggg | 5880 | |
| cggagcctat ggaaaaacgc cagcaacgcg gccttttac ggttcctggc cttttgctgg | 5940 | |
| ccttttgctc acatgttctt tcctgcgtta tcccctgatt ctgtggataa ccgtattacc | 6000 | |
| gcctttgagt gagctgatac cgctcgccgc agccgaacga ccgagcgcag cgagtcagtg | 6060 | |
| agcgaggaag cggaaga | 6077 | |

```
<210> SEQ ID NO 111
<211> LENGTH: 15790
<212> TYPE: DNA
<213> ORGANISM: binary vector pBPSMM350
<220> FEATURE:
<221> NAME/KEY: misc_recomb
<222> LOCATION: (5254)..(5276)
<223> OTHER INFORMATION: Gateway cloning technology attachement site:
      attR2. (sequence is complementary)
<220> FEATURE:
<221> NAME/KEY: promoter
<222> LOCATION: (5341)..(6276)
<223> OTHER INFORMATION: Zea mais Ubiquitin promoter
<220> FEATURE:
<221> NAME/KEY: Intron
<222> LOCATION: (6303)..(6886)
<223> OTHER INFORMATION: BPSI.1
<220> FEATURE:
<221> NAME/KEY: gene
<222> LOCATION: (6942)..(8942)
<223> OTHER INFORMATION: GUS gene
<220> FEATURE:
<221> NAME/KEY: terminator
<222> LOCATION: (9003)..(9282)
<223> OTHER INFORMATION: Nopalin synthase terminator sequence (NosT)
<220> FEATURE:
<221> NAME/KEY: misc_recomb
<222> LOCATION: (9551)..(9651)
<223> OTHER INFORMATION: Gateway cloning technology attachement site:
      attR1. (sequence is complementary)
```

<400> SEQUENCE: 111

| | | |
|---|---|---|
| aattgactag tggcgcgccc acgtgttaat taaggcgcgc caagcttgca tgcctgcagg | 60 | |
| catgcaagct tccgcggctg cagtgcagcg tgacccggtc gtgcccctct ctagagataa | 120 | |
| tgagcattgc atgtctaagt tataaaaaat taccacatat ttttttttgtc acacttgttt | 180 | |
| gaagtgcagt ttatctatct ttatacatat atttaaactt tactctacga ataatataat | 240 | |
| ctatagtact acaataatat cagtgtttta gagaatcata taaatgaaca gttagacatg | 300 | |
| gtctaaagga caattgagta ttttgacaac aggactctac agtttatct ttttagtgtg | 360 | |
| catgtgttct ccttttttt tgcaaatagc ttcacctata taatacttca tccatttat | 420 | |
| tagtacatcc atttagggtt tagggttaat ggttttttata gactaatttt tttagtacat | 480 | |
| ctatttatt ctattttagc ctctaaatta agaaaactaa aactctattt tagttttttt | 540 | |
| atttaatagt ttagatataa aatagaataa aataaagtga ctaaaaatta aacaaatacc | 600 | |
| ctttaagaaa ttaaaaaaac taaggaaaca tttttcttgt ttcgagtaga taatgccagc | 660 | |
| ctgttaaacg ccgtcgacga gtctaacgga caccaaccag cgaaccagca gcgtcgcgtc | 720 | |
| gggccaagcg aagcagacgg cacggcatct ctgtcgctgc ctctggaccc ctctcgagag | 780 | |
| ttccgctcca ccgttggact tgctccgctg tcggcatcca gaaattgcgt ggcggagcgg | 840 | |
| cagacgtgag ccggcacggc aggcggcctc ctcctcctct cacggcaccg gcagctacgg | 900 | |
| gggattcctt tcccaccgct ccttcgcttt cccttcctcg cccgccgtaa taaatagaca | 960 | |
| ccccctccac accctctttc cccaacctcg tgttgttcgg agcgcacaca cacacaacca | 1020 | |

```
gatctccccc aaatccaccc gtcggcacct ccgcttcaag gtacgccgct cgtcctcccc    1080 ccccccccc ctctctacct tctctagatc ggcgttccgg tccatggtta gggcccggta     1140
gttctacttc tgttcatgtt tgtgttagat ccgtgtttgt gttagatccg tgctgctagc    1200
gttcgtacac ggatgcgacc tgtacgtcag acacgttctg attgctaact tgccagtgtt    1260
tctctttggg gaatcctggg atggctctag ccgttccgca gacgggatcg atttcatgat    1320 ttttttttgtt tcgttgcata gggtttggtt tgcccttttc ctttatttca atatatgccg   1380
tgcacttgtt tgtcgggtca tcttttcatg ctttttttg tcttggttgt gatgatgtgg    1440
tctggttggg cggtcgttct agatcggagt agaattctgt ttcaaactac ctggtggatt    1500
tattaatttt ggatctgtat gtgtgtgcca tacatattca tagttacgaa ttgaagatga    1560
tggatggaaa tatcgatcta ggataggtat acatgttgat gcgggtttta ctgatgcata    1620
tacagagatg cttttttgttc gcttggttgt gatgatgtgg tgtggttggg cggtcgttca   1680
ttcgttctag atcggagtag aatactgttt caaactacct ggtgtattta ttaattttgg    1740
aactgtatgt gtgtgtcata catcttcata gttacgagtt taagatggat ggaaatatcg    1800
atctaggata ggtatacatg ttgatgtggg ttttactgat gcatatacat gatggcatat    1860
gcagcatcta ttcatatgct ctaaccttga gtacctatct attataataa acaagtatgt    1920
tttataatta tttcgatctt gatatacttg gatgatggca tatgcagcag ctatatgtgg    1980 attttttttag ccctgccttc atacgctatt tatttgcttg gtactgtttc ttttgtcgat   2040
gctcaccctg ttgtttggtg ttacttctgc agggtacccc cggggatcc actagttcta    2100 gaaaccatgg ccaccgccgc cgccgcgtct accgcgctca ctggcgccac taccgctgcg    2160
cccaaggcga ggcgccgggc gcacctcctg gccaccgcc gcgccctcgc cgcgcccatc     2220
aggtgctcag cggcgtcacc cgccatgccg atggctcccc cggccacccc gctccggccg    2280
tggggcccca ccgatccccg caagggcgcg acatcctcg tcgagtccct cgagcgctgc    2340
ggcgtccgcg acgtcttcgc ctaccccggc ggcgcgtcca tggagatcca ccaggcactc    2400
acccgctccc ccgtcatcgc caaccacctc ttccgccacg agcaagggga ggcctttgcg    2460
gcctccggct acgcgcgctc ctcgggccgc gtcggcgtct gcatcgccac ctccggcccc    2520
ggcgccacca accttgtctc cgcgctcgcc gacgcgctgc tcgattccgt ccccatggtc    2580
gccatcacgg gacaggtgcc gcgacgcatg attggcaccg acgccttcca ggagacgccc    2640
atcgtcgagg tcacccgctc catcaccaag cacaactacc tggtcctcga cgtcgacgac    2700
atcccccgcg tcgtgcagga ggcttttctt ctcgcctcct ctggtcgacc ggggccggtg    2760
cttgtcgaca tccccaagga catccagcag cagatggcgg tgcctgtctg gacaagccc    2820 atgagtctgc ctgggtacat tgcgcgcctt cccaagcccc ctgcgactga gttgcttgag    2880
caggtgctgc gtcttgttgg tgaatcccgg cgccctgttc tttatgttgg cggtggctgc    2940
gcagcatctg gtgaggagtt gcgacgcttt gtggagctga ctggaatccc ggtcacaact    3000
actcttatgg gcctcggcaa cttccccagc gacgacccac tgtctctgcg catgctaggt    3060
atgcatggca cggtgtatgc aaattatgca gtggataagg ccgatctgtt gcttgcactt    3120
ggtgtgcggt ttgatgatcg tgtgacaggg aagattgagg cttttgcaag cagggctaag    3180
attgtgcacg ttgatattga tccggctgag attggcaaga acaagcagcc acatgtgtcc    3240
atctgtgcag atgttaagct tgctttgcag ggcatgaatg ctcttcttga aggaagcaca    3300
tcaaagaaga gctttgactt tggctcatgg aacgatgagt tggatcagca gaagagggaa    3360 ttccccccttg ggtataaaac atctaatgag gagatccagc cacaatatgc tattcaggtt    3420
```

```
cttgatgagc tgacgaaagg cgaggccatc atcggcacag gtgttgggca gcaccagatg    3480
tgggcggcac agtactacac ttacaagcgg ccaaggcagt ggttgtcttc agctggtctt    3540
ggggctatgg gatttggttt gccggctgct gctggtgctt ctgtggccaa cccaggtgtt    3600
actgttgttg acatcgatgg agatggtagc tttctcatga acgttcagga gctagctatg    3660
atccgaattg agaacctccc ggtgaaggtc tttgtgctaa acaaccagca cctggggatg    3720
gtggtgcagt gggaggacag gttctataag gccaacagag cgcacacata cttgggaaac    3780
ccagagaatg aaagtgagat atatccagat ttcgtgacga tcgccaaagg gttcaacatt    3840
ccagcggtcc gtgtgacaaa gaagaacgaa gtccgcgcag cgataaagaa gatgctcgag    3900
actccagggc cgtacctctt ggatataatc gtcccacacc aggagcatgt gttgcctatg    3960
atccctaatg gtggggcttt caaggatatg atcctggatg gtgatggcag gactgtgtac    4020
tgatctaaaa tccagcaagc aactgatcta aaatccagca agcaccgcct ccctgctagt    4080
acaagggtga tatgttttta tctgtgtgat gttctcctgt attctatctt ttttttgtagg    4140 ccgtcagcta tctgttatgg taatcctatg tagcttccga ccttgtaatt gtgtagtctg    4200 ttgtttttcct tctggcatgt gtcataagag atcatttaag tgccttttgc tacatataaa    4260
taagataata agcactgcta tgcagtggtt ctgaattggc ttctgttgcc aaatttaagt    4320
gtccaactgg tccttgcttt tgttttcgct attttttttcc ttttttagtt attattatat    4380
tggtaatttc aactcaacat atgatgtatg gaataatgct agggctgcaa tttcaaacta    4440
ttttacaaac cagaatggca ttttcgtggt tgaggggag tgaaaaaaaa tgaggcattt    4500
gactgaatta gttacctgat ccatttcgt ggtttggatc attggaatta aattccattc    4560
taataatagt aattttggca tatatcaatt aagttaattc ggttttatgc aaaatatatt    4620
tgtatactat tattatcaag atgtcggaga tatttatatg ctacatttt actatacagg    4680 agtgagatga agagtgtcat gtaagttaca cagtagaaac aaattctatt aatgcataaa    4740
atcatttcca tcatccaccc tatgaatttg agatagacct atatctaaac tttgaaaagt    4800
ggttgaatat caaattccaa attaaataag ttatttttatt gagtgaattc taatttctct    4860
aaaacgaagg gatctaaacg ccctctaaag ctaatttgga aactcaaact ttcttagcat    4920
tggaggggat tgagaaaaaa tattaattca ttttcatctc aatcattcaa tctccaaaga    4980
gatttgagtt ccttattagt ctgttccatg catcaaatcg gctcaatgtg tcattatttg    5040
ccatgacgat tgacgagttg ttctggggcc tagcgctttc cacgccgatg tgctggggcc    5100
tggtcctgga agacagct tgatatttaa agctatcaat tgtttcaatt gattcccact    5160
tcatttttct aaatgtagaa aacggtgacg tataagaaaa agaatgaatt aggacttta    5220 ttccgtacac taatctagag cggccgtttt atcaccactt tgtacaagaa agctgggtcg    5280
gcgcgccaag cttgcatgcc tgcaggtcga ctctagagga tccccatcga attcctgcag    5340
tgcagcgtga cccggtcgtg cccctctcta gagataatga gcattgcatg tctaagttat    5400 aaaaattac cacatatttt ttttgtcaca cttgtttgaa gtgcagttta tctatcttta    5460
tacatatatt taaacttac tctacgaata atataatcta tagtactaca ataatatcag    5520
tgttttagag aatcatataa atgaacagtt agacatggtc taaaggacaa ttgagtattt    5580
tgacaacagg actctacagt tttatctttt tagtgtgcat gtgttctcct ttttttttgc    5640
aaatagcttc acctatataa tacttcatcc attttattag tacatccatt tagggtttag    5700
ggttaatggt tttatagac taattttttt agtacatcta ttttattcta ttttagcctc    5760
taaattaaga aaactaaaac tctattttag tttttttatt taataattta gatataaaat    5820
```

```
agaataaaat aaagtgacta aaaattaaac aaatacccct taagaaatta aaaaaactaa    5880
ggaaacattt ttcttgtttc gagtagataa tgccagcctg ttaaacgccg tcgacgagtc    5940
taacggacac caaccagcga accagcagcg tcgcgtcggg ccaagcgaag cagacggcac    6000
ggcatctctg tcgctgcctc tggacccctc tcgagagttc cgctccaccg ttggacttgc    6060
tccgctgtcg gcatccagaa attgcgtggc ggagcggcag acgtgagccg gcacggcagg    6120
cggcctcctc ctcctctcac ggcacggcag ctacggggga ttcctttccc accgctcctt    6180
cgctttccct tcctcgcccg ccgtaataaa tagacacccc ctccacaccc tctttcccca    6240
acctcgtgtt gttcggagcg cacacacaca caaccagatc cccgggcctt cacctgcgga    6300
gggtaagatc cgatcaccat cttctgaatt tctgttcttg atctgtcatg tataataact    6360
gtctagtctt ggtgttggtg agatggaaat tcggtggatc tcggaaggga tattgttcgt    6420
ttgctggggt tttttttgtg tgttgtgatc cgtagagaat ttgtgtttat ccatgttgtt    6480
gatcttggta tgtattcatg acatattgac atgcatgtgt tgtatgtgtc atatgtgtgc    6540
ctctccttgg gatttgtttt ggataataga acatgttatg gactcaatag tctgtgaaca    6600
aatcttttt tagatggtgg ccaaatctga tgatgatctt tcttgagagg aaaaagttca    6660
tgatagaaaa atctttttg agatggtggc ttaatgtgat gatgatcttt cttgagagga    6720
aaaaaaagat tcattatagg agattttgat ttagctcctt tccaccgata ttaaatgagg    6780
agcatgcatg ctgatggctg ataaggatct gattttttt atccctctt ctttgaacag    6840
acaagaaata ggctctgaat ttctgattga ttatttgtac atgcagatgc aagatgtaca    6900
acggtccgcc tcagcgcgat cgccttaagg tttgggtggt catgttacgt cctgtagaaa    6960
ccccaacccg tgaaatcaaa aaactcgacg gcctgtgggc attcagtctg atcgcgaaa    7020
actgtggaat tggtcagcgt tggtgggaaa gcgcgttaca agaaagccgg gcaattgctg    7080
tgccaggcag ttttaacgat cagttcgccg atgcagatat tcgtaattat gcgggcaacg    7140
tctggtatca gcgcgaagtc tttataccga aaggttgggc aggccagcgt atcgtgctgc    7200
gtttcgatgc ggtcactcat tacggcaaag tgtgggtcaa taatcaggaa gtgatggagc    7260
atcagggcgg ctatacgcca tttgaagccg atgtcacgcc gtatgttatt gccgggaaaa    7320
gtgtacgtaa gtttctgctt ctacctttga tatatatata ataattatca ttaattagta    7380
gtaatataat atttcaaata ttttttttcaa aataaaagaa tgtagtatat agcaattgct    7440
tttctgtagt ttataagtgt gtatatttta atttataact tttctaatat atgaccaaaa    7500
tttgttgatg tgcaggtatc accgtttgtg tgaacaacga actgaactgg cagactatcc    7560
cgccgggaat ggtgattacc gacgaaaacg gcaagaaaaa gcagtcttac ttccatgatt    7620
tctttaacta tgccggaatc catcgcagcg taatgctcta caccacgccg aacacctggg    7680
tggacgatat caccgtggtg acgcatgtcg cgcaagactg taaccacgcg tctgttgact    7740
ggcaggtggt ggccaatggt gatgtcagcg ttgaactgcg tgatgcggat caacaggtgg    7800
ttgcaactgg acaaggcact agcgggactt tgcaagtggt gaatccgcac ctctggcaac    7860
cgggtgaagg ttatctctat gaactgtgcg tcacagccaa aagccagaca gagtgtgata    7920
tctacccgct tcgcgtcggc atccggtcag tggcagtgaa gggcgaacag ttcctgatta    7980
accacaaacc gttctacttt actggctttg gtcgtcatga agatgcggac ttgcgtggca    8040
aaggattcga taacgtgctg atggtgcacg accacgcatt aatggactgg attggggcca    8100
actcctaccg tacctcgcat tacccttacg ctgaagagat gctcgactgg gcagatgaac    8160
atggcatcgt ggtgattgat gaaactgctg ctgtcggctt taacctctct ttaggcattg    8220
```

```
gtttcgaagc gggcaacaag ccgaaagaac tgtacagcga agaggcagtc aacggggaaa   8280
ctcagcaagc gcacttacag gcgattaaag agctgatagc gcgtgacaaa aaccacccaa   8340
gcgtggtgat gtggagtatt gccaacgaac cggataccgc tccgcaaggt gcacgggaat   8400
atttcgcgcc actggcggaa gcaacgcgta aactcgaccc gacgcgtccg atcacctgcg   8460
tcaatgtaat gttctgcgac gctcacaccg ataccatcag cgatctcttt gatgtgctgt   8520
gcctgaaccg ttattacgga tggtatgtcc aaagcggcga tttggaaacg gcagagaagg   8580
tactggaaaa agaacttctg gcctggcagg agaaactgca tcagccgatt atcatcaccg   8640
aatacggcgt ggatacgtta gccgggctgc actcaatgta caccgacatg tggagtgaag   8700
agtatcagtg tgcatggctg gatatgtatc accgcgtctt tgatcgcgtc agcgccgtcg   8760
tcggtgaaca ggtatggaat ttcgccgatt ttgcgacctc gcaaggcata ttgcgcgttg   8820
gcggtaacaa gaaagggatc ttcactcgcg accgcaaacc gaagtcggcg gcttttctgc   8880
tgcaaaaacg ctggactggc atgaacttcg gtgaaaaacc gcagcaggga ggcaaacaat   8940
gaatcaacaa ctctcctggc gcaccatcgt cggctacagc ctcgggaatt gctaccgagc   9000
tcgaatttcc ccgatcgttc aaacatttgg caataaagtt tcttaagatt gaatcctgtt   9060
gccggtcttg cgatgattat catataattt ctgttgaatt acgttaagca tgtaataatt   9120
aacatgtaat gcatgacgtt atttatgaga tgggttttta tgattagagt cccgcaatta   9180
tacatttaat acgcgataga aaacaaaata tagcgcgcaa actaggataa attatcgcgc   9240
gcggtgtcat ctatgttact agatcgggaa ttggcatgca agcttggcac tggccgtcgt   9300
tttacaacgt cgtgactggg aaaaccctgg cgttacccaa cttaatcgcc ttgcagcaca   9360
tccccctttc gccagctggc gtaatagcga agaggcccgc accgatcgcc cttcccaaca   9420
gttgcgcagc ctgaatggcg aatgctagag cagcttgagc ttggatcaga ttgtcgtttc   9480
ccgccttcag tttaaacgat agcggtgaag ggggcggccg cggcatagtg actggatatg   9540
ttgtgtttta cagtattatg tagtctgttt tttatgcaaa atctaattta atatattgat   9600
atttatatca ttttacgttt ctcgttcagc tttttgtac aaacttgtga taaactatca   9660
gtgtttgaca ggatatattg gcgggtaaac ctaagagaaa agagcgttta ttagaataac   9720
ggatatttaa aagggcgtga aaaggtttat ccgttcgtcc atttgtatgt gcatgccaac   9780
cacagggttc ccctcgggag tgcttggcat tccgtacgat aatgacttct gttcaaccac   9840
ccaaacgtcg gaaagcctga cgacggagca gcattccaaa aagatccctt ggctcgtctg   9900
ggtcggctag aaggtcgagt gggctgctgt ggccttgatc ctcaacgcgg tcgcggacgt   9960
agcgcagcgc cgaaaaatcc tcgatcgcaa atccgacgct gtcgaaaagc gtgatctgct  10020
tgtcgctctt tcggccgacg tcctggccag tcatcacgcg ccaaagttcc gtcacaggat  10080
gatctggcgc gagttgctgg atctcgcctt caatccgggt ctgtggcggg aactccacga  10140
aaatatccga acgcagcaag atcgtcgacc aattcttgaa gacgaaaggg cctcgtgata  10200
cgcctatttt tataggttaa tgtcatgata ataatggttt cttagacgtc aggtggcact  10260
tttcggggaa atgtgcgcgg aacccctatt tgtttatttt tctaaataca ttcaaatatg  10320
tatccgctca tgagacaata accctgataa atgcttcaat aatattgaaa aaggaagagt  10380
atgagtattc aacatttccg tgtcgccctt attccctttt ttgcggcatt tgccttcct   10440
gtttttgctc acccagaaac gctggtgaaa gtaaaagatg ctgaagatca gttgggtgca  10500
cgagtgggtt acatcgaact ggatctcaac agcggtaaga tccttgagag ttttcgcccc  10560
gaagaacgtt ttccaatgat gagcactttt aaagttctgc tatgtggcgc ggtattatcc  10620
```

```
cgtgttgacg ccgggcaaga gcaactcggt cgccgcatac actattctca gaatgacttg   10680
gttgagtact caccagtcac agaaaagcat cttacggatg gcatgacagt aagagaatta   10740
tgcagtgctg ccataaccat gagtgataac actgcggcca acttacttct gacaacgatc   10800
ggaggaccga aggagctaac cgctttttg cacaacatgg gggatcatgt aactcgcctt   10860
gatcgttggg aaccggagct gaatgaagcc ataccaaacg acgagcgtga caccacgatg   10920
cctgcagggg gggggggggg gggacatga ggttgccccg tattcagtgt cgctgatttg   10980
tattgtctga agttgttttt acgttaagtt gatgcagatc aattaatacg atacctgcgt   11040
cataattgat tatttgacgt ggtttgatgg cctccacgca cgttgtgata tgtagatgat   11100
aatcattatc actttacggg tcctttccgg tgatccgaca ggttacgggg cggcgacctc   11160
gcgggttttc gctatttatg aaattttcc ggtttaaggc gtttccgttc ttcttcgtca   11220
taacttaatg ttttttattta aaataccctc tgaaagaaa ggaaacgaca ggtgctgaaa   11280
gcgaggcttt ttggcctctg tcgtttcctt tctctgtttt tgtccgtgga atgaacaatg   11340
gaagtccccc ccccccccc cccctgcagc aatggcaaca acgttgcgca aactattaac   11400
tggcgaacta cttactctag cttcccggca acaattaata gactggatgg aggcggataa   11460
agttgcagga ccacttctgc gctcggccct tccggctggc tggtttattg ctgataaatc   11520
tggagccggt gagcgtgggt ctcgcggtat cattgcagca ctggggccag atggtaagcc   11580
ctcccgtatc gtagttatct acacgacggg gagtcaggca actatggatg aacgaaatag   11640
acagatcgct gagataggtg cctcactgat taagcattgg taactgtcag accaagttta   11700
ctcatatata ctttagattg atttaaaact tcatttttaa tttaaaagga tctaggtgaa   11760 gatcctttt gataatctca tgaccaaaat cccttaacgt gagttttcgt tccactgagc   11820
gtcagacccc gtagaaaaga tcaaaggatc ttcttgagat ccttttttt tgcgcgtaat   11880 ctgctgcttg caaacaaaaa aaccaccgct accagcggtg gtttgtttgc cggatcaaga   11940
gctaccaact ctttttccga aggtaactgg cttcagcaga gcgcagatac caaatactgt   12000
ccttctagtg tagccgtagt taggccacca cttcaagaac tctgtagcac cgcctacata   12060
cctcgctctg ctaatcctgt taccagtggc tgctgccagt ggcgataagt cgtgtcttac   12120
cgggttggac tcaagacgat agttaccgga taaggcgcag cggtcgggct gaacggggg   12180 ttcgtgcaca cagcccagct tggagcgaac gacctacacc gaactgagat acctacagcg   12240
tgagctatga gaaagcgcca cgcttcccga agggagaaag gcggacaggt atccggtaag   12300
cggcagggtc ggaacaggag agcgcacgag ggagcttcca gggggaaacg cctggtatct   12360
ttatagtcct gtcgggtttc gccacctctg acttgagcgt cgatttttgt gatgctcgtc   12420 aggggggcg agcctatgga aaacgccag caacgcggcc ttttacggt tcctggcctt   12480 ttgctggcct tttgctcaca tgttctttcc tgcgttatcc cctgattctg tggataaccg   12540
tattaccgcc tttgagtgag ctgataccgc tcgccgcagc cgaacgaccg agcgcagcga   12600
gtcagtgagc gaggaagcgg aagagcgcct gatgcggtat tttctcctta cgcatctgtg   12660
cggtatttca caccgcatat ggtgcactct cagtacaatc tgctctgatg ccgcatagtt   12720
aagccagtat acactccgct atcgctacgt gactgggtca tggctgcgcc ccgacacccg   12780
ccaacacccg ctgacgcgcc ctgacgggct tgtctgctcc cggcatccgc ttacagacaa   12840
gctgtgaccg tctccgggag ctgcatgtgt cagaggtttt caccgtcatc accgaaacgc   12900
gcgaggcagc agatccccg atcaagtaga tacactacat atatctacaa tagacatcga   12960
gccggaaggt gatgtttact ttcctgaaat ccccagcaat tttaggccag ttttaccca   13020
```

| | | | | | |
|---|---|---|---|---|---|
| agacttcgcc | tctaacataa | attatagtta | ccaaatctgg | caaaagggtt | aacaagtggc | 13080 |
| agcaacggat | tcgcaaacct | gtcacgcctt | ttgtgccaaa | agccgcgcca | ggtttgcgat | 13140 |
| ccgctgtgcc | aggcgttagg | cgtcatatga | agatttcggt | gatccctgag | caggtggcgg | 13200 |
| aaacattgga | tgctgagaac | catttcattg | ttcgtgaagt | gttcgatgtg | cacctatccg | 13260 |
| accaaggctt | tgaactatct | accagaagtg | tgagccccta | ccggaaggat | tacatctcgg | 13320 |
| atgatgactc | tgatgaagac | tctgcttgct | atggcgcatt | catcgaccaa | gagcttgtcg | 13380 |
| ggaagattga | actcaactca | acatggaacg | atctagcctc | tatcgaacac | attgttgtgt | 13440 |
| cgcacacgca | ccgaggcaaa | ggagtcgcgc | acagtctcat | cgaatttgcg | aaaaagtggg | 13500 |
| cactaagcag | acagctcctt | ggcatacgat | tagagacaca | aacgaacaat | gtacctgcct | 13560 |
| gcaatttgta | cgcaaaatgt | ggctttactc | tcggcggcat | tgacctgttc | acgtataaaa | 13620 |
| ctagacctca | agtctcgaac | gaaacagcga | tgtactggta | ctggttctcg | ggagcacagg | 13680 |
| atgacgccta | acaattcatt | caagcccgaca | ccgcttcgcg | cgcgcggctta | attcaggagt | 13740 |
| taaacatcat | gagggaagcg | gtgatcgccg | aagtatcgac | tcaactatca | gaggtagttg | 13800 |
| gcgtcatcga | gcgccatctc | gaaccgacgt | tgctggccgt | acatttgtac | ggctccgcag | 13860 |
| tggatggcgg | cctgaagcca | cacagtgata | ttgatttgct | ggttacggtg | accgtaaggc | 13920 |
| ttgatgaaac | aacgcggcga | gctttgatca | acgaccttt | ggaaacttcg | gcttccctg | 13980 |
| gagagagcga | gattctccgc | gctgtagaag | tcaccattgt | tgtgcacgac | gacatcattc | 14040 |
| cgtggcgtta | tccagctaag | cgcgaactgc | aatttggaga | atggcagcgc | aatgacattc | 14100 |
| ttgcaggtat | cttcgagcca | gccacgatcg | acattgatct | ggctatcttg | ctgacaaaag | 14160 |
| caagagaaca | tagcgttgcc | ttggtaggtc | cagcggcgga | ggaactcttt | gatccggttc | 14220 |
| ctgaacagga | tctatttgag | gcgctaaatg | aaaccttaac | gctatggaac | tcgccgcccg | 14280 |
| actgggctgg | cgatgagcga | aatgtagtgc | ttacgttgtc | ccgcatttgg | tacagcgcag | 14340 |
| taaccggcaa | aatcgcgccg | aaggatgtcg | ctgccgactg | ggcaatggag | cgcctgccgg | 14400 |
| cccagtatca | gcccgtcata | cttgaagcta | ggcaggctta | tcttggacaa | gaagatcgct | 14460 |
| tggcctcgcg | cgcagatcag | ttggaagaat | ttgttcacta | cgtgaaaggc | gagatcacca | 14520 |
| aggtagtcgg | caaataatgt | ctaacaattc | gttcaagccg | acgccgcttc | gcggcgcggc | 14580 |
| ttaactcaag | cgttagagag | ctggggaaga | ctatgcgcga | tctgttgaag | gtggttctaa | 14640 |
| gcctcgtact | tgcgatggca | tcggggcagg | cacttgctga | cctgccaatt | gttttagtgg | 14700 |
| atgaagctcg | tcttccctat | gactactccc | catccaacta | cgacatttct | ccaagcaact | 14760 |
| acgacaactc | cataagcaat | tacgacaata | gtccatcaaa | ttacgacaac | tctgagagca | 14820 |
| actacgataa | tagttcatcc | aattacgaca | atagtcgcaa | cggaaatcgt | aggcttatat | 14880 |
| atagcgcaaa | tgggtctcgc | actttcgccg | gctactacgt | cattgccaac | aatgggacaa | 14940 |
| cgaacttctt | ttccacatct | ggcaaaagga | tgttctacac | cccaaagggg | gggcgcggcg | 15000 |
| tctatggcgg | caaagatggg | agcttctgcg | gggcattggt | cgtcataaat | ggccaatttt | 15060 |
| cgcttgccct | gacagataac | ggcctgaaga | tcatgtatct | aagcaactag | cctgctctct | 15120 |
| aataaaatgt | taggcctcaa | catctagtcg | caagctgagg | ggaaccacta | gtgtcatacg | 15180 |
| aacctccaag | agacggttac | acaaacgggt | acattgttga | tgtcatgtat | gacaatcgcc | 15240 |
| caagtaagta | tccagctgtg | ttcagaacgt | acgtccgaat | taattcatcg | gggtacggtc | 15300 |
| gacgatcgtc | aacgttcact | tctaaagaaa | tagcgccact | cagcttcctc | agcggcttta | 15360 |
| tccagcgatt | tcctattatg | tcggcatagt | tctcaagatc | gacagcctgt | cacggttaag | 15420 |

-continued

```
cgagaaatga ataagaaggc tgataattcg gatctctgcg agggagatga tatttgatca   15480
caggcagcaa cgctctgtca tcgttacaat caacatgcta ccctccgcga gatcatccgt   15540
gtttcaaacc cggcagctta gttgccgttc ttccgaatag catcggtaac atgagcaaag   15600
tctgccgcct tacaacggct ctcccgctga cgccgtcccg gactgatggg ctgcctgtat   15660
cgagtggtga ttttgtgccg agctgccggt cggggagctg ttggctggct ggtggcagga   15720
tatattgtgg tgtaaacaaa ttgacgctta gacaacttaa taacacattg cggacgtttt   15780
taatgtactg                                                         15790
```

<210> SEQ ID NO 112
<211> LENGTH: 10196
<212> TYPE: DNA
<213> ORGANISM: binary vector pBPSLM139
<220> FEATURE:
<221> NAME/KEY: gene
<222> LOCATION: (2178)..(4094)
<223> OTHER INFORMATION: Zea mais Als gene: mutated allele, herbicide
      insensitive genproduct
<220> FEATURE:
<221> NAME/KEY: Intron
<222> LOCATION: (8945)..(9760)
<223> OTHER INFORMATION: first intron of the Zea mais Ubiquitin gene
<220> FEATURE:
<221> NAME/KEY: Terminator
<222> LOCATION: (8945)..(9760)
<220> FEATURE:
<221> NAME/KEY: gene
<222> LOCATION: (8945)..(9760)
<223> OTHER INFORMATION: kanamycin resistance cassette, Transposon Tn903

<400> SEQUENCE: 112

```
tttgtgccga gctgccggtc ggggagctgt tggctggctg gtggcaggat atattgtggt     60
gtaaacaaat tgacgcttag acaacttaat aacacattgc ggacgttttt aatgtactga    120
attggatccg cccgggcggt accaagcttc cgcggctgca gtgcagcgtg acccggtcgt    180 gccctctct agagataatg agcattgcat gtctaagtta taaaaaatta ccacatattt    240
tttttgtcac acttgtttga agtgcagttt atctatcttt atacatatat ttaaacttta    300
ctctacgaat aatataatct atagtactac aataatatca gtgttttaga gaatcatata    360
aatgaacagt tagacatggt ctaaaggaca attgagtatt ttgacaacag gactctacag    420
ttttatcttt ttagtgtgca tgtgttctcc ttttttttttg caaatagctt cacctatata    480
atacttcatc cattttatta gtacatccat ttagggttta gggttaatgg ttttttataga   540 ctaatttttt tagtacatct attttattct attttagcct ctaaattaag aaaactaaaa    600
ctctatttta gttttttttat ttaatagttt agatataaaa tagaataaaa taaagtgact    660
aaaaattaaa caaataccct ttaagaaatt aaaaaaacta aggaaacatt tttcttgttt    720
cgagtagata atgccagcct gttaaacgcc gtcgacgagt ctaacggaca ccaaccagcg    780
aaccagcagc gtcgcgtcgg gccaagcgaa gcagacggca cggcatctct gtcgctgcct    840
ctggacccct ctcgagagtt ccgctccacc gttggacttg ctccgctgtc ggcatccaga    900
aattgcgtgg cggagcggca gacgtgagcc ggcacggcag gcggcctcct cctcctctca    960
cggcaccggc agctacgggg gattcctttc ccaccgctcc ttcgctttcc cttcctcgcc    1020
cgccgtaata aatagacacc cctccacac cctctttccc caacctcgtg ttgttcggag    1080
cgcacacaca cacaaccaga tctcccccaa atccacccgt cggcacctcc gcttcaaggt    1140
acgccgctcg tcctcccccc ccccccccct ctctaccttc tctagatcgg cgttccggtc    1200
catggttagg gcccggtagt tctacttctg ttcatgtttg tgttagatcc gtgtttgtgt    1260
```

```
tagatccgtg ctgctagcgt tcgtacacgg atgcgacctg tacgtcagac acgttctgat    1320
tgctaacttg ccagtgtttc tctttgggga atcctgggat ggctctagcc gttccgcaga    1380
cgggatcgat ttcatgattt tttttgtttc gttgcatagg gtttggtttg ccctttttcct   1440
ttatttcaat atatgccgtg cacttgtttg tcgggtcatc ttttcatgct ttttttttgtc   1500
ttggttgtga tgatgtggtc tggttgggcg gtcgttctag atcggagtag aattctgttt    1560
caaactacct ggtggattta ttaattttgg atctgtatgt gtgtgccata catattcata    1620
gttacgaatt gaagatgatg gatggaaata tcgatctagg ataggtatac atgttgatgc    1680
gggttttact gatgcatata cagagatgct ttttgttcgc ttggttgtga tgatgtggtg    1740
tggttgggcg gtcgttcatt cgttctagat cggagtagaa tactgtttca aactacctgg    1800
tgtatttatt aattttggaa ctgtatgtgt gtgtcataca tcttcatagt tacgagttta    1860
agatggatgg aaatatcgat ctaggatagg tatacatgtt gatgtgggtt ttactgatgc    1920
atatacatga tggcatatgc agcatctatt catatgctct aaccttgagt acctatctat    1980
tataataaac aagtatgttt tataattatt tcgatcttga tatacttgga tgatggcata    2040
tgcagcagct atatgtggat ttttttagcc ctgccttcat acgctattta tttgcttggt    2100
actgtttctt ttgtcgatgc tcaccctgtt gtttggtgtt acttctgcag ggtacggatc    2160
cactagttct agaaaccatg ccaccgccg ccgccgcgtc taccgcgctc actggcgcca    2220
ctaccgctgc gcccaaggcg aggcgccggg cgcacctcct ggccaccgc gcgcccctcg    2280
ccgcgcccat caggtgctca gcggcgtcac ccgccatgcc gatggctccc ccggccaccc   2340
cgctccggcc gtggggcccc accgatcccc gcaagggcgc cgacatcctc gtcgagtccc    2400
tcgagcgctg cggcgtccgc gacgtcttcg cctaccccgg cggcgcgtcc atggagatcc    2460
accaggcact caccccgctcc cccgtcatcg ccaaccacct cttccgccac gagcaagggg   2520
aggccttgc ggcctccggc tacgcgcgct cctcgggccg cgtcggcgtc tgcatcgcca    2580
cctccggccc cggcgccacc aaccttgtct ccgcgctcgc cgacgcgctg ctcgattccg    2640
tccccatggt cgccatcacg ggacaggtgc cgcgacgcat gattggcacc gacgccttcc    2700
aggagacgcc catcgtcgag gtcacccgct ccatcaccaa gcacaactac ctggtcctcg    2760
acgtcgacga catccccgc gtcgtgcagg aggctttctt cctcgcctcc tctggtcgac    2820
cggggccggt gcttgtcgac atccccaagg acatccagca gcagatggcg gtgcctgtct    2880
gggacaagcc catgagtctg cctgggtaca ttgcgcgcct tcccaagccc cctgcgactg    2940
agttgcttga gcaggtgctg cgtcttgttg gtgaatcccg gcgccctgtt ctttatgttg    3000
gcggtggctg cgcagcatct ggtgaggagt tgcgacgctt tgtggagctg actggaatcc    3060
cggtcacaac tactcttatg ggcctcggca acttccccag cgacgaccca ctgtctctgc    3120
gcatgctagg tatgcatggc acggtgtatg caaattatgc agtggataag gccgatctgt    3180
tgcttgcact tggtgtgcgg tttgatgatc gtgtgacagg gaagattgag gcttttgcaa    3240
gcagggctaa gattgtgcac gttgatattg atccggctga gattggcaag aacaagcagc    3300
cacatgtgtc catctgtgca gatgttaagc ttgctttgca gggcatgaat gctcttcttg    3360
aaggaagcac atcaaagaag agctttgact ttggctcatg gaacgatgag ttggatcagc    3420
agaagaggga attccccctt gggtataaaa catctaatga ggagatccag ccacaatatg    3480
ctattcaggt tcttgatgag ctgacgaaag gcgaggccat catcggcaca ggtgttgggc    3540
agcaccagat gtgggcggca cagtactaca cttacaagcg gccaaggcag tggttgtctt    3600
cagctggtct tggggctatg ggatttggtt tgccggctgc tgctggtgct tctgtggcca    3660
```

| | |
|---|---|
| acccaggtgt tactgttgtt gacatcgatg gagatggtag ctttctcatg aacgttcagg | 3720 |
| agctagctat gatccgaatt gagaacctcc cggtgaaggt ctttgtgcta acaaccagc | 3780 |
| acctggggat ggtggtgcag tgggaggaca ggttctataa ggccaacaga gcgcacacat | 3840 |
| acttgggaaa cccagagaat gaaagtgaga tatatccaga tttcgtgacg atcgccaaag | 3900 |
| ggttcaacat tccagcggtc cgtgtgacaa agaagaacga agtccgcgca gcgataaaga | 3960 |
| agatgctcga gactccaggg ccgtacctct tggatataat cgtcccacac caggagcatg | 4020 |
| tgttgcctat gatccctaat ggtggggctt tcaaggatat gatcctggat ggtgatggca | 4080 |
| ggactgtgta ctgatctaaa atccagcaag caactgatct aaaatccagc aagcaccgcc | 4140 |
| tccctgctag tacaagggtg atatgttttt atctgtgtga tgttctcctg tattctatct | 4200 |
| tttttttgtag gccgtcagct atctgttatg gtaatcctat gtagcttccg accttgtaat | 4260 |
| tgtgtagtct gttgttttcc ttctggcatg tgtcataaga gatcatttaa gtgccttttg | 4320 |
| ctacatataa ataagataat aagcactgct atgcagtggt tctgaattgg cttctgttgc | 4380 |
| caaatttaag tgtccaactg gtccttgctt ttgttttcgc tattttttc cttttttagt | 4440 |
| tattattata ttggtaattt caactcaaca tatgatgtat ggaataatgc tagggctgca | 4500 |
| atttcaaact attttacaaa ccagaatggc attttcgtgg tttgagggga gtgaaaaaaa | 4560 |
| atgaggcatt tgactgaatt agttacctga tccattttcg tggtttggat cattggaatt | 4620 |
| aaattccatt ctaataatag taattttggc atatatcaat taagttaatt cggttttatg | 4680 |
| caaaatatat ttgtatacta ttattatcaa gatgtcggag atatttatat gctacatttt | 4740 |
| tactatacag gagtgagatg aagagtgtca tgtaagttac acagtagaaa caaattctat | 4800 |
| taatgcataa aatcatttcc atcatccacc ctatgaattt gagatagacc tatatctaaa | 4860 |
| ctttgaaaag tggttgaata tcaaattcca aattaaataa gttattttat tgagtgaatt | 4920 |
| ctaatttctc taaaacgaag ggatctaaac gccctctaaa gctaatttgg aaactcaaac | 4980 |
| tttcttagca ttggagggga ttgagaaaaa atattaattc attttcatct caatcattca | 5040 |
| atctccaaag agatttgagt tccttattag tctgttccat gcatcaaatc ggctcaatgt | 5100 |
| gtcattattt gccatgacga ttgacagagtt gttctggggc ctagcgcttt ccacgccgat | 5160 |
| gtgctggggc ctggtcctgg agaagacagc ttgatattta aagctatcaa ttgtttcaat | 5220 |
| tgattcccac ttcatttttc taaatgtaga aaacggtgac gtataagaaa agaatgaat | 5280 |
| taggactttt attccgtaca ctaatctaga gcggccgcaa gcttgtacaa cgcgtaccgg | 5340 |
| ttaattaatc tagaggcgcg ccgggcccgg ccggccagat cttgattgtc gtttcccgcc | 5400 |
| ttcagtttaa actatcagtg tttgacagga tatattggcg ggtaaaccta agagaaaaga | 5460 |
| gcgtttatta gaataatcgg atattaaaa gggcgtgaaa aggtttatcc gttcgtccat | 5520 |
| ttgtatgtgc atgccaacca cagggttccc ctcgggagtg cttggcattc cgtgcgataa | 5580 |
| tgacttctgt tcaaccaccc aaacgtcgga aagcctgacg acggagcagc attccaaaaa | 5640 |
| gatcccttgg ctcgtctggg tcggctagaa ggtcgagtgg gctgctgtgg cttgatccct | 5700 |
| caacgcggtc gcggacgtag cgcagcgccg aaaaatcctc gatcgcaaat ccgacgctgt | 5760 |
| cgaaaagcgt gatctgcttg tcgctctttc ggccgacgtc ctggccagtc atcacgcgcc | 5820 |
| aaagttccgt cacaggatga tctgcgcga ttgctggat ctcgccttca atccgggtct | 5880 |
| gtggcgggaa ctccacgaaa atatccgaac gcagcaagat cgtcgaccaa ttcttgaaga | 5940 |
| cgaaagggcc tcgtgatacg cctattttta taggttaatg tcatgataat aatggtttct | 6000 |
| tagacgtcag gtggcacttt tcggggaaat gtgcgcggaa cccctatttg tttatttttc | 6060 |

```
taaatacatt caaatatgta tccgctcatg agacaataac cctgataaat gcttcaataa    6120
tattgaaaaa ggaagagtat gagtattcaa catttccgtg tcgcccttat tcccttttt     6180
gcggcatttt gccttcctgt ttttgctcac ccagaaacgc tggtgaaagt aaaagatgct    6240
gaagatcagt tgggtgcacg agtgggttac atcgaactgg atctcaacag cggtaagatc    6300
cttgagagtt ttcgccccga agaacgtttt ccaatgatga gcacttttaa agttctgcta    6360
tgtggcgcgg tattatcccg tgttgacgcc gggcaagagc aactcggtcg ccgcatacac    6420
tattctcaga atgacttggt tgagtactca ccagtcacag aaaagcatct tacggatggc    6480
atgacagtaa gagaattatg cagtgctgcc ataaccatga gtgataacac tgcggccaac    6540
ttacttctga caacgatcgg aggaccgaag gagctaaccg cttttttgca acatggggg     6600
gatcatgtaa ctcgccttga tcgttgggaa ccggagctga atgaagccat accaaacgac    6660
gagcgtgaca ccacgatgcc gggggggggg ggggggaca tgaggttgcc ccgtattcag     6720
tgtcgctgat ttgtattgtc tgaagttgtt tttacgttaa gttgatgcag atcaattaat    6780
acgatacctg cgtcataatt gattatttga cgtggtttga tggcctccac gcacgttgtg    6840
atatgtagat gataatcatt atcactttac gggtccttt cggtgatccg acaggttacg     6900
gggcggcgac ctcgcgggtt tcgctatttt atgaaaattt tccggtttaa ggcgtttccg    6960
ttcttcttcg tcataactta atgttttat ttaaaatacc ctctgaaaag aaaggaaacg     7020
acaggtgctg aaagcgagct ttttggcctc tgtcgtttcc tttctctgtt tttgtccgtg    7080
gaatgaacaa tggaaccccc ccccccccc cctgcagcaa tggcaacaac gttgcgcaaa     7140
ctattaactg gcgaactact tactctagct tcccggcaac aattaataga ctggatggag    7200
gcggataaag ttgcaggacc acttctgcgc tcggcccttc cggctggctg gtttattgct    7260
gataaatctg gagccggtga gcgtgggtct cgcggtatca ttgcagcact ggggccagat    7320
ggtaagccct cccgtatcgt agttatctac acgacgggga gtcaggcaac tatggatgaa    7380
cgaaatagac agatcgctga ataggtgcc tcactgatta gcattggta actgtcagac      7440
caagtttact catatatact ttagattgat ttaaaacttc attttttaat taaaaggatc    7500
taggtgaaga tcctttttga taatctcatg accaaaatcc cttaacgtga gttttcgttc    7560
cactgagcgt cagaccccgt agaaaagatc aaaggatctt cttgagatcc ttttttctg     7620
cgcgtaatct gctgcttgca acaaaaaaa ccaccgctac cagcggtggt ttgtttgccg    7680
gatcaagagc taccaactct ttttccgaag gtaactggct tcagcagagc gcagatacca    7740
aatactgtcc ttctagtgta gccgtagtta ggccaccact tcaagaactc tgtagcaccg    7800
cctacatacc tcgctctgct aatcctgtta ccagtggctg ctgccagtgg cgataagtcg    7860
tgtcttaccg ggttggactc aagacgatag ttaccggata aggcgcagcg gtcgggctga    7920
acggggggtt cgtgcacaca gcccagcttg gagcgaacga cctacaccga actgagatac    7980
ctacagcgtg agctatgaga aagcgccacg cttcccgaag ggagaaaggc ggacaggtat    8040
ccggtaagcg gcagggtcgg aacaggagag cgcacgaggg agcttccagg gggaaacgcc    8100
tggtatcttt atagtcctgt cgggtttcgc cacctctgac ttgagcgtcg atttttgtga    8160
tgctcgtcag ggggggggag cctatggaaa aacgccagca acgcggcctt tttacggttc    8220
ctggcctttt gctggccttt tgctcacatg ttctttcctg cgttatcccc tgattctgtg    8280
gataaccgta ttaccgcctt tgagtgagct gataccgctc gccgcagccg aacgaccgag    8340
cgcagcgagt cagtgagcga ggaagcggaa gagcgcctga tgcggtattt tctccttacg    8400
catctgtgcg gtatttcaca ccgcatatgg tgcactctca gtacaatctg ctctgatgcc    8460
```

-continued

| | |
|---|---|
| gcatagttaa gccagtatac actccgctat cgctacgtga ctgggtcatg gctgcgcccc | 8520 |
| gacacccgcc aacacccgct gacgcgccct gacgggcttg tctgctcccg gcatccgctt | 8580 |
| acagacaagc tgtgaccgtc tccgggagct gcatgtgtca gaggttttca ccgtcatcac | 8640 |
| cgaaacgcgc gaggcagcag atcccccgat caagtagata cactacatat atctacaata | 8700 |
| gacatcgagc cggaaggtga tgtttacttt cctgaaatcc ccagcaattt taggccagtt | 8760 |
| tttacccaag acttcgcctc taacataaat tatagttacc aaatctggca aaagggttga | 8820 |
| ccgggggggg gggaaagcc acgttgtgtc tcaaaatctc tgatgttaca ttgcacaaga | 8880 |
| taaaaatata tcatcatgaa caataaaact gtctgcttac ataaacagta atacaagggg | 8940 |
| tgttatgagc catattcaac gggaaacgtc ttgctcgagg ccgcgattaa attccaacat | 9000 |
| ggatgctgat ttatatgggt ataaatgggc tcgcgataat gtcgggcaat caggtgcgac | 9060 |
| aatctatcga ttgtatggga agcccgatgc gccagagttg tttctgaaac atggcaaagg | 9120 |
| tagcgttgcc aatgatgtta cagatgagat ggtcagacta aactggctga cggaatttat | 9180 |
| gcctcttccg accatcaagc atttttatccg tactcctgat gatgcatggt tactcaccac | 9240 |
| tgcgatcccc gggaaaacag cattccaggt attagaagaa tatcctgatt caggtgaaaa | 9300 |
| tattgttgat gcgctggcag tgttcctgcg ccggttgcat tcgattcctg tttgtaattg | 9360 |
| tccttttaac agcgatcgcg tatttcgtct cgctcaggcg caatcacgaa tgaataacgg | 9420 |
| tttggttgat gcgagtgatt ttgatgacga gcgtaatggc tggcctgttg aacaagtctg | 9480 |
| gaaagaaatg cataagcttt tgccattctc accggattca gtcgtcactc atggtgattt | 9540 |
| ctcacttgat aaccttattt ttgacgaggg gaaattaata ggttgtattg atgttggacg | 9600 |
| agtcggaatc gcagaccgat accaggatct tgccatccta tggaactgcc tcggtgagtt | 9660 |
| ttctccttca ttacagaaac ggcttttttca aaaatatggt attgataatc ctgatatgaa | 9720 |
| taaattgcag tttcatttga tgctcgatga gttttttctaa tcagaattgg ttaattggtt | 9780 |
| gtaacactgg cagagcatta cgctgacttg acggacggc ggctttgttg aataaatcga | 9840 |
| acttttgctg agttgaagga tcagatcacg catcttcccg acaacgcaga ccgttccgtg | 9900 |
| gcaaagcaaa agttcaaaat caccaactgg tccacctaca acaaagctct catcaaccgt | 9960 |
| ggctccctca ctttctggct ggatgatggg gcgattcagg gatcacaggc agcaacgctc | 10020 |
| tgtcatcgtt acaatcaaca tgctaccctc cgcgagatca tccgtgtttc aaacccggca | 10080 |
| gcttagttgc cgttcttccg aatagcatcg gtaacatgag caaagtctgc cgccttacaa | 10140 |
| cggctctccc gctgacgccg tcccggactg atgggctgcc tgtatcgagt ggtgat | 10196 |

<210> SEQ ID NO 113
<211> LENGTH: 1470
<212> TYPE: DNA
<213> ORGANISM: Artificial sequence
<220> FEATURE:
<223> OTHER INFORMATION: cassette from vector pBPSMM355 (OsCP12::BPSI.1)
<220> FEATURE:
<221> NAME/KEY: promoter
<222> LOCATION: (1)..(854)
<223> OTHER INFORMATION: Os CP12 promoter
<220> FEATURE:
<221> NAME/KEY: Intron
<222> LOCATION: (888)..(1470)
<223> OTHER INFORMATION: IME-Intron: BPSI.1 intron

<400> SEQUENCE: 113

| | |
|---|---|
| gaattctcgg cagggtggca gcatgggcct aaggcccagt caactgtggg cctataagcg | 60 |
| actaatccgg ctgtaactgg gccttgcaag aggcttgtct tgttggtccg aactcaggaa | 120 |

```
gtccaggttg cggggacaac ttcaaggcca tctggtttcc acttctctta ccacctcaat    180
tccgctcttg atccgagcta gcttagtccc aatctaaaaa ctttacaaag aaagaaccat    240
acgcacctat tgggcaaaat gaaaataat ttgctactca ccaaataatt tgagcacctc     300
tgcacctgta cactaaataa ctctgttcca ccaaaatagt tgagatatct aggacgtttc    360 atttttgtccg ttcttcacca aacttttcca tagtatctca gatattttcg agaccgaaag  420
tgatctttct ggccttagac cgagttcact tccctacaag ccattctttg ctggcacaac   480
acgaacctct acatcaattt cgtatccaac ctgaacttct gcatacatgt acacacccac   540
agtcatctgc tcatgttttc acggtcaaat taaaactgct tctctcacct tagattcacc   600
caagggaaaa gaaaaagatc tcctttgcca agtccccatt tcgcatgaaa tatctcaaaa   660
tacagcccac gtggcacacg acgattggct gaggaggcga taagaaacga gtgcacgtcg    720
tcgaatcctc tctccccttc tcccccaccc cacggagcta tatatatata aaccccatct    780
cttcaatccg tgcaacgaac gcctcgtcgc aacagctaca aacgcccaca tcacacgcag    840
aaatccgcat caacagagct cggtacccgg gccttcacct gcggagggta agatccgatc    900
accatcttct gaatttctgt tcttgatctg tcatgtataa taactgtcta gtcttggtgt   960
tggtgagatg gaaattcggt ggatctcgga agggatattg ttcgtttgct gggtttttt    1020 ttgtgtgttg tgatccgtag agaatttgtg tttatccatg ttgttgatct tggtatgtat   1080
tcatgacata ttgacatgca tgtgttgtat gtgtcatatg tgtgcctctc cttgggattt   1140
gttttggata atagaacatg ttatggactc aatagtctgt gaacaaatct ttttttagat   1200
ggtggccaaa tctgatgatg atctttcttg agaggaaaaa gttcatgata gaaaaatctt   1260
ttttgagatg gtggcttaat gtgatgatga tctttcttga gaggaaaaaa aagattcatt   1320
ataggagatt ttgatttagc tccttttccac cgatattaaa tgaggagcat gcatgctgat  1380
tgctgataag gatctgattt ttttatcccc tcttctttga acagacaaga aataggctct   1440
gaatttctga ttgattattt gtacatgcag                                    1470
```

<210> SEQ ID NO 114
<211> LENGTH: 1799
<212> TYPE: DNA
<213> ORGANISM: Artificial sequence
<220> FEATURE:
<223> OTHER INFORMATION: cassette from vector pBPSMM355 (ZmHRGP::BPSI.1)
    Zea mays promoter, oryza sativa intron
<220> FEATURE:
<221> NAME/KEY: promoter
<222> LOCATION: (1)..(1184)
<223> OTHER INFORMATION: Maize [HRGP] hydroxyproline-rich glycoprotein
    (extensin) 5'/UTR promoter
<220> FEATURE:
<221> NAME/KEY: Intron
<222> LOCATION: (1217)..(1799)
<223> OTHER INFORMATION: IME-Intron: BPSI.1 intron

<400> SEQUENCE: 114

```
ccggtgacct tcttgcttct tcgatcgtct ggacgtcgag gagccccgcg gcagcgcacg    60
cgtctgcacc gttatggtgg ccgcgctcgc gatggaatag aagggtaat gatgatccg     120 gccaggaagg ccacgacatc gacggatcca accggcaaga cggcgatccg gttaaataga   180
cgacggatct agctgggaag gtagactcta cattaaatga ggttgcacat gccctaataa   240
ctttataaat ctaatttatt cagaggcaag gtagtagtat tatctttccc aacgatagt    300 tatctgatct gccgttcagc ttgatcgata actttataaa tctaatttat tcagaggccg   360
gcggcagcgc acacgtctgc accagtaatg ttagccgcgc ctgtgcgta atagaagggg   420
```

-continued

```
taacgatgga tccgaccaga aaggcctcga cattgacgga tccagacggc gatccggtca    480
aagagacgac gaatctagcc gagaaggtag atctctcgag agagttcata ttaaatgatg    540
ttgtacatgc cataataact ctataaatct aatttattca taggcgaagg tagtagtatt    600
atctttccca gcggatcgtt atctgatctg ccgttcagct tgatcgatcc acgtcgtttg    660
atctcggcga gcagcacatg gcggctcttc ttgtgtacag gtctcactct ctgctacttc    720
agtgcaaggc ggagtgaatg cacacaataa cgtgagtatt gtgggaacta cttgtagatg    780
caaacgatgt aaatccacct gctccaccaa gtgcccgccc ggctctatcc attccattcg    840
tcaacatgca ggttcagact ggcccgtgct ggaccagtga gcggtgccgg tgaaccccaa    900
tgcaagcgaa gcgagtgacc atcggggaag cctcccgtgc tgcccccaca tggcttgcct    960
gaatgcctct ctctcgccgc agtgccctct ctctctcctc ctcctctccg tcgaagggcg   1020
tcacgagagc ccagagggca tccgaggccc ccaccccacc ccttcctccg tgtatataag   1080
cagtggcagg gtgagcgtct ctcctcagac caccactgcg ccattggcca gctagagcca   1140
accagaagag cttgcagtta ctgagagtgt gtgtgagaga gagggagctc ggtacccggg   1200
ccttcacctg cggagggtaa gatccgatca ccatcttctg aatttctgtt cttgatctgt   1260
catgtataat aactgtctag tcttggtgtt ggtgagatgg aaattcggtg gatctcggaa   1320
gggatattgt tcgtttgctg gggttttttt tgtgtgttgt gatccgtaga gaatttgtgt   1380
ttatccatgt tgttgatctt ggtatgtatt catgacatat tgacatgcat gtgttgtatg   1440
tgtcatatgt gtgcctctcc ttgggatttg ttttggataa tagaacatgt tatggactca   1500
atagtctgtg aacaaatctt ttttttagatg gtggccaaat ctgatgatga tctttcttga   1560
gaggaaaaag ttcatgatag aaaaatcttt tttgagatgg tggcttaatg tgatgatgat   1620 cttttcttgag aggaaaaaaa agattcatta taggagattt tgatttagct cctttccacc   1680
gatattaaat gaggagcatg catgctgatt gctgataagg atctgatttt tttatcccct   1740
cttctttgaa cagacaagaa ataggctctg aatttctgat tgattatttg tacatgcag    1799
```

<210> SEQ ID NO 115
<211> LENGTH: 1701
<212> TYPE: DNA
<213> ORGANISM: Artificial sequence
<220> FEATURE:
<223> OTHER INFORMATION: cassette from vector pBPSMM358
    (OsCCoAMT1::BPSI.1)
<220> FEATURE:
<221> NAME/KEY: promoter
<222> LOCATION: (1)..(1034)
<223> OTHER INFORMATION: p-caffeoyl-CoA 3-O-methyltransferase [CCoAMT1]
    promoter
<220> FEATURE:
<221> NAME/KEY: Intron
<222> LOCATION: (1119)..(1701)
<223> OTHER INFORMATION: IME-Intron: BPSI.1 intron

<400> SEQUENCE: 115

```
caactactgc acggtaaaag tgataggaat cggtcggaaa cagtattaat gttttttatta    60 ttttacaaa aacgaattga ataattgga aattttcata tttatatatt aaactattca   120
gtatcaactt caattcgacg tcaatagaaa ttagaaaagc ataattatac acagtaatag   180
gcgttcaaga tattattgtt attatttagt tttgtggaaa tggtatcaac gtgatcggaa   240
aattttgtac atgttttcac cctgcgggat atctcaattc cttctcctcc ctctaccgcc   300
atatcagcac acgttttaga gcaccaatca taacccataa atccgtgggc tactcactta   360
tttaatttat atgtgaattc gtgacctgac tcactcacat actatcaaaa atttgtctca   420
```

```
gtcacccatc tccttctttc ctggtccgat aagggtttat cctacggttc gacggttatc    480
acgatagtcg tgcggttact gaggtatacc gtgatttaaa aatatgataa agttaccgca    540
ggttttaact gcgcggtttg gtaaacctgt tcctcctcac caaccttctc ctccggtctc    600
cttatgtgtc tcaccgaggc gagccgccgc gagaccgcat ggacgcggtc cacgcacctg    660
gcggtgcacc tcctcctccc cggcgaagaa gacgtggagg agagtaaatg agcaatcagg    720
cccacggccc aatcgccgtc caccaccac cccctcagc gacccaaaac cacctcacca     780
acccaactct gtaccgtact gtacccgccc tcccctccca ctgacactcc gggcccacct    840
gtcggcgcga ctcttccacg gtccccttct ctcctcagag attttttcca cgcatttttt    900
aatttttttt tctgcagttc acatgctctt ctcccactct tccgccgcgc tatataaacc    960
gcgcgaggcg tcgttgcctc gtcggcgaag tcaatccggc gatccccggc gagcgagaga   1020
tcgaagcaag ctgcaagggc gaattctgca gatatccatc acactggcgg ccgctcgagc   1080
atgcatctag aggatccccg ggccttcacc tgcggagggt aagatccgat caccatcttc   1140
tgaatttctg ttcttgatct gtcatgtata ataactgtct agtcttggtg ttggtgagat   1200
ggaaattcgg tggatctcgg aagggatatt gttcgtttgc tggggttttt tttgtgtgtt   1260
gtgatccgta gagaatttgt gtttatccat gttgttgatc ttggtatgta ttcatgacat   1320
attgacatgc atgtgttgta tgtgtcatat gtgtgcctct ccttgggatt gttttggat    1380 aatagaacat gttatggact caatagtctg tgaacaaatc ttttttaga tggtggccaa    1440 atctgatgat gatctttctt gagaggaaaa agttcatgat agaaaatct ttttgagat     1500 ggtggcttaa tgtgatgatg atctttcttg agaggaaaaa aagattcat tataggagat    1560 tttgatttag ctcctttcca ccgatattaa atgaggagca tgcatgctga ttgctgataa   1620
ggatctgatt tttttatccc ctcttctttg aacagacaag aaataggctc tgaatttctg   1680
attgattatt tgtacatgca g                                            1701

<210> SEQ ID NO 116
<211> LENGTH: 1999
<212> TYPE: DNA
<213> ORGANISM: Artificial sequence
<220> FEATURE:
<223> OTHER INFORMATION: cassette from vector EXS1025
      (ZmGlobulin1::BPSI.1) Zea mays promoter, Oryza sativa intron
<220> FEATURE:
<221> NAME/KEY: promoter
<222> LOCATION: (1)..(1440)
<223> OTHER INFORMATION: Maize Globulin-1 [ZmGlb1] promoter (W64A)
<220> FEATURE:
<221> NAME/KEY: Intron
<222> LOCATION: (1443)..(1999)
<223> OTHER INFORMATION: IME-Intron: BPSI.1 intron

<400> SEQUENCE: 116
agcttcccgg gccgagtgcc atccttggac actcgataaa gtatattta ttttttttat     60 tttgccaacc aaacttttg tggtatgttc ctacactatg tagatctaca tgtaccattt    120
tggcacaatt acatatttac aaaaatgttt tctataaata ttagatttag ttcgtttatt   180
tgaatttctt cggaaaattc acatttaaac tgcaagtcac tcgaaacatg gaaaccgtg    240 catgcaaaat aaatgatatg catgttatct agcacaagtt acgaccgatt tcagaagcag    300
accagaatct tcaagcacca tgctcactaa acatgaccgt gaacttgtta tctagttgtt   360
taaaaattgt ataaaacaca ataaagtca gaaattaatg aaacttgtcc acatgtcatg    420
atatcatata tagaggttgt gataaaaatt tgataatgtt tcggtaaagt tgtgacgtac   480
tatgtgtaga aacctaagtg acctacacat aaaatcatag agtttcaatg tagttcactc   540
```

```
gacaaagact tgtcaagtg tccgataaaa agtactcgac aaagaagccg ttgtcgatgt    600
actgttcgtc gagatctctt tgtcgagtgt cacactaggc aaagtcttta cggagtgttt    660
ttcaggcttt gacactcggc aaagcgctcg attccagtag tgacagtaat ttgcatcaaa    720
aatagctgag agatttaggc cccgtttcaa tctcacggga taaagtttag cttcctgcta    780
aactttagct atatgaattg aagtgctaaa gtttagtttc aattaccacc attagctctc    840
ctgtttagat tacaaatggc taaaagtagc taaaaaatag ctgctaaagt ttatctcgcg    900
agattgaaac agggccttaa aatgagtcaa ctaatagacc aactaattat tagctattag    960
tcgttagctt ctttaatcta agctaaaacc aactaatagc ttatttgttg aattacaatt   1020
agctcaacgg aattctctgt tttttctata aaaaaaggga aactgcccct catttacagc   1080
aaattgtccg ctgcctgtcg tccagataca atgaacgtac ctagtaggaa ctcttttaca   1140
cgctcggtcg ctcgccgcgg atcggagtcc caggaacacg acaccactgt gtaacacgac   1200
aaagtctgct cagaggcggc cacaccctgg cgtgcaccga gccggagccc ggataagcac   1260
ggtaaggaga gtacggcggg acgtggcgac ccgtgtgtct gctgccacgc agccttcctc   1320
cacgtagccg cgcggccgcg ccacgtacca gggcccggcg ctggtataaa tgcgcgctac   1380
ctccgcttta gttctgcata cagccaaccc aaccatgtaa gatccgatca ccatcttctg   1440
aatttctgtt cttgatctgt catgtataat aactgtctag tcttggtgtt ggtgagatgg   1500
aaattcggtg gatctcggaa gggatattgt tcgtttgctg gggttttttt tgtgtgttgt   1560
gatccgtaga gaatttgtgt ttatccatgt tgttgatctt ggtatgtatt catgacatat   1620
tgacatgcat gtgttgtatg tgtcatatgt gtgcctctcc ttgggatttg ttttggataa   1680
tagaacatgt tatggactca atagtctgtg aacaaatctt ttttttagatg gtggccaaat   1740 ctgatgatga tctttcttga gaggaaaaag ttcatgatag aaaaatcttt tttgagatgg   1800
tggcttaatg tgatgatgat ctttcttgag aggaaaaaaa agattcatta taggagattt   1860
tgatttagct cctttccacc gatattaaat gaggagcatg catgctgatt gctgataagg   1920
atctgatttt tttatcccct cttctttgaa cagacaagaa ataggctctg aatttctgat   1980
tgattatttg tacatgcag                                                 1999
```

<210> SEQ ID NO 117
<211> LENGTH: 2198
<212> TYPE: DNA
<213> ORGANISM: Artificial sequence
<220> FEATURE:
<223> OTHER INFORMATION: cassette from vector pBPSMM369
      (OsV-ATPase::BPSI.1)
<220> FEATURE:
<221> NAME/KEY: promoter
<222> LOCATION: (1)..(1589)
<223> OTHER INFORMATION: putative Rice H+-transporting ATP synthase
      5'/UTR promoter; 99% homology to #AP002901 Oryza sativa (japonica
      cultivar-group) genomic DNA, chromosome 1.
<220> FEATURE:
<221> NAME/KEY: Intron
<222> LOCATION: (1616)..(2198)
<223> OTHER INFORMATION: IME-Intron: BPSI.1 intron

<400> SEQUENCE: 117

```
tccacaactg cacaagcaag caggcggacg gccagatcat accagctctc aaagatccaa     60
cggctcacgc atggcatgga actgttaccc tgtagcagaa tgcagcgttc tcgcgtaggg    120
tgttactgtg ggcaggaaaa ctaaagattt aatatgatat gatatgatat gatatgcacg    180
cacagaaacc gtataaaact cttatgtgca tatgggccta aggcccaaaa tggtggttaa    240
```

```
cgttgggctt caagcccaac caaaagccga ggaggactcc gagtctccga ctaggccttg    300
gccatgctgt agtctggacg gcggtgcacg ttggccaacg tgcccagacg cttcgacaag    360
gtggggccca caggaacaaa tcacgctgtc acgccgatcc gggccgtccg atcccgccac    420
gtggacgacg gaaaccccct ggtctctcga acatggcgga tcaaatcggg gacgagacga    480
cgacgcccaa aacaaaaccg ctaatctgac tggaaaccca gatcgccttc ttcgctgggg    540
gtggggcgac gaaacttgcg cgatctcccc tctcctctcc tccgctcgaa tctgcggtac    600
gcacgcctcc ctcctcctcc tcctcctcct cctcactcct tccggccccg atcctatagc    660
tcctccgctc gccgcgggga tctgcttacg acgaggcccg gcaccccgc cgccgccgga    720 tcgtggtttg gcgcttcaga cccgtgcgta gcgtgtagga tcaattggcg ctccacgttc    780
cccgatgttg ccgaatttc agagtttgtt gggtagattg accccgcta cctccactgt    840 ggaggtatgc agagctgccc gtgcgaggag atggggtttg tcgattagtg ttctgtcgag    900
agcgctagga ctaggatctt cgtagtgttg ttgtttaaga agtgagatac agtacaaagc    960
tcgtttctgc ctcagttctt ctagggagct tacatgtaat gatcaatgtg tctgaaacat   1020
gatttttttt ttcagagatg tagggttggt ttttggacta gaaagggttc tggtgaagta   1080
catatgattc gattggcgat gttctatcac tgccttttat gttttactg cttactagaa   1140 tagtagctca tggagctaga tccttctagt atttccagaa aattggaaca acataatctt   1200
tctagagtta atcttttgct aattcgaata gcaggatagt gtttgcctat ttggcatatc   1260
tactaactat acatttcacc ttgtagttga tatcagcttt agctttgtca gcatctgatt   1320
gattttagat tggcaaagta tctggccttt gttgctggta atttaggaaa tatagaagtg   1380
acagttaatg ccatgaattt gttgttttaa tttctaatct aaatcgcaaa actaaaagag   1440
aagataagta tgcggccagt gaagaaaggg tttaatggtg atgcataccc catttatcta   1500
gggaacttga gaaacagat acacgacaga ttgtccatag aatattcttc tgagtatatt   1560
ttattgactc aaatacttac ctacagcagg atccccgggc cttcacctgc ggagggtaag   1620
atccgatcac catcttctga atttctgttc ttgatctgtc atgtataata actgtctagt   1680
cttggtgttg gtgagatgga aattcggtgg atctcggaag ggatattgtt cgtttgctgg   1740 ggttttttt gtgtgttgtg atccgtagag aatttgtgtt tatccatgtt gttgatcttg   1800
gtatgtattc atgacatatt gacatgcatg tgttgtatgt gtcatatgtg tgcctctcct   1860
tgggatttgt tttggataat agaacatgtt atggactcaa tagtctgtga acaaatcttt   1920
ttttagatgg tggccaaatc tgatgatgat cttcttgag aggaaaaagt tcatgataga   1980
aaaatctttt ttgagatggt ggcttaatgt gatgatgatc tttcttgaga ggaaaaaaaa   2040
gattcattat aggagatttt gatttagctc ctttccaccg atattaaatg aggagcatgc   2100
atgctgattg ctgataagga tctgattttt ttatccccct ttctttgaac agacaagaaa   2160
taggctctga atttctgatt gattatttgt acatgcag                           2198
```

<210> SEQ ID NO 118
<211> LENGTH: 1409
<212> TYPE: DNA
<213> ORGANISM: Artificial sequence
<220> FEATURE:
<223> OTHER INFORMATION: cassette from vector pBPSMM366
   (OsC8,7SI::BPSI.1)
<220> FEATURE:
<221> NAME/KEY: promoter
<222> LOCATION: (1)..(796)
<223> OTHER INFORMATION: Putative Rice C-8,7 Sterol isomerase promoter;
   99%+ homology to #AP002969 Oryza sativa (japonica cultivar-group)
   genomic DNA, chromosome 1

```
<220> FEATURE:
<221> NAME/KEY: Intron
<222> LOCATION: (827)..(1409)
<223> OTHER INFORMATION: IME-Intron: BPSI.1 intron

<400> SEQUENCE: 118
cctcgattcg accgtgtaat ggaatgaagg tggtgggccc ccaccccac  aagccactct      60
ccacactttg gtgttcctgg tatgtcacct agaccaacaa ctatgttaag ccatatgttc     120
cacagtgcaa aatctacaag accacgatac aagtaggtat ggtggactac cacattttca    180
cttctctttc actttcccct ctctctcccc tctctcttcc tttcccccac cgcagagagc    240
ctggcgcgcg gagacggcga cggcgccgga ccaagcagtg gtggagcgac ggcagggcga    300
cagcgccgag cggcgggatg cgctcgccgg cgcaccaccc cctcctctcc ccccgagcg     360
gcggggctgc tcggagcagc agggcggcgg cggcatgtcg gcggcgggca gacgacttgg    420
agcgggagac ggcgacgggc ggatgcgagg cggcggtcgg cgccctcctc ccctggagtt    480
cggctgcttc gcccctctc  ctctctcctc tagcggtggt gtgggtccca ctgagctgag    540
gagggcgcgc ggttggacga cgaggcaaag gaatactagt cttcgctttt ttgggttgag    600
gctgaatgcc acgtcggccc attgtgaatg ccctttaaca aaacaagggt ttatggctat    660
gggatctggc tgaggcattg acctaccttg gtccttggca gagagagaga gagactcccc    720
ctcactcctt ccccgacgac ctgctcgatc cgatccaatc agctcctctc cagtccagat    780
cggaaggaag ccaggagctc ggtacccggg ccttcacctg cggagggtaa gatccgatca    840
ccatcttctg aatttctgtt cttgatctgt catgtataat aactgtctag tcttggtgtt    900
ggtgagatgg aaattcggtg gatctcggaa gggatattgt tcgtttgctg gggttttttt    960
tgtgtgttgt gatccgtaga gaatttgtgt ttatccatgt tgttgatctt ggtatgtatt   1020
catgacatat tgacatgcat gtgttgtatg tgtcatatgt gtgcctctcc ttgggatttg   1080
ttttggataa tagaacatgt tatggactca atagtctgtg aacaaatctt tttttagatg   1140
gtggccaaat ctgatgatga tctttcttga gaggaaaaag ttcatgatag aaaaatcttt   1200
tttgagatgg tggcttaatg tgatgatgat ctttcttgag aggaaaaaaa agattcatta   1260
taggagattt tgatttagct cctttccacc gatattaaat gaggagcatg catgctgatt   1320
gctgataagg atctgatttt tttatccccct cttctttgaa cagacaagaa ataggctctg   1380
aatttctgat tgattatttg tacatgcag                                     1409

<210> SEQ ID NO 119
<211> LENGTH: 1677
<212> TYPE: DNA
<213> ORGANISM: Artificial sequence
<220> FEATURE:
<223> OTHER INFORMATION: cassette from vector pBPSMM357 (ZmLDH::BPSI.1)
<220> FEATURE:
<221> NAME/KEY: promoter
<222> LOCATION: (1)..(1062)
<223> OTHER INFORMATION: Z.mays gene Lactate Dehydrogenase 5'/UTR
       promoter
<220> FEATURE:
<221> NAME/KEY: Intron
<222> LOCATION: (1095)..(1677)
<223> OTHER INFORMATION: IME-Intron: BPSI.1 intron

<400> SEQUENCE: 119
aacaaatggc gtacttatat aaccacaatg tactggtgct gcgtcattat tttatactac      60
gcatatatta tttataagtag agaaagctca caaaaccatg cgcgcgcccc cctgtttgtt    120
tcggtcgcta attacaccct ttgtatcgtt ggttgatgat ggtctccacc ggccgtacga    180
```

```
gtcatcgatc gttgatttat ttttatcacc gacttgcacg cctttcgaac aaagacgcaa      240
caaaggaaag cgaaagcgtc acgaacgagg ttgttccctg acagttgttc gactaataca      300
actgcaagac actgaataag cagtaaaaat caatatagat taaagttaaa cgaacatgct      360
caacatcgaa tactactcat atgtgttatt attaagagaa taccaccaag gtagaaaagt      420
taaaggacct aaactgttgt gccgggagag ttgtgcgacg aacagatgta aatatgataa      480
aataagttca aagttcatat agatagcacg atcacactta gggctagttt gaagccataa      540
aaatggaaga gattaaatga gataaaattc acttatttaa ttttaaataa gaagagagtt      600
ttaacccctc taattctctc cagtatttta gctcctaaac tagctcttac agcagtaaaa      660
gacccttgat ggtagcgtat gcaaagagaa ggaactattc aatgaattgt ttttttaatc      720
actagtagta tggtgggtaa ctgtcgtcaa ccggccctat ctacttcagt ttagtgaagc      780
actaaaccgc accttggtat gttcaaattt aagattttt ttgaaacgaa acaattttaa      840
ccagcggctc caaccggtg aagtggtttg gtctttggtg tggggccagg gtattaatgg       900
aattgaatat ataaagagca gggtggtgga cctttcccct cccacgagtc gagtagccat      960
tgcccattgc cattccttcc ttcctccaca gagaaatccg atccgcggag atttgaccca     1020
accagatcat atcacacacg taatcccatc ccattccgcc cggagctcgg tacccgggcc     1080
ttcacctgcg gagggtaaga tccgatcacc atcttctgaa tttctgttct tgatctgtca     1140
tgtataataa ctgtctagtc ttggtgttgg tgagatggaa attcggtgga tctcggaagg     1200
gatattgttc gtttgctggg gttttttttg tgtgttgtga tccgtagaga atttgtgttt     1260
atccatgttg ttgatcttgg tatgtattca tgacatattg acatgcatgt gttgtatgtg     1320
tcatatgtgt gcctctcctt gggatttgtt ttggataata gaacatgtta tggactcaat     1380
agtctgtgaa caaatctttt tttagatggt ggccaaatct gatgatgatc tttcttgaga     1440
ggaaaaagtt catgatagaa aaatcttttt tgagatggtg gcttaatgtg atgatgatct     1500
ttcttgagag gaaaaaaaag attcattata ggagattttg atttagctcc tttccaccga     1560
tattaaatga ggagcatgca tgctgattgc tgataaggat ctgatttttt tatcccctct     1620
tctttgaaca gacaagaaat aggctctgaa tttctgattg attatttgta catgcag        1677
```

<210> SEQ ID NO 120
<211> LENGTH: 1318
<212> TYPE: DNA
<213> ORGANISM: Artificial sequence
<220> FEATURE:
<223> OTHER INFORMATION: cassette from vector pBPSLM229 (ZmLDH::BPSI.5)
<220> FEATURE:
<221> NAME/KEY: promoter
<222> LOCATION: (1)..(1062)
<223> OTHER INFORMATION: Z.mays gene Lactate Dehydrogenase 5'/UTR
      promoter
<220> FEATURE:
<221> NAME/KEY: Intron
<222> LOCATION: (1068)..(1318)
<223> OTHER INFORMATION: IME-Intron: BPSI.5 intron

<400> SEQUENCE: 120

```
aacaaatggc gtacttatat aaccacaatg tactggtgct gcgtcattat tttatactac       60
gcatatatta ttataagtag agaaagctca caaaaccatg cgcgcgcccc cctgtttgtt      120
tcggtcgcta attacaccct ttgtatcgtt ggttgatgat ggtctccacc ggccgtacga      180
gtcatcgatc gttgatttat ttttatcacc gacttgcacg cctttcgaac aaagacgcaa      240
caaaggaaag cgaaagcgtc acgaacgagg ttgttccctg acagttgttc gactaataca      300
actgcaagac actgaataag cagtaaaaat caatatagat taaagttaaa cgaacatgct      360
```

```
caacatcgaa tactactcat atgtgttatt attaagagaa taccaccaag gtagaaaagt      420
taaaggacct aaactgttgt gccgggagag ttgtgcgacg aacagatgta aatatgataa      480
aataagttca aagttcatat agatagcacg atcacactta gggctagttt gaagccataa      540
aaatggaaga gattaaatga gataaaattc acttatttaa ttttaaataa gaagagagtt      600 ttaaccccte taattctctc cagtatttta gctcctaaac tagctcttac agcagtaaaa      660 gaccettgat ggtagcgtat gcaaagagaa ggaactattc aatgaattgt tttttaatc      720 actagtagta tggtgggtaa ctgtcgtcaa ccggccctat ctacttcagt ttagtgaagc      780
actaaaccgc accttggtat gttcaaattt aagattttt ttgaaacgaa acaattttaa      840
ccagcggctc caaaccggtg aagtggtttg gtctttggtg tggggccagg gtattaatgg      900
aattgaatat ataagagca gggtggtgga cctttcccct cccacgagtc gagtagccat      960
tgcccattgc cattccttcc ttcctccaca gagaaatccg atccgcggag atttgaccca     1020
accagatcat atcacacacg taatcccatc ccattccgcc cggagctctc tggtggctga     1080
ggtaagttct gttattacct cataaactgc ctgctgataa tactttaaca atgtgctaat     1140
attagtcttt gtaataagat agtactatac tgaaaatatt ttagcgagta tgagtaattt     1200
aacttacata ttgtattgct gttcctcttt ttcaaccctg tcatattggt tgcttttttt     1260
cacagcctaa catgctcttg tttggtcatt ttccctgtt ttcaggtttt cctgtccg       1318

<210> SEQ ID NO 121
<211> LENGTH: 2001
<212> TYPE: DNA
<213> ORGANISM: Artificial sequence
<220> FEATURE:
<223> OTHER INFORMATION: cassette from vector pBPSMM371 (OsLea::BPSI.1)
<220> FEATURE:
<221> NAME/KEY: promoter
<222> LOCATION: (1)..(1386)
<220> FEATURE:
<221> NAME/KEY: promoter
<222> LOCATION: (1)..(1386)
<223> OTHER INFORMATION: Oryza sativa Lea (Late Embryogenesis Abundant)
      promoter
<220> FEATURE:
<221> NAME/KEY: Intron
<222> LOCATION: (1387)..(2001)
<223> OTHER INFORMATION: IME-Intron: BPSI.1 intron

<400> SEQUENCE: 121
tcgggttgct atctggcccg tcccaagacg agttctgatc ggatccggcc cagctcagcc       60
aatgccaagc tgcagatgat gaacaagaag catatggcct tatcttatct tttcgtttat      120
atttatactt atcagacaaa atttaaaatt ttaacactag atttaaaact aattttcagg      180
tttttctcat taaaatttgt ttttcaatct ttgcttttag gtcgttaaga acacgtatat      240 aaaaattta tccacaaatt acttctcatt tacggatatg ccgtttggcc aaccaatagg      300
catctgaagg tgcaggtgac gggagcgaac aagttccagg gcctccttcc attctgctca      360
agcagcagca gggggaggaa gaagtagtta ccagcagttt attaattagg ccgagtggac      420
aagatcgatg gcgcagaaaa cgtacccttc cacaactgta taatctagat taaattttac      480
aaaaactaca tgtattttac attatttata acaaaactat aaatttaaaa gcttgttttt      540
ttcgctggga tggtgaagaa tgccgaccga tgtatattaa ggaaagggaa aaactgtac       600 aaacctcctc gggaggaggc acaaatgtag tgcatcaaaa gcaccgcctt tacaacatta      660
agcaagtttc aaaggctata atctctctaa agctggtgct gcggcaacac tcaatgagct      720
aactagccct gctaattttc aagtttccca ttcatcacac atgatcgcac acagttgtgt      780
```

```
gaccgacgag cttgttttat aaaattacaa attcagcgtc tccgtttatc acgaaactag    840
acatacttcg tgcaatatat ccatcaacac agataatctc tatatcggta atcactaatt    900
agtgagcaga tcatccatca acatagataa gatctacaat taattcgtta cgaatgaccg    960
gtttcgtagt ggtggtggag agggaggccg ccgaccaaac caaggtcctg cggccgggaa   1020
aacgatgtgg cttttagtag caggagtcgg cagaaagcat gttggtcgga gaagaacata   1080
tgccgtacgt tttgtacagg tggtgcatcc agaaaaatct cgatcgcaac tagcggggac   1140
gtgtgtccag tcctggtgtt ccgatcgatc gacgtggtgt acatgcatcg cgtccacgta   1200
acagccattc atgcatgatg atcgtcttcg tccatcgacc aaagtcgtcc aagtgcagca   1260
tatatataat cggatgcaac tcgagcaacc ttacttccca tcatacgcac tgcaagctta   1320
gcttggtgag gatcgatcga tcggagaaga tcatcagatt gataattaaa gtaagaaagg   1380
tcgagggagc tcggtacccg ggccttcacc tgcggagggt aagatccgat caccatcttc   1440
tgaatttctg ttcttgatct gtcatgtata ataactgtct agtcttggtg ttggtgagat   1500
ggaaattcgg tggatctcgg aagggatatt gttcgtttgc tggggttttt tttgtgtgtt   1560
gtgatccgta gagaatttgt gtttatccat gttgttgatc ttggtatgta ttcatgacat   1620
attgacatgc atgtgttgta tgtgtcatat gtgtgcctct ccttgggatt tgttttggat   1680
aatagaacat gttatggact caatagtctg tgaacaaatc ttttttttaga tggtggccaa   1740 atctgatgat gatctttctt gagaggaaaa agttcatgat agaaaaatct tttttgagat   1800
ggtggcttaa tgtgatgatg atctttcttg agaggaaaaa aaagattcat tataggagat   1860
tttgatttag ctccttttcca ccgatattaa atgaggagca tgcatgctga ttgctgataa   1920
ggatctgatt tttttatccc ctcttctttg aacagacaag aaataggctc tgaatttctg   1980
attgattatt tgtacatgca g                                              2001
```